(12) United States Patent
Reed et al.

(10) Patent No.: US 6,911,426 B2
(45) Date of Patent: Jun. 28, 2005

(54) METHODS AND COMPOSITIONS FOR DEREPRESSION OF IAP-INHIBITED CASPASE

(75) Inventors: John C. Reed, Rancho Santa Fe, CA (US); Richard A. Houghten, Solana Beach, CA (US); Adel Nefzi, San Diego, CA (US); John M. Ostresh, Encinitas, CA (US); Clemencia Pinilla, Cardiff, CA (US); Kate Welsh, San Diego, CA (US)

(73) Assignees: The Burnham Institute, La Jolla, CA (US); Torrey Pines Institute for Molecular Studies, San Diego, CA (US)

( * ) Notice: Subject to any disclaimer, the term of this patent is extended or adjusted under 35 U.S.C. 154(b) by 26 days.

(21) Appl. No.: 10/302,811

(22) Filed: Nov. 21, 2002

(65) Prior Publication Data

US 2003/0180805 A1 Sep. 25, 2003

Related U.S. Application Data

(60) Provisional application No. 60/331,957, filed on Nov. 21, 2001.

(51) Int. Cl.$^7$ .............................................. A61K 38/00
(52) U.S. Cl. ......................................................... 514/2
(58) Field of Search ............................................. 514/2

(56) References Cited

U.S. PATENT DOCUMENTS

| | | | |
|---|---|---|---|
| 4,631,211 A | 12/1986 | Houghten | 428/35 |
| 5,556,762 A | 9/1996 | Pinilla et al. | 435/7.21 |
| 6,159,709 A | 12/2000 | Korneluk et al. | 435/69.1 |
| 6,228,603 B1 | 5/2001 | Reed et al. | 435/18 |

FOREIGN PATENT DOCUMENTS

WO      WO 92/09300      6/1992

OTHER PUBLICATIONS

Ambrosini et al., "A novel anti-apoptosis gene, *survivin*, expressed in cancer and lymphoma," *Nature Med.* 3:917–921 (1997).
Birnbaum et al., "An Apoptosis–Inhibiting Gene from a Nuclear Polyhedrosis Virus Encoding a Polypeptide with Cys/His Sequence Motifs," *J. Virol.* 68:2521–2528 (1994).
Boldin et al., "Involvement of Mach, a Novel Mort1/FAD-D–Interacting Protease, in Fas/APO–1– and TNF Receptor–Induced Cell Death," *Cell* 85:803–815 (1996).
Casciola–Rosen et al., "Apopain/CPP32 Cleaves Proteins That Are Essential for Cellular Repair: a Fundamental Principle of Apoptotic Death," *J. Exp. Med.* 183:1957–1964 (1996).
Chai et al., "Structural and biochemical basis of apoptotic activation by Smac/DIABLO," *Nature* 406:855–862 (2000).

Chen et al., "A Human IAP–Family Gene, *Apollon*, Expressed in Human Brain Cancer Cells," *Biochem. Biophys. Res. Commun.* 264:847–854 (1999).
Deveraux et al., "IAPs block apoptotic events induced by caspase–8 and cytochrome c by direct inhibition of distinct caspases," *EMBO J.* 17:2215–2223 (1998).
Deveraux and Reed, "IAP family proteins–suppressors of apoptosis," *Genes and Development* 13:239–252 (1999).
Dooley et al., "An All D–Amino Acid Opioid Peptide with Central Analgesic Activity from a Combinatorial Library," *Science* 266:2019–2022 (1994).
Du et al., "Smac, a Mitochondrial Protein That Promotes Cytochrome c—Dependent Caspase Activation by Eliminating IAP Inhibition," *Cell* 102:33–42 (2000).
Houghten et al., "Generation and Use of synthetic peptide combinatorial libraries for basic research and drug discovery," *Nature* 354:84–86 (1991).
Kasof and Gomes, "Livin, a Novel Inhibitor of Apoptosis Protein Family Member," *J. Biol. Chem.* 276:3238–3246 (2001).
Kharbanda et al., "Role for Bcl–$x_L$ as an inhibitor of cytosolic cytochrome C accumulation in DNA damage–induced apoptosis," *Proc. Natl. Acad. Sci. USA* 94:6939–6942 (1997).
Kluck et al., "The Release of Cytochrome c from Mitochondria: a Primary Site for Bcl–2 Regulation of Apoptosis," *Science* 275:1132–1136 (1997).
Li et al., "Cytochrome c and dATP–Dependent Formation of Apaf–1/Caspase–9 Complex Initiates an Apoptotic Protease Cascade," *Cell* 91:479–489 (1997).
Liston et al., "Suppression of apoptosis in mammalian cells by NAIP and a related family of IAP genes," *Nature* 379:349–353 (1996).

(Continued)

*Primary Examiner*—Christopher R. Tate
*Assistant Examiner*—Maury Audet
(74) *Attorney, Agent, or Firm*—McDermott Will & Emery LLP

(57) ABSTRACT

The invention provides isolated agents having a core peptide selected from the group consisting of Core peptides 5 through 39 and 42 through 55, wherein the agent derepresses an IAP-inhibited caspase. Also provided is an isolated agent having a core structure selected from any of the structures shown in FIGS. 5, 9, 10, 14B, and 21–24 wherein said agent derepresses an IAP-inhibited caspase. The invention further provides a method of derepressing an IAP-inhibited caspase. The method consists of contacting an IAP-inhibited caspase with an effective amount of an agent to derepress an IAP-inhibited caspase, the agent having a core motif selected from the group consisting of a core peptide having a sequence set forth in any of Core peptides 4 through 39 and 42 through 55, and a core structure selected from the group consisting of TPI759, TPI882, TPI914 or TPI927. The methods of the invention also can be used for promoting apoptosis in a cell and for reducing the severity of a pathology characterized by reduced levels of apoptosis. Methods for identifying agents that derepress an IAP-inhibited caspase are also provided.

12 Claims, 122 Drawing Sheets

OTHER PUBLICATIONS

Liu et al., "Induction of Apoptotic Program in Cell–Free Extracts: Requirement for dATP and Cytochrome c," *Cell* 86:147–157 (1996).

Liu et al., "DFF, a Heterodimeric Protein That Functions Downstream of Caspase–3 to Trigger DNA Fragmentation During Apoptosis," *Cell* 89:175–184 (1997).

Liu et al., "Structural basis for binding of Smac/DIABLO to the XIAP BIR3 domain," *Nature* 408:1004–1008 (2000).

Martin and Green, "Protease Activation During Apoptosis: Death by a Thousand Cuts?," *Cell* 82:349–352 (1995).

Muzio et al., "FLICE, a Novel FADD–Homologous ICE/CED–3–like Protease, Is Recruited to the CD95 (Fas/APO–1) Death—Inducing Signaling Complex," *Cell* 85:817–827 (1996).

Reed and Tomaselli, "Drug discovery opportunities from apoptosis research," *Cur. Opin. Biotech.* 11:586–592 (2000).

Reed, J., "Apoptosis–regulating proteins as targets for drug discovery," *Trends Mol. Med.* 7:314–319 (2001).

Riedl et al., "Structural Basis for the Inhibition of Caspase–3 by XIAP," *Cell* 104:791–800 (2001).

Rothe et al., "The TNFR2–TRAF Signaling Complex Contains Two Novel Proteins Related to Baculoviral Inhibitor of Apoptosis Proteins," *Cell* 83:1243–1252 (1995).

Roy et al., "The c–IAP–1 and c–IAP–2 proteins are direct inhibitors of specific caspases," *EMBO J.* 16:6914–6925 (1997).

Sun et al., "NMR structure and mutagenesis of the inhibitor–of–apoptosis protein XIAP," *Nature* 401:818–822 (1999).

Srinivasula et al., "Molecular Determinants of the Caspase–promoting Activity of Smac/DIABLO and its Role in the Death Receptor Pathway," *J. Bio. Chem.* 275:36152–36157 (2000).

Srinivasula et al., "A conserved XIAP–interaction motif in caspase–9 and Smac/DIABLO regulates caspase activity and apoptosis," *Nature* 410:112–116 (2001).

Takahashi et al., "Cleavage of lamin A by Mch2α but not CPP32: Multiple interleukin 1β–converting enzyme–related proteases with distinct substrate recognition properties are active in apoptosis," *Proc. Natl. Acad. Sci. USA* 93:8395–8400 (1996).

Takahashi et al., A Single BIR Domain of XIAP Sufficient for Inhibiting Caspases, *J. Biol. Chem.* 273:7787–7790 (1998).

Ubeda and Habener, "The Large Subunit of the DNA Replication Complex C (DSEB/RF–C140) Cleaved and Inactivated by Caspase–3 (CPP32/YAMA) During Fas–induced Apoptosis," *J. Biol. Chem.* 272:19562–19568 (1997).

Verhagen et al., "Identification of DIABLO, a Mammalian Protein that Promotes Apoptosis by Binding to and Antagonizing IAP Proteins," *Cell* 102:43–53 (2000).

Vucic et al., "ML–IAP, a novel inhibitor of apoptosis that is preferentially expressed in human melanomas," *Cur. Biol.* 10:1359–1366 (2000).

Wang et al., "Cleavage of sterol regulatory element binding proteins (SREBPs) by CPP32 during apoptosis," *EMBO J.* 15:1012–1020 (1996).

Wu et al., "Structural basis of IAP recognition by Smac/DIABLO," *Nature* 408:1008–1012 (2000).

Yang et al., "Prevention of Apoptosis by Bcl–2: Release of Cytochrome c from Mitochondria Blocked," *Science* 275:1129–1132 (1997).

Zou et al., "Apaf–1, a Human Protein Homologous to C. elegans CED–4, Participates in Cytochrome c–Dependent Activation of Caspase–3," *Cell* 90:405–413 (1997).

Zhou et al., "Target Protease Specificity of the Viral Serpin CrmA. Analysis of Five Caspases," *J. Biol. Chem.* 272:7797–7800 (1997).

Zhou et al., "IL–10 Inhibits Apoptosis of Promyeloid Cells by Activating Insulin Receptor Substrate–2 and Phosphatidylinositol 3'–Kinase," *J. Immunol.* 167:4436–4442 (2001).

TPI 1313

| | 1 | 2 | 3 | 4 | | | | | Ratio>1.9 | |
|---|---|---|---|---|---|---|---|---|---|---|
| | L-Thiala | D-pCl-Phe | D-OEt-Tyr | D-pCl-Phe | | | | | | |
| | D-Thiala | D-OEt-Tyr | D-Nal | D-pNO2-Phe | | | | | | |
| | Phe | D-Phe | | D-Thiala | | | | | | |

| | | | | | | Ratio Caspase3/Xiap | | Ratio peptide/xiap | |
|---|---|---|---|---|---|---|---|---|---|
| Vial# | 1 | 2 | 3 | 4 | | Avg | std | AVG | std |
| 1 | L-Thiala | D-pCl-Phe | D-OEt-Tyr | D-pCl-Phe | -NH2 | 0.9 | 0.036 | 1.3 | 0.20 |
| 2 | L-Thiala | D-pCl-Phe | D-OEt-Tyr | D-pNO2-Phe | -NH2 | 0.9 | 0.035 | 1.3 | 0.22 |
| 3 | L-Thiala | D-pCl-Phe | D-OEt-Tyr | D-Thiala | -NH2 | 0.9 | 0.031 | 0.9 | 0.10 |
| 4 | L-Thiala | D-pCl-Phe | D-Nal | D-pCl-Phe | -NH2 | 0.9 | 0.031 | 2.3 | 0.60 |
| 5 | L-Thiala | D-pCl-Phe | D-Nal | D-pNO2-Phe | -NH2 | 0.9 | 0.033 | 1.7 | 0.24 |
| 6 | L-Thiala | D-pCl-Phe | D-Nal | D-Thiala | -NH2 | 0.9 | 0.029 | 1.3 | 0.17 |
| 7 | L-Thiala | D-OEt-Tyr | D-OEt-Tyr | D-pCl-Phe | -NH2 | 0.9 | 0.024 | 2.7 | 0.37 |
| 8 | L-Thiala | D-OEt-Tyr | D-OEt-Tyr | D-pNO2-Phe | -NH2 | 0.9 | 0.027 | 1.4 | 0.21 |
| 9 | L-Thiala | D-OEt-Tyr | D-OEt-Tyr | D-Thiala | -NH2 | 0.9 | 0.032 | 0.9 | 0.05 |
| 10 | L-Thiala | D-OEt-Tyr | D-Nal | D-pCl-Phe | -NH2 | 0.9 | 0.029 | 0.7 | 0.09 |
| 11 | L-Thiala | D-OEt-Tyr | D-Nal | D-pNO2-Phe | -NH2 | 0.9 | 0.031 | 0.9 | 0.18 |
| 12 | L-Thiala | D-OEt-Tyr | D-Nal | D-Thiala | -NH2 | 0.9 | 0.029 | 0.9 | 0.13 |
| 13 | L-Thiala | D-Phe | D-OEt-Tyr | D-pCl-Phe | -NH2 | 0.9 | 0.028 | 0.6 | 0.08 |
| 14 | L-Thiala | D-Phe | D-OEt-Tyr | D-pNO2-Phe | -NH2 | 0.9 | 0.028 | 0.6 | 0.08 |
| 15 | L-Thiala | D-Phe | D-OEt-Tyr | D-Thiala | -NH2 | 0.9 | 0.025 | 0.6 | 0.07 |
| 16 | L-Thiala | D-Phe | D-Nal | D-pCl-Phe | -NH2 | 0.9 | 0.029 | 0.8 | 0.09 |
| 17 | L-Thiala | D-Phe | D-Nal | D-pNO2-Phe | -NH2 | 0.9 | 0.032 | 1.1 | 0.10 |
| 18 | L-Thiala | D-Phe | D-Nal | D-Thiala | -NH2 | 0.9 | 0.029 | 0.9 | 0.08 |
| 19 | D-Thiala | D-pCl-Phe | D-OEt-Tyr | D-pCl-Phe | -NH2 | 0.9 | 0.031 | 1.5 | 0.24 |
| 20 | D-Thiala | D-pCl-Phe | D-OEt-Tyr | D-pNO2-Phe | -NH2 | 0.8 | 0.042 | 1.3 | 0.30 |
| 21 | D-Thiala | D-pCl-Phe | D-OEt-Tyr | D-Thiala | -NH2 | 0.9 | 0.030 | 0.9 | 0.10 |

Figure 2A

TPI 1313

| | 1 | 2 | 3 | 4 | |
|---|---|---|---|---|---|
| | L-Thiala | D-pCl-Phe | D-OEt-Tyr | D-pCl-Phe | |
| | D-Thiala | D-OEt-Tyr | D-Nal | D-pNO2-Phe | |
| | Phe | D-Phe | | D-Thiala | |

| Vial# | 1 | 2 | 3 | 4 | | Ratio Caspase3/Xiap Avg | std | Ratio peptide/xiap AVG | std |
|---|---|---|---|---|---|---|---|---|---|
| 22 | D-Thiala | D-pCl-Phe | D-Nal | D-pCl-Phe | -NH2 | 0.9 | 0.030 | 1.0 | 0.14 |
| 23 | D-Thiala | D-pCl-Phe | D-Nal | D-pNO2-Phe | -NH2 | 0.9 | 0.022 | 1.0 | 0.10 |
| 24 | D-Thiala | D-pCl-Phe | D-Nal | D-Thiala | -NH2 | 0.9 | 0.024 | 1.3 | 0.16 |
| 25 | D-Thiala | D-OEt-Tyr | D-OEt-Tyr | D-pCl-Phe | -NH2 | 1.0 | 0.028 | 1.6 | 0.20 |
| 26 | D-Thiala | D-OEt-Tyr | D-OEt-Tyr | D-pNO2-Phe | -NH2 | 0.8 | 0.027 | 1.1 | 0.14 |
| 27 | D-Thiala | D-OEt-Tyr | D-OEt-Tyr | D-Thiala | -NH2 | 0.9 | 0.037 | 1.1 | 0.12 |
| 28 | D-Thiala | D-OEt-Tyr | D-Nal | D-pCl-Phe | -NH2 | 0.9 | 0.041 | 1.1 | 0.11 |
| 29 | D-Thiala | D-OEt-Tyr | D-Nal | D-pNO2-Phe | -NH2 | 0.9 | 0.032 | 1.1 | 0.14 |
| 30 | D-Thiala | D-OEt-Tyr | D-Nal | D-Thiala | -NH2 | 0.9 | 0.043 | 1.2 | 0.12 |
| 31 | D-Thiala | D-Phe | D-OEt-Tyr | D-pCl-Phe | -NH2 | 0.9 | 0.038 | 1.3 | 0.15 |
| 32 | D-Thiala | D-Phe | D-OEt-Tyr | D-pNO2-Phe | -NH2 | 1.0 | 0.036 | 1.1 | 0.08 |
| 33 | D-Thiala | D-Phe | D-OEt-Tyr | D-Thiala | -NH2 | 0.9 | 0.034 | 1.0 | 0.08 |
| 34 | D-Thiala | D-Phe | D-Nal | D-pCl-Phe | -NH2 | 0.9 | 0.027 | 1.0 | 0.13 |
| 35 | D-Thiala | D-Phe | D-Nal | D-pNO2-Phe | -NH2 | 0.9 | 0.029 | 0.9 | 0.12 |
| 36 | D-Thiala | D-Phe | D-Nal | D-Thiala | -NH2 | 0.9 | 0.032 | 1.1 | 0.13 |
| 37 | Phe | D-pCl-Phe | D-OEt-Tyr | D-pCl-Phe | -NH2 | 0.9 | 0.042 | 1.3 | 0.14 |
| 38 | Phe | D-pCl-Phe | D-OEt-Tyr | D-pNO2-Phe | -NH2 | 0.9 | 0.030 | 0.8 | 0.12 |
| 39 | Phe | D-pCl-Phe | D-OEt-Tyr | D-Thiala | -NH2 | 0.9 | 0.029 | 0.9 | 0.11 |
| 40 | Phe | D-pCl-Phe | D-Nal | D-pCl-Phe | -NH2 | 1.0 | 0.026 | 1.9 | 0.13 |
| 41 | Phe | D-pCl-Phe | D-Nal | D-pNO2-Phe | -NH2 | 1.0 | 0.120 | 0.9 | 0.07 |
| 42 | Phe | D-pCl-Phe | D-Nal | D-Thiala | -NH2 | 0.9 | 0.045 | 1.0 | 0.27 |

Ratio > 1.9

Figure 2B

TPI 1313

| Vial# | 1 | 2 | 3 | 4 | | Ratio Caspase3/Xiap Avg | std | Ratio peptide/xiap AVG | std |
|---|---|---|---|---|---|---|---|---|---|
| | L-Thiala | D-pCl-Phe | D-OEt-Tyr | D-pCl-Phe | | | | Ratio>1.9 | |
| | D-Thiala | D-OEt-Tyr | D-Nal | D-pNO2-Phe | | | | | |
| | Phe | D-Phe | | D-Thiala | | | | | |
| 43 | Phe | D-OEt-Tyr | D-OEt-Tyr | D-pCl-Phe | -NH2 | 1.0 | 0.098 | 0.9 | 0.14 |
| 44 | Phe | D-OEt-Tyr | D-OEt-Tyr | D-pNO2-Phe | -NH2 | 1.0 | 0.139 | 1.0 | 0.07 |
| 45 | Phe | D-OEt-Tyr | D-OEt-Tyr | D-Thiala | -NH2 | 1.0 | 0.114 | 0.8 | 0.23 |
| 46 | Phe | D-OEt-Tyr | D-Nal | D-pCl-Phe | -NH2 | 1.0 | 0.124 | 0.9 | 0.26 |
| 47 | Phe | D-OEt-Tyr | D-Nal | D-pNO2-Phe | -NH2 | 0.9 | 0.100 | 1.0 | 0.33 |
| 48 | Phe | D-OEt-Tyr | D-Nal | D-Thiala | -NH2 | 1.0 | 0.068 | 1.0 | 0.05 |
| 49 | Phe | D-Phe | D-OEt-Tyr | D-pCl-Phe | -NH2 | 1.0 | 0.057 | 1.1 | 0.09 |
| 50 | Phe | D-Phe | D-OEt-Tyr | D-pNO2-Phe | -NH2 | 0.9 | 0.106 | 0.9 | 0.07 |
| 51 | Phe | D-Phe | D-OEt-Tyr | D-Thiala | -NH2 | 1.0 | 0.056 | 0.9 | 0.03 |
| 52 | Phe | D-Phe | D-Nal | D-pCl-Phe | -NH2 | 0.9 | 0.083 | 1.0 | 0.14 |
| 53 | Phe | D-Phe | D-Nal | D-pNO2-Phe | -NH2 | 0.9 | 0.080 | 0.9 | 0.06 |
| 54 | Phe | D-Phe | D-Nal | D-Thiala | -NH2 | 1.0 | 0.127 | 0.9 | 0.03 |

Figure 2C

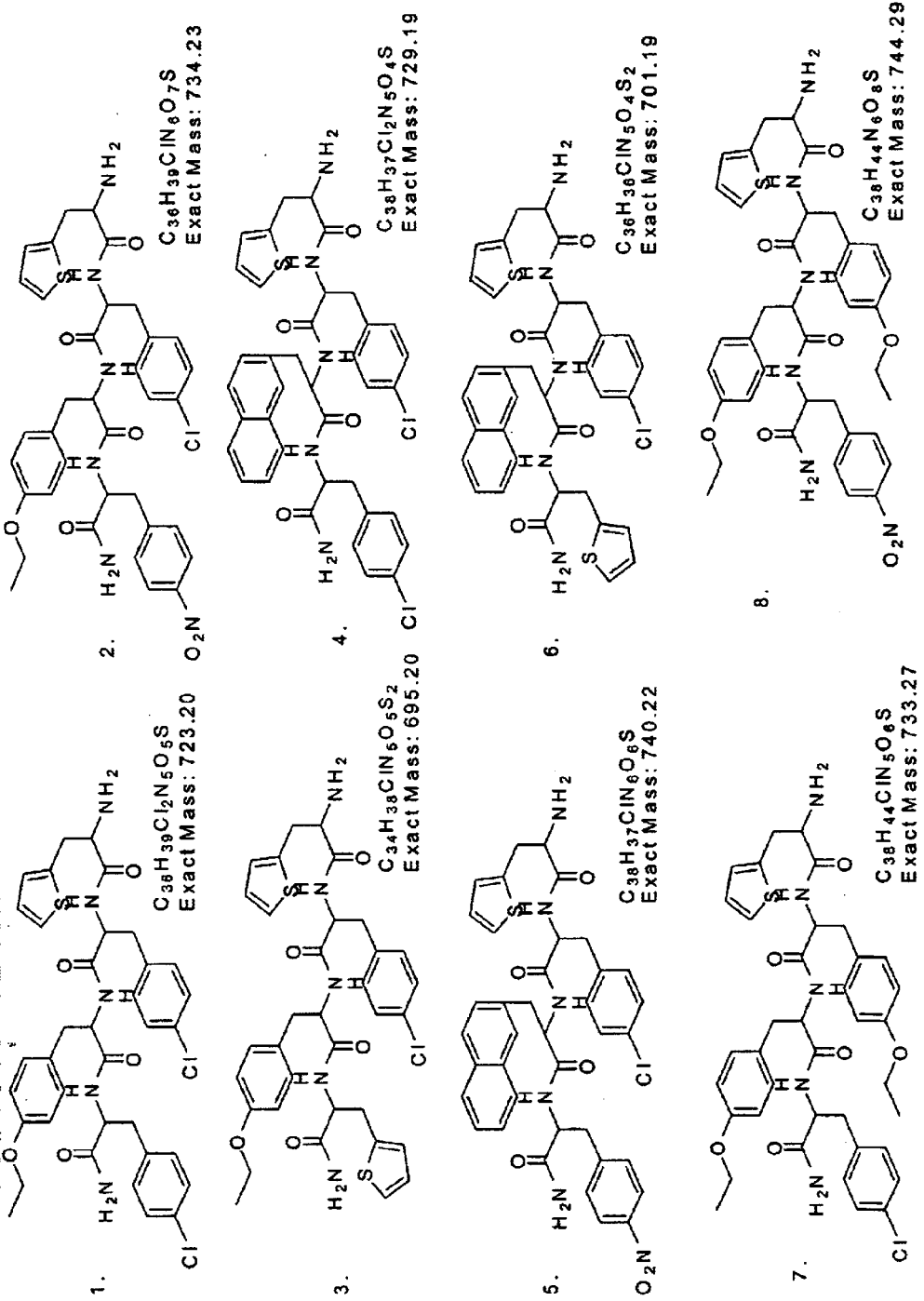

TPI 882

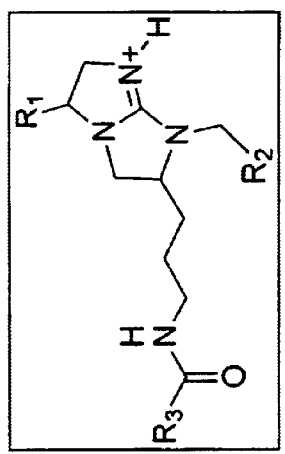

R1

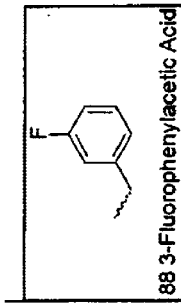
16 L-cyclohexylalanine
cyclohexylmethyl

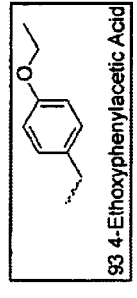
17 D-cyclohexylalanine
cyclohexylmethyl

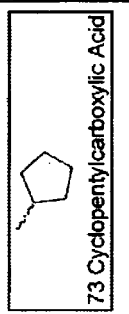
44 2-Phenylbutyric Acid
1-phenylpropyl

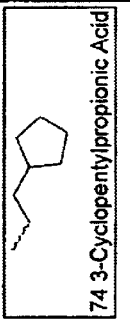
45 3-Phenylbutyric Acid
2-phenylpropyl

R2

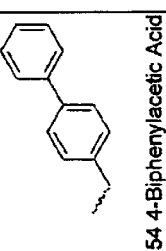
54 4-Biphenylacetic Acid
1-biphenylmethyl

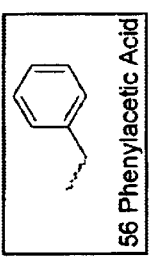
56 Phenylacetic Acid
benzyl

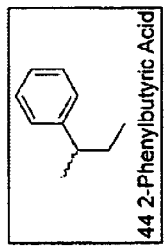
73 Cyclopentylcarboxylic Acid
cyclopentyl

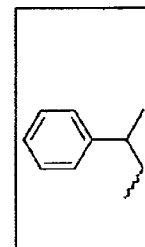
74 3-Cyclopentylpropionic Acid
cyclopentylethyl

R3

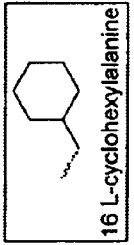
88 3-Fluorophenylacetic Acid
3-fluorobenzyl 93 4-Ethoxyphenylacetic Acid
4-ethoxybenzyl

Figure 7A

TPI 882
R3
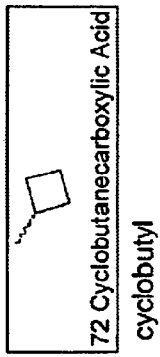
R2
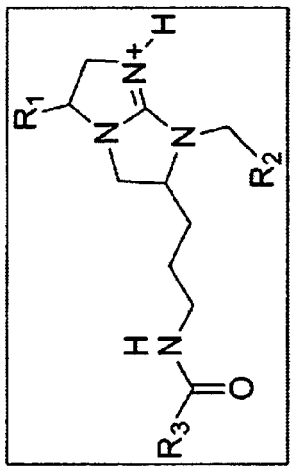
| 72 Cyclobutanecarboxylic Acid | cyclobutyl |
R1
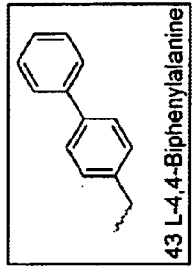
| 43 L-4,4-Biphenylalanine | 4-biphenylmethyl |
Figure 7F

TPI 759 N-Benzyl-1,4,5-trisubstited-2,3-diketopiperazines

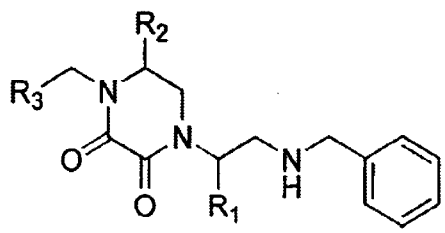

Selections:

| R1 | R2 | R3 |
|---|---|---|
| 21 Fmoc-Nle | 43 Fmoc-leu | 65 4-Isobutyl-alpha-Methylphenylacetic Acid |
| 22 Fmoc-nle | 52 Fmoc-NapAla | 67 3,5-Bis(Trifluoromethyl)-Phenylacetic Acid |
| 25 Fmoc-NapAla | 41 Fmoc-phe | 72 Heptanoic Acid |
| 29 Fmoc-chala | 31 Fmoc-Phe | 60 (Alpha-Alpha-Alpha-Trifluoro-m-Tolvi) acetic acid |
| 28 Fmoc-ChAla | 42 Fmoc-ile | 87 4-tert-Butvl-cvclohexanecarboxvlic Acid |
| 5 Fmoc-Lys(Boc) | 33 Fmoc-Ile | 58 m-Tolyacetic Acid |
| 24 Fmoc-nva | 46 Fmoc-val | 66 3,4-Dichlorophenylacetic Acid |
| 23 Fmoc-Nva | 34 Fmoc-Leu | 89 3,3-Diphenyl propionic Acid |
| 19 Fmoc-val | | 90 Dicyclohexlacetic Acid |
| | | 81 Cycloheptanecarboxylic Acid |
| | | 61 p-Tolylacetic Acid |
| | | 80 Cyclohexanebutyric Acid |

| R1 | R2 | R3 |
|---|---|---|
| 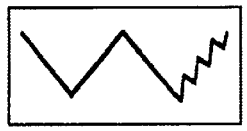 |  | 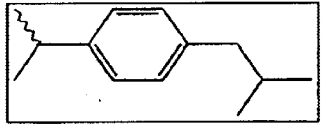 |
| 21 Norleucine butyl | 43 leucine isobutyl | 65 4-Isobutyl-alpha-Methylphenylacetic Acid 1-(4-isobutyl-phenyl)-ethyl |
| 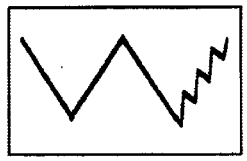 | 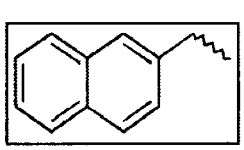 | 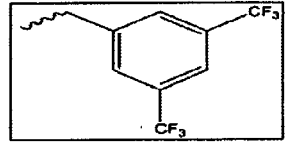 |
| 22 norleucine butyl | 52 NapAla 2-naphtylmethyl | 67 3,5-Bis(Trifluoromethyl)-Phenylacetic Acid 3,5-bis(Trifluoromethyl)-phenylmethyl |

Figure 8A

TPI 759 N-Benzyl-1,4,5-trisubstited-2,3-diketopiperazines

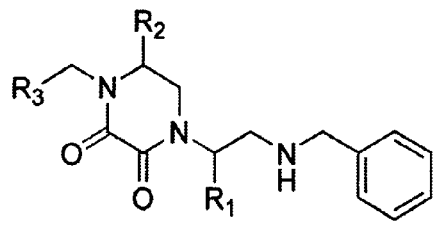

Selections:

| RI | R2 | R3 |
|---|---|---|
| 21 Fmoc-Nle | 43 Fmoc-leu | 65 4-Isobutyl-alpha-Methylphenylacetic Acid |
| 22 Fmoc-nle | 52 Fmoc-NapAla | 67 3,5-Bis(Trifluoromethyl)-Phenylacetic Acid |
| 25 Fmoc-NapAla | 41 Fmoc-phe | 72 Heptanoic Acid |
| 29 Fmoc-chala | 31 Fmoc-Phe | 60 (Alpha-Alpha-Alpha-Trifluoro-m-Tolyi) acetic acid |
| 28 Fmoc-ChAla | 42 Fmoc-ile | 87 4-tert-Butyl-cyclohexanecarboxylic Acid |
| 5 Fmoc-Lys(Boc) | 33 Fmoc-Ile | 58 m-Tolyacetic Acid |
| 24 Fmoc-nva | 46 Fmoc-val | 66 3,4-Dichlorophenylacetic Acid |
| 23 Fmoc-Nva | 34 Fmoc-Leu | 89 3,3-Diphenyl propionic Acid |
| 19 Fmoc-val | | 90 Dicyclohexlacetic Acid |
| | | 81 Cycloheptanecarboxylic Acid |
| | | 61 p-Tolylacetic Acid |
| | | 80 Cyclohexanebutyric Acid |

| R1 | R2 | R3 |
|---|---|---|
| 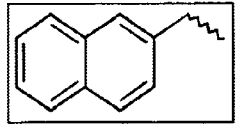 | 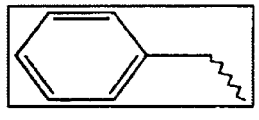 |  |
| 25 NapAla<br>2-naphtylmethyl | 41 phenylalanine<br>benzyl | 72 Heptanoic acid<br>hexyl |

| | | |
|---|---|---|
| 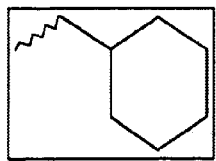 | 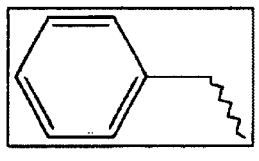 | 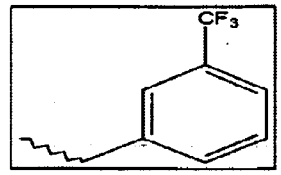 |
| 29 cyclohexylalanine<br>cyclohexylmethyl | 31 Phenylalanine<br>benzyl | 60 (Alpha-Alpha-Alpha-Trifluoro-m-Tolyl) Acetic Acid<br>3-trifluoromethylbenzyl |

Figure 8B

TPI 759 N-Benzyl-1,4,5-trisubstited-2,3-diketopiperazines

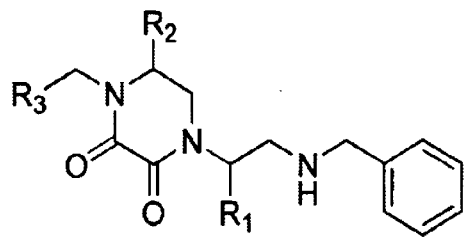

Selections:

| R1 | R2 | R3 |
|---|---|---|
| 21 Fmoc-Nle | 43 Fmoc-leu | 65 4-Isobutyl-alpha-Methylphenylacetic Acid |
| 22 Fmoc-nle | 52 Fmoc-NapAla | 67 3,5-Bis(Trifluoromethyl)-Phenylacetic Acid |
| 25 Fmoc-NapAla | 41 Fmoc-phe | 72 Heptanoic Acid |
| 29 Fmoc-chala | 31 Fmoc-Phe | 60 (Alpha-Alpha-Alpha-Trifluoro-m-Tolvi) acetic acid |
| 28 Fmoc-ChAla | 42 Fmoc-ile | 87 4-tert-Butvl-cvclohexanecarboxvlic Acid |
| 5 Fmoc-Lys(Boc) | 33 Fmoc-Ile | 58 m-Tolyacetic Acid |
| 24 Fmoc-nva | 46 Fmoc-val | 66 3,4-Dichlorophenylacetic Acid |
| 23 Fmoc-Nva | 34 Fmoc-Leu | 89 3,3-Diphenyl propionic Acid |
| 19 Fmoc-val | | 90 Dicyclohexlacetic Acid |
| | | 81 Cycloheptanecarboxylic Acid |
| | | 61 p-Tolylacetic Acid |
| | | 80 Cyclohexanebutyric Acid |

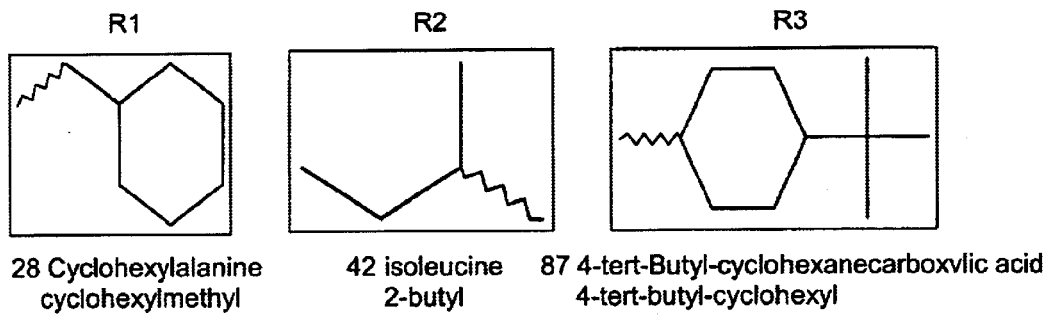

28 Cyclohexylalanine  42 isoleucine  87 4-tert-Butyl-cyclohexanecarboxvlic acid
cyclohexylmethyl      2-butyl       4-tert-butyl-cyclohexyl

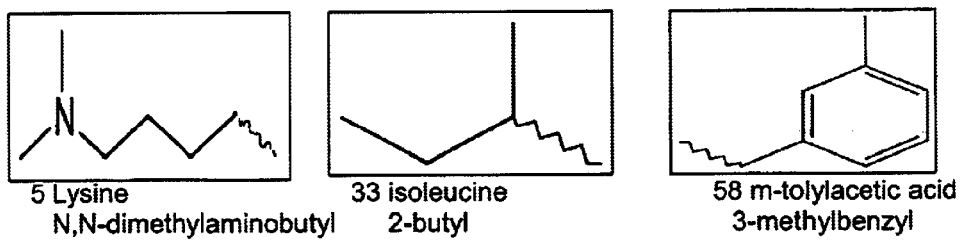

5 Lysine                33 isoleucine   58 m-tolylacetic acid
N,N-dimethylaminobutyl  2-butyl         3-methylbenzyl

Figure 8C

TPI 759 N-Benzyl-1,4,5-trisubstited-2,3-diketopiperazines

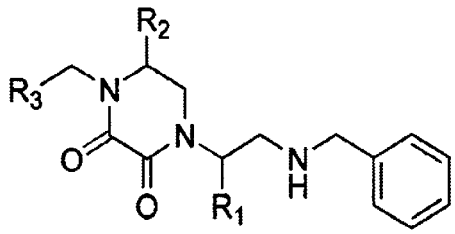

Selections:

| R1 | R2 | R3 |
|---|---|---|
| 21 Fmoc-Nle | 43 Fmoc-leu | 65 4-Isobutyl-alpha-Methylphenylacetic Acid |
| 22 Fmoc-nle | 52 Fmoc-NapAla | 67 3,5-Bis(Trifluoromethyl)-Phenylacetic Acid |
| 25 Fmoc-NapAla | 41 Fmoc-phe | 72 Heptanoic Acid |
| 29 Fmoc-chala | 31 Fmoc-Phe | 60 (Alpha-Alpha-Alpha-Trifluoro-m-Tolvi) acetic acid |
| 28 Fmoc-ChAla | 42 Fmoc-Ile | 87 4-tert-Butvl-cvclohexanecarboxvlic Acid |
| 5 Fmoc-Lys(Boc) | 33 Fmoc-Ile | 58 m-Tolyacetic Acid |
| 24 Fmoc-nva | 46 Fmoc-val | 66 3,4-Dichlorophenylacetic Acid |
| 23 Fmoc-Nva | 34 Fmoc-Leu | 89 3,3-Diphenyl propionic Acid |
| 19 Fmoc-val | | 90 Dicyclohexlacetic Acid |
| | | 81 Cycloheptanecarboxylic Acid |
| | | 61 p-Tolylacetic Acid |
| | | 80 Cyclohexanebutyric Acid |

| R1 | R2 | R3 |
|---|---|---|
| 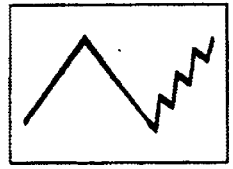 | 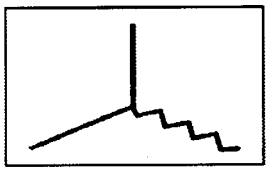 | 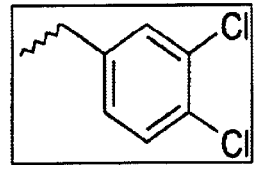 |
| 24 norvaline propyl | 46 valine isopropyl | 66 3,4-Dichlorophenylacetic Acid 3,4-dichlorobenzyl |
| 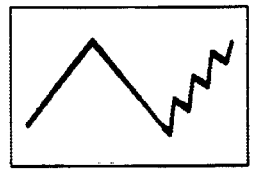 | 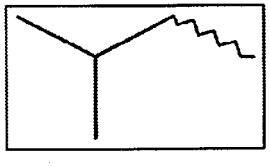 | 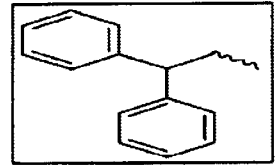 |
| 23 Norvaline propyl | 34 Leucine isobutyl | 89 3,3-Diphenylpropionic Acid 2,2-diphenylethyl |

Figure 8D

TPI 759 N-Benzyl-1,4,5-trisubstited-2,3-diketopiperazines

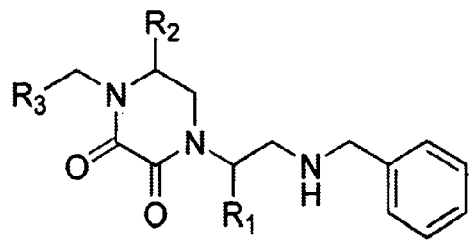

Selections:

| R1 | R2 | R3 |
|---|---|---|
| 21 Fmoc-Nle | 43 Fmoc-leu | 65 4-Isobutyl-alpha-Methylphenylacetic Acid |
| 22 Fmoc-nle | 52 Fmoc-NapAla | 67 3,5-Bis(Trifluoromethyl)-Phenylacetic Acid |
| 25 Fmoc-NapAla | 41 Fmoc-phe | 72 Heptanoic Acid |
| 29 Fmoc-chala | 31 Fmoc-Phe | 60 (Alpha-Alpha-Alpha-Trifluoro-m-Tolvl) acetic acid |
| 28 Fmoc-ChAla | 42 Fmoc-ile | 87 4-tert-Butvl-cvclohexanecarboxvlic Acid |
| 5 Fmoc-Lys(Boc) | 33 Fmoc-Ile | 58 m-Tolyacetic Acid |
| 24 Fmoc-nva | 46 Fmoc-val | 66 3,4-Dichlorophenylacetic Acid |
| 23 Fmoc-Nva | 34 Fmoc-Leu | 89 3,3-Diphenyl propionic Acid |
| 19 Fmoc-val | | 90 Dicyclohexlacetic Acid |
| | | 81 Cycloheptanecarboxylic Acid |
| | | 61 p-Tolylacetic Acid |
| | | 80 Cyclohexanebutyric Acid |

R1

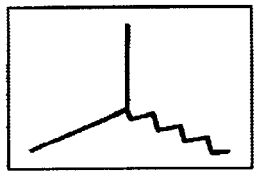

19 valine
isopropyl

R2

R3

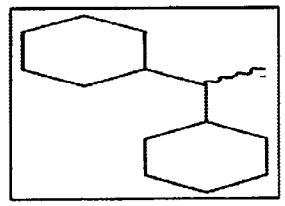

90 Dicyclohexylacetic Acid
2,2-dicyclohexylmethyl

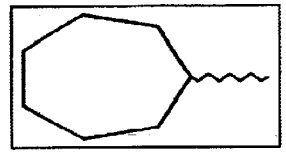

81 Cycloheptanecarboxylic Acid
cycloheptyl

Figure 8E

TPI 759 N-Benzyl-1,4,5-trisubstited-2,3-diketopiperazines

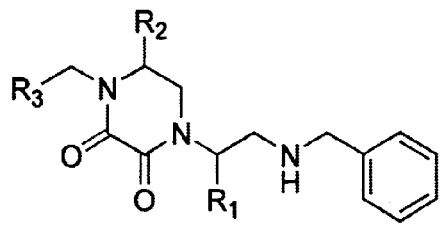

Selections:

| R1 | R2 | R3 |
|---|---|---|
| 21 Fmoc-Nle | 43 Fmoc-leu | 65 4-Isobutyl-alpha-Methylphenylacetic Acid |
| 22 Fmoc-nle | 52 Fmoc-NapAla | 67 3,5-Bis(Trifluoromethyl)-Phenylacetic Acid |
| 25 Fmoc-NapAla | 41 Fmoc-phe | 72 Heptanoic Acid |
| 29 Fmoc-chala | 31 Fmoc-Phe | 60 (Alpha-Alpha-Alpha-Trifluoro-m-Tolyl) acetic acid |
| 28 Fmoc-ChAla | 42 Fmoc-ile | 87 4-tert-Butyl-cyclohexanecarboxylic Acid |
| 5 Fmoc-Lys(Boc) | 33 Fmoc-Ile | 58 m-Tolyacetic Acid |
| 24 Fmoc-nva | 46 Fmoc-val | 66 3,4-Dichlorophenylacetic Acid |
| 23 Fmoc-Nva | 34 Fmoc-Leu | 89 3,3-Diphenyl propionic Acid |
| 19 Fmoc-val | | 90 Dicyclohexlacetic Acid |
| | | 81 Cycloheptanecarboxylic Acid |
| | | 61 p-Tolylacetic Acid |
| | | 80 Cyclohexanebutyric Acid |

R1      R2      R3

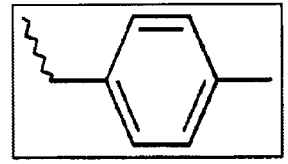

61 p-Tolylacetic acid
4-methylbenzyl

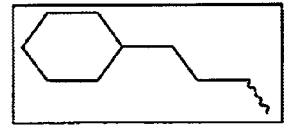

80 Cyclohexanebutyric Acid
cyclohexylpropyl

Figure 8F

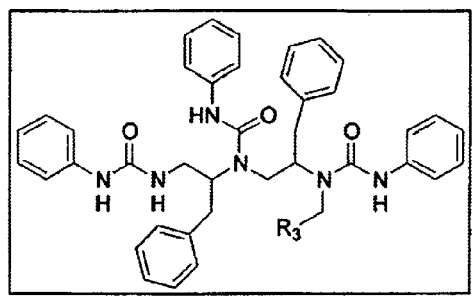
R3
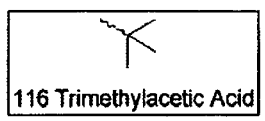
tert-butyl
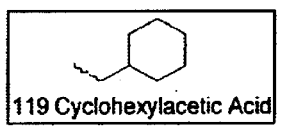
cyclohexylmethyl
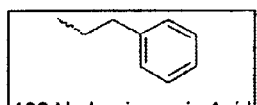
phenethyl
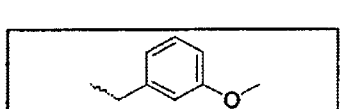
3-methoxybenzyl
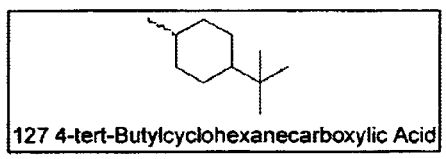
4-t-butyl-cyclohexyl
propyl
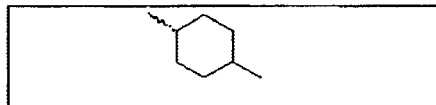
4-methylcyclohexyl
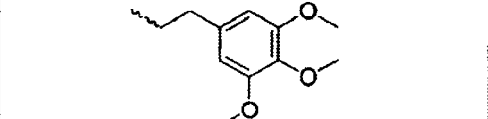
3,4,5-trimethoxyphenethyl
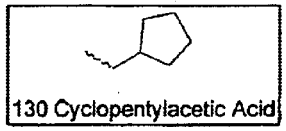
cyclopentylmethyl
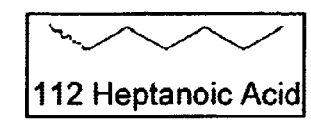
hexyl
Figure 9A

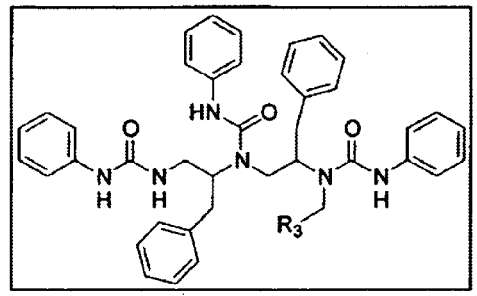
R3
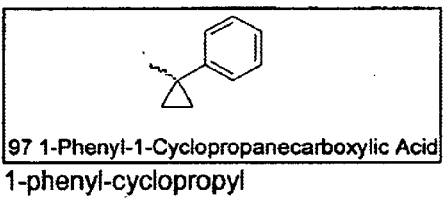
1-phenyl-cyclopropyl
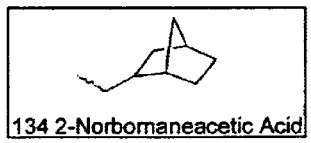
2-norbornylmethyl
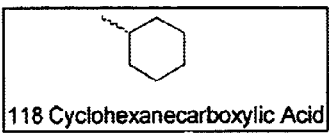
cyclohexyl
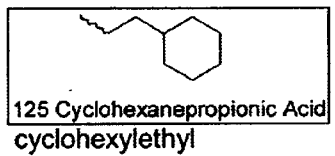
cyclohexylethyl
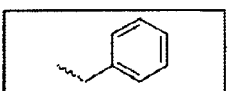
benzyl
tert-butylmethyl
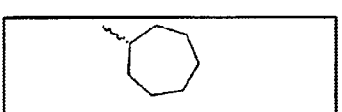
cycloheptyl
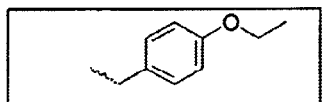
4-ethoxybenzyl
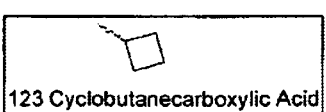
cyclobutyl
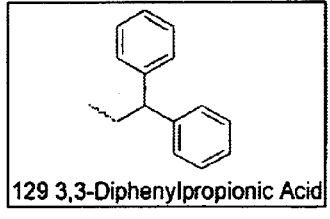
2,2-diphenylethyl
Figure 9B

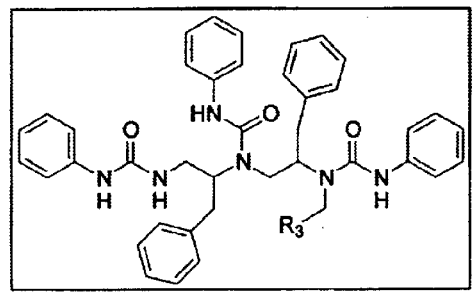
R3
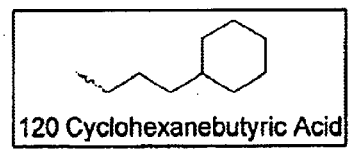
120 Cyclohexanebutyric Acid
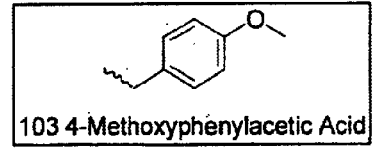
103 4-Methoxyphenylacetic Acid
4-methoxybenzyl
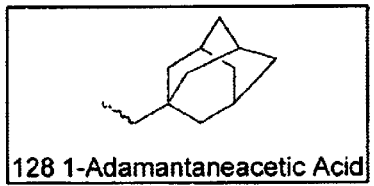
128 1-Adamantaneacetic Acid
1-adamantylmethyl
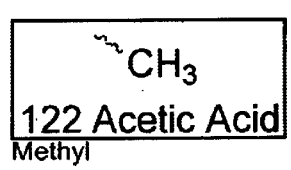
$CH_3$
122 Acetic Acid
Methyl
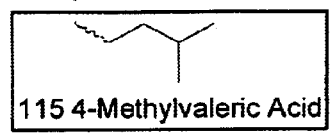
115 4-Methylvaleric Acid
3-methylbutyl
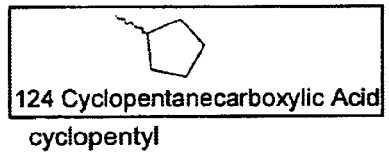
124 Cyclopentanecarboxylic Acid
cyclopentyl
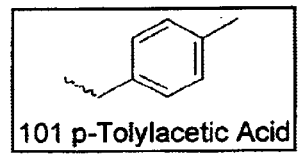
101 p-Tolylacetic Acid
4-methylbenzyl
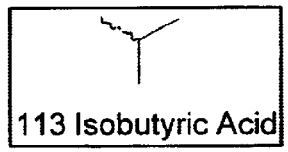
113 Isobutyric Acid
isopropyl
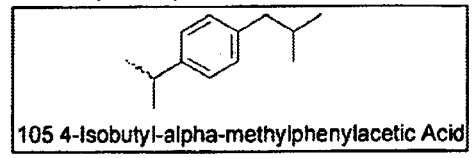
105 4-Isobutyl-alpha-methylphenylacetic Acid
1-(4-isobutyl-phenyl)-ethyl
Figure 9C

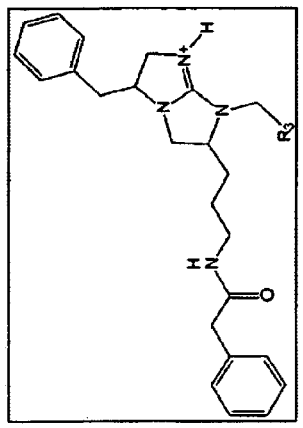
R3
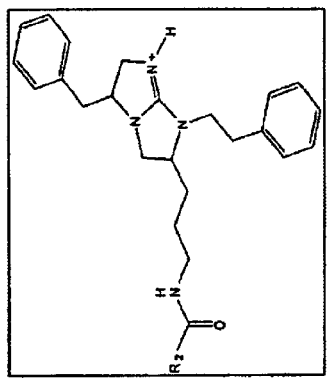
R2
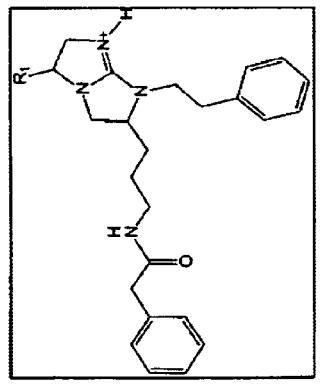
R1
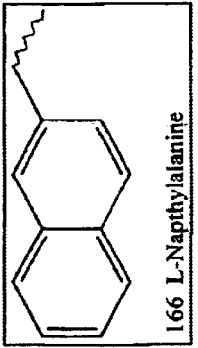
166 L-Napthylalanine
2-naphthylmethyl
Figure 10F Hexape-1
TPI 1239
Caspase 3-XIAP
From File 032001-IC50 of selected TPI 1239
Note that Smac is only tested at 1 mM All mix are N-terminal free and C-terminal amide TPI1239 dose responses (sort)

Caspase effect

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| Caspase 3 | 1.0 | 0.0 | 1.0 | 0.0 | 1.0 | 0.0 | 1.0 | 0.0 |
| Xiap+C3 | 0.4 | 0.0 | 0.4 | 0.0 | 0.4 | 0.0 | 0.4 | 0.0 |
| SMAC | 0.9 | 0.1 | 0.9 | 0.1 | 0.9 | 0.1 | 0.9 | 0.1 |
| XXXAWW | 1.0 | 0.0 | 1.1 | 0.0 | 1.1 | 0.0 | 1.0 | 0.0 |
| XXXHWW | 1.0 | 0.1 | 1.1 | 0.0 | 1.1 | 0.0 | 1.0 | 0.1 |
| XXXKWW | 1.0 | 0.0 | 1.0 | 0.0 | 1.0 | 0.0 | 1.0 | 0.1 |
| XXXNWW | 1.0 | 0.0 | 1.0 | 0.0 | 1.0 | 0.0 | 1.0 | 0.0 |
| XXXQWW | 1.0 | 0.0 | 1.0 | 0.0 | 1.0 | 0.0 | 1.0 | 0.0 |
| XXXRWW | 1.0 | 0.0 | 1.0 | 0.0 | 1.0 | 0.0 | 1.0 | 0.1 |
| XXXSWW | 1.0 | 0.0 | 1.0 | 0.0 | 1.0 | 0.0 | 1.0 | 0.0 |
| XXXTWW | 1.1 | 0.0 | 1.1 | 0.0 | 1.1 | 0.0 | 1.0 | 0.0 |

Figure 11A

Hexape-1
TPI 1239       All mix are N-terminal free and C-terminal amide
Caspase 3-XIAP
From File 032001-IC50 of selected TPI 1239
Note that Smac is only tested at 1 mM TPI1239 dose responses (sort)

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| XXXVWW | 1.0 | 0.0 | 0.9 | 0.0 | 1.0 | 0.1 | 1.0 | 0.0 |
| XXXXWW | 1.0 | 0.0 | 1.1 | 0.0 | 1.0 | 0.0 | 1.1 | 0.0 |

XIAP effect

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| Caspase 3 | 2.2 | 0.0 | 2.2 | 0.0 | 2.2 | 0.0 | 2.2 | 0.0 |
| Xiap + C3 | 1.0 | 0.0 | 1.0 | 0.0 | 1.0 | 0.0 | 1.0 | 0.0 |
| SMAC | 2.0 | 0.1 | 2.0 | 0.1 | 2.0 | 0.1 | 2.0 | 0.1 |
| XXXAWW | 2.2 | 0.0 | 2.0 | 0.0 | 1.7 | 0.0 | 1.4 | 0.0 |
| XXXKWW | 2.2 | 0.1 | 2.0 | 0.2 | 1.6 | 0.1 | 1.2 | 0.1 |
| XXXTWW | 2.1 | 0.0 | 1.8 | 0.0 | 1.6 | 0.0 | 1.2 | 0.1 |
| XXXSWW | 2.1 | 0.2 | 1.8 | 0.1 | 1.4 | 0.1 | 1.3 | 0.3 |

Figure 11B

Hexape-1
TPI 1239    All mix are N-terminal free and C-terminal amide
Caspase 3-XIAP
From File 032001-IC50 of selected TPI 1239
Note that Smac is only tested at 1 mM TPI1239 dose responses (sort)

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| XXXNWW | 1.8 | 0.2 | 1.4 | 0.0 | 1.2 | 0.1 | 1.1 | 0.1 |
| XXXVWW | 1.7 | 0.0 | 1.4 | 0.0 | 1.2 | 0.2 | 1.0 | 0.1 |
| XXXXWW | 1.8 | 0.1 | 1.4 | 0.1 | 1.1 | 0.1 | 1.1 | 0.3 |
| XXXHWW | 1.8 | 0.1 | 1.1 | 0.0 | 1.1 | 0.1 | 1.0 | 0.1 |
| XXXRVW | 1.4 | 0.1 | 1.3 | 0.0 | 1.1 | 0.1 | 0.9 | 0.1 |
| XXXQWW | 1.54 | 0.0 | | | | | 0.9 | |

Figure 11C

Tetra-peptide antagonists of XIAP
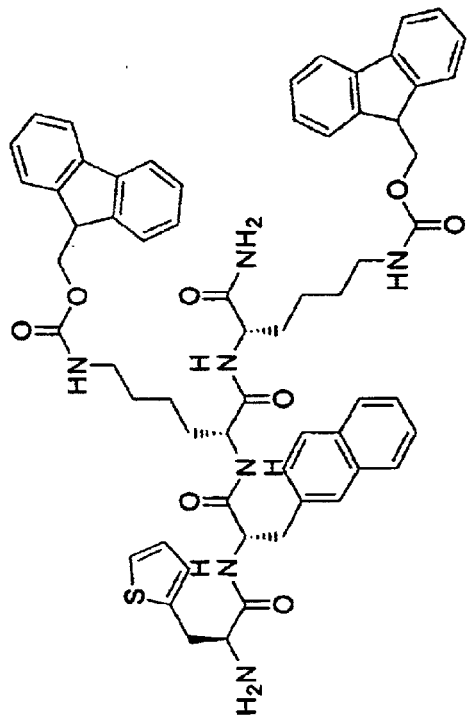
792-35
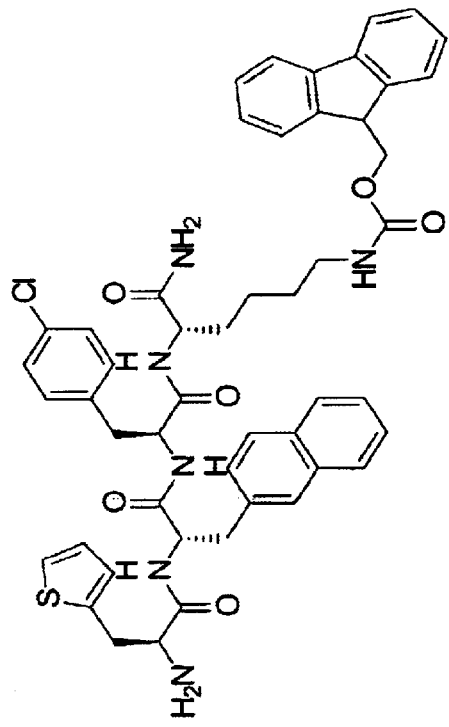
792-33
Figure 12

A   TPI 1391
N-Benzyl-1,4,5-trisubstited-2,3-diketopiperazines
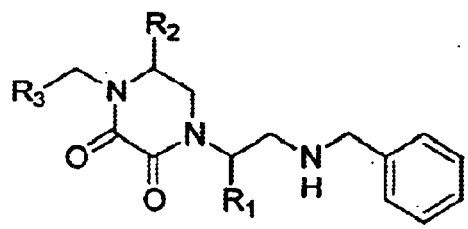
TPI 1396
Polyphenylureas
Diphenyl or Triphenylureas
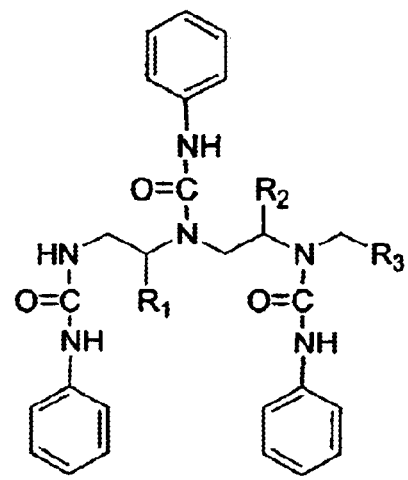
Figure 14A B
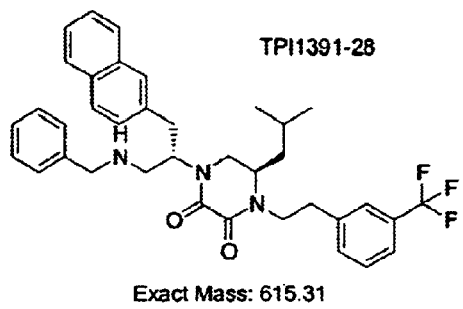
TPI1391-28
Exact Mass: 615.31
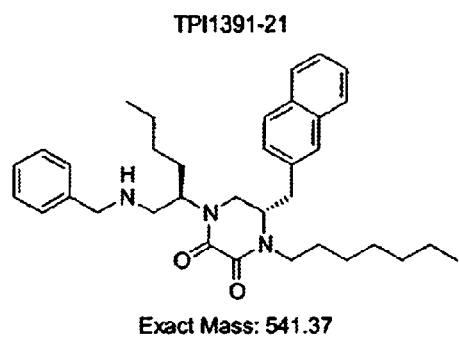
TPI1391-21
Exact Mass: 541.37
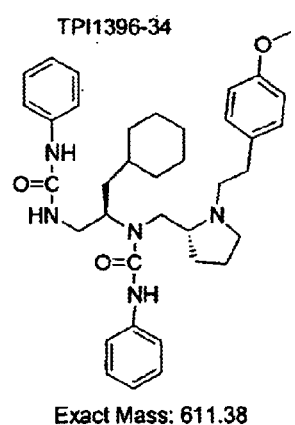
TPI1396-34
Exact Mass: 611.38
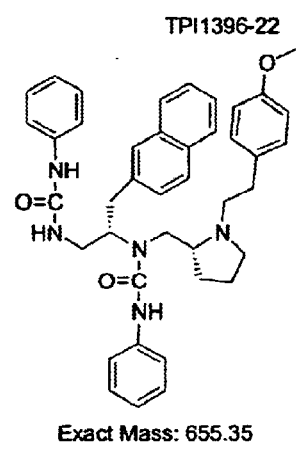
TPI1396-22
Exact Mass: 655.35
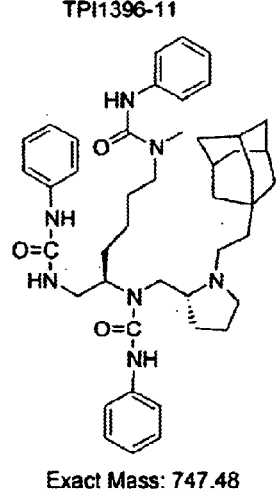
TPI1396-11
Exact Mass: 747.48
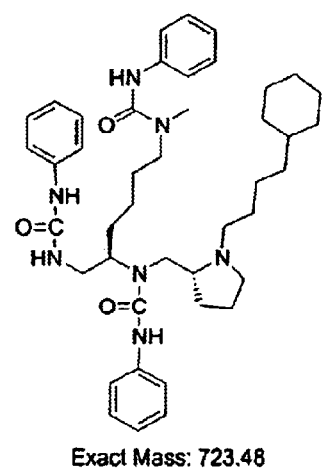
TPI1396-12
Exact Mass: 723.48
Figure 14B

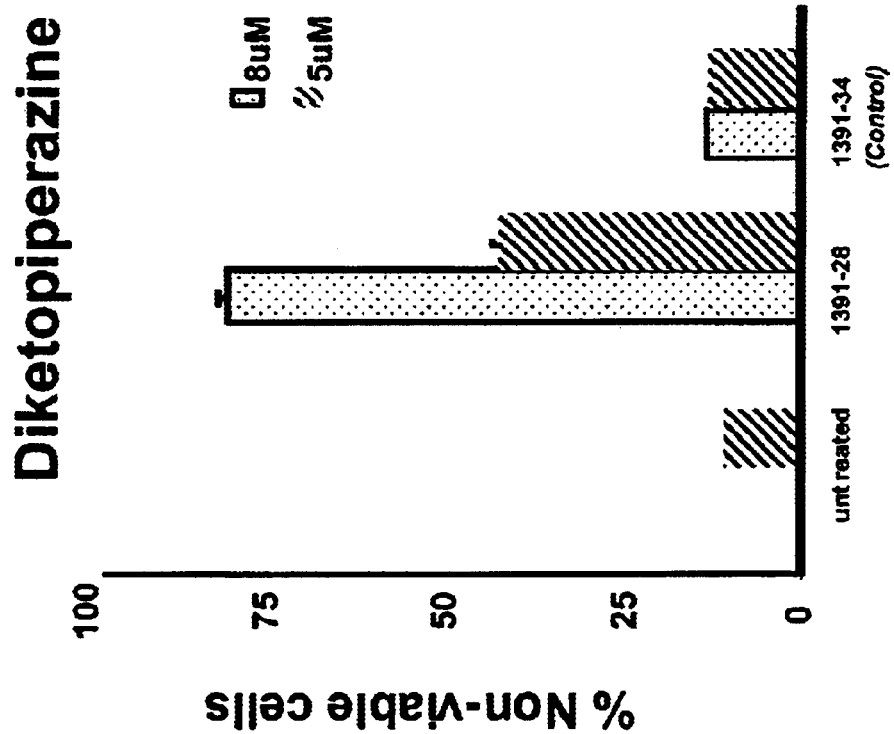
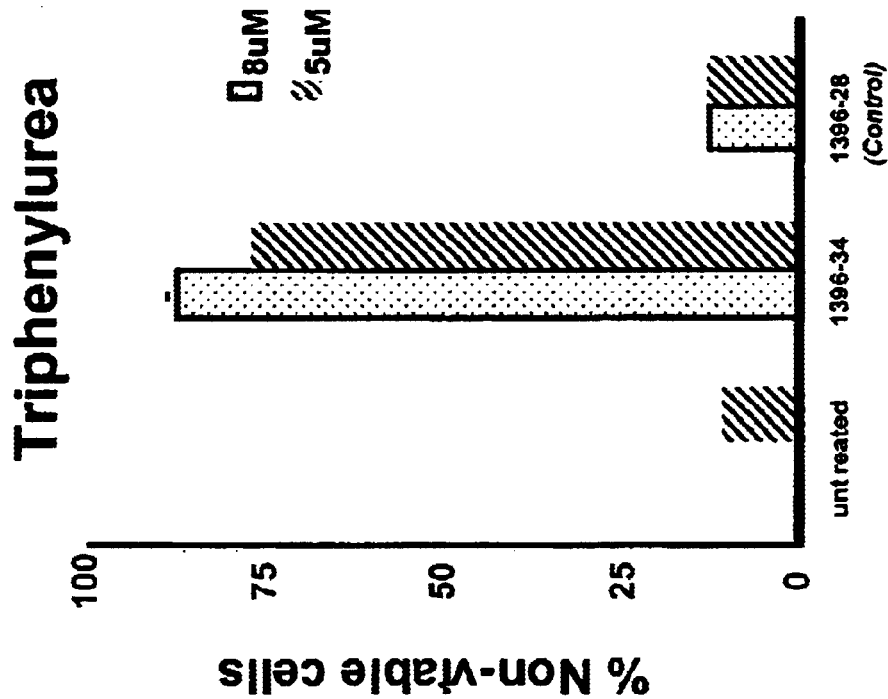
Figure 16

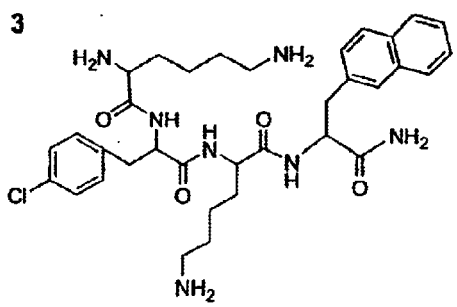
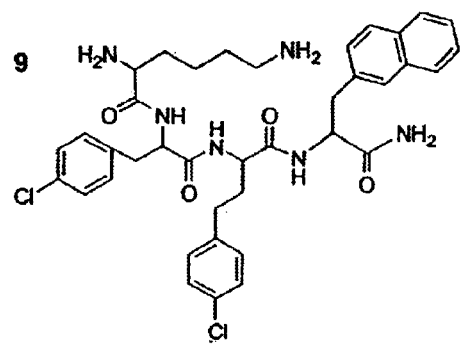
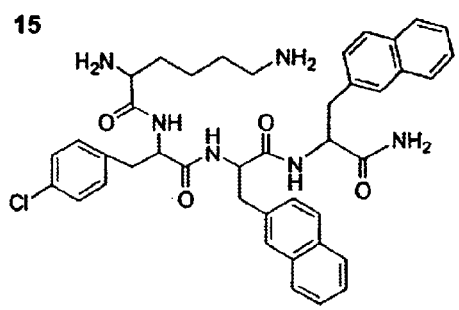
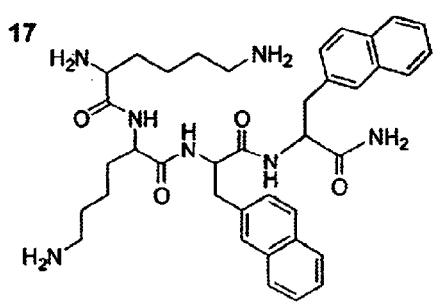
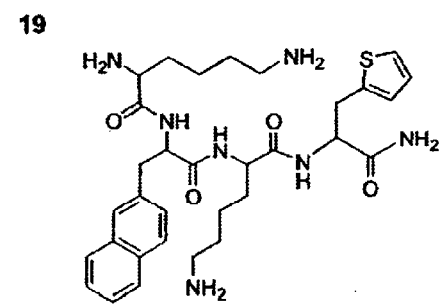
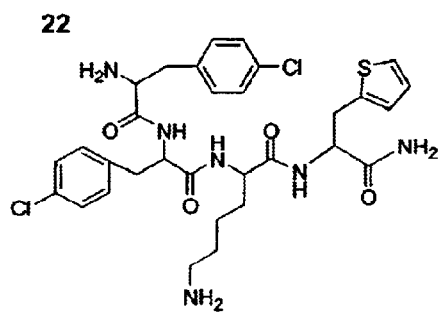
Figure 20A 27
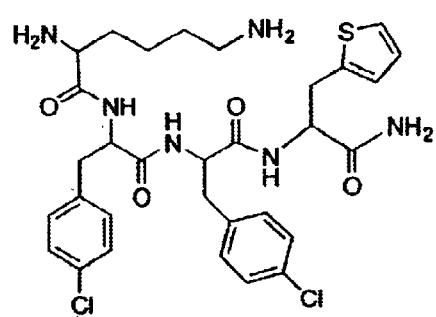
33
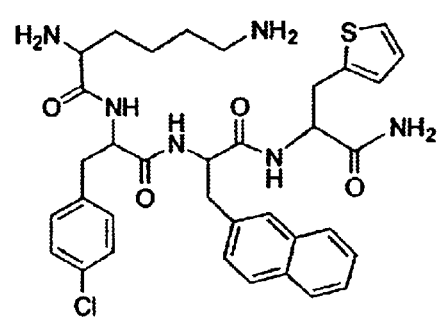
35
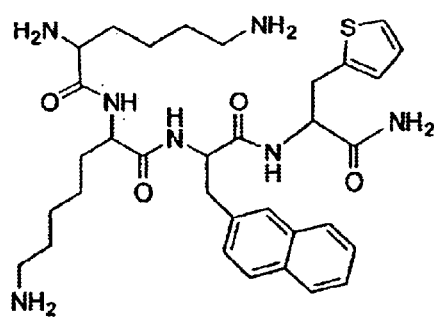
Figure 20B

| TPI1349 | Structures | MW | Exact Mass | [lowest] ug/ml * |
|---|---|---|---|---|
| 1 | 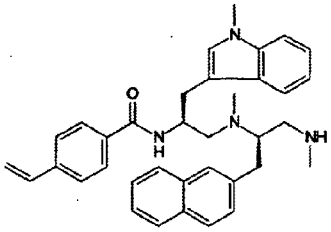 [Boc-D-(2-Naphthyl)-alanine][Boc-L-Tryptophan(Formyl)][4-Vinylbenzoic acid] | 544.74 | 544.32 | 1 |
| 2 | 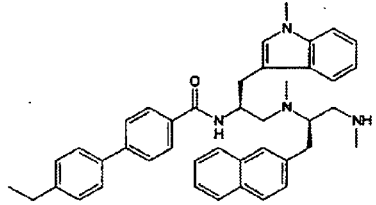 [Boc-D-(2-Naphthyl)-alanine][Boc-L-Tryptophan(Formyl)][4-Ethyl-4-Biphenylcarboxylic acid] | 622.86 | 622.37 | 5 |
| 3 | 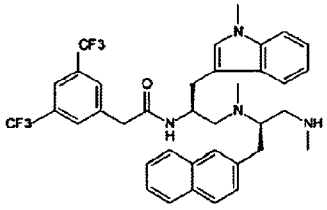 [Boc-D-(2-Naphthyl)-alanine][Boc-L-Tryptophan(Formyl)][3,5-Bis-(trifluoromethyl)-phenylacetic acid] | 668.73 | 668.29 | 5 |
Figure 21A

| TPI1349 | Structures | MW | Exact Mass | [lowest] ug/ml * |
|---|---|---|---|---|
| 4 | 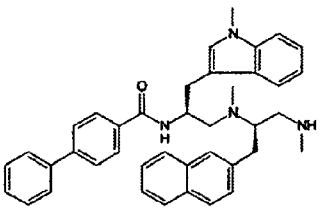 [Boc-D-(2-Naphthyl)-alanine][Boc-L-Tryptophan(Formyl)][4-Biphenylcarboxylic acid] | 594.80 | 594.34 | 5 |
| 5 | 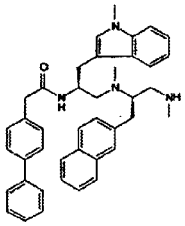 [Boc-D-(2-Naphthyl)-alanine][Boc-L-Tryptophan(Formyl)][4-Biphenylacetic acid] | 608.83 | 608.35 | 5 |
| 6 | 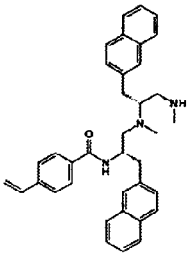 [Boc-D-(2-Naphthyl)-alanine][Boc-L-(2-Naphthyl)-alanine][4-Vinylbenzoic acid] | 541.74 | 541.31 | 5 |
Figure 21B

| TPI1349 | Structures | MW | Exact Mass | [lowest] ug/ml * |
|---|---|---|---|---|
| 7 | 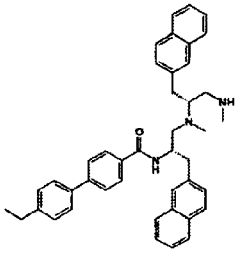 [Boc-D-(2-Naphthyl)-alanine][Boc-L-(2-Naphthyl)-alanine][4-Ethyl-4-Biphenylcarboxylic acid] | 619.85 | 619.36 | 5 |
| 8 | 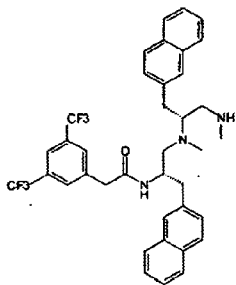 [Boc-D-(2-Naphthyl)-alanine][Boc-L-(2-Naphthyl)-alanine][3,5-Bis-(trifluoromethyl)-phenylacetic acid] | 665.72 | 665.28 | 1 |
| 9 | 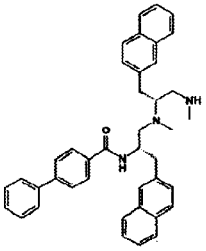 [Boc-D-(2-Naphthyl)-alanine][Boc-L-(2-Naphthyl)-alanine][4-Biphenylcarboxylic acid] | 591.80 | 591.32 | 15 |
Figure 21C

| TPI1349 | Structures | MW | Exact Mass | [lowest] ug/ml * |
|---|---|---|---|---|
| 10 | 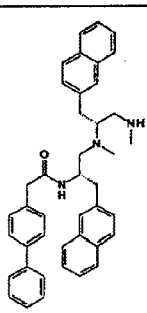 [Boc-D-(2-Naphthyl)-alanine][Boc-L-(2-Naphthyl)-alanine][4-Biphenylacetic acid] | 605.83 | 605.34 | 25 |
| 11 | 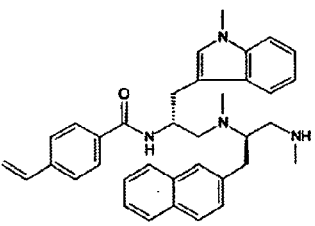 [Boc-D-(2-Naphthyl)-alanine][Boc-D-Tryptophan][4-Vinylbenzoic acid] | 544.74 | 544.32 | 15 |
| 12 | 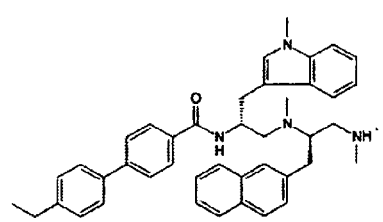 [Boc-D-(2-Naphthyl)-alanine][Boc-D-Tryptophan][4-Ethyl-4-Biphenylcarboxylic acid] | 622.86 | 622.37 | 15 |
Figure 21D

| TPI1349 | Structures | MW | Exact Mass | [lowest] ug/ml * |
|---|---|---|---|---|
| 13 | 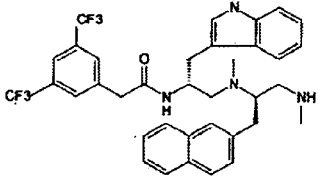 [Boc-D-(2-Naphthyl)-alanine][Boc-D-Tryptophan][3,5-Bis-(trifluoromethyl)-phenylacetic acid] | 668.73 | 668.29 | 25 |
| 14 | 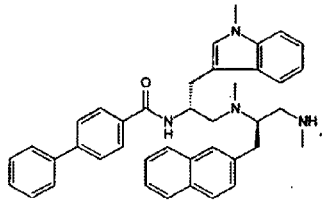 [Boc-D-(2-Naphthyl)-alanine][Boc-D-Tryptophan][4-Biphenylcarboxylic acid] | 594.80 | 594.34 | 15 |
| 15 | 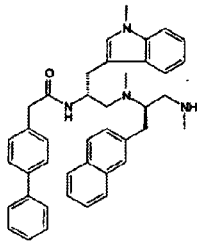 [Boc-D-(2-Naphthyl)-alanine][Boc-D-Tryptophan][4-Biphenylacetic acid] | 608.83 | 608.35 | 25 |
Figure 21E

| TPI1349 | Structures | MW | Exact Mass | [lowest] ug/ml * |
|---|---|---|---|---|
| 16 | 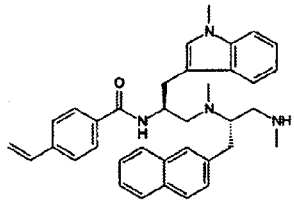 [Boc-L-(2-Naphthyl)-alanine][Boc-L-Tryptophan(Formyl)][4-Vinylbenzoic acid] | 544.74 | 544.32 | 15 |
| 17 | 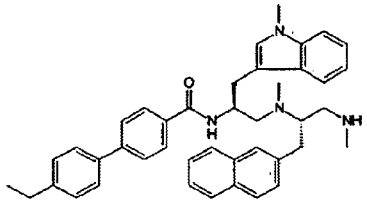 [Boc-L-(2-Naphthyl)-alanine][Boc-L-Tryptophan(Formyl)][4-Ethyl-4-Biphenylcarboxylic acid] | 622.86 | 622.37 | 5 |
| 18 | 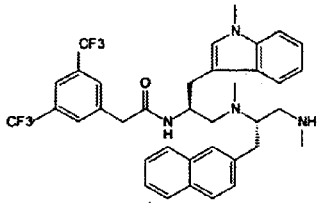 [Boc-L-(2-Naphthyl)-alanine][Boc-L-Tryptophan(Formyl)][3,5-Bis-(trifluoromethyl)-phenylacetic acid] | 668.73 | 668.29 | 25 |
Figure 21F

| TPI1349 | Structures | MW | Exact Mass | [lowest] ug/ml * |
|---|---|---|---|---|
| 19 | 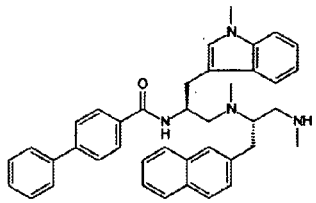 [Boc-L-(2-Naphthyl)-alanine][Boc-L-Tryptophan(Formyl)][4-Biphenylcarboxylic acid] | 594.80 | 594.34 | 5 |
| 20 | 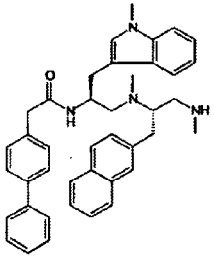 [Boc-L-(2-Naphthyl)-alanine][Boc-L-Tryptophan(Formyl)][4-Biphenylacetic acid] | 608.83 | 608.35 | 5 |
| 21 | 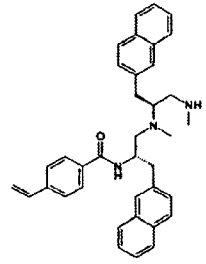 [Boc-L-(2-Naphthyl)-alanine][Boc-L-(2-Naphthyl)-alanine][4-Vinylbenzoic acid] | 541.74 | 541.31 | 15 |
Figure 21G

| TPI1349 | Structures | MW | Exact Mass | [lowest] ug/ml * |
|---|---|---|---|---|
| 22 | 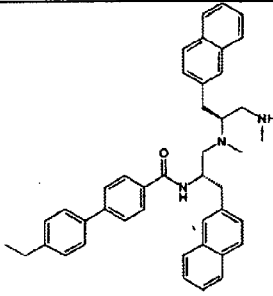 [Boc-L-(2-Naphthyl)-alanine][Boc-L-(2-Naphthyl)-alanine][4-Ethyl-4-Biphenylcarboxylic acid] | 619.85 | 619.36 | .5 |
| 23 | 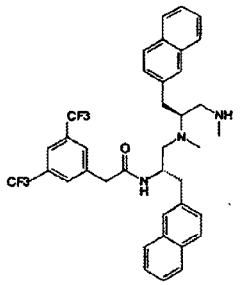 [Boc-L-(2-Naphthyl)-alanine][Boc-L-(2-Naphthyl)-alanine][3,5-Bis-(trifluoromethyl)-phenylacetic acid] | 665.72 | 665.28 | 5 |
| 24 | 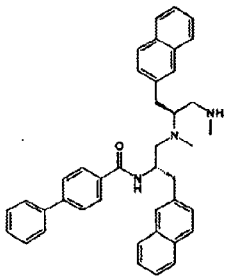 [Boc-L-(2-Naphthyl)-alanine][Boc-L-(2-Naphthyl)-alanine][4-Biphenylcarboxylic acid] | 591.80 | 591.32 | 1 |
Figure 21H

| TPI1349 | Structures | MW | Exact Mass | [lowest] ug/ml * |
|---|---|---|---|---|
| 25 | 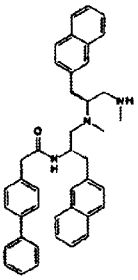 [Boc-L-(2-Naphthyl)-alanine][Boc-L-(2-Naphthyl)-alanine][4-Biphenylacetic acid] | 605.83 | 605.34 | 1 |
| 26 | 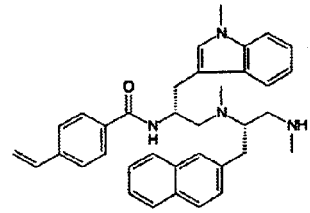 [Boc-L-(2-Naphthyl)-alanine][Boc-D-Tryptophan][4-Vinylbenzoic acid] | 544.74 | 544.32 | 5 |
| 27 | 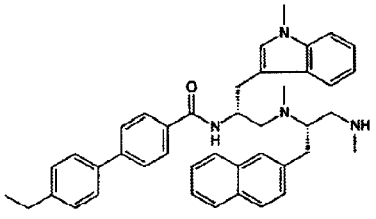 [Boc-L-(2-Naphthyl)-alanine][Boc-D-Tryptophan][4-Ethyl-4-Biphenylcarboxylic acid] | 622.86 | 622.37 | 5 |
Figure 21I

| TPI1349 | Structures | MW | Exact Mass | [lowest] ug/ml * |
|---|---|---|---|---|
| 28 | 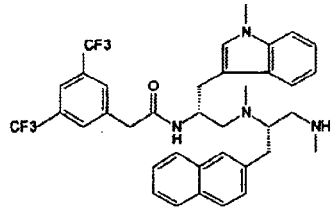 [Boc-L-(2-Naphthyl)-alanine][Boc-D-Tryptophan][3,5-Bis-(trifluoromethyl)-phenylacetic acid] | 668.73 | 668.29 | 5 |
| 29 | 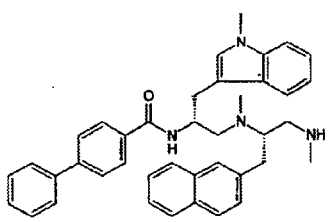 [Boc-L-(2-Naphthyl)-alanine][Boc-D-Tryptophan][4-Biphenylcarboxylic acid] | 594.80 | 594.34 | 5 |
| 30 | 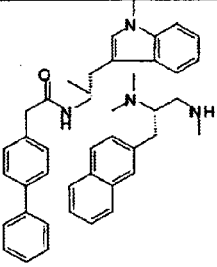 [Boc-L-(2-Naphthyl)-alanine][Boc-D-Tryptophan][4-Biphenylacetic acid] | 608.83 | 608.35 | 5 |
Figure 21J

| TPI1349 | Structures | MW | Exact Mass | [lowest] ug/ml * |
|---|---|---|---|---|
| 31 | [Boc-L-Leucine][Boc-D-Tryptophan][Acetic acid] | 372.56 | 372.29 | 25 |
| 32 | [Boc-L-Leucine][Boc-L-Phenylalanine][3,5-Bis-(trifluoromethyl)-phenylacetic acid] | 531.58 | 531.27 | 1 |
| 33 | [Boc-L-Leucine][Boc-L-Phenylalanine][4-Vinylbenzoic acid] | 407.60 | 407.29 | >25 |

Figure 21K

| TPI1349 | Structures | MW | Exact Mass | [lowest] ug/ml * |
|---|---|---|---|---|
| 34 | <br>[Boc-L-Leucine][Boc-L-Phenylalanine][4-Ethyl-4-Biphenylcarboxylic acid] | 485.72 | 485.34 | >25 |

| TPI1396 | Structures | MW | Exact Mass | [lowest] ug/ml * |
|---|---|---|---|---|
| 1 | 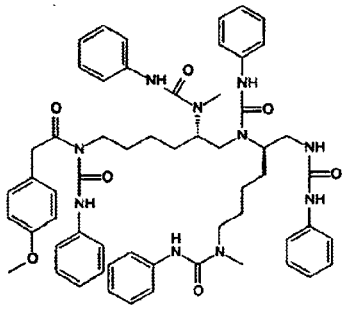 [Boc-D-Lysine(2-Cl-Z)][a-ClZ-L-Lysine(e-Boc)][4-Methoxyphenylacetic acid] | 1017.24 | 1016.53 | >25 |
| 2 | 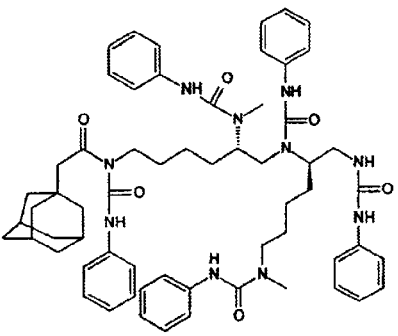 [Boc-D-Lysine(2-Cl-Z)][a-ClZ-L-Lysine(e-Boc)][1-Adamantaneacetic acid] | 1045.34 | 1044.59 | 25 |
Figure 22A

| TPI1396 | Structures | MW | Exact Mass | [lowest] ug/ml * |
|---|---|---|---|---|
| 3 | 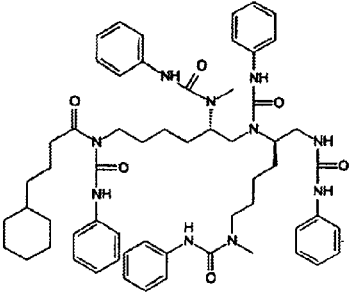 [Boc-D-Lysine(2-Cl-Z)][a-ClZ-L-Lysine(e-Boc)][Cyclohexanebutyric acid] | 1021.32 | 1020.59 | >25 |
| 4 | 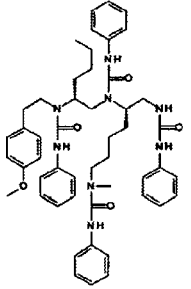 [Boc-D-Lysine(2-Cl-Z)][Boc-L-Norleucine][4-Methoxyphenylacetic acid] | 855.10 | 854.48 | >25 |
| 5 | 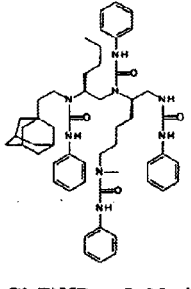 [Boc-D-Lysine(2-Cl-Z)][Boc-L-Norleucine][1-Adamantaneacetic acid] | 883.19 | 882.55 | >25 |
Figure 22B

| TPI1396 | Structures | MW | Exact Mass | [lowest] ug/ml * |
|---|---|---|---|---|
| 6 | 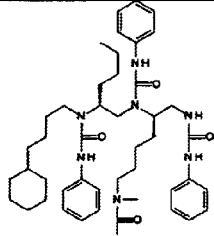 [Boc-D-Lysine(2-Cl-Z)][Boc-L-Norleucine][Cyclohexanebutyric acid] | 859.17 | 858.55 | >25 |
| 7 | 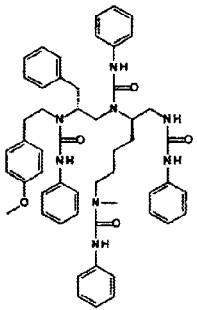 [Boc-D-Lysine(2-Cl-Z)][Boc-D-Phenylalanine][4-Methoxyphenylacetic acid] | 889.11 | 88.47 | >25 |
| 8 | 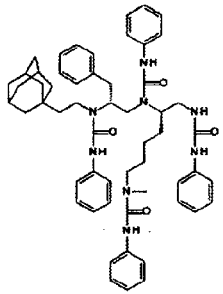 [Boc-D-Lysine(2-Cl-Z)][Boc-D-Phenylalanine][1-Adamantaneacetic acid] | 917.21 | 916.54 | >25 |
Figure 22C

| TPI1396 | Structures | MW | Exact Mass | [lowest] ug/ml * |
|---|---|---|---|---|
| 9 | 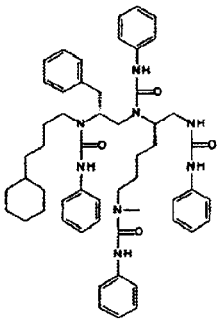 [Boc-D-Lysine(2-Cl-Z)][Boc-D-Phenylalanine][Cyclohexanebutyric acid] | 893.19 | 892.54 | >25 |
| 10 | 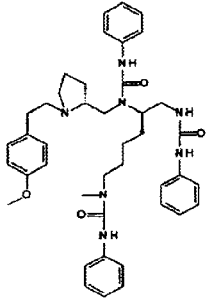 [Boc-D-Lysine(2-Cl-Z)][Boc-D-Proline][4-Methoxyphenylacetic acid] | 719.93 | 719.42 | 13 |
Figure 22D

| TPI1396 | Structures | MW | Exact Mass | [lowest] ug/ml * |
|---|---|---|---|---|
| 11 | [Boc-D-Lysine(2-Cl-Z)][Boc-D-Proline][1-Adamantaneacetic acid] | 748.03 | 747.48 | 6 |
| 12 | [Boc-D-Lysine(2-Cl-Z)][Boc-D-Proline][Cyclohexanebutyric acid] | 724.01 | 723.48 | 6 |
| 13 | [Boc-L-3-(2-Naphthyl)-Alanine][a-ClZ-L-Lysine(e-Boc)][4-Methoxyphenylacetic acid] | 953.16 | 952.46 | >25 |

Figure 22E

| TPI1396 | Structures | MW | Exact Mass | [lowest] ug/ml * |
|---|---|---|---|---|
| 14 | 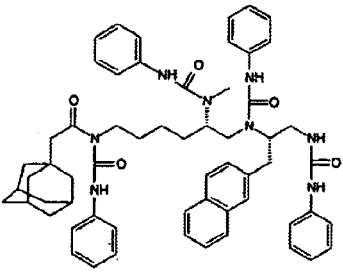 [Boc-L-3-(2-Naphthyl)-Alanine][a-ClZ-L-Lysine(e-Boc)][1-Adamantaneacetic acid] | 981.25 | 980.53 | >25 |
| 15 | 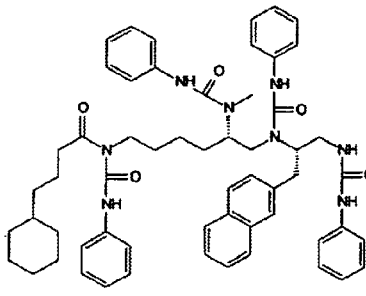 [Boc-L-3-(2-Naphthyl)-Alanine][a-ClZ-L-Lysine(e-Boc)][Cyclohexanebutyric acid] | 957.23 | 956.53 | >25 |
| 16 | 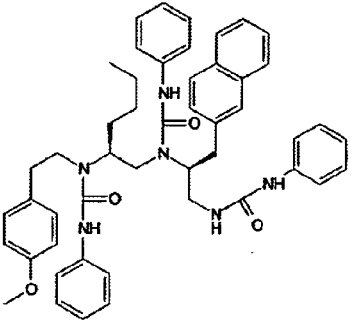 [Boc-L-3-(2-Naphthyl)-Alanine][Boc-L-Norleucine][4-Methoxyphenylacetic acid] | 791.01 | 790.42 | >25 |
Figure 22F

| TPI1396 | Structures | MW | Exact Mass | [lowest] ug/ml * |
|---|---|---|---|---|
| 17 | 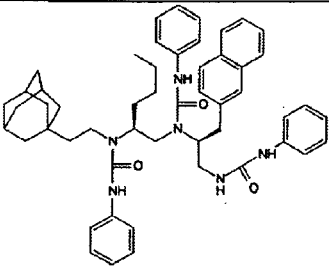 [Boc-L-3-(2-Naphthyl)-Alanine][Boc-L-Norleucine][1-Adamantaneacetic acid] | 819.11 | 818.49 | >25 |
| 18 | 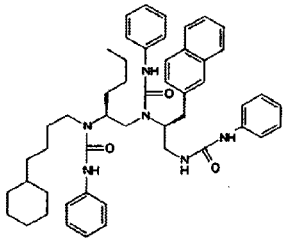 [Boc-L-3-(2-Naphthyl)-Alanine][Boc-L-Norleucine][Cyclohexanebutyric acid] | 795.08 | 794.49 | >25 |
| 19 | 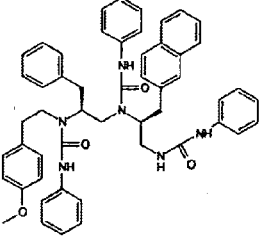 [Boc-L-3-(2-Naphthyl)-Alanine][Boc-D-Phenylalanine][4-Methoxyphenylacetic acid] | 825.03 | 824.40 | >25 |
Figure 22G

| TPI1396 | Structures | MW | Exact Mass | [lowest] ug/ml * |
|---|---|---|---|---|
| 20 | 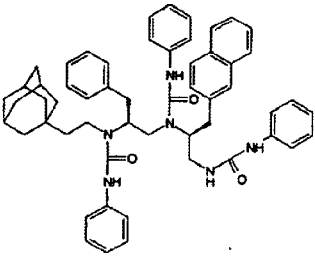 [Boc-L-3-(2-Naphthyl)-Alanine][Boc-D-Phenylalanine][1-Adamantaneacetic acid] | 853.12 | 852.47 | >25 |
| 21 | 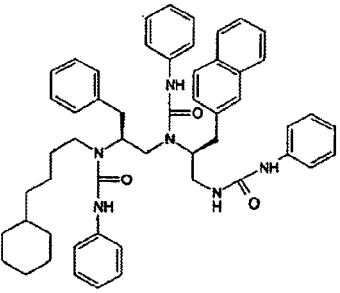 [Boc-L-3-(2-Naphthyl)-Alanine][Boc-D-Phenylalanine][Cyclohexanebutyric acid] | 829.10 | 828.47 | >25 |
| 22 | 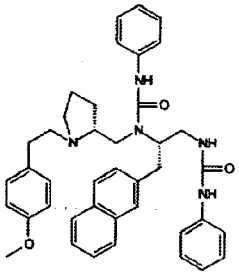 [Boc-L-3-(2-Naphthyl)-Alanine][Boc-D-Proline][4-Methoxyphenylacetic acid] | 655.84 | 655.35 | 25 |
Figure 22H

| TPI1396 | Structures | MW | Exact Mass | [lowest] ug/ml * |
|---|---|---|---|---|
| 23 | 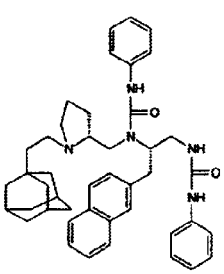 [Boc-L-3-(2-Naphthyl)-Alanine][Boc-D-Proline][1-Adamantaneacetic acid] | 683.94 | 683.42 | 25 |
| 24 | 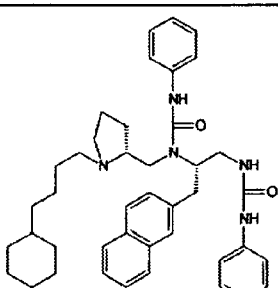 [Boc-L-3-(2-Naphthyl)-Alanine][Boc-D-Proline][Cyclohexanebutyric acid] | 659.92 | 659.42 | 25 |
| 25 | 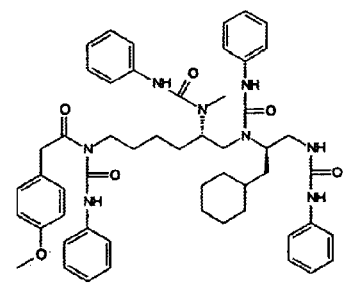 [Boc-D-Cyclohexylalanine][a-ClZ-L-Lysine(e-Boc)][4-Methoxyphenylacetic acid] | 909.14 | 908.49 | >25 |
Figure 22I

| TPI1396 | Structures | MW | Exact Mass | [lowest] ug/ml * |
|---|---|---|---|---|
| 26 | 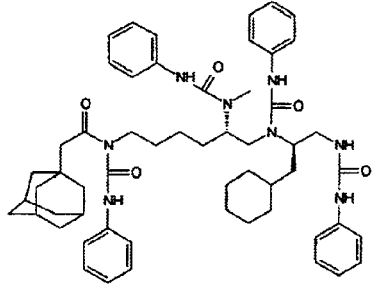 [Boc-D-Cyclohexylalanine][a-ClZ-L-Lysine(e-Boc)][1-Adamantaneacetic acid] | 937.24 | 936.56 | >25 |
| 27 | 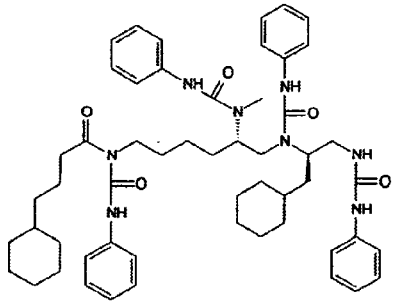 [Boc-D-Cyclohexylalanine][a-ClZ-L-Lysine(e-Boc)][Cyclohexanebutyric acid] | 913.22 | 912.56 | >25 |
| 28 | 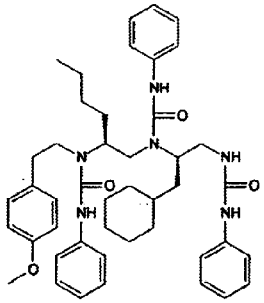 [Boc-D-Cyclohexylalanine][Boc-L-Norleucine][4-Methoxyphenylacetic acid] | 747.00 | 746.45 | >25 |
Figure 22J

| TPI1396 | Structures | MW | Exact Mass | [lowest] ug/ml * |
|---|---|---|---|---|
| 29 | 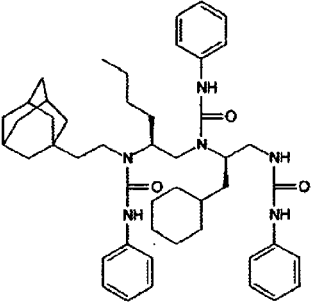 [Boc-D-Cyclohexylalanine][Boc-L-Norleucine][1-Adamantaneacetic acid] | 775.09 | 774.52 | >25 |
| 30 | 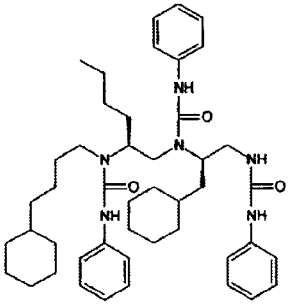 [Boc-D-Cyclohexylalanine][Boc-L-Norleucine][Cyclohexanebutyric acid] | 751.07 | 750.52 | >25 |
| 31 | 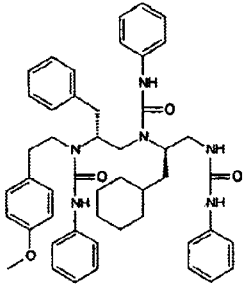 [Boc-D-Cyclohexylalanine][Boc-D-Phenylalanine][4-Methoxyphenylacetic acid] | 781.01 | 780.44 | >25 |
Figure 22K

| TPI1396 | Structures | MW | Exact Mass | [lowest] ug/ml * |
|---|---|---|---|---|
| 32 | 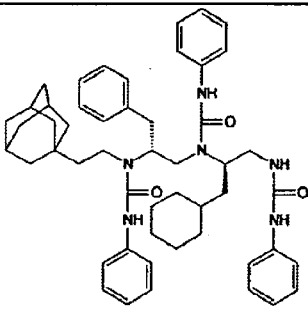<br>[Boc-D-Cyclohexylalanine][Boc-D-Phenylalanine][1-Adamantaneacetic acid] | 809.11 | 808.50 | >25 |
| 33 | 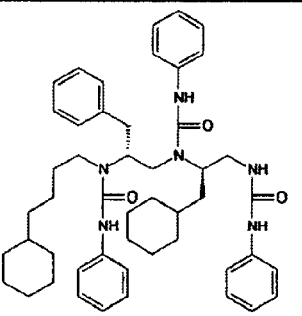<br>[Boc-D-Cyclohexylalanine][Boc-D-Phenylalanine][Cyclohexanebutyric acid] | 785.09 | 784.50 | >25 |
| 34 | 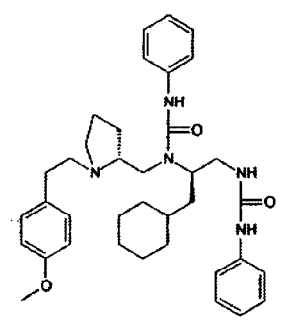<br>[Boc-D-Cyclohexylalanine][Boc-D-Proline][4-Methoxyphenylacetic acid] | 611.83 | 611.38 | 13 |
Figure 22L

| TPI1396 | Structures | MW | Exact Mass | [lowest] ug/ml * |
|---|---|---|---|---|
| 35 | 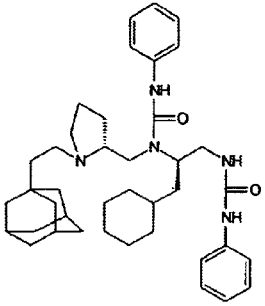 [Boc-D-Cyclohexylalanine][Boc-D-Proline][1-Adamantaneacetic acid] | 639.93 | 639.45 | 25 |
| 36 | 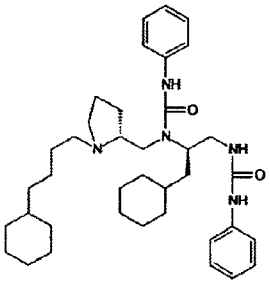 [Boc-D-Cyclohexylalanine][Boc-D-Proline][Cyclohexanebutyric acid] | 615.91 | 615.45 | >25 |
| 37 | 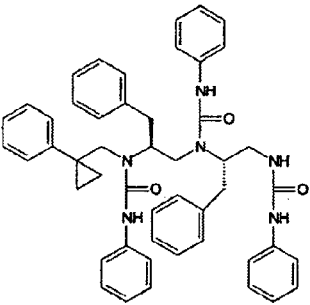 [Boc-L-Phenylalanine][Boc-L-Phenylalanine][1-Phenyl-1-Cyclopropanecarboxylic acid] | 770.98 | 770.39 | >25 |
Figure 22M

| TPI1396 | Structures | MW | Exact Mass | [lowest] ug/ml * |
|---|---|---|---|---|
| 38 | 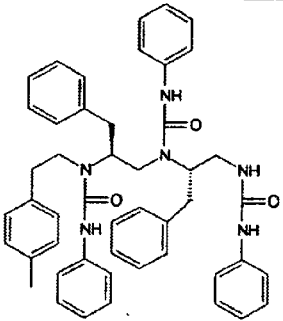 [Boc-L-Phenylalanine][Boc-L-Phenylalanine][p-Tolylacetic acid] | 758.97 | 758.39 | >25 |
| 39 | 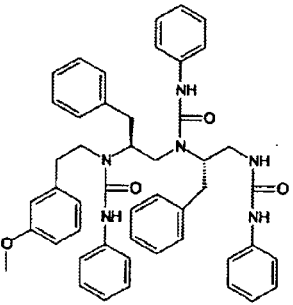 [Boc-L-Phenylalanine][Boc-L-Phenylalanine][3-Methoxyphenylacetic acid] | 774.97 | 774.39 | >25 |
| 40 | 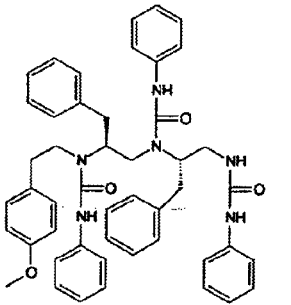 [Boc-L-Phenylalanine][Boc-L-Phenylalanine][4-Methoxyphenylacetic acid] | 774.97 | 774.39 | >25 |
Figure 22N

| TPI1396 | Structures | MW | Exact Mass | [lowest] ug/ml * |
|---|---|---|---|---|
| 41 | 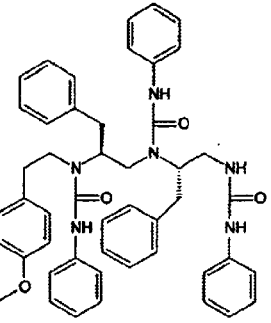 [Boc-L-Phenylalanine][Boc-L-Phenylalanine][4-Ethoxyphenylacetic acid] | 788.99 | 788.40 | 25 |
| 42 | 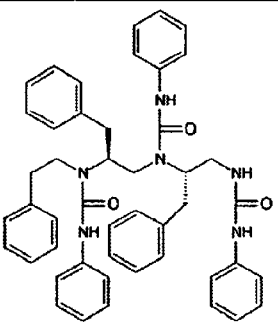 [Boc-L-Phenylalanine][Boc-L-Phenylalanine][Phenylacetic acid] | 744.94 | 744.38 | 25 |
| 43 | 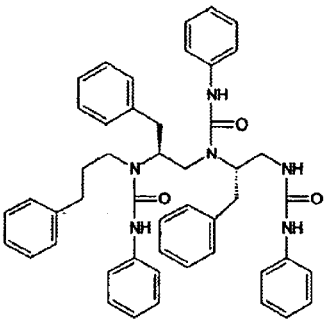 [Boc-L-Phenylalanine][Boc-L-Phenylalanine][Hydrocinnamic acid] | 758.97 | 758.39 | >25 |
Figure 22O

| TPI1396 | Structures | MW | Exact Mass | [lowest] ug/ml * |
|---|---|---|---|---|
| 44 | [Boc-L-Phenylalanine][Boc-L-Phenylalanine][Butyric acid] | 696.90 | 696.38 | >25 |
| 45 | [Boc-L-Phenylalanine][Boc-L-Phenylalanine][Heptanoic acid] | 738.98 | 738.43 | >25 |
| 46 | [Boc-L-Phenylalanine][Boc-L-Phenylalanine][Isobutyric acid] | 696.90 | 696.38 | 25 |

Figure 22P

| TPI1396 | Structures | MW | Exact Mass | [lowest] ug/ml * |
|---|---|---|---|---|
| 47 | 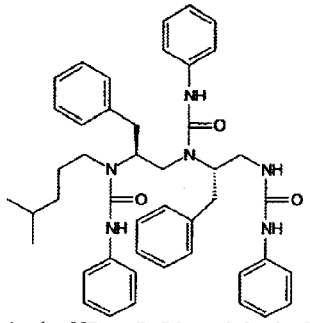 [Boc-L-Phenylalanine][Boc-L-Phenylalanine][4-Methylvaleric acid] | 724.95 | 724.41 | >25 |
| 48 | 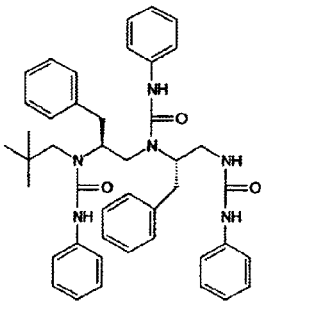 [Boc-L-Phenylalanine][Boc-L-Phenylalanine][Trimethylacetic acid] | 741.92 | 710.39 | 25 |
| 49 | 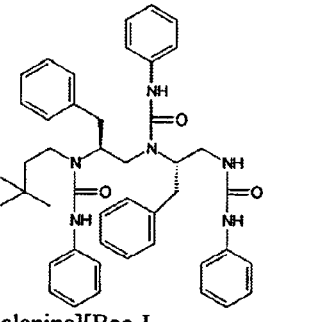 [Boc-L-Phenylalanine][Boc-L-Phenylalanine][tert-Butylacetic acid] | 724.95 | 724.41 | 25 |
Figure 22Q

| TPI1396 | Structures | MW | Exact Mass | [lowest] ug/ml * |
|---|---|---|---|---|
| 50 | 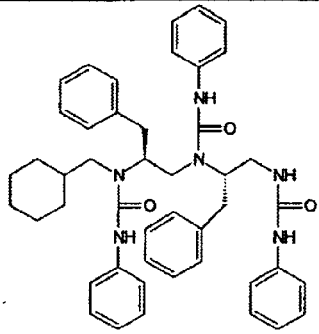 [Boc-L-Phenylalanine][Boc-L-Phenylalanine][Cyclohexanecarboxylic acid] | 736.96 | 736.41 | 25 |
| 51 | 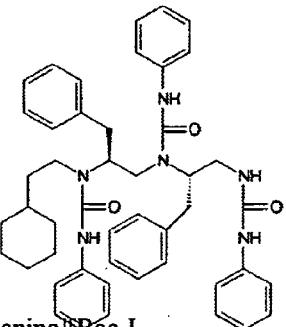 [Boc-L-Phenylalanine][Boc-L-Phenylalanine][Cyclohexylacetic acid] | 750.99 | 750.43 | >25 |
| 52 | 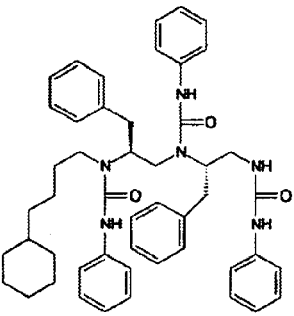 [Boc-L-Phenylalanine][Boc-L-Phenylalanine][Cyclohexanebutyric acid] | 779.04 | 778.46 | 25 |
Figure 22R

| TPI1396 | Structures | MW | Exact Mass | [lowest] ug/ml * |
|---|---|---|---|---|
| 53 | 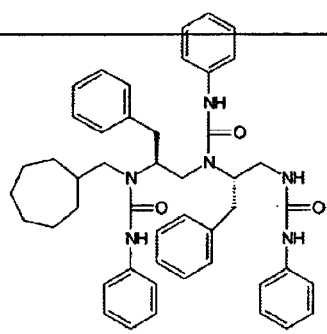 [Boc-L-Phenylalanine][Boc-L-Phenylalanine][Cycloheptanecarboxylic acid] | 750.99 | 750.43 | 25 |
| 54 | 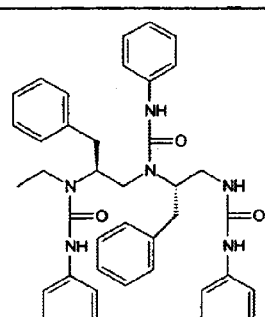 [Boc-L-Phenylalanine][Boc-L-Phenylalanine][Acetic acid] | 668.84 | 668.35 | >25 |
| 55 | 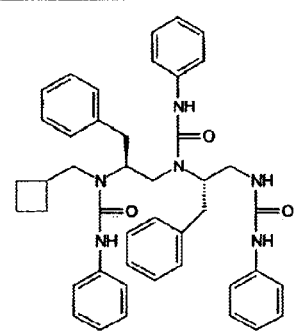 [Boc-L-Phenylalanine][Boc-L-Phenylalanine][Cyclobutanecarboxylic acid] | 708.91 | 708.38 | 25 |
Figure 22S

| TPI1396 | Structures | MW | Exact Mass | [lowest] ug/ml * |
|---|---|---|---|---|
| 56 | 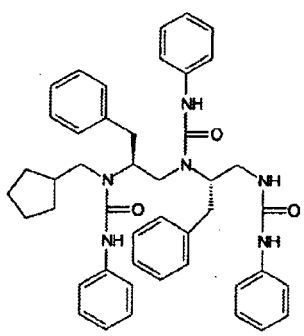 [Boc-L-Phenylalanine][Boc-L-Phenylalanine][Cyclopentanecarboxylic acid] | 722.93 | 722.39 | 25 |
| 57 | 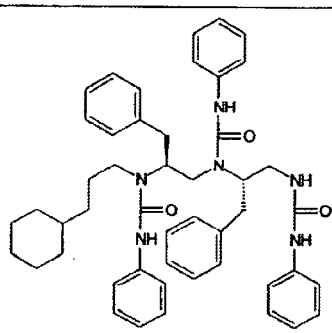 [Boc-L-Phenylalanine][Boc-L-Phenylalanine][Cyclohexanepropionic acid] | 765.01 | 764.44 | >25 |
| 58 | 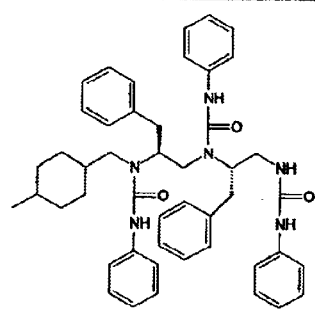 [Boc-L-Phenylalanine][Boc-L-Phenylalanine][4-Methyl-1-cyclohexanecarboxylic acid] | 750.99 | 750.43 | >25 |
Figure 22T

| TPI1396 | Structures | MW | Exact Mass | [lowest] ug/ml * |
|---|---|---|---|---|
| 59 | 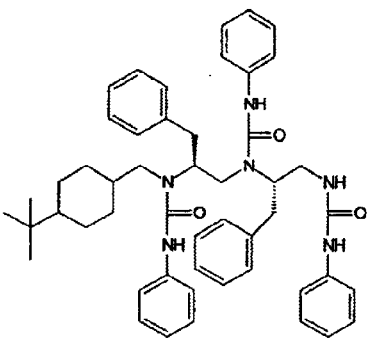 [Boc-L-Phenylalanine][Boc-L-Phenylalanine][4-tert-Butyl-cyclohexanecarboxylic acid] | 793.07 | 792.47 | >25 |
| 60 | 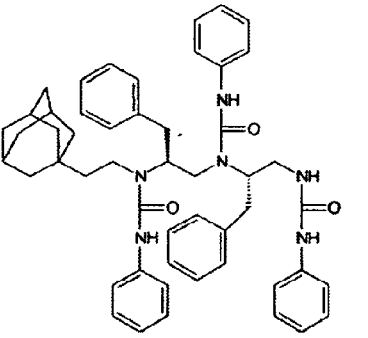 [Boc-L-Phenylalanine][Boc-L-Phenylalanine][1-Adamantaneacetic acid] | 803.06 | 802.46 | >25 |
| 61 | 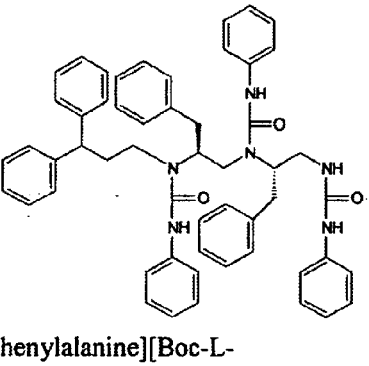 [Boc-L-Phenylalanine][Boc-L-Phenylalanine][3,3-Diphenylpropionic acid] | 835.06 | 834.43 | >25 |
Figure 22U

| TPI1396 | Structures | MW | Exact Mass | [lowest] ug/ml * |
|---|---|---|---|---|
| 62 | [Boc-L-Phenylalanine][Boc-L-Phenylalanine][Cyclopentylacetic acid] | 736.96 | 736.41 | >25 |
| 63 | [Boc-L-Phenylalanine][Boc-L-Phenylalanine][Indole-3-acetic acid] | 783.98 | 783.39 | 25 |
| 64 | [Boc-L-Phenylalanine][Boc-L-Phenylalanine][3-(3,4,5)-Trimethoxyphenylpropionic acid] | 849.04 | 848.43 | >25 |

Figure 22V

| TPI1396 | Structures | MW | Exact Mass | [lowest] ug/ml * |
|---|---|---|---|---|
| 65 | <br>[Boc-L-Phenylalanine][Boc-L-Phenylalanine][2-Norbornaneacetic acid] | 763.00 | 762.43 | 25 |

| TPI1391 | Structures | MW | Exact Mass | [lowest] ug/ml * |
|---|---|---|---|---|
| 1 | 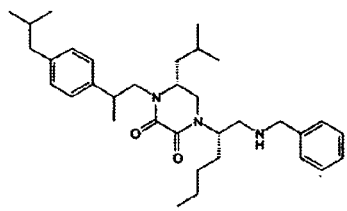 [Fmoc-L-Norleucine][Fmoc-D-Leucine][4-Isobutyl-alpha-Methylphenylacetic Acid] | 533.40 | 533.40 | 5 |
| 2 | 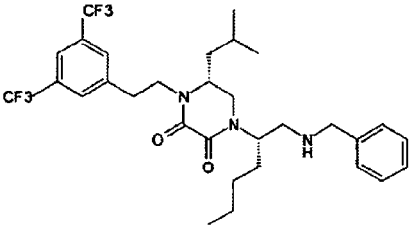 [Fmoc-L-Norleucine][Fmoc-D-Leucine][3,5-Bis(Trifluoromethyl)-Phenylacetic Acid] | 599.66 | 599.29 | 10 |
| 3 | 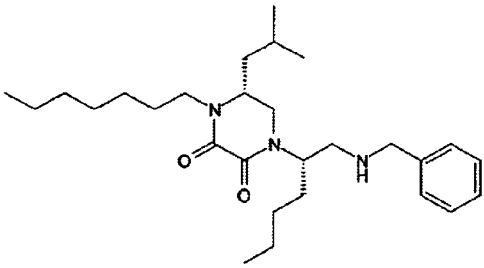 [Fmoc-L-Norleucine][Fmoc-D-Leucine][Heptanoic acid] | 457.70 | 457.37 | >25 |
Figure 23A

| TPI1391 | Structures | MW | Exact Mass | [lowest] ug/ml * |
|---|---|---|---|---|
| 4 | 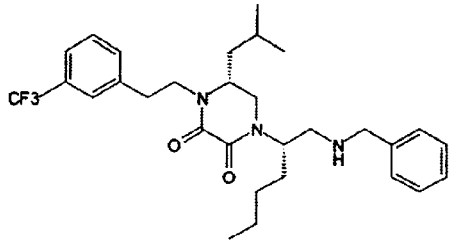 [Fmoc-L-Norleucine][Fmoc-D-Leucine][(Alpha-Alpha-Alpha-Trifluoro-m-Tolyl) acetic acid] | 531.66 | 531.31 | 5 |
| 5 | 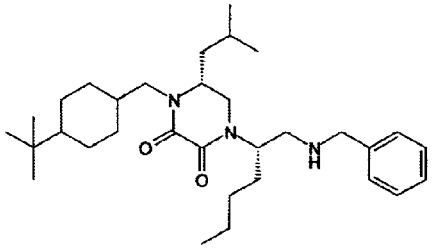 [Fmoc-L-Norleucine][Fmoc-D-Leucine][4-tert-Butyl-cyclohexanecarboxylic acid] | 511.79 | 511.41 | 10 |
| 6 | 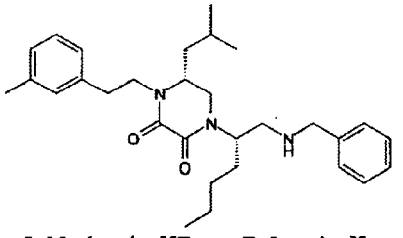 [Fmoc-L-Norleucine][Fmoc-D-Leucine][m-Tolylacetic acid] | 477.69 | 477.34 | >25 |
Figure 23B

| TPI1391 | Structures | MW | Exact Mass | [lowest] ug/ml * |
|---|---|---|---|---|
| 7 | 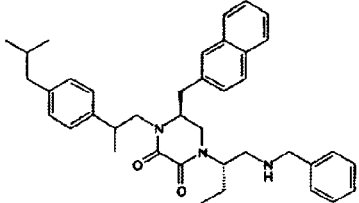 [Fmoc-L-Norleucine][Fmoc-L-2-Naphthylalanine][4-Isobutyl-alpha-Methylphenylacetic Acid] | 617.88 | 617.40 | >25 |
| 8 | 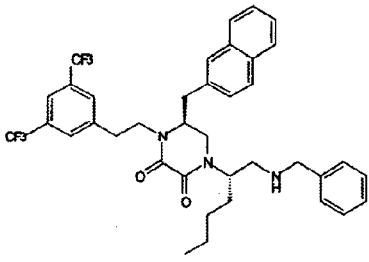 [Fmoc-L-Norleucine][Fmoc-L-2-Naphthylalanine][3,5-Bis(Trifluoromethyl)-Phenylacetic Acid] | 683.74 | 683.29 | >25 |
| 9 | 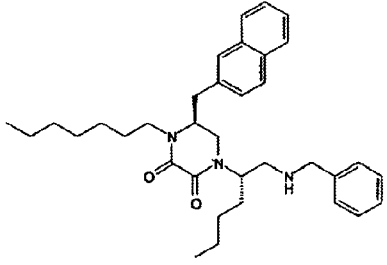 [Fmoc-L-Norleucine][Fmoc-L-2-Naphthylalanine][Heptanoic acid] | 541.78 | 541.37 | >25 |
Figure 23C

| TPI1391 | Structures | MW | Exact Mass | [lowest] ug/ml * |
|---|---|---|---|---|
| 10 | 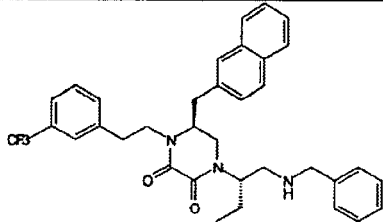 [Fmoc-L-Norleucine][Fmoc-L-2-Naphthylalanine][(Alpha-Alpha-Alpha-Trifluoro-m-Tolyl) acetic acid] | 615.74 | 615.31 | >25 |
| 11 | 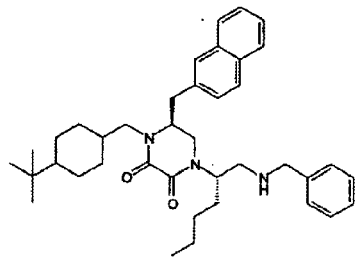 [Fmoc-L-Norleucine][Fmoc-L-2-Naphthylalanine][4-tert-Butyl-cyclohexanecarboxylic acid] | 595.87 | 595.41 | >25 |
| 12 | 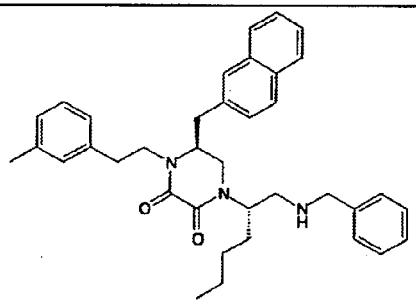 [Fmoc-L-Norleucine][Fmoc-L-2-Naphthylalanine][m-Tolylacetic acid] | 561.77 | 561.34 | >25 |
Figure 23D

| TPI1391 | Structures | MW | Exact Mass | [lowest] ug/ml * |
|---|---|---|---|---|
| 13 | 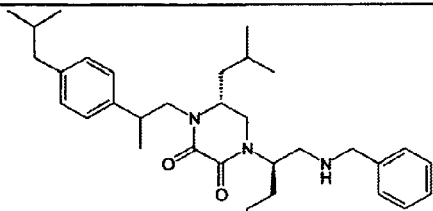 [Fmoc-D-Norleucine][Fmoc-D-Leucine][4-Isobutyl-alpha-Methylphenylacetic Acid] | 533.80 | 533.40 | 10 |
| 14 | 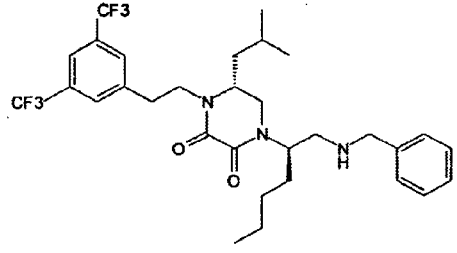 [Fmoc-D-Norleucine][Fmoc-D-Leucine][3,5-Bis(Trifluoromethyl)-Phenylacetic Acid] | 599.66 | 599.29 | 10 |
| 15 | 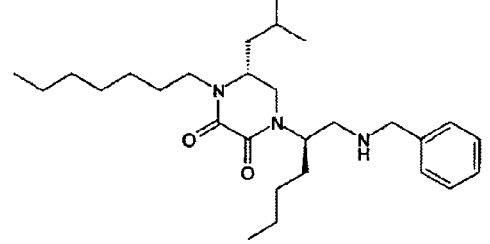 [Fmoc-D-Norleucine][Fmoc-D-Leucine][Heptanoic acid] | 457.70 | 457.37 | 10 |
Figure 23E

| TPI1391 | Structures | MW | Exact Mass | [lowest] ug/ml * |
|---|---|---|---|---|
| 16 | 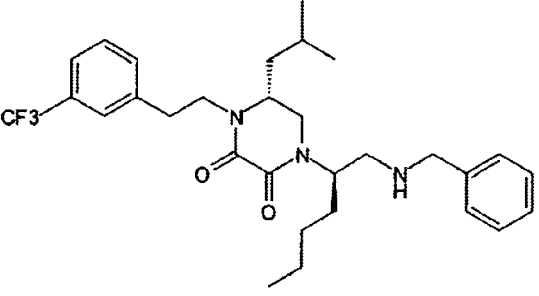 [Fmoc-D-Norleucine][Fmoc-D-Leucine][(Alpha-Alpha-Alpha-Trifluoro-m-Tolyl) acetic acid] | 531.66 | 531.31 | 10 |
| 17 | 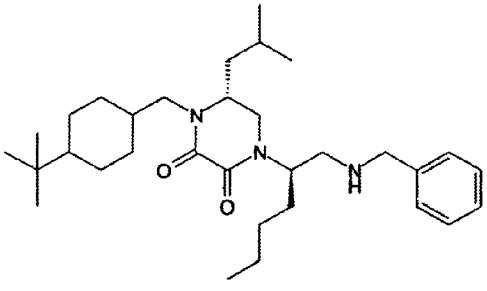 [Fmoc-D-Norleucine][Fmoc-D-Leucine][4-tert-Butyl-cyclohexanecarboxylic acid] | 511.79 | 511.41 | 10 |
| 18 | 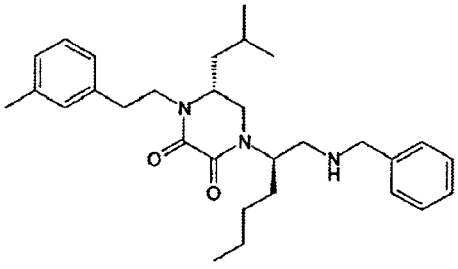 [Fmoc-D-Norleucine][Fmoc-D-Leucine][m-Tolylacetic acid] | 477.69 | 477.34 | >25 |
Figure 23F

| TPI1391 | Structures | MW | Exact Mass | [lowest] ug/ml * |
|---|---|---|---|---|
| 19 | 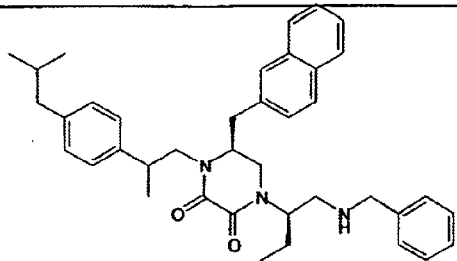 [Fmoc-D-Norleucine][Fmoc-L-2-Naphthylalanine][4-Isobutyl-alpha-Methylphenylacetic Acid] | 617.88 | 617.40 | >25 |
| 20 | 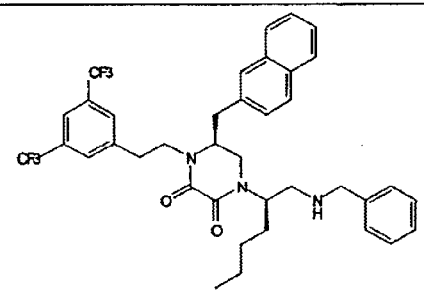 [Fmoc-D-Norleucine][Fmoc-L-2-Naphthylalanine][3,5-Bis(Trifluoromethyl)-Phenylacetic Acid] | 683.74 | 683.29 | >25 |
| 21 | 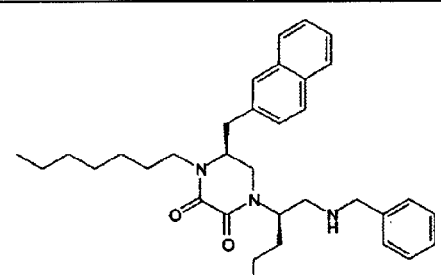 [Fmoc-D-Norleucine][Fmoc-L-2-Naphthylalanine][Heptanoic acid] | 541.78 | 541.37 | 10 |
Figure 23G

| TPI1391 | Structures | MW | Exact Mass | [lowest] ug/ml * |
|---|---|---|---|---|
| 22 | 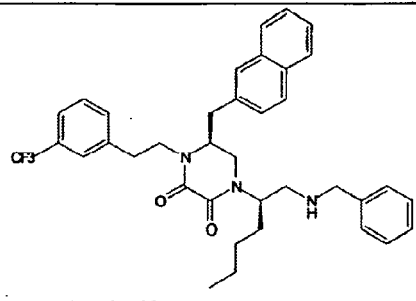 [Fmoc-D-Norleucine][Fmoc-L-2-Naphthylalanine][(Alpha-Alpha-Alpha-Trifluoro-m-Tolyl) acetic acid] | 615.74 | 615.31 | 10 |
| 23 | 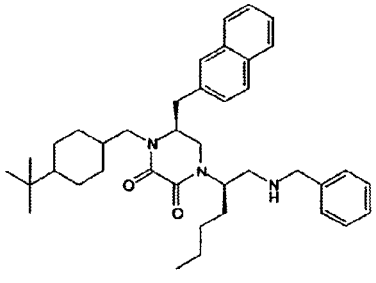 [Fmoc-D-Norleucine][Fmoc-L-2-Naphthylalanine][4-tert-Butyl-cyclohexanecarboxylic acid] | 595.87 | 595.41 | >25 |
| 24 | 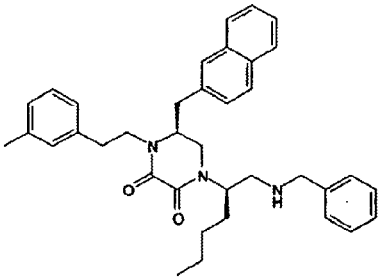 [Fmoc-D-Norleucine][Fmoc-L-2-Naphthylalanine][m-Tolylacetic acid] | 561.77 | 561.34 | 10 |
Figure 23H

| TPI1391 | Structures | MW | Exact Mass | [lowest] ug/ml * |
|---|---|---|---|---|
| 25 | 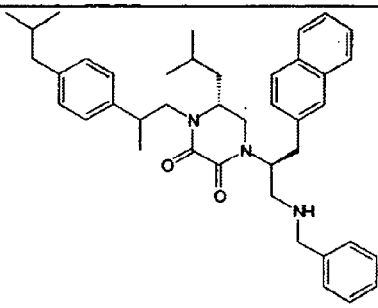 [Fmoc-L-2-Naphthylalanine][Fmoc-D-Leucine][4-Isobutyl-alpha-Methylphenylacetic Acid] | 617.88 | 617.40 | 10 |
| 26 | 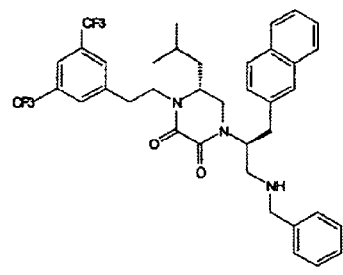 [Fmoc-L-2-Naphthylalanine][Fmoc-D-Leucine][3,5-Bis(Trifluoromethyl)-Phenylacetic Acid] | 683.74 | 683.29 | 10 |
| 27 | 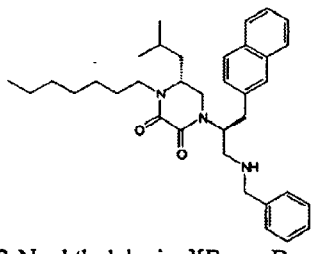 [Fmoc-L-2-Naphthylalanine][Fmoc-D-Leucine][Heptanoic acid] | 541.78 | 541.37 | 10 |
Figure 23I

| TPI1391 | Structures | MW | Exact Mass | [lowest] ug/ml * |
|---|---|---|---|---|
| 28 | 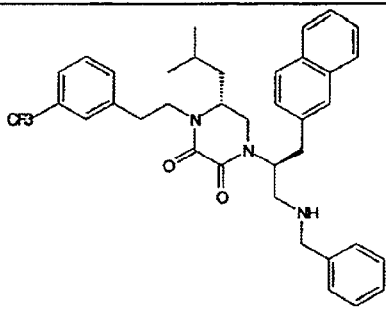 [Fmoc-L-2-Naphthylalanine][Fmoc-D-Leucine][(Alpha-Alpha-Alpha-Trifluoro-m-Tolyl) acetic acid] | 615.74 | 615.31 | 10 |
| 29 | 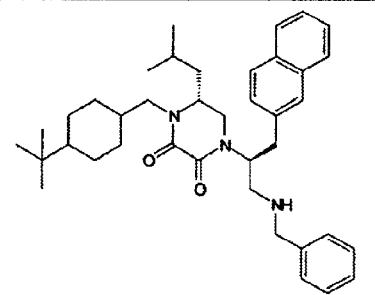 [Fmoc-L-2-Naphthylalanine][Fmoc-D-Leucine][4-tert-Butyl-cyclohexanecarboxylic acid] | 595.87 | 595.41 | 10 |
| 30 | 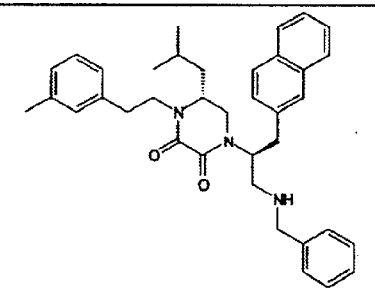 [Fmoc-L-2-Naphthylalanine][Fmoc-D-Leucine][m-Tolylacetic acid] | 561.77 | 561.34 | 10 |
Figure 23J

| TPI1391 | Structures | MW | Exact Mass | [lowest] ug/ml * |
|---|---|---|---|---|
| 31 | 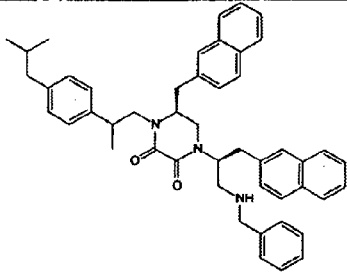 [Fmoc-L-2-Naphthylalanine][Fmoc-L-2-Naphthylalanine][4-Isobutyl-alpha-Methylphenylacetic Acid] | 701.95 | 701.40 | >25 |
| 32 | 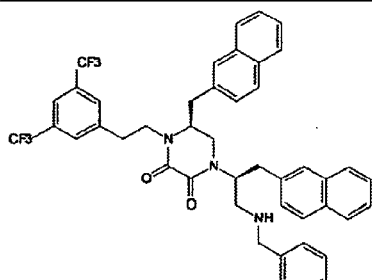 [Fmoc-L-2-Naphthylalanine][Fmoc-L-2-Naphthylalanine][3,5-Bis(Trifluoromethyl)-Phenylacetic Acid] | 767.81 | 767.29 | >25 |
| 33 | 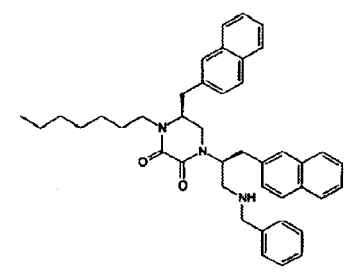 [Fmoc-L-2-Naphthylalanine][Fmoc-L-2-Naphthylalanine][Heptanoic acid] | 625.86 | 625.37 | >25 |
Figure 23K

| TPI1391 | Structures | MW | Exact Mass | [lowest] ug/ml * |
|---|---|---|---|---|
| 34 | 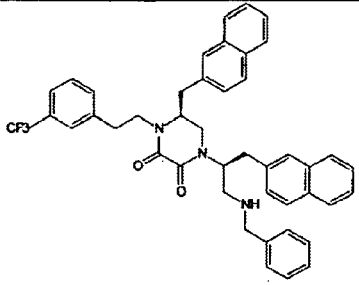 [Fmoc-L-2-Naphthylalanine][Fmoc-L-2-Naphthylalanine][(Alpha-Alpha-Alpha-Trifluoro-m-Tolyl) acetic acid] | 699.82 | 699.31 | >25 |
| 35 | 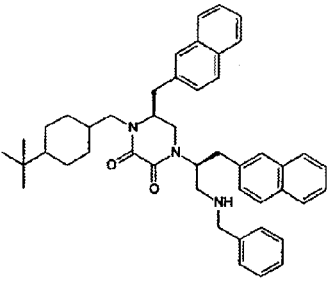 [Fmoc-L-2-Naphthylalanine][Fmoc-L-2-Naphthylalanine][4-tert-Butyl-cyclohexanecarboxylic acid] | 679.95 | 679.41 | >25 |
| 36 | 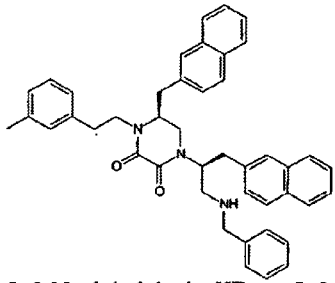 [Fmoc-L-2-Naphthylalanine][Fmoc-L-2-Naphthylalanine][m-Tolylacetic acid] | 645.85 | 645.34 | >25 |
Figure 23L

| TPI1400 | Structures | MW | Exact Mass | [lowest] ug/ml * |
|---|---|---|---|---|
| 1 | 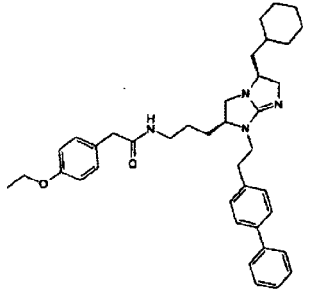<br>[Boc-L-Cyclohexylalanine][4-Biphenylacetic acid][4-Ethoxyphenylacetic acid] | 606.855 | 606.393351 | 13 |
| 2 | 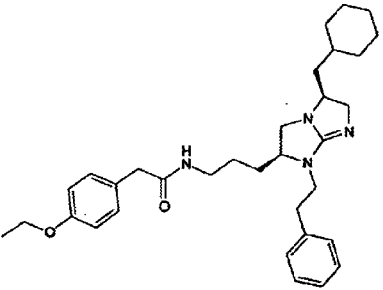<br>[Boc-L-Cyclohexylalanine][Phenylacetic acid][4-Ethoxyphenylacetic acid] | 530.757 | 530.362051 | 25 |
| 3 | 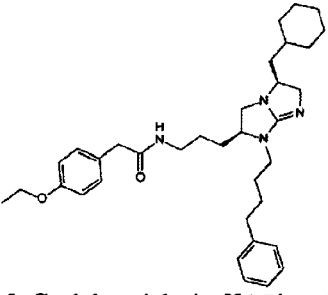<br>[Boc-L-Cyclohexylalanine][4-Phenylbutyric acid][4-Ethoxyphenylacetic acid] | 558.811 | 558.393351 | 25 |
Figure 24A

| TPI1400 | Structures | MW | Exact Mass | [lowest] ug/ml * |
|---|---|---|---|---|
| 4 | 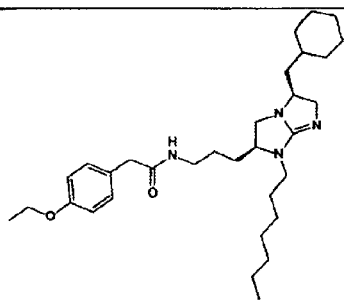 [Boc-L-Cyclohexylalanine][Heptanoic acid][4-Ethoxyphenylacetic acid] | 524.794 | 524.409001 | 13 |
| 5 | 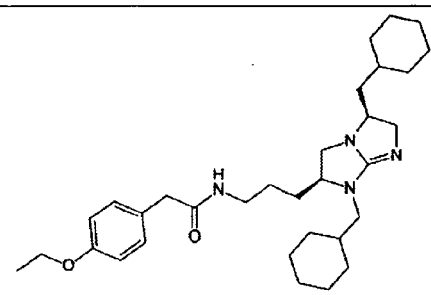 [Boc-L-Cyclohexylalanine][Cyclohexanecarboxylic acid][4-Ethoxyphenylacetic acid] | 522.778 | 522.393351 | 25 |
| 6 | 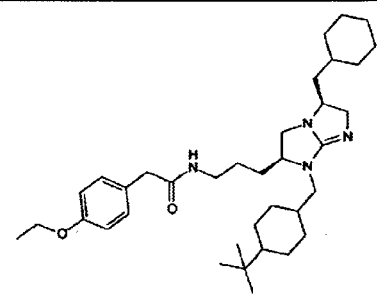 [Boc-L-Cyclohexylalanine][4-tert-Butyl-cyclohexanecarboxylic acid][4-Ethoxyphenylacetic acid] | 578.886 | 578.455951 | 6 |
Figure 24B

| TPI1400 | Structures | MW | Exact Mass | [lowest] ug/ml * |
|---|---|---|---|---|
| 7 | 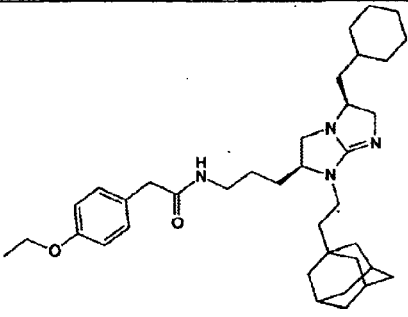 [Boc-L-Cyclohexylalanine][1-Adamantaneacetic acid][4-Ethoxyphenylacetic acid] | 588.881 | 588.440301 | 6 |
| 8 | 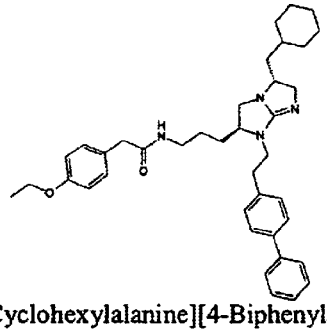 [Boc-D-Cyclohexylalanine][4-Biphenylacetic acid][4-Ethoxyphenylacetic acid] | 606.855 | 606.393351 | 13 |
| 9 | 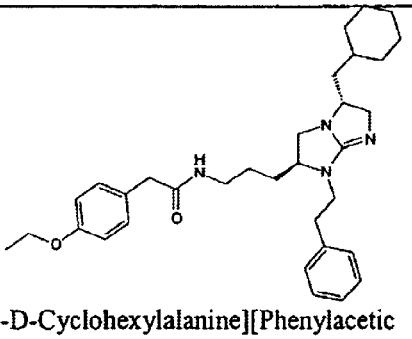 [Boc-D-Cyclohexylalanine][Phenylacetic acid][4-Ethoxyphenylacetic acid] | 530.757 | 530.362051 | 25 |
Figure 24C

| TPI1400 | Structures | MW | Exact Mass | [lowest] ug/ml * |
|---|---|---|---|---|
| 10 | 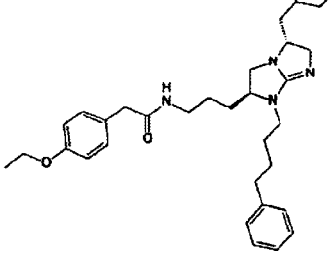 [Boc-D-Cyclohexylalanine][4-Phenylbutyric acid][4-Ethoxyphenylacetic acid] | 558.811 | 558.393351 | 25 |
| 11 | 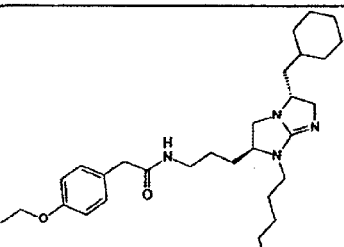 [Boc-D-Cyclohexylalanine][Heptanoic acid][4-Ethoxyphenylacetic acid] | 524.794 | 524.409001 | 25 |
| 12 | 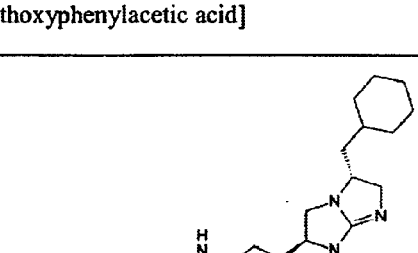 [Boc-D-Cyclohexylalanine][Cyclohexanecarboxylic acid][4-Ethoxyphenylacetic acid] | 522.778 | 522.393351 | 25 |
Figure 24D

| TPI1400 | Structures | MW | Exact Mass | [lowest] ug/ml * |
|---|---|---|---|---|
| 13 | 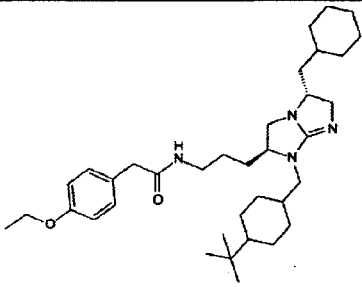 [Boc-D-Cyclohexylalanine][4-tert-Butyl-cyclohexanecarboxylic acid][4-Ethoxyphenylacetic acid] | 578.886 | 578.455951 | 25 |
| 14 | 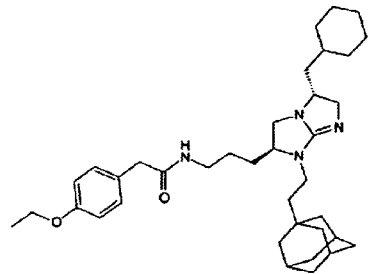 [Boc-D-Cyclohexylalanine][1-Adamantaneacetic acid][4-Ethoxyphenylacetic acid] | 588.881 | 588.440301 | 6 |
| 15 | 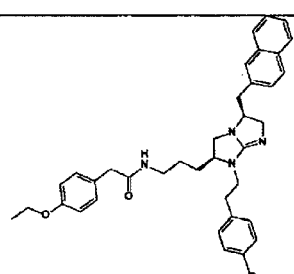 [Boc-L-Naphthylalanine][4-Biphenylacetic acid][4-Ethoxyphenylacetic acid] | 650.867 | 650.362051 | 10 |
Figure 24E

| TPI1400 | Structures | MW | Exact Mass | [lowest] ug/ml * |
|---|---|---|---|---|
| 16 | 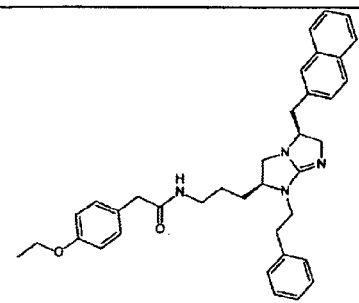 [Boc-L-Naphthylalanine][Phenylacetic acid][4-Ethoxyphenylacetic acid] | 574.769 | 574.330751 | 25 |
| 17 | 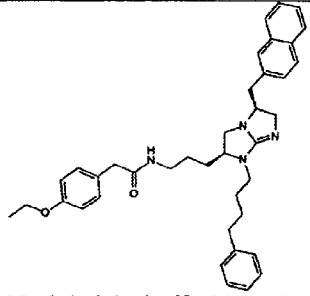 [Boc-L-Naphthylalanine][4-Phenylbutyric acid][4-Ethoxyphenylacetic acid] | 602.823 | 602.362051 | 25 |
| 18 | 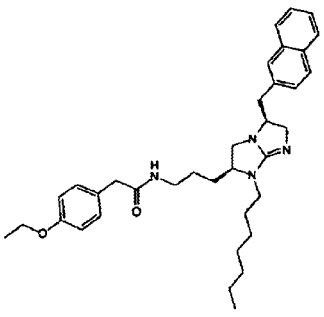 [Boc-L-Naphthylalanine][Heptanoic acid][4-Ethoxyphenylacetic acid] | 568.806 | 568.377701 | 25 |
Figure 24F

| TPI1400 | Structures | MW | Exact Mass | [lowest] ug/ml * |
|---|---|---|---|---|
| 19 | 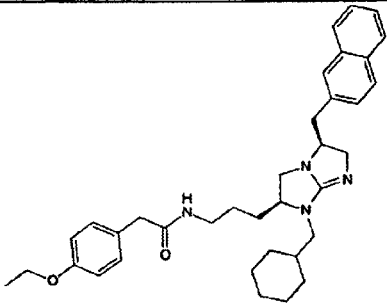 [Boc-L-Naphthylalanine][Cyclohexanecarboxylic acid][4-Ethoxyphenylacetic acid] | 566.79 | 566.362051 | 25 |
| 20 | 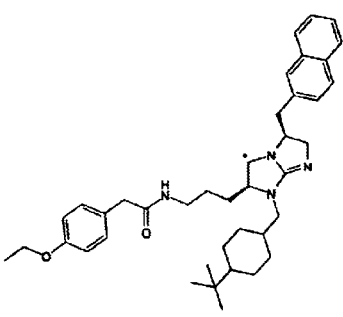 [Boc-L-Naphthylalanine][4-tert-Butyl-cyclohexanecarboxylic acid][4-Ethoxyphenylacetic acid] | 622.898 | 622.424651 | 10 |
| 21 | 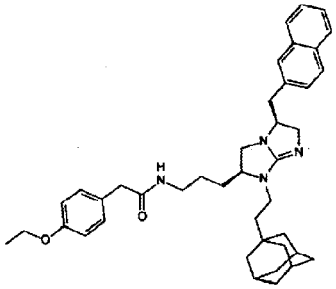 [Boc-L-Naphthylalanine][1-Adamantaneacetic acid][4-Ethoxyphenylacetic acid] | 632.893 | 632.409001 | >25 |
Figure 24G

| TPI1400 | Structures | MW | Exact Mass | [lowest] ug/ml * |
|---|---|---|---|---|
| 22 | 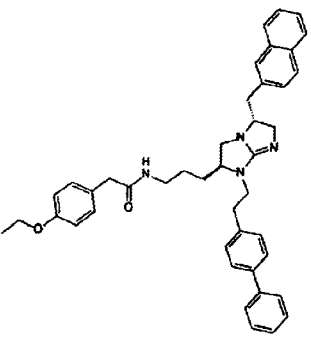 [Boc-D-Naphthylalanine][4-Biphenylacetic acid][4-Ethoxyphenylacetic acid] | 650.867 | 650.362051 | 25 |
| 23 | 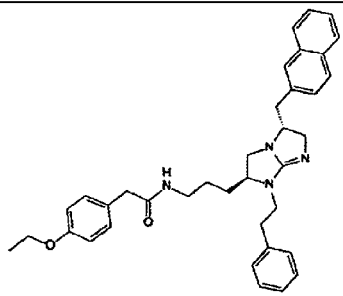 [Boc-D-Naphthylalanine][Phenylacetic acid][4-Ethoxyphenylacetic acid] | 574.769 | 574.330751 | 25 |
| 24 | 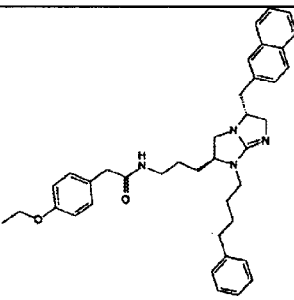 [Boc-D-Naphthylalanine][4-Phenylbutyric acid][4-Ethoxyphenylacetic acid] | 602.823 | 602.362051 | 25 |
Figure 24H

| TPI1400 | Structures | MW | Exact Mass | [lowest] ug/ml * |
|---|---|---|---|---|
| 25 | [Boc-D-Naphthylalanine][Heptanoic acid][4-Ethoxyphenylacetic acid] | 568.806 | 568.377701 | 10 |
| 26 | [Boc-D-Naphthylalanine][Cyclohexanecarboxylic acid][4-Ethoxyphenylacetic acid] | 566.79 | 566.362051 | 25 |
| 27 | [Boc-D-Naphthylalanine][4-tert-Butyl-cyclohexanecarboxylic acid][4-Ethoxyphenylacetic acid] | 622.898 | 622.424651 | 25 |

Figure 24I

| TPI1400 | Structures | MW | Exact Mass | [lowest] ug/ml * |
|---|---|---|---|---|
| 28 | 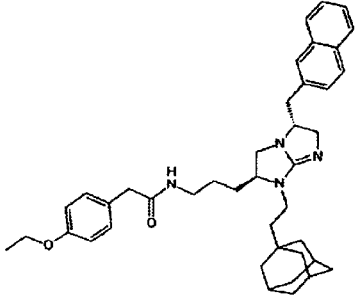 [Boc-D-Naphthylalanine][1-Adamantaneacetic acid][4-Ethoxyphenylacetic acid] | 632.893 | 632.409001 | 13 |
| 29 | 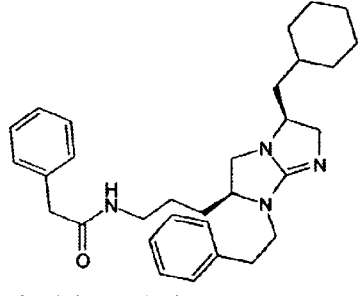 [Boc-L-Cyclohexylalanine][Phenylacetic acid][Phenylacetic acid] | 486.704 | 486.33584 | 25 |
| 30 | 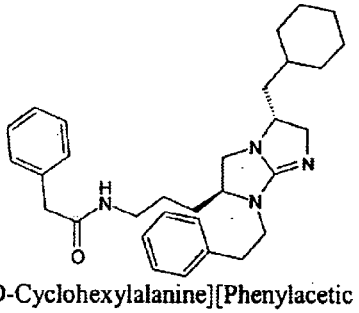 [Boc-D-Cyclohexylalanine][Phenylacetic acid][Phenylacetic acid] | 486.704 | 486.33584 | 25 |
Figure 24J

| TPI1400 | Structures | MW | Exact Mass | [lowest] ug/ml * |
|---|---|---|---|---|
| 31 | 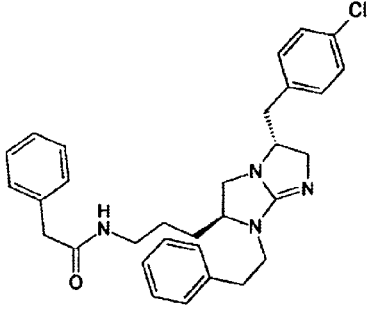 [Boc-D-p-Chloro-Phenylalanine][Phenylacetic acid][Phenylacetic acid] | 515.101 | 514.249915 | >25 |
| 32 | 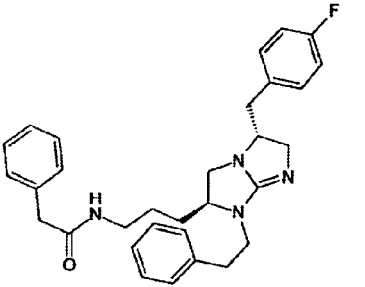 [Boc-D-p-Fluoro-Phenylalanine][Phenylacetic acid][Phenylacetic acid] | 498.646 | 498.279465 | 25 |
| 33 | 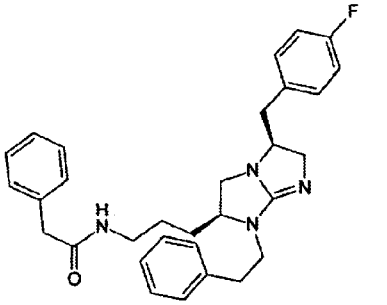 [Boc-L-p-Fluoro-Phenylalanine][Phenylacetic acid][Phenylacetic acid] | 498.646 | 498.279465 | >25 |
Figure 24K

| TPI1400 | Structures | MW | Exact Mass | [lowest] ug/ml * |
|---|---|---|---|---|
| 34 | 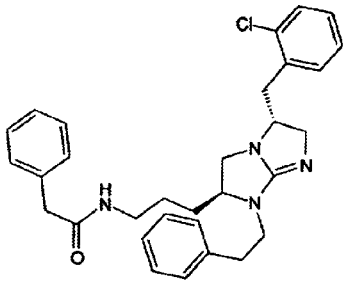 [Boc-D-2-Chloro-Phenylalanine][Phenylacetic acid][Phenylacetic acid] | 515.101 | 514.249915 | >25 |
| 35 | 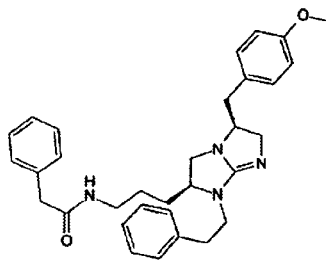 [Boc-L-O-Ethyl-Tyrosine][Phenylacetic acid][Phenylacetic acid] | 524.709 | 524.315101 | >25 |
| 36 | 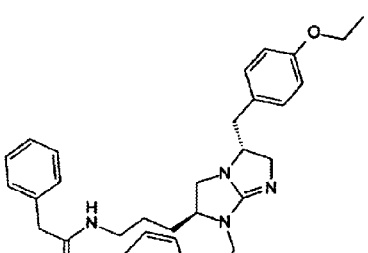 [Boc-D-O-Ethyl-Tyrosine][Phenylacetic acid][Phenylacetic acid] | 524.709 | 524.315101 | >25 |
Figure 24L

| TPI1400 | Structures | MW | Exact Mass | [lowest] ug/ml * |
|---|---|---|---|---|
| 37 | 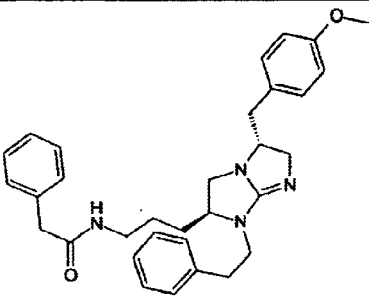 [Boc-D-O-Methyl-Tyrosine][Phenylacetic acid][Phenylacetic acid] | 510.682 | 510.299451 | >25 |
| 38 | 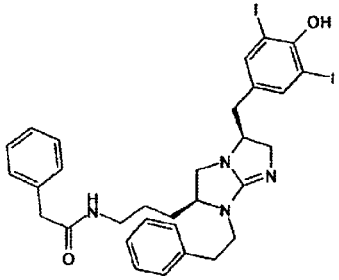 [Boc-L-3,5-Diiodo-Tyrosine(BrZ)][Phenylacetic acid][Phenylacetic acid] | 748.447 | 748.068947 | >25 |
| 39 | 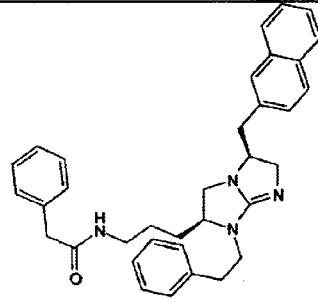 [Boc-L-Naphthylalanine][Phenylacetic acid][Phenylacetic acid] | 530.716 | 530.30454 | 25 |
Figure 24M

| TPI1400 | Structures | MW | Exact Mass | [lowest] ug/ml * |
|---|---|---|---|---|
| 40 | 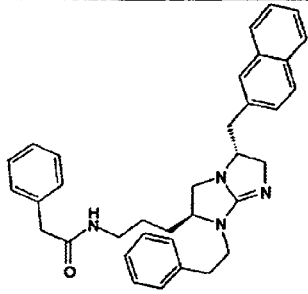 [Boc-D-Naphthylalanine][Phenylacetic acid][Phenylacetic acid] | 530.716 | 530.30454 | 25 |
| 41 | 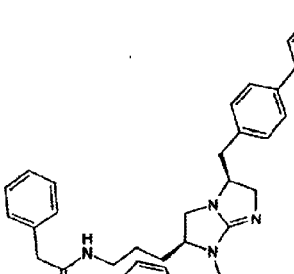 [Boc-L-4,4'-Biphenyl-Alanine][Phenylacetic acid][Phenylacetic acid] | 556.754 | 556.32019 | 25 |
| 42 | 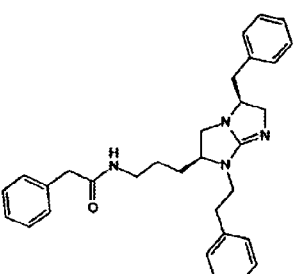 [Boc-L-Phenylalanine][p-Tolylacetic acid][Phenylacetic acid] | 494.683 | 494.30454 | >25 |
Figure 24N

| TPI1400 | Structures | MW | Exact Mass | [lowest] ug/ml * |
|---|---|---|---|---|
| 43 | 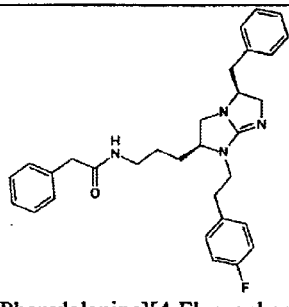 [Boc-L-Phenylalanine][4-Fluorophenylacetic acid][Phenylacetic acid] | 498.646 | 498.279465 | >25 |
| 44 | 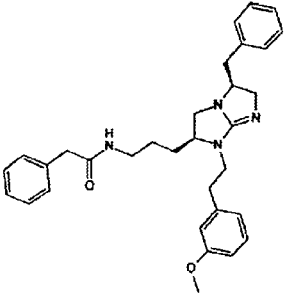 [Boc-L-Phenylalanine][3-Methoxyphenylacetic acid][Phenylacetic acid] | 510.682 | 510.299451 | >25 |
| 45 | 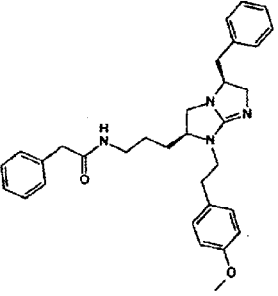 [Boc-L-Phenylalanine][4-Methoxyphenylacetic acid][Phenylacetic acid] | 510.682 | 510.299451 | >25 |
Figure 240

| TPI1400 | Structures | MW | Exact Mass | [lowest] ug/ml * |
|---|---|---|---|---|
| 46 | 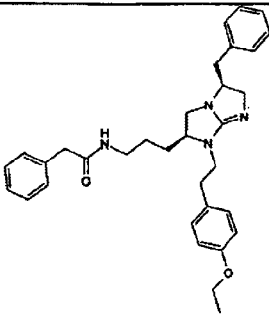 [Boc-L-Phenylalanine][4-Ethoxyphenylacetic acid][Phenylacetic acid] | 524.709 | 524.315101 | >25 |
| 47 | 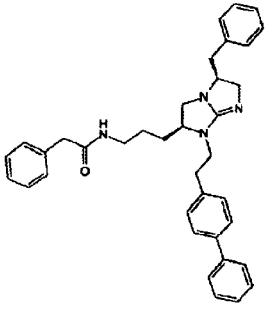 [Boc-L-Phenylalanine][4-Biphenylacetic acid][Phenylacetic acid] | 556.754 | 556.32019 | 25 |
| 48 | 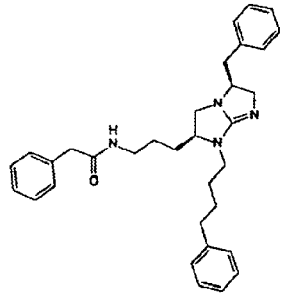 [Boc-L-Phenylalanine][4-Phenylbutyric acid][Phenylacetic acid] | 508.71 | 508.32019 | >25 |
Figure 24P

| TPI1400 | Structures | MW | Exact Mass | [lowest] ug/ml * |
|---|---|---|---|---|
| 49 | 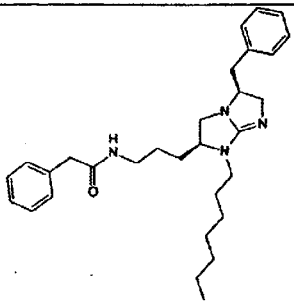 [Boc-L-Phenylalanine][Heptanoic acid][Phenylacetic acid] | 474.693 | 474.33584 | 25 |
| 50 | 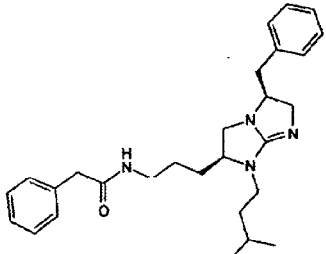 [Boc-L-Phenylalanine][3-Methylvaleric acid][Phenylacetic acid] | 460.666 | 460.32019 | >25 |
| 51 | 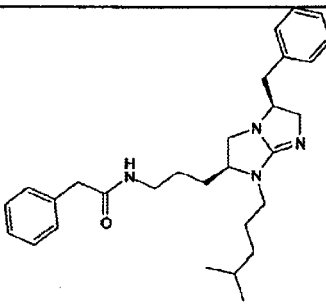 [Boc-L-Phenylalanine][4-Methylvaleric acid][Phenylacetic acid] | 460.666 | 460.32019 | >25 |
Figure 24Q

| TPI1400 | Structures | MW | Exact Mass | [lowest] ug/ml * |
|---|---|---|---|---|
| 52 | 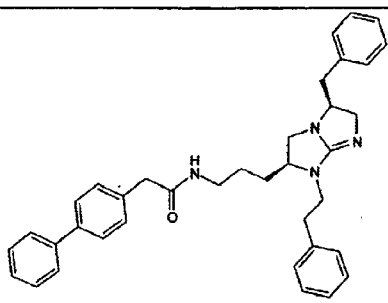 [Boc-L-Phenylalanine][Phenylacetic acid][4-Biphenylacetic acid] | 556.754 | 556.32019 | 25 |
| 53 | 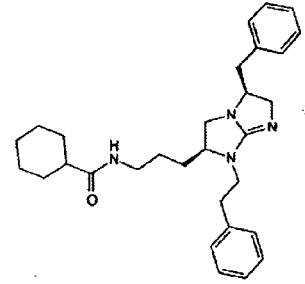 [Boc-L-Phenylalanine][Phenylacetic acid][Cyclohexanecarboxylic acid] | 472.677 | 472.32019 | >25 |
| 54 | 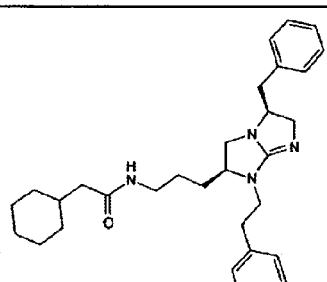 [Boc-L-Phenylalanine][Phenylacetic acid][Cyclohexaneacetic acid] | 486.704 | 486.33584 | >25 |
Figure 24R

| TPI1400 | Structures | MW | Exact Mass | [lowest] ug/ml * |
|---|---|---|---|---|
| 55 | [Boc-L-Phenylalanine][Phenylacetic acid][Cyclohexanebutyric acid] | 514.758 | 514.367141 | 25 |
| 56 | [Boc-L-Phenylalanine][Phenylacetic acid][Cycloheptanecarboxylic acid] | 486.704 | 486.335484 | 25 |
| 57 | [Boc-L-Phenylalanine][Phenylacetic acid][3-Cyclopentylpropionic acid] | 486.704 | 486.33584 | >25 |

Figure 24S

| TPI1400 | Structures | MW | Exact Mass | [lowest] ug/ml * |
|---|---|---|---|---|
| 58 | <br>[Boc-L-Phenylalanine][Phenylacetic acid][3,5-bis-(Trifluoromethyl)-phenylacetic acid] | 616.65 | 616.263639 | 25 |

METHODS AND COMPOSITIONS FOR DEREPRESSION OF IAP-INHIBITED CASPASE

This application claims benefit of the filing date of U.S. Provisional Application No. 60/331,957, filed Nov. 21, 2001, and which is incorporated herein by reference.

This invention was made with government support under grant number CA78040 awarded by The National Institute of Health/National Cancer Institute. The United States Government has certain rights in this invention.

BACKGROUND OF THE INVENTION

The present invention relates generally to molecular medicine and more specifically to compositions and methods for altering molecular interactions involved in regulating programmed cell death.

Normal tissues in the body are formed either by cells that have reached a terminally differentiated state and no longer divide or by cells that die after a period of time and are replaced from a pool of dividing cells. For example, nervous tissue is formed early in development and the cells of the nervous system reach a terminally differentiated state soon after birth. In contrast, the body has a number of self renewing tissues such as skin, gut, bone marrow and sex organs which undergo a balanced flux of cell birth and death. This flux, which results in the production of 50–70 billion cells per day in an average adult and amounting to a mass of cells equivalent to an entire body weight over a years time, is balanced by the regulated eradication of an equivalent number of cells. In self renewing tissues the eradication is maintained, in part, due to the process of programmed cell death, known as apoptosis, in which the cells are genetically "programmed" to die after a certain period of time.

Apoptosis is particularly prominent during the development of an organism, where cells that perform transitory functions are programmed to die after their function no longer is required. In addition, apoptosis can occur in cells that have undergone major genetic alterations, thus providing the organism with a means to rid itself of defective and potentially cancer forming cells. Apoptosis also can be induced due to exposure of an organism to various external stimuli, including, for example, bacterial toxins, ethanol and ultraviolet radiation. Chemotherapeutic agents for treating cancer also are potent inducers of apoptosis.

The regulation of programmed cell death is a complex process involving numerous pathways and, on occasion, defects occur in the regulation of programmed cell death. Given the critical role of this process in maintaining a steady-state number of cells in a tissue or in maintaining the appropriate cells during development of an organism, defects in programmed cell death often are associated with pathologic conditions. It is estimated that either too little or too much cell death is involved in over half of the diseases for which adequate therapies do not currently exist.

Various disease states occur due to aberrant regulation of programmed cell death in an organism. For example, defects that result in a decreased level of apoptosis in a tissue as compared to the normal level required to maintain the steady-state of the tissue can result in an increased number of cells in the tissue. Such a mechanism of increasing cell numbers has been identified in various cancers, where the formation of a tumor occurs not because the cancer cells necessarily are dividing more rapidly than their normal counterparts, but because the cells are not dying at their normal rate.

Thus, a need exists for agents capable of modulating programmed cell death pathways and methods for treating individuals experiencing diseases associated with aberrant regulation of programmed cell death. The present invention satisfies this need and provides additional advantages as well.

SUMMARY OF THE INVENTION

The invention provides isolated agents having a core peptide selected from the group consisting of Core peptides 4 through 39 and 42 through 55, wherein the agent derepresses an IAP-inhibited caspase. Also provided is an isolated agent having a core structure selected from any of the structures shown in FIGS. 5, 9A–9C, 10A–I, 14B, and 21A–24T, wherein the agent derepresses an IAP-inhibited caspase. The invention further provides a method of derepressing an IAP-inhibited caspase. The method consists of contacting an IAP-inhibited caspase with an effective amount of an agent to derepress an IAP-inhibited caspase, the agent having a core motif selected from the group consisting of a core peptide having a sequence set forth in any of Core peptides 4 through 39 and 42 through 55, and a core structure selected from the group consisting of TPI759, TPI882, TPI914 or TPI927. The methods of the invention also can be used for promoting apoptosis in a cell and for reducing the severity of a pathology characterized by reduced levels of apoptosis. Methods for identifying agents that derepress an IAP-inhibited caspase are also provided.

BRIEF DESCRIPTION OF THE DRAWINGS

FIGS. 2A, 2B and 2C show a table listing individual tetrapeptides of the TPI1313 library and the ratio of $V_{max}$ for hydrolysis of Ac-DEVD-AFC in the presence and absence of each peptide species. The ratio=($V_{max}$ when peptide, caspase 3 and XIAP are present)/($V_{max}$ when caspase 3 and XIAP are present).

FIGS. 3A–3I show structures for the individual species of tetrapeptides in the TPI1313 library.

FIGS. 7A–7F show structures of the defined functionalities in the mixtures found to be derepressors of an XIAP-inhibited caspase in the TPI882 C-6-acylamino bicyclic guanidine library. The chemical name in each box is for the reagent from which the R group was derived and the chemical name below each box is the name of the functional group at the respective R position. Each functional group has the same steriochemistry as the reagent from which it was derived.

FIGS. 8A–8F show structures of the defined functionalities in the mixtures found to be derepressors of an XIAP-inhibited caspase in the TPI759 N-benzyl-1,4,5-trisusbstituted-2,3-diketopiperazine positional scanning combinatorial library. The first chemical name listed below each box is for the reagent from which the R group was derived and the second chemical name listed below each box is the name of the functional group at the respective R position. Each functional group has the same steriochemistry as the reagent from which it was derived.

FIGS. 9A–9C show structures for individual compounds found to be derepressors of an XIAP-inhibited caspase in the TPI927 polyphenylurea library. The chemical name in each box is for the reagent from which the R group was derived and the chemical name below each box is the name of the functional group at the respective R position. Each functional group has the same steriochemistry as the reagent from which it was derived.

FIGS. 10A–10F show structures for individual compounds found to be derepressors of an XIAP-inhibited caspase in the TPI882 C-6-acylamino bicyclic guanidine library. The chemical name in each box is for the reagent from which the R group was derived and the chemical name below each box is the name of the functional group at the respective R position. Each functional group has the same steriochemistry as the reagent from which it was derived.

FIGS. 11A–11C show dose response of mixtures identified as derepressors of XIAP-inhibited caspase from the TPI 1239 library. Values shown are for the ratio of $V_{max}$ for hydrolysis of AC-DEVD-AFC in the presence and absence of each mixture. Caspase or XIAP were present at the doses listed at the top of each column.

FIG. 12 shows the structures of L-3-(2-thienyl)-alanyl-L-(2-naphthyl)-alanyl-L-p-chloro-phenylalanyl-L-(e-fluorenylmethyloxycarbonyl)-lysine (TPI792-33; Core peptide 16) and L-3-(2-thienyl)-alanyl, L-(2-naphthyl)-alanyl-D-(e-fluorenylmethyloxycarbonyl)-lysyl-L-(e-fluorenylmethyloxycarbonyl)-lysine (TPI792-35; Core peptide 17).

FIG. 14 shows the generalized structures for phenyl urea compounds in the TPI1396 library and diketopiperazine compounds in the TPI1391 library (Panel A) and structures for compounds TPI1391-28, TPI1391-21, TPI1396-34, TPI1396-22, TPI1396-11, TPI1396-12 (Panel B).

FIG. 16 shows killing of Jurkat leukemia cells by TPI1391-28 and TPI1396-34 compared to control compounds having similar core pharmacophores, respectively, but different R groups.

FIG. 20A shows structures for TPI792-3, TPI792-9, TPI792-15, TPI792-17, TPI792-19 and TPI792-22; FIG. 20B shows structures for TPI792-27, TPI792-33 and TPI792-35.

FIGS. 22A–22W show structures for agents TPI1396-1 through TPI1396-65 along with respective molecular weights, masses and lowest concentration of each agent having a ratio of 1.8 or higher in SMAC competition assays.

FIGS. 23A–23L show structures for agents TPI1391-1 through TPI1391-36 along with respective molecular weights, masses and lowest concentration of each agent having a ratio of 1.8 or higher in SMAC competition assays.

FIGS. 24A–24T show structures for agents TPI1400-1 through TPI1400-58 along with respective molecular weights, masses and lowest concentration of each agent having a ratio of 1.8 or higher in SMAC competition assays.

DETAILED DESCRIPTION OF THE INVENTION

Figure 1A:
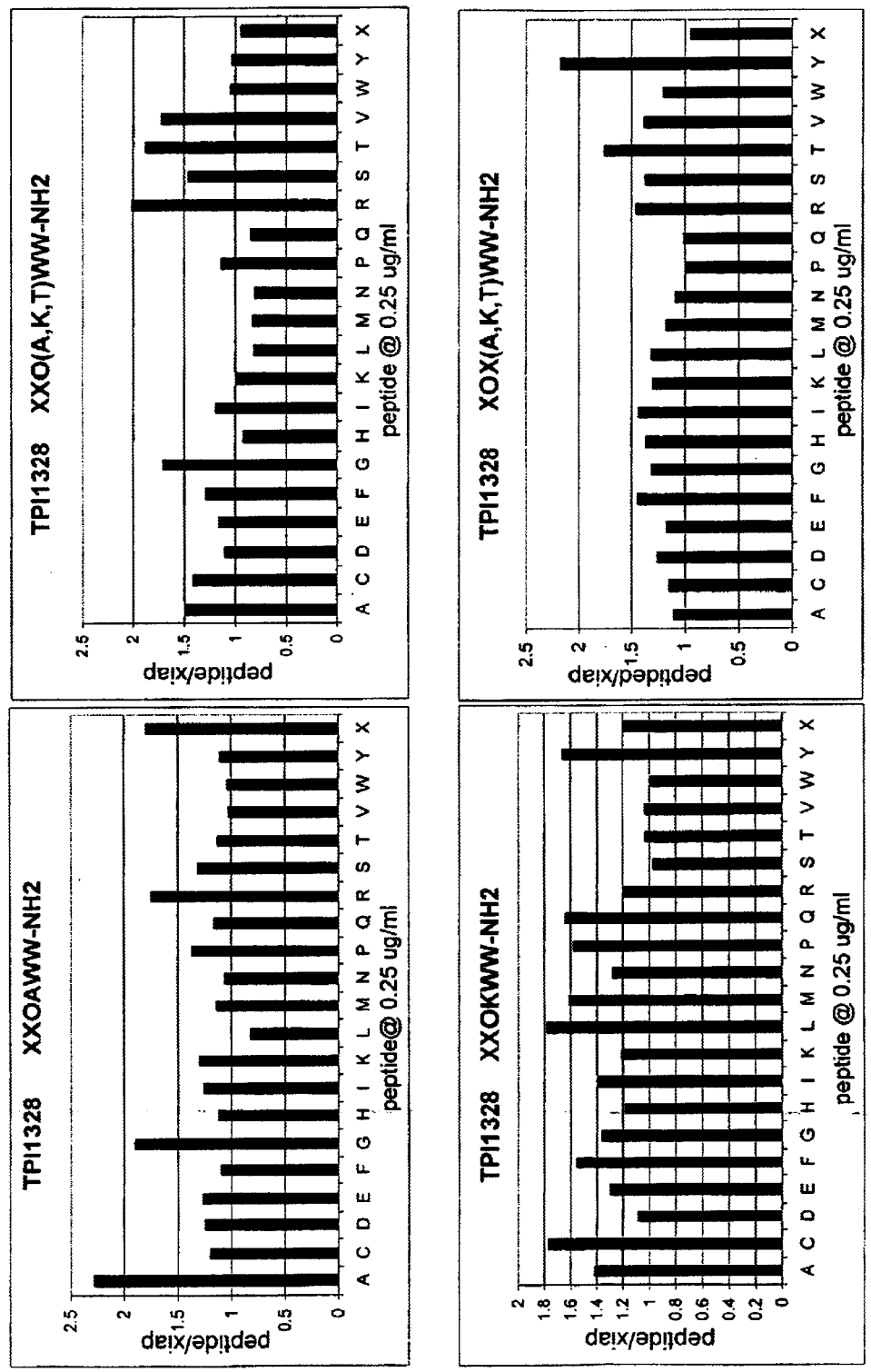
FIGS. 1A and 1B show a plot of values obtained for the ratio of $V_{max}$ (where $V_{max}$ is equal to RFU/min) for hydrolysis of Acetyl-DEVD-7-amino-4-trifluoromethyl-coumarin (Ac-DEVD-AFC) in the presence and absence of each species of the TPI1328 library, composed of mixtures of hexapeptides.

The present invention provides agents that suppress an inhibitor of apoptosis protein (IAP) from inhibiting the protease activity of a caspase or from binding to a caspase. An advantage of an agent of the invention is that it can be used to allow apoptosis to occur in a cell where apoptosis is being prevented by the regulatory activity of an IAP. Accordingly, the invention provides methods for reducing the ability of a population of cells to survive in vitro or ex vivo by administering to the cells an agent that derepresses an IAP-inhibited caspase. Use of an agent having specificity for a particular IAP-inhibited caspase in such a method can selectively target and kill a sub-population of cells in a larger mixed population. Also provided is a method of treating an individual having a condition characterized by a pathologically reduced level of apoptosis, such as cancer or hyperplasia, by administering to the individual an agent of the invention, wherein the agent derepresses an IAP inhibited caspase, thereby increasing the level of apoptosis.

The invention further provides methods for identifying agents that modulate inhibitors of apoptosis. Using the methods of the invention a candidate agent can be tested for the ability to suppress an inhibitor of apoptosis (IAP) protein from inhibiting a protease activity of a caspase or from binding to a caspase. A caspase when uninhibited mediates apoptosis. Thus, an agent determined by the methods to derepress an IAP-inhibited caspase is identified as an agent that allows apoptosis to occur in the presence of negative regulatory components. An advantage of the methods of the invention is that they can be performed in a high throughput format such that large libraries of candidate agents can be efficiently screened for identification of a variety of derepressors of an IAP-inhibited caspase.

As used herein the term "caspase" is intended to mean a member of the family of cysteine aspartyl-specific proteases that cleave C-terminal to an aspartic acid residue in a polypeptide and are involved in cell death pathways leading to apoptosis. The term is intended to be consistent with its use in the art as described, for example, in Martin and Green, *Cell* 82:349–352 (1995). The caspases previously were referred to as the "Ice" proteases, based on their homology to the first identified member of the family, the interleukin-1β (IL-1β) converting enzyme (Ice), which converts the inactive 33 kiloDalton (kDa) form of IL-1β to the active 17.5 kDa form. The Ice protease was found to be homologous to the *Caenorhabditis elegans* ced-3 gene, which is involved in apoptosis during *C. elegans* development, and transfection experiments showed that expression of Ice in fibroblasts induced apoptosis in the cells (see Martin and Green, supra, 1995). Therefore, the term includes Ice and ced-3.

Additional polypeptides sharing homology with Ice andced-3 have been identified and are referred to as caspases, each caspase being distinguished by a number. For example, the originally identified Ice protease now is referred to as caspase-1, the protease referred to as caspase-3 previously was known variously as CPP32, YAMA and apopain, and the protease now designated caspase-9 previously was known as Mch6 or ICE-LAP6. The caspase family of proteases are characterized in that each is a cysteine protease that cleaves C-terminal to an aspartic acid residue and each has a conserved active site cysteine comprising generally the amino acid sequence QACXG (SEQ ID NO:1), where X can be any amino acid and often is arginine. The caspases are further subcategorized into those that have DEVD (SEQ ID NO:2) cleaving activity, including caspase-3 and caspase-7, and those that have YVAD (SEQ ID NO:3) cleaving activity, including caspase-1 (Martin and Green, supra, 1995).

As used herein the term "IAP" or "inhibitor of apoptosis" is intended to mean a protein that inhibits the proteolytic activity of a caspase. The term can include a protein that when bound to a caspase inhibits the proteolytic activity of the caspase. The term can also include a protein that inhibits the proteolytic activity of a downstream caspase by inhibiting the ability of an upstream caspase to process a precursor of the caspase to a mature form. Also included in the term is a protein that induces ubiquitination and degradation of a caspase.

Members of the Inhibitor of Apoptosis (IAP) protein family of antiapoptotic proteins are conserved across evolution with homologues found in both vertebrate and invertebrate animal species. The baculovirus IAPs, Cp-IAP and Op-IAP, were the first members of this family to be identified based on their ability to functionally complement defects in the cell death inhibitor p35, a baculovirus protein that binds to and inhibits caspase. Subsequently, at least seven additional human homologues have been identified and demonstrated to inhibit cell death including X chromosome linked IAP (XIAP, Genbank accession number U32974); cellular IAP proteins, c-IAP-1/HIAP-2/hMIHB and c-IAP-2/HIAP-1/hMIHC (Liston et al., *Nature* 379:349–353 (1996); Rothe et al., *Cell* 83:1243–1252 (1995)); neuronal apoptosis inhibitory protein, NAIP (Roy et al., *Cell* 80:167–178 (1995)); ML-IAP also referred to as LIVIN (Vucic et al., *Cur. Biol.* 10:1359–1366 (2000) and Kasof et al.,*J. Biol. Chem.* 276:3238–3246 (2001)); Apollon (Chen et al.,*Biochem. Biophys. Res. Commun.* 264:847–854 (1999)); and survivin (Ambrosini et al., *Nature Med.* 3:917–921 (1997)). Two Drosophila homologues (DIAP1 and DIAP2) have also been identified and demonstrated to inhibit cell death (Deveraux et al., *Genes and Development* 13:239–252 (1999)). A central role for IAP-family proteins in programmed cell death regulation in Drosophila has been suggested by the finding that several apoptosis-inducing proteins in flies, including reaper, hid, and grim bind to IAPs as part of their cytotoxic mechanism. Other IAP proteins include viral IAPs such as CiIAP, PoIAP, CpIAP and ASFIAP (Deveraux et al., supra (1999)).

IAP proteins of the invention include those that inhibit the activity of an effector caspase such as caspase-3 or caspase-7 and those that inhibit an initiator caspase such as caspase-9. The human IAPs (XIAP, cIAP1, and cIAP2) have been reported to bind and potently inhibit caspase-3 and -7, with Kis in the range of 0.2–10 nM. These caspases operate in the distal portions of apoptotic protease cascades, functioning as effectors rather than initiators of apoptosis.

A common structural feature of all IAP family members is a ~70 amino acid motif termed baculoviral IAP repeat (BIR), which is present in one to three copies as described, for example, in Deveraux et al., *Genes and Development* 13:239–252 (1999). The conserved presence and spacing of cysteine and histidine residues observed within BIR domains indicates that the structure represents a zinc binding domain. BIR domains have been shown to exhibit distinct functions. For example, the second BIR domain of XIAP (BIR2) is a potent inhibitor for caspase-3, whereas the third BIR domain of XIAP (BIR3) targets caspase-9 (see Wu et al., *Nature* 408:1008–1012 (2000)). In addition to the BIR motif located at the N-terminal and central portions of IAP, a RING finger domain is located in the C-terminal portion of members of the IAP protein family (Birnbaum et al.,*J. Virol.* 68:2521–2528 (1994)).

As used herein the term "IAP-inhibited caspase" is intended to mean a cysteine aspartyl-specific protease that is prevented or suppressed from proteolytic activity due to the presence of an inhibitor of apoptosis protein. The term can include a cysteine aspartyl-specific protease having reduced activity due to a bound inhibitor of apoptosis protein. The term can also include a cysteine aspartyl-specific protease that is prevented or suppressed from being processed to a mature form capable of proteolytic activity due to the presence of an inhibitor of apoptosis protein. An example of a non-processed cysteine aspartyl-specific protease that is useful in the invention is a pro-caspase having an attached pro-domain. Alternatively, the compositions and methods of the invention can be directed to an IAP-inhibited caspase that does not contain a prodomain or is not a procaspase.

As used herein the term "derepress," when used in reference to an IAP-inhibited caspase, is intended to mean reduction, inhibition or prevention of the ability of the IAP to inhibit the proteolytic activity of the caspase. Accordingly, a derepressor of a IAP-inhibited caspase is a molecule that inhibits or prevents the ability of the IAP to inhibit caspase proteolytic activity. The term can include inhibition or prevention of the ability of an IAP to induce ubiquitination and degradation of caspases.

As used herein, the term "agent" means a synthetic or isolated biological molecule such as a simple or complex organic molecule, a peptide, a peptidomimetic, a protein or an oligonucleotide that is capable of derepressing an IAP-inhibited caspase.

As used herein, the term "pharmaceutically acceptable carrier" is intended to mean a medium having sufficient purity and quality for use in humans. Such a medium can be a human pharmaceutical grade, sterile medium, such as water, sodium phosphate buffer, phosphate buffered saline, normal saline or Ringer's solution or other physiologically buffered saline, or other solvent or vehicle such as a glycol, glycerol, an oil such as olive oil or an injectable organic ester. Pharmaceutically acceptable media are substantially free from contaminating particles and organisms.

As used herein the term "inhibiting," when used in reference to a protein activity, is intended to mean a reduction in the activity by decreasing affinity of the protein for a substrate or decreasing the catalytic rate at which the protein converts a substrate to product. The term includes, for example, decreasing the affinity of an IAP for a caspase substrate, decreasing the affinity of a caspase for a polypeptide substrate, decreasing the rate at which a caspase cleaves a polypeptide C-terminal to an aspartic acid residue, or decreasing the rate at which a caspase is ubiquitinated or proteolytically degraded.

As used herein the term "isolated," when used in reference to an agent, means that the agent is separated from 1 or more reagent, precursor or other reaction product. Therefore, an isolated agent is an agent that is free from one or more compounds found in the synthetic reaction or reaction pathway that produces the agent. Also included in the term is an agent that is free from one or more compound that it is found with in nature. An isolated agent also includes a substantially pure agent. The term can include a molecule that has been produced by a combinatorial chemistry method and separated from precursors and other products by chemical purification or by binding to second molecule with sufficient stability to be co-purified with the second molecule. The term can include naturally occurring agents such as products of biosynthetic reactions or non-naturally occurring agents.

As used herein the term "peptide" refers to a molecule containing two or more amino acids linked by a covalent bond between the carboxyl of one amino acid and the amino group of another. Invention peptides can be included in larger molecules or agents, such as larger peptides, proteins, fragments of proteins, peptoids, peptidomimetics and the like. A peptide can be a non-naturally occurring molecule, which does not occur in nature, but is produced as a result of in vitro methods, or can be a naturally occurring molecule such as a protein or fragment thereof expressed from a cDNA library. Peptides can be either linear, cyclic or multivalent, and the like, which conformations can be achieved using methods well-known in the art. The term includes molecules having naturally occurring proteogenic amino acids as well as non-naturally occurring amino acids such as D-amino acids and amino acid analogs, any of which can be incorporated into a peptide using methods known in the art. In view of this definition, one skilled in the art would know that reference herein to an amino acid, unless specifically indicated otherwise, includes, for example, naturally occurring proteogenic L-amino acids, D-amino acids, chemically modified amino acids such as amino acid analogs, naturally occurring non-proteogenic amino acids such as norleucine, and chemically synthesized agents. Exemplary amino acids useful in the invention are described further below.

As used herein, the term "proteogenic," when used in reference to an amino acid, indicates that the amino acid can be incorporated into a protein in a cell through well known metabolic pathways. The amino acids are designated as D or L in reference to the configuration at the alpha carbon. Amino acids referred to herein without specific reference to configuration are understood to have the L configuration at the alpha carbon. Proteogenic amino acids are indicated herein using the single letter or three letter code and are intended to be consistent with the nomenclature used in the art as described for Example in Branden and Tooze *Introduction to Protein Structure,* Garland Publishing, New York, pp6–7 (1991). Other amino acids are indicated using nomenclature known in the art, wherein, for example, pClPhe refers to p-chloro-phenylalanine, ThiAla refers to 2-thienyl-alanine, Nal refers to 3-(2-napthyl)-alanine, 3I-Tyr refers to 3-iodo-Tyrosine, Cha refers to cyclohexylalanine, Lys-ε-Fmoc refers to lysine (ε-fluorenylmethloxycarbonyl) and OEt-Tyr refers to Tyrosine (O-ethyl).

As used herein the term "core" is intended to mean a chemical structure or motif of a molecule, or portion thereof. The chemical structure or motif can be, for example, an amino acid sequence of a peptide or peptide containing molecule, or a chemical formula representing the covalent attachment of atoms in a molecule. A chemical structure or motif included in the term can be further defined with respect to chirality. A core peptide or other chemical entity need not be located at the center of a molecule.

The present invention provides isolated agents that derepresses an IAP-inhibited caspase. An agent that derepresses an IAP-inhibited caspase can have a core peptide or amino acid sequence motif corresponding to:

| (L-Ala)-$X_1$-(L-Trp)-$X_2$ | (Core peptide 4) | where $X_1$ is L-Trp or D-Trp and $X_2$ is L-ThiAla or L-pClPhe. Exemplary core peptides included in Core peptide 4 include, for example:

| (L-Ala)-(L-Trp)-(L-Trp)-(L-ThiAla) | (Core peptide 5), |
| (L-Ala)-(L-Trp)-(L-Trp)-(L-pClPhe) | (Core peptide 6) and |
| (L-Ala)-(D-Trp)-(L-Trp)-(L-ThiAla) | (Core peptide 7). |

An agent that derepresses an IAP-inhibited caspase can have a core peptide or amino acid sequence motif corresponding to:

| $X_1$-$X_2$-$X_3$-$X_4$ | (Core peptide 23) | where $X_1$ is L-Ala, L-Cha, L-Nal, D-Trp or D-Trp(CHO); $X_2$ is D-Nal, D-Trp, D-Trp(CHO), L-Trp, L-Trp(CHO), D-Cha or D-ThiAla; $X_3$ is L-Trp, L-Trp(CHO) or D-Phe; and $X_4$ is L-Nal, D-Nal, D-Trp, D-Trp(CHO), L-ThiAla, L-3I-Tyr or L-pClPhe. Exemplary core peptides included in Core peptide 23 include, for example:

| (L-Ala)-(D-Nal)-(L-Trp)-(L-Nal) | (Core peptide 24) |
| (D-Trp)-(D-Trp)-(L-Trp)-(D-Nal) | (Core peptide 25) |
| (L-Cha)-(D-Nal)-(L-Trp)-(L-ThiAla) | (Core peptide 26) |
| (L-Ala)-(L-Trp)-(L-Trp)-(L-3I-Tyr) | (Core peptide 27) |
| (L-Ala)-(D-Trp)-(L-Trp)-(L-ThiAla) | (Core peptide 28) |
| (L-Cha)-(L-Trp)-(L-Trp)-(L-pClPhe) | (Core peptide 29) |
| (L-Ala)-(D-Trp)-(L-Trp)-(D-Trp) | (Core peptide 30) |
| (L-Ala)-(D-Trp)-(D-Phe)-(D-Trp) | (Core peptide 31) |
| (L-Nal)-(D-Trp)-(D-Phe)-(D-Trp) | (Core peptide 32) |
| (L-Nal)-(D-Cha)-(L-Trp)-(D-Trp) | (Core peptide 33) |
| (L-Nal)-(D-ThiAla)-(D-Phe)-(D-Trp) | (Core peptide 34). |

An agent that derepresses an IAP-inhibited caspase can have a core peptide or amino acid sequence motif corresponding to:

X₁-X₂-X₃-X₄ (Core peptide 8)

where X₁ is D-Nal or L-ThiAla; X₂ is Lys-εFmoc, D-pClPhe or L-Nal; X₃ is D-Nal, L-pClPhe or D-Lys(Fm); and X₄ is Lys-εFmoc or D-pFPhe. Exemplary core peptides included in Core peptide 8 include, for example:

| | |
|---|---|
| (D-Nal)-(Lys-εFmoc)-(L-pClPhe)-(Lys-εFmoc) | (Core peptide 9) |
| (D-Nal)-(D-pClPhe)-(L-pClPhe)-(Lys-εFmoc) | (Core peptide 10) |
| (D-Nal)-(L-Nal)-(L-pClPhe)-(Lys-εFmoc) | (Core peptide 11) |
| (D-Nal)-(L-Nal)-(D-Lys-εFmoc)-(Lys-εFmoc) | (Core peptide 12) |
| (L-ThiAla)-(Lys-εFmoc)-(D-Nal)-(Lys-εFmoc) | (Core peptide 13) |
| (L-ThiAla)-(Lys-εFmoc)-(L-pClPhe)-(pF-D-F) | (Core peptide 14) |
| (L-ThiAla)-(D-pClPhe)-(L-pClPhe)-(Lys-εFmoc) | (Core peptide 15) |
| (L-ThiAla)-(L-Nal)-(L-pClPhe)-(Lys-εFmoc) | (Core peptide 16) |
| (L-ThiAla)-(L-Nal)-(D-Lys-εFmoc)-(Lys-εFmoc) | (Core peptide 17). |

An agent that derepresses an IAP-inhibited caspase can have a core peptide or amino acid sequence motif corresponding to:

X₁-X₂-X₃-X₄ (Core peptide 35)

where X₁ is L-ThiAla or Phe; X₂ is D-pClPhe or D-OEt-Tyr X₃ is D-Nal, or D-OEt-Tyr; and X₄ is D-pClPhe or D-pNO₂Phe. Exemplary core peptides included in Core peptide 35 include, for example:

| | |
|---|---|
| (L-ThiAla)-(D-pClPhe)-(D-Nal)-(D-pClPhe) | (Core peptide 36) |
| (L-ThiAla)-(D-pClPhe)-(D-Nal)-(D-pNO₂Phe) | (Core peptide 37) |
| (L-ThiAla)-(D-OEt-Tyr)-(D-OEt-Tyr)-(D-pClPhe) | (Core peptide 38) |
| (Phe)-(D-pClPhe)-(D-Nal)-(D-pClPhe) | (Core peptide 39). |

An agent that derepresses an IAP-inhibited caspase can have a core peptide or amino acid sequence motif corresponding to:

A-X₁-X₂-X₃ (Core peptide 18)

where X₁ is Met, Ser, Thr, Trp, or ThiAla and X₂ and X₃ are selected from Ala, Asp, Glu, Phe, Gly, His, Ile, Lys, Leu, Met, Asn, Pro, Gln, Arg, Ser, Thr, Val, Trp, Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, L-Nle, D-Nle, L-Cha, D-Cha, L-PyrAla, D-PyrAla, L-ThiAla, D-ThiAla, L-Tic, D-Tic, L-pClPhe, D-pClPhe, L-pIPhe, D-pIPhe, L-pNO₂Phe, D-pNO₂Phe, L-Nal, D-Nal, beta-Ala, e-Aminocaproic acid, L-Met[O2], L-dehydPro, or L-3I-Tyr.

An agent that derepresses an IAP-inhibited caspase can have a core peptide or amino acid sequence motif corresponding to:

X₁-X₂-(L-Trp)-(D-Trp) (Core peptide 19)

where X₁ and X₂ are selected from Ala, Asp, Glu, Phe, Gly, His, Ile, Lys, Leu, Met, Asn, Pro, Gln, Arg, Ser, Thr, Val, Trp, Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, L-Nle, D-Nle, L-Cha, D-Cha, L-PyrAla, D-PyrAla, L-ThiAla, D-ThiAla, L-Tic, D-Tic, L-pClPhe, D-pClPhe, L-pIPhe, D-pIPhe, L-pNO₂Phe, D-pNO₂Phe, L-Nal, D-Nal, beta-Ala, e-Aminocaproic acid, L-Met[O2], L-dehydPro, or L-3I-Tyr.

An agent that derepresses an IAP-inhibited caspase can have a core peptide or amino acid sequence motif corresponding to:

X₁-X₂-X₃-X₄-W-W (Core peptide 55), where X₁, X₂ and X₃ are selected from Ala, Asp, Glu, Phe, Gly, His, Ile, Lys, Leu, Met, Asn, Pro, Gln, Arg, Ser, Thr, Val, Trp, Cys or Tyr and X₄ is selected from Ala, His, Lys, Asn, Gln, Arg, Ser, Thr or Val.

An agent that derepresses an IAP-inhibited caspase can have a core peptide or amino acid sequence motif corresponding to any of:

| | |
|---|---|
| X₁-X₂-A-A-W-W | (Core peptide 43) SEQ ID NO: 7, |
| X₁-X₂-G-A-W-W | (Core peptide 44) SEQ ID NO: 8, |
| X₁-X₂-R-A-W-W | (Core peptide 45) SEQ ID NO: 9, |
| X₁-X₂-X₄-A-W-W | (Core peptide 46), |
| X₁-X₂-C-K-W-W | (Core peptide 47) SEQ ID NO: 10, |
| X₁-X₂-L-X₃-W-W | (Core peptide 20), |
| X₁-X₂-R-X₃-W-W | (Core peptide 21), |
| X₁-X₂-G-X₃-W-W | (Core peptide 22), |
| X₁-X₂-T-X₃-W-W | (Core peptide 42), |
| X₁-X₂-V-X₃-W-W | (Core peptide 48), |
| X₁-T-X₂-X₃-W-W | (Core peptide 49), |
| X₁-Y-X₂-X₃-W-W | (Core peptide 50), |
| A-X₁-X₂-X₃-W-W | (Core peptide 51), |
| C-X₁-X₂-X₃-W-W | (Core peptide 52), |
| F-X₁-X₂-X₃-W-W | (Core peptide 53), or |
| K-X₁-X₂-X₃-W-W | (Core peptide 54), | where X₁, X₂ and X₄ are selected from Ala, Asp, Glu, Phe, Gly, His, Ile, Lys, Leu, Met, Asn, Pro, Gln, Arg, Ser, Thr, Val, Trp, Cys or Tyr and X₃ is selected from Ala, Lys, Ser or Thr.

The core peptide sequences of the invention can be those of a molecule or a portion of a molecule. For example, the above-described sequences having four positions can be tetrapeptide molecules and the above-described sequences having four or six positions can be hexapeptide molecules. A core peptide of the invention can also be included in larger molecules including, for example, a molecule having at least 5 amino acids, at least 6 amino acids, at least 7 amino acids, at least 8 amino acids, at least 9 amino acids, at least 10 amino acids, at least 20 amino acids or at least 25 amino acids. In some embodiments, the amino acid lengths of molecules comprising invention peptides can be defined by a maximum length including, for example, no more than about 4, no more than about 5, no more than about 6, no more than about 7, no more than about 8, no more than about 9, no more than about 10, no more than about 20, no more than about 25, no more than about 50, no more than about 100, no more than about 150, or no more than about 200 or more amino acids in length so long as the peptide is capable of derepressing an IAP-inhibited caspase. A molecule having a core peptide of the invention can also be defined within a size range delimited by a combination of any of the above described minimum and maximum lengths.

The invention further provides agents that are effective derepressors of an IAP-inhibited caspase having non-peptide based core structures. Thus, the invention provides an agent that derepresses an IAP-inhibited caspase and having a core structure corresponding to an N-benzyl-1,4,5-trisubstituted-2,3-diketopiperazine such as TPI759 shown in FIGS. 8A–8F. An agent having the TPI759 core structure can be substituted, for example, at position R1 derived from an amino acid side chain group of norleucine, NapAla, cyclohexylalanine, Lys, norvaleucine or valine; at R2 derived from an amino acid side chain group of Leu, NapAla, Phe, Ile or Val; and at R3 with the functional group derived from 4-isobutyl-alpha-methylphenylacetic acid, 3,5-bis(trifluoromethyl)-phenylacetic acid, heptanoic acid, (alpha-alpha-alpha-trifluoro-m-tolyl)acetic acid, 4-tert-butyl-cyclohexane carboxylic acid, m-tolylacetic acid, 3,4-dichlorophenylacetic acid, 3,3-diphenyl propionic acid, dicyclohexylacetic acid, cycloheptanecarboxylic acid, p-Tolylacetic acid or cyclohexanebutyric acid as shown in FIGS. 8A–8F.

An agent that derepresses an IAP-inhibited caspase can have a core structure corresponding to a C-6-acylamino bicyclic guanidine such as TPI882 shown in FIGS. 7A–7F. An agent having the TPI882 core structure can be substituted, for example, at position R1 derived from an amino acid side chain group of L-cyclohexylalanine, D-cyclohexylalanine, D-2-chloroPhe, O-ethyl-D-Tyr, p-iodo-L-Phe, p-iodo-D-Phe, D-homo-Phe, L-homo-Phe, L-napthylAla, D-napthylAla or L-4,4-biphenylalanine; at position R2 with the functional group derived from 2-phenylbutyric acid, 3-phenylbutyric acid, m-tolylacetic acid, 3-fluorophenylacetic acid, p-tolylacetic acid, 4-fluorophenylacetic acid, 3-methoxyphenylacetic acid, 4-methoxyphenylacetic acid, 4-ethoxyphenylacetic acid, 4-biphenylacetic acid, phenylacetic acid, 4-phenylbutyric acid, heptanoic acid, 4-methylvaleric acid, tert-butyric acid, cyclohexylcarboxylic acid, cyclohexylacetic acid, cyclohexylbutyric acid, cycloheptanecarboxylic acid, cyclobutanecarboxylic acid, cyclopentylcarboxylic acid, 3-cyclopentylpropionic acid, cyclohexylpropionic acid, 4-methyl-1-cyclohexylcarboxylic acid, 4-t-butylcyclohexylcarboxylic acid, 2-norbornaneacetic acid, 1-adamantane acetic acid, 2-ethylbutyric acid, 3,3-diphenylpropionic acid or cyclopentylacetic acid; and at position R3 with the functional group derived from 3-fluorophenylacetic acid, 4-ethoxyphenylacetic acid, 4-biphenylacetic acid or 3,5-bis(trifluoromethyl) phenylacetic acid as shown in FIGS. 7A–7F. An agent having the TPI882 core structure can be substituted at R2 and R3 with the functional group derived from phenylacetic acid and at R1 derived from an amino acid side chain group of L-cyclohexylalanine, D-cyclohexylalanine, D-p-chloro-Phe, D-p-fluoro-Phe, L-p-fluoro-Phe, D-2-chloro-Phe, O-ethyl-L-Tyr, O-ethyl-D-Tyr, O-methyl-D-Tyr, 3,5-diiodo-Tyr or L-napthylAla; at R1 with an amino acid side chain group of Phe; at R3 with the functional group derived from phenylacetic acid and at R2 with the functional group derived from p-tolylacetic acid, 4-fluorophenylacetic acid, 3-methoxyphenylacetic acid, 4-methoxyphenylacetic acid, 4-ethoxyphenylacetic acid, 4-biphenylacetic acid, phenylacetic acid, 4-phenylbutyric acid, heptanoic acid, 3-methylvaleric acid or 4-methylvaleric acid; or at R1 with an amino acid side chain group of Phe; at R2 with the functional group derived from phenylacetic acid; and at R3 with the functional group derived from 4-biphenylacetic acid, cyclohexanecarboxylic acid, cyclohexylacetic acid, cyclohexylbutyric acid, cycloheptanecarboxylic acid, 3-cyclopentylpropionic acid or 3,5-bis(trifluoromethyl) phenylacetic acid as shown in FIGS. 10A–10F.

Figure 6A:
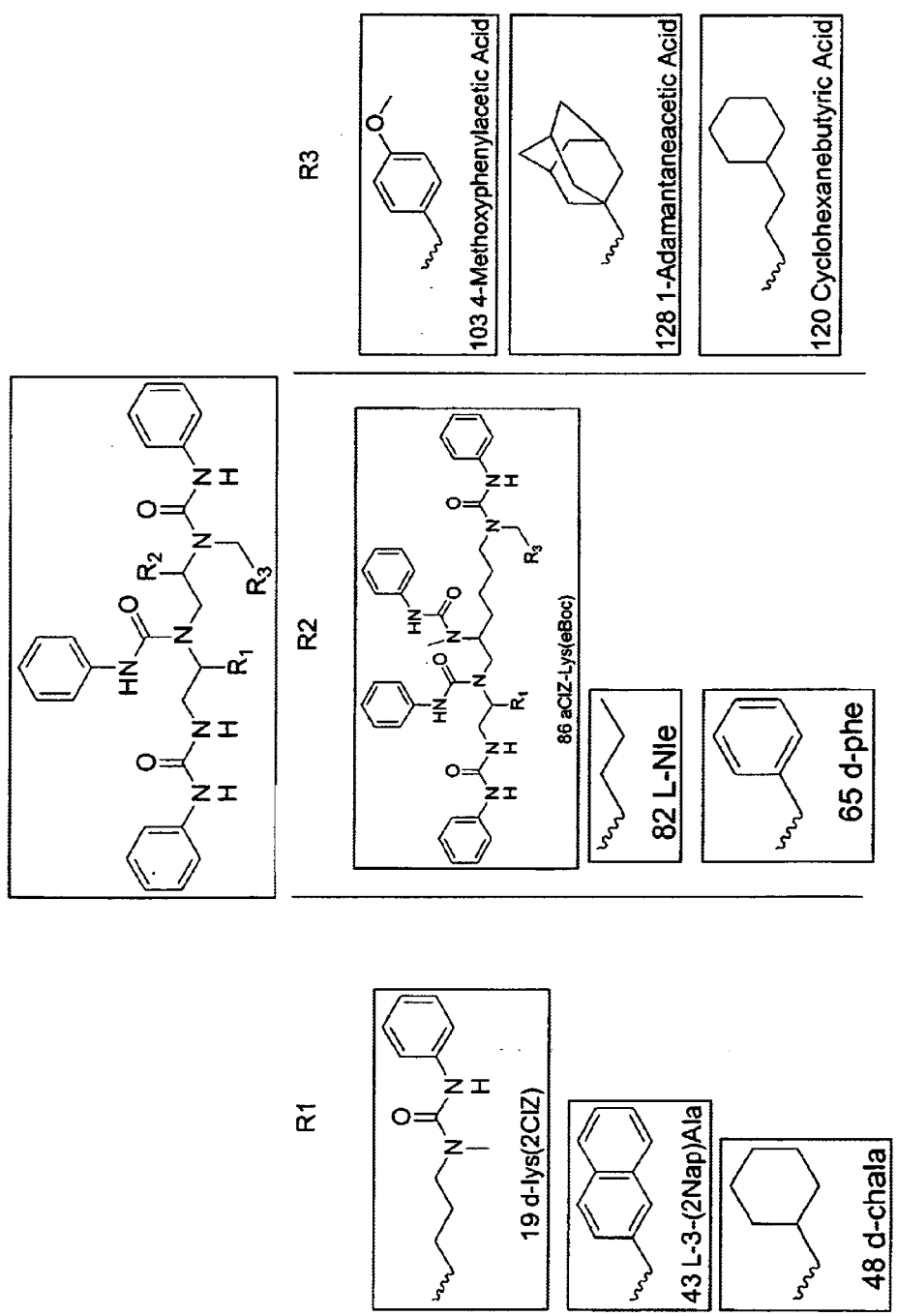
FIGS. 6A and 6B show structures of the defined functionalities in the mixtures found to be derepressors of an XIAP-inhibited caspase in the TPI927 polyphenylurea positional scanning combinatorial library. The chemical name in each box is for the reagent from which the R group was derived and the chemical name below each box is the name of the functional group at the respective R position. Each functional group has the same steriochemistry as the reagent from which it was derived. For structures 25, 73, 86 and 88, where the core structure of the molecule is modified, the resulting modified core structure and R group is shown.
Figure 6B:
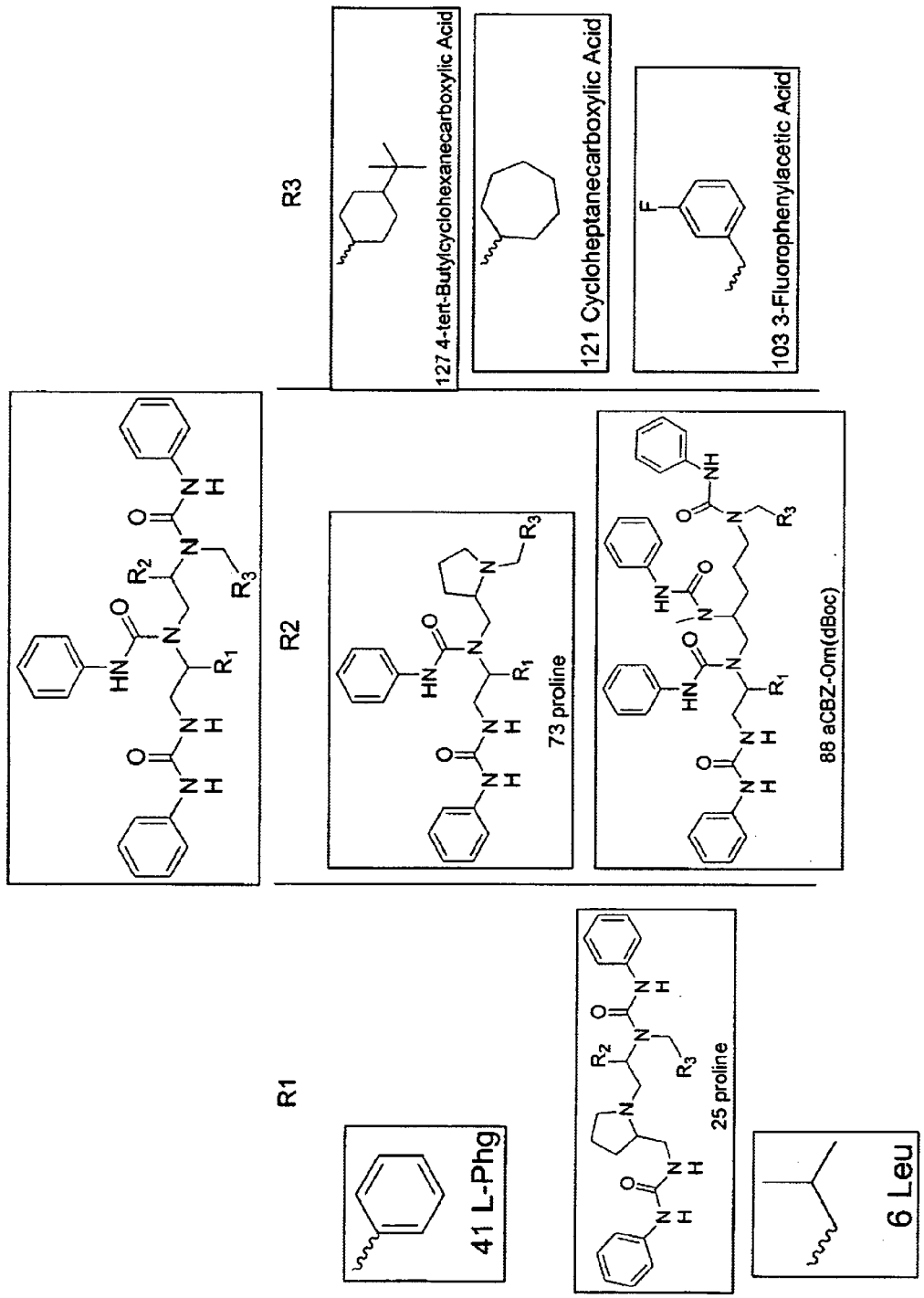
Figure 6C:
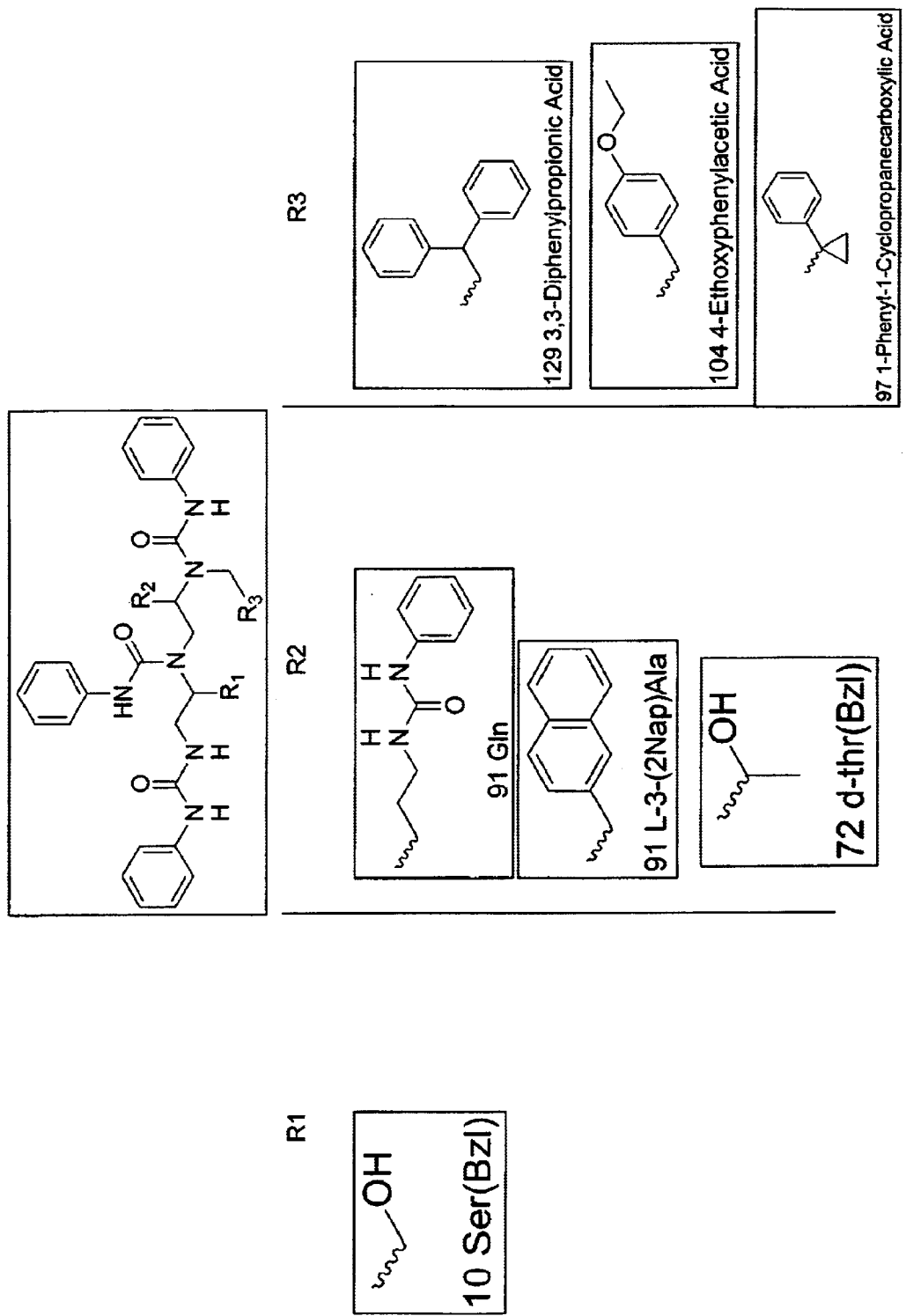
Figure 6D:
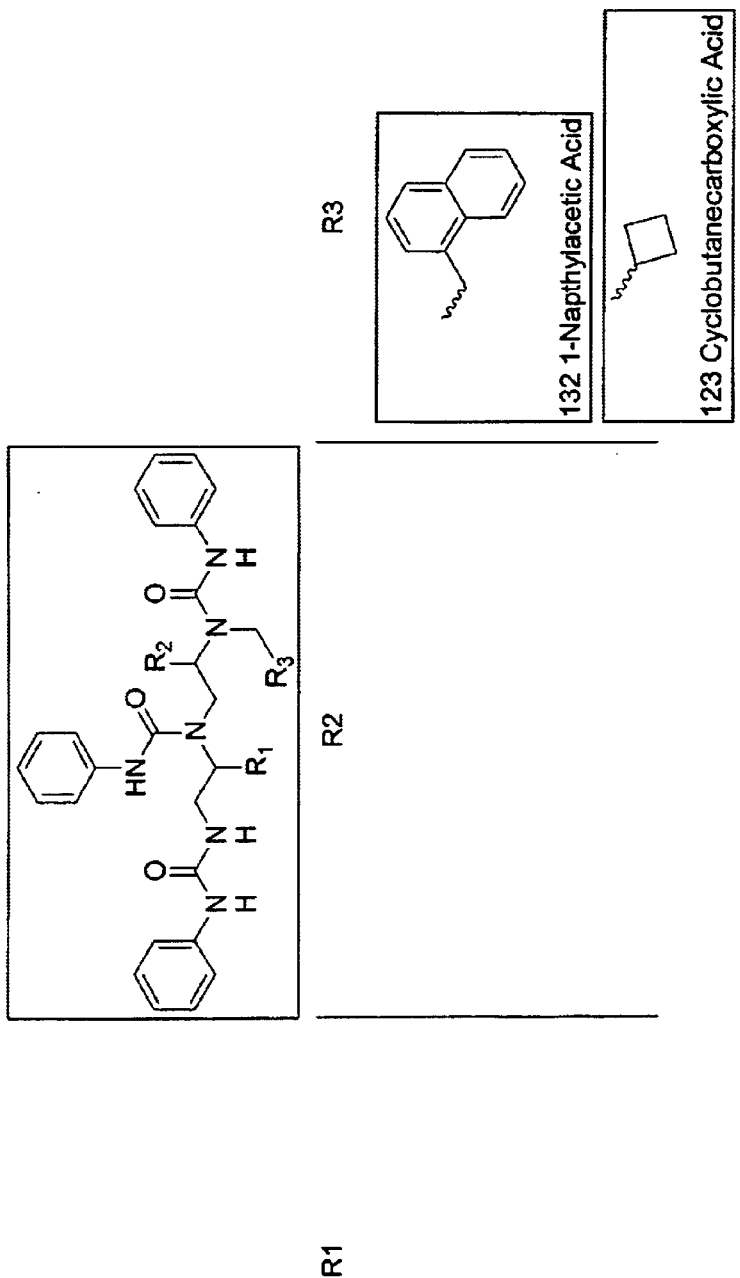
Figure 7B:
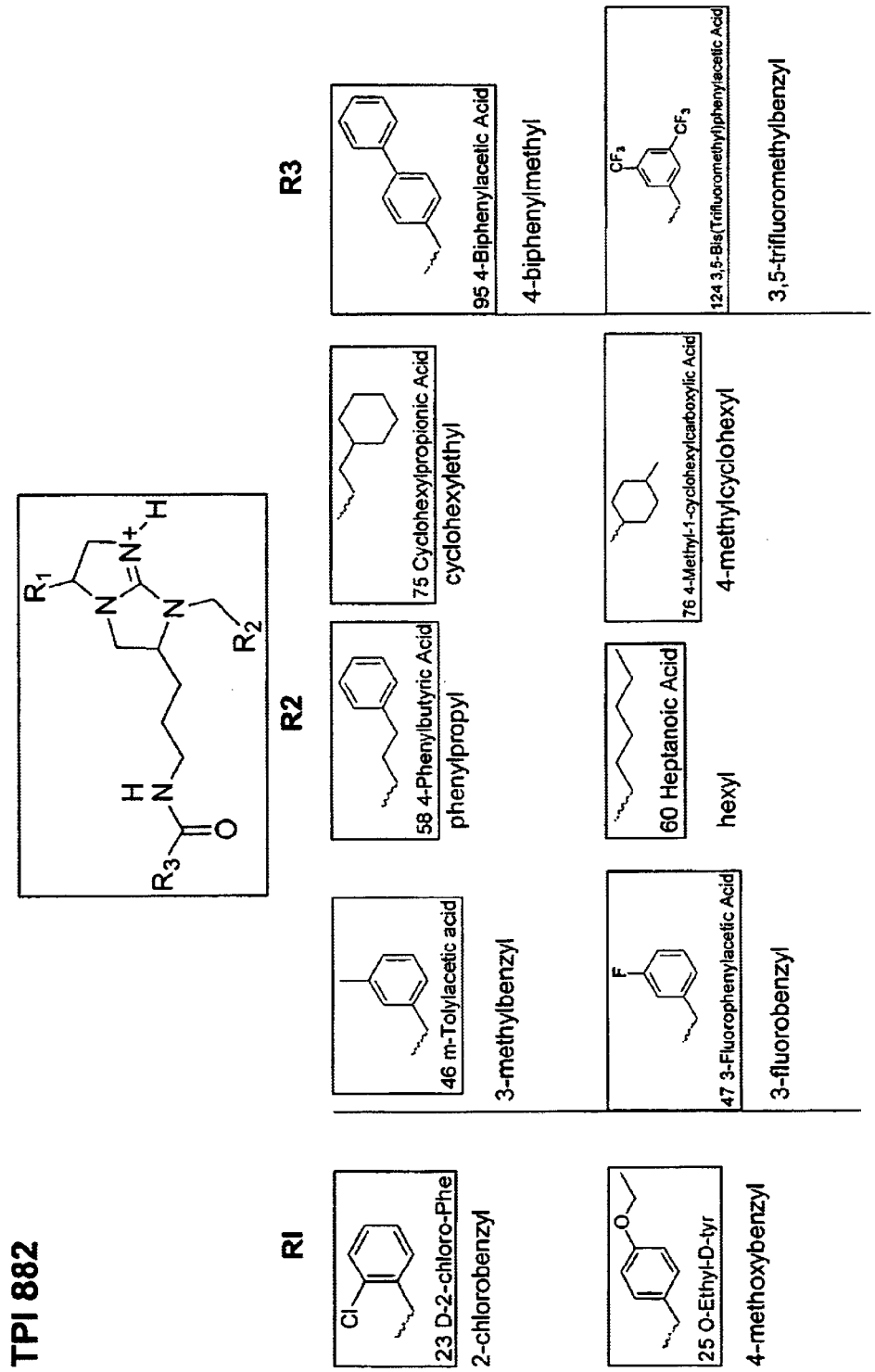
Figure 7C:
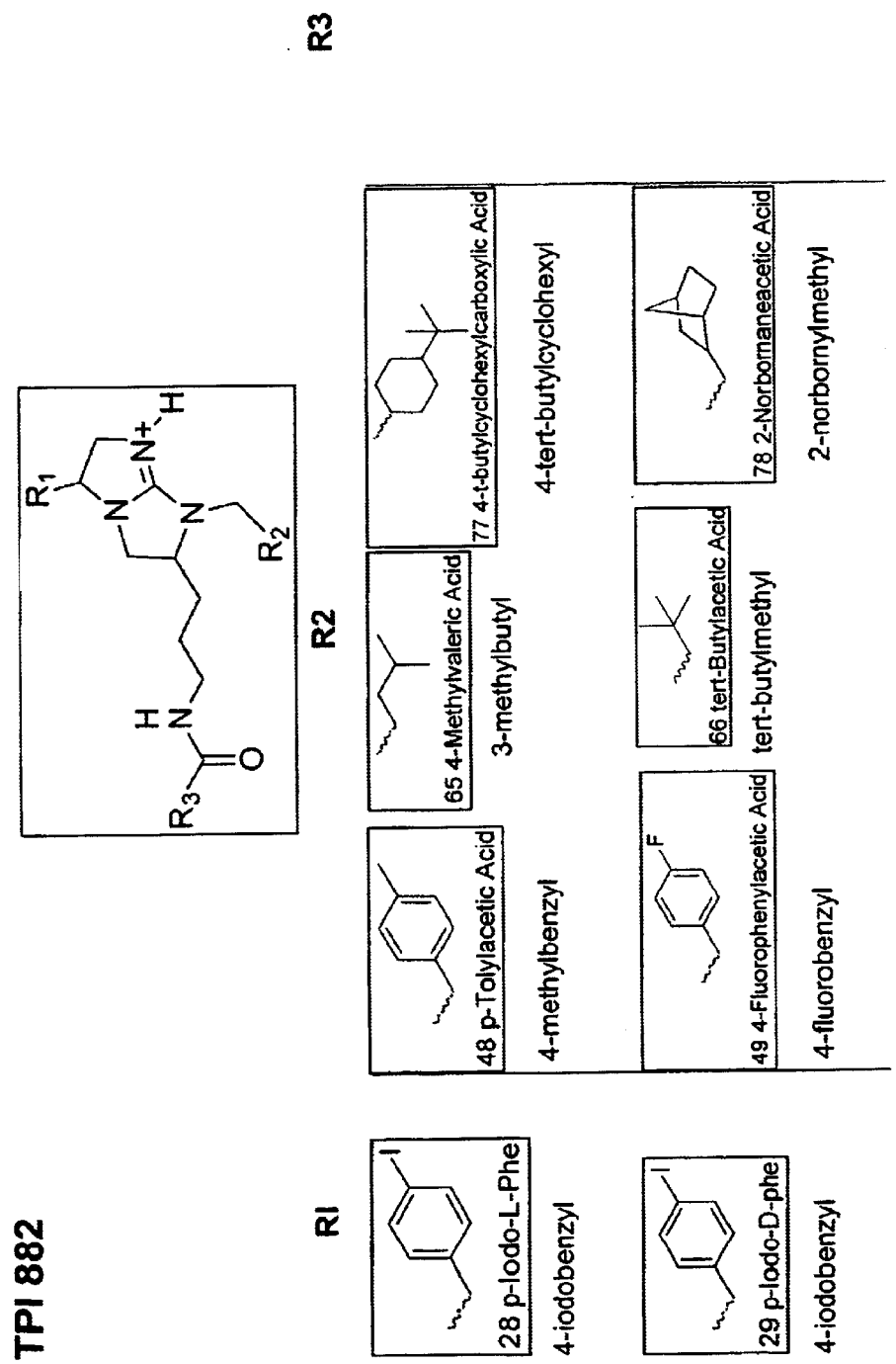
Figure 7D:
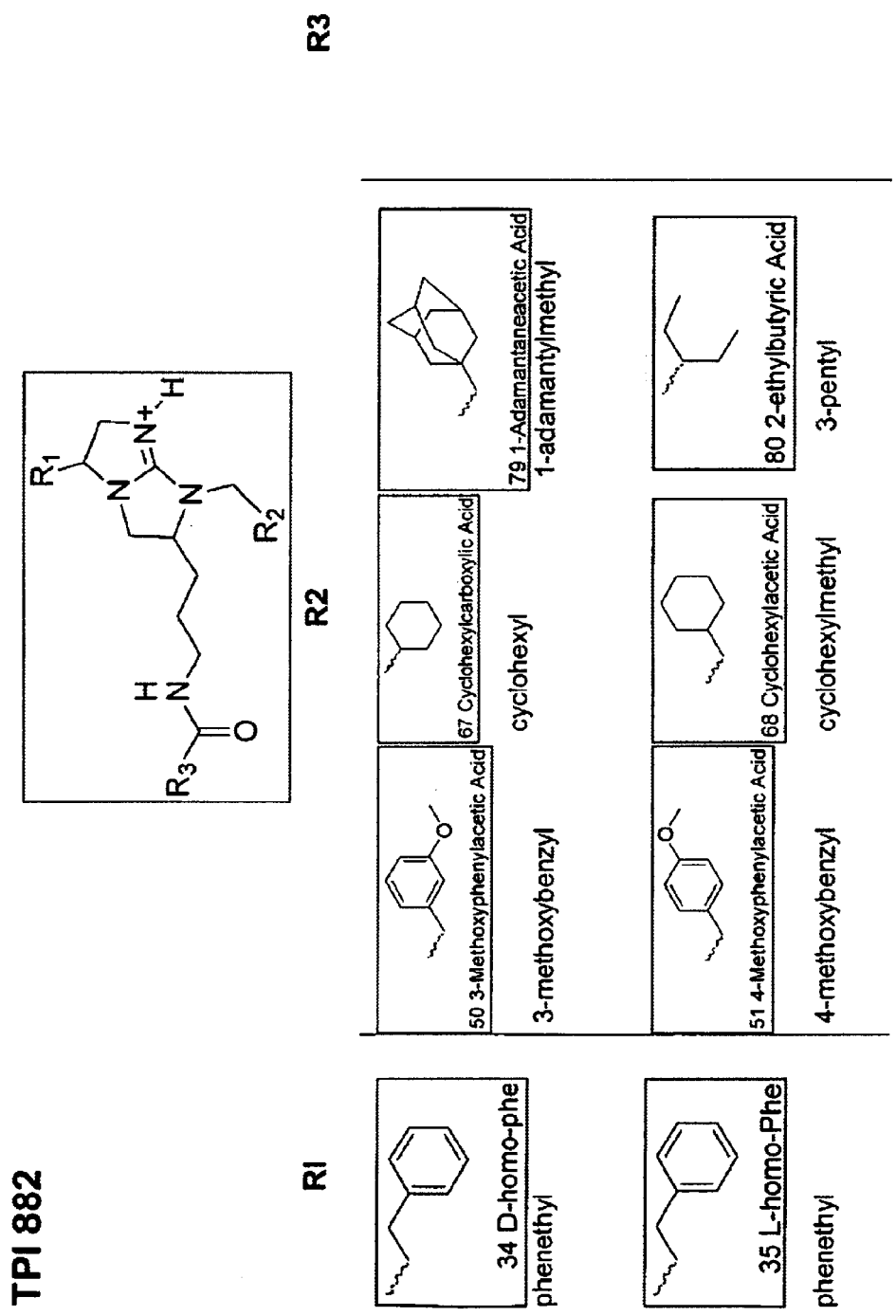
Figure 7E:
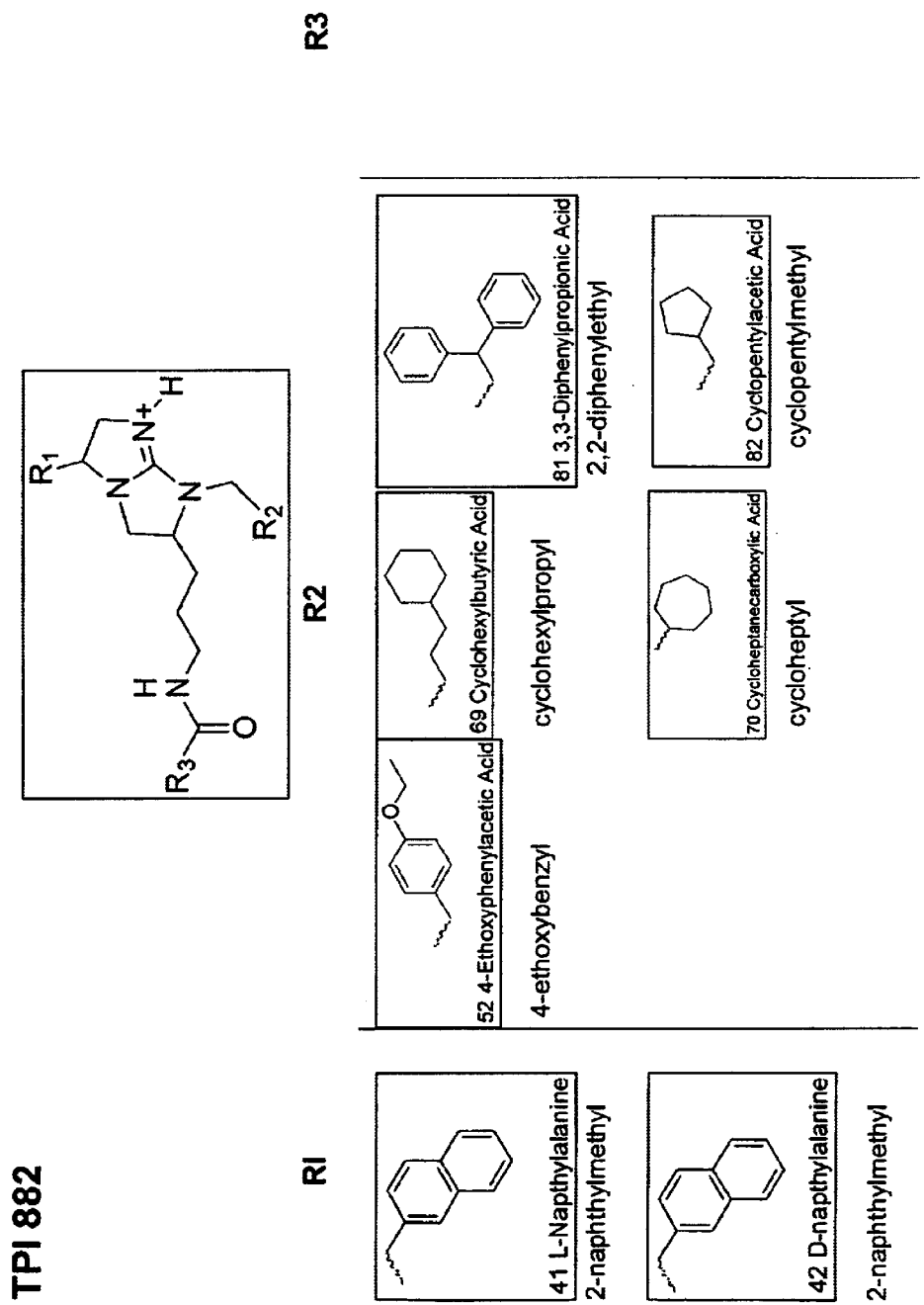
Figure 10A:
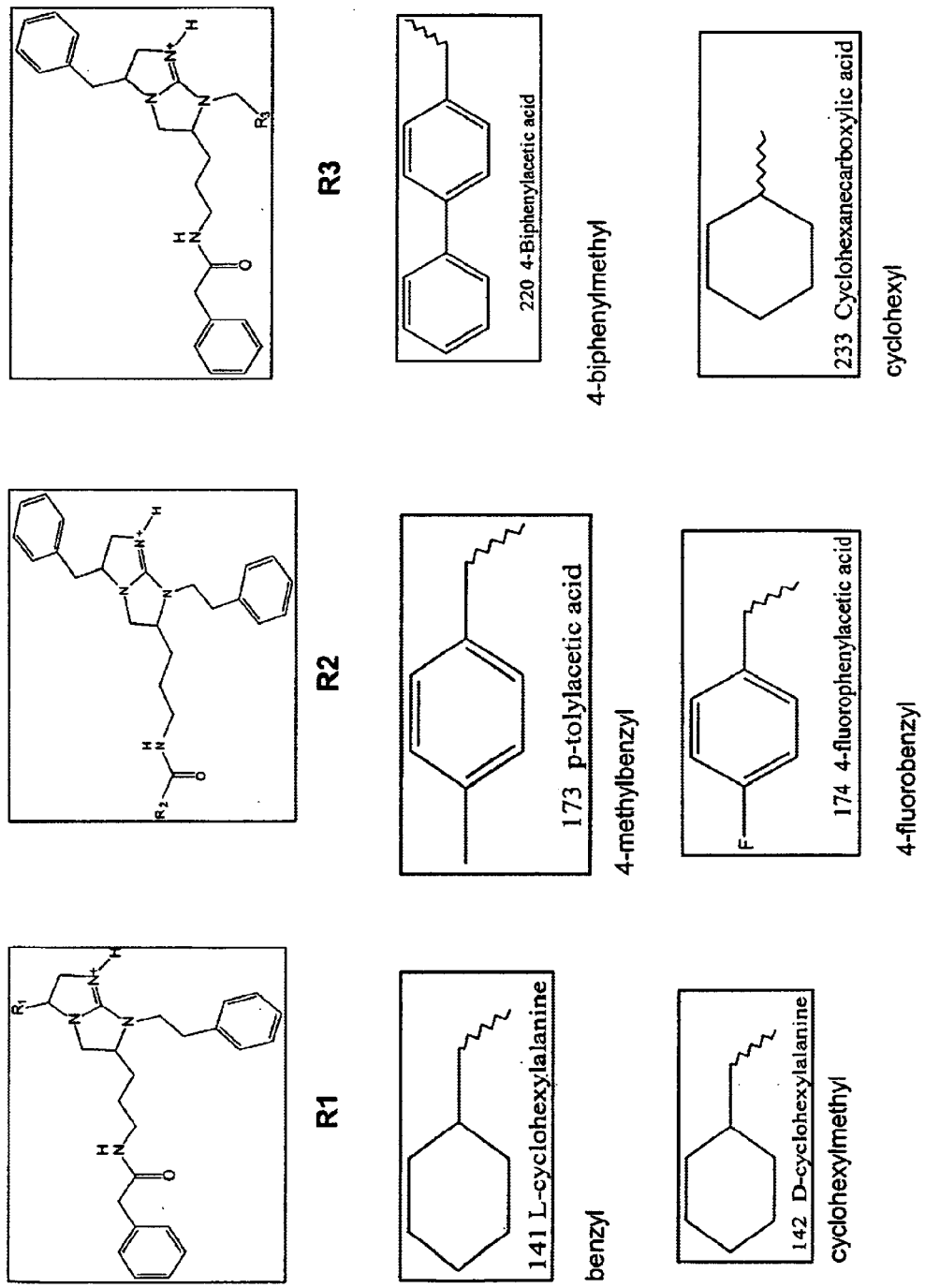
Figure 10B:
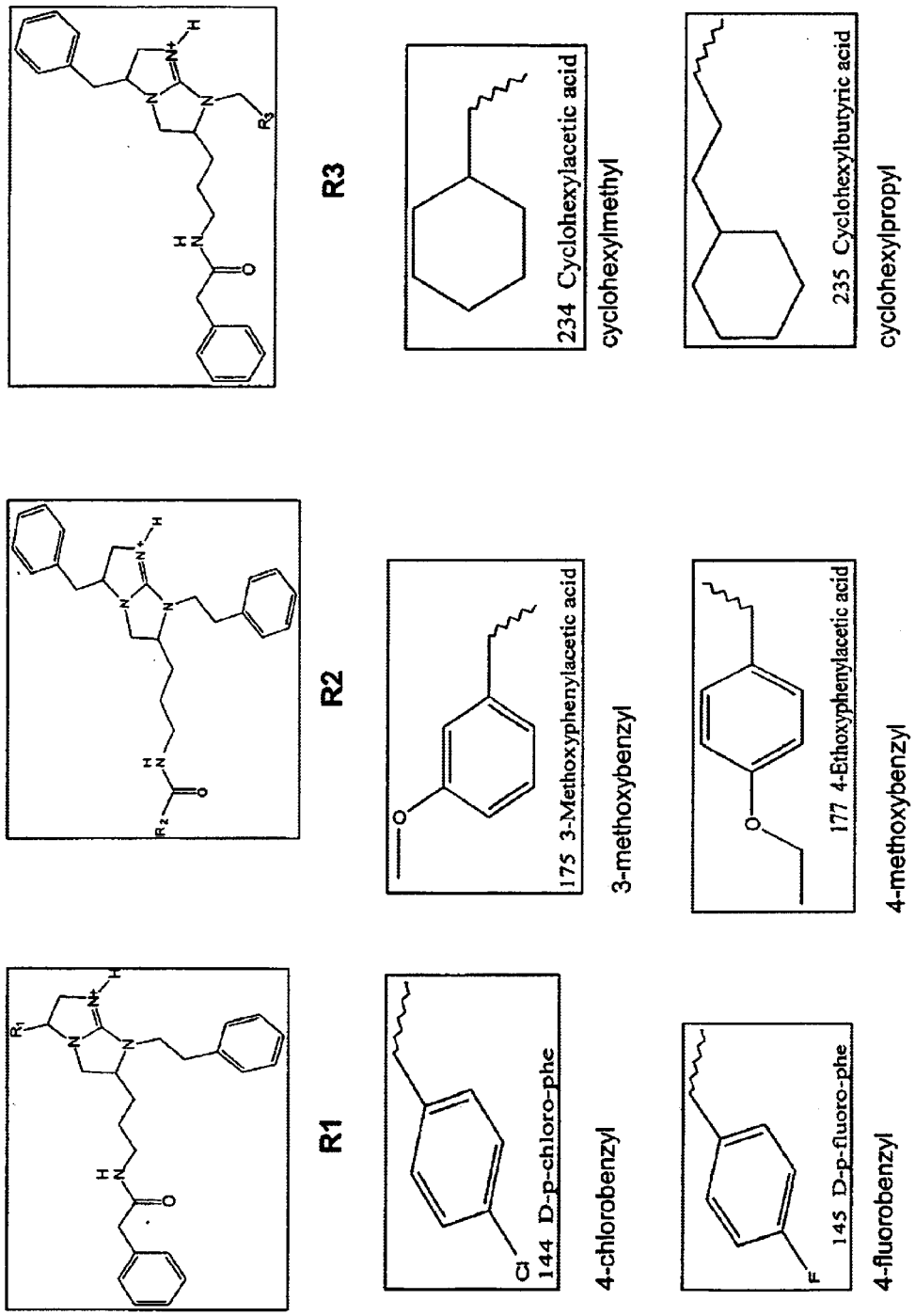
Figure 10C:
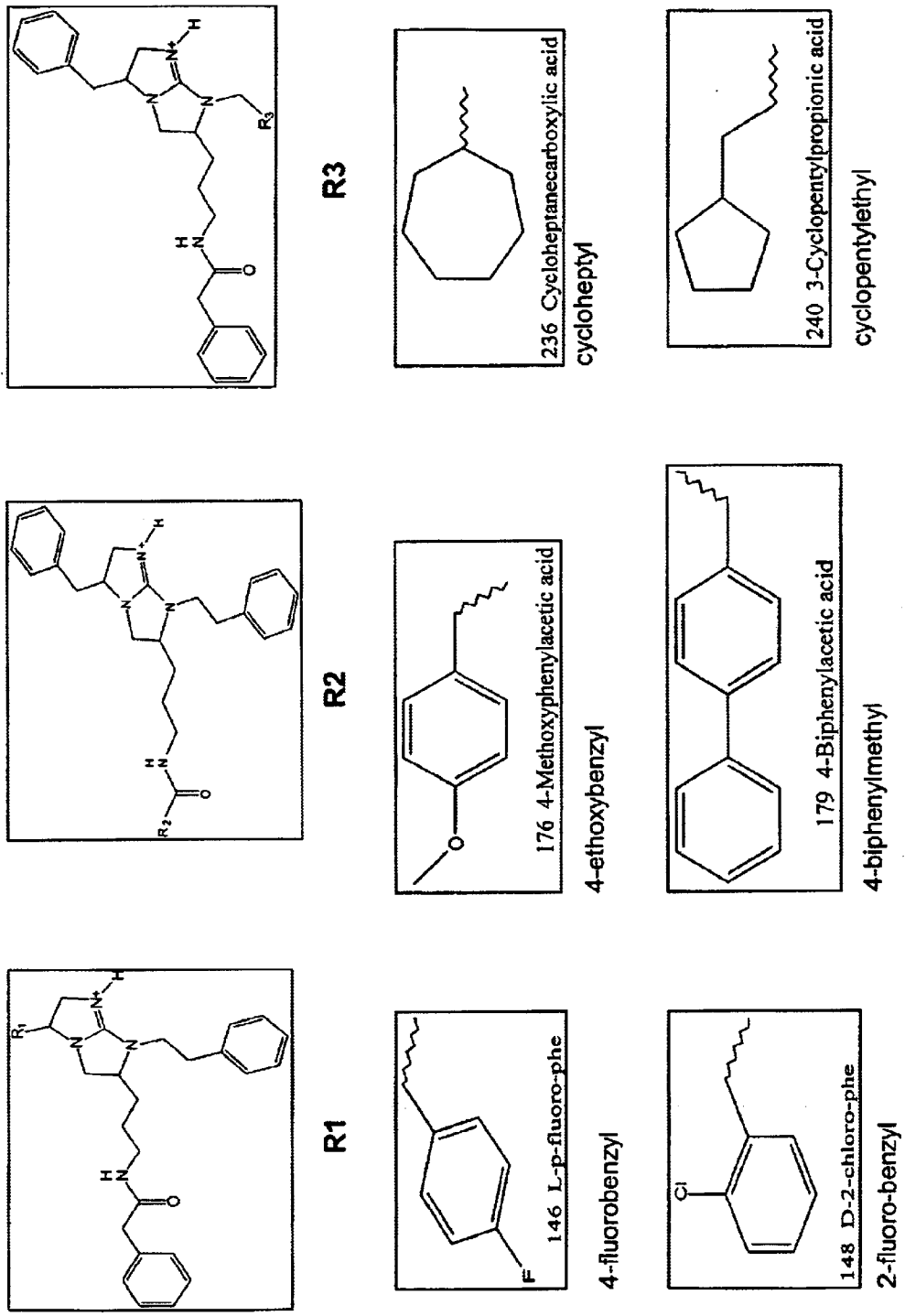
Figure 10D:
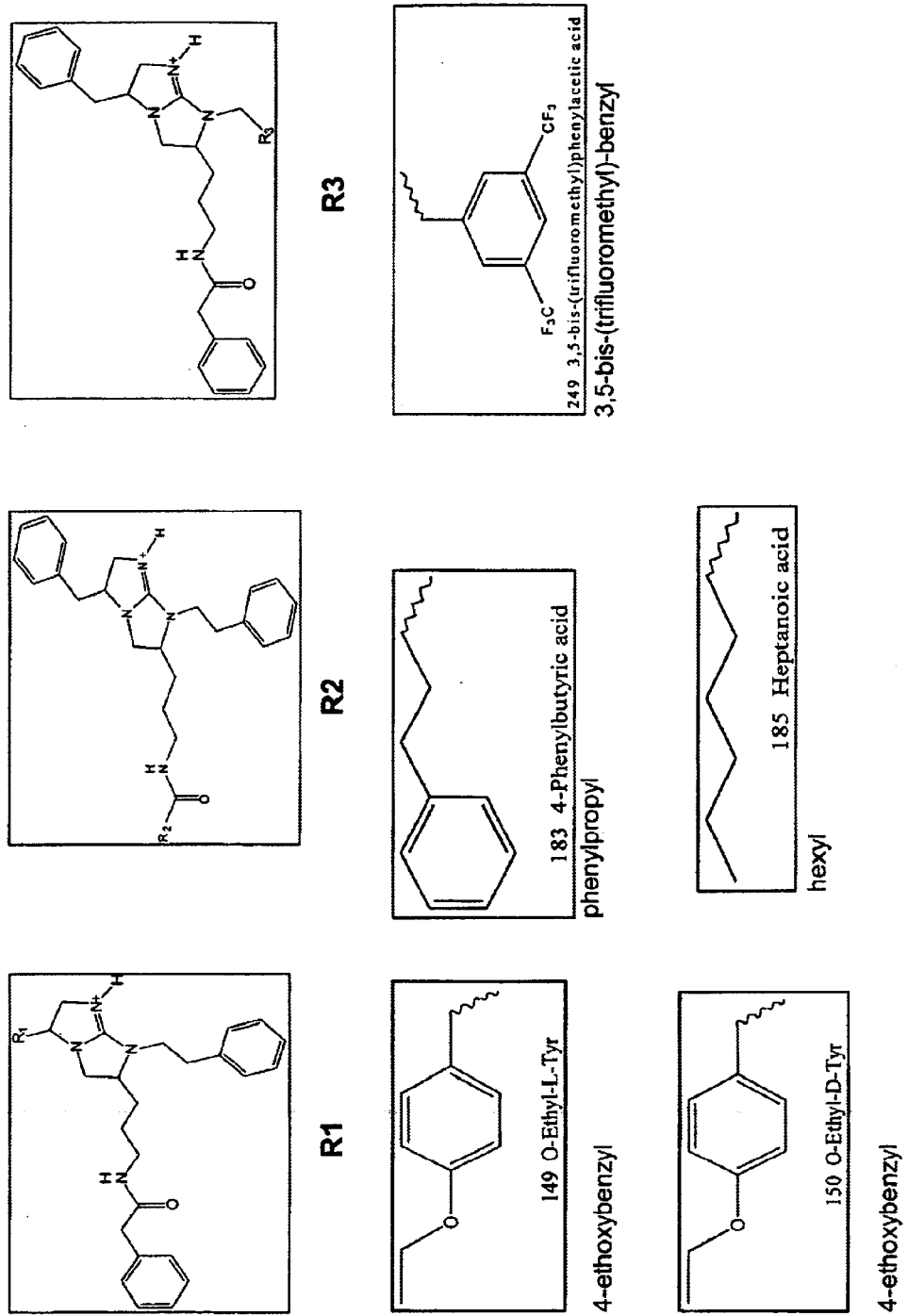
Figure 10E:
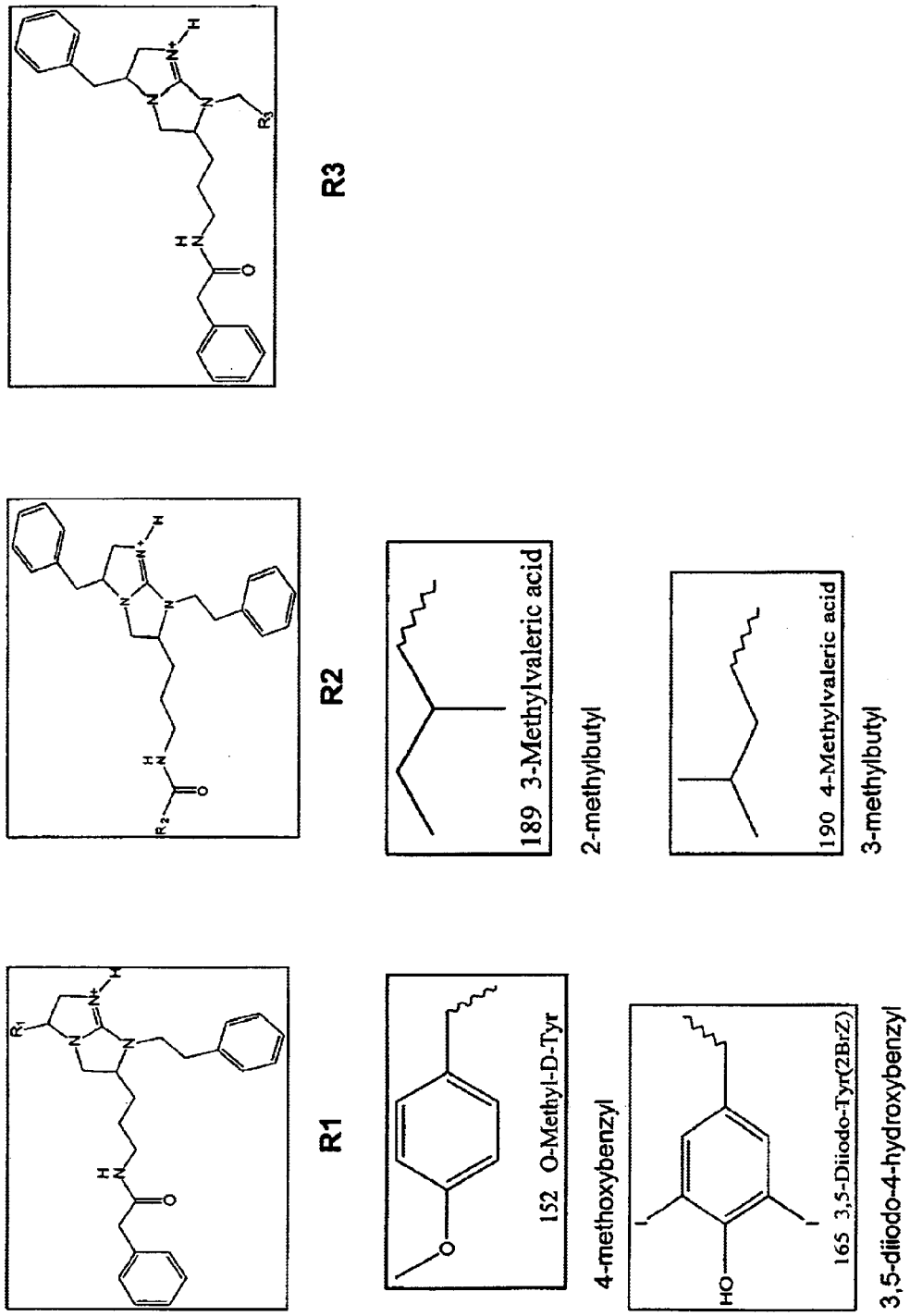

An agent that derepresses an IAP-inhibited caspase can have a core structure corresponding to a polyphenylurea such as TPI927 shown in FIGS. 6A and 6B. An agent having the TPI927 core structure can be substituted, for example, at position R1 derived from an amino acid side chain group of D-Lys(Me), L-3-(2Nap)Ala, D-Chala, L-Phe, Pro, Leu or Ser; at position R2 derived from an amino acid side chain group of ε-Lys, L-Nle, D-Phe, Pro, D-Orn(Me), Gln, L-3-(2-Nap)Ala or D-Thr; and at position R3 with the functional group derived from 4-methoxyphenylacetic acid, 1-adamantaneacetic acid, cyclohexanebutyric acid, 4-tert-butylcyclohexanecarboxylic acid, cycloheptanecarboxylic acid, 3-fluorophenylacetic acid, 3,3-diphenylpropionic acid, 4-ethoxyphenylacetic acid, 1-phenyl-1-cyclopropanecarboxylic acid, 1-napthylacetic acid, or cyclobutane carboxylic acid as shown in FIGS. 6A and 6B. An agent having the TPI927 core structure can be substituted at R1 and R2 with an amino acid side chain group of Phe and at R3 with the functional group derived from trimethylacetic acid, hydrocinnamic acid, 4-tert-butylcyclohexane carboxylic acid, 4-methyl-1-cyclohexanecarboxylic acid, cyclopentylacetic acid, 1-phenyl-1-cyclopropanecarboxylic acid, cyclohexanecarboxylic acid, phenylacetic acid, cycloheptanecarboxylic acid, cyclobutane carboxylic acid, cyclohexanebutyric acid, 1-adamantaneacetic acid, cyclopentanecarboxylic acid, isobutyric acid, cyclohexylacetic acid; 3-methoxyphenylacetic acid, butyric acid, 3-(3,4,5)-trimethoxyphenylpropionic acid; heptanoic acid; 2-norbornaneacetic acid, cyclohexanepropionic acid, tert-butyric acid, 4-ethoxyphenylacetic acid, 3,3-diphenylpropionic acid, 4-methoxyphenylacetic acid, acetic acid, methylvaleric acid p-tolylacetic acid or 4-isobutyl-alpha-methylphenylacetic acid as shown in FIGS. 9A–9C.

Figure 4:
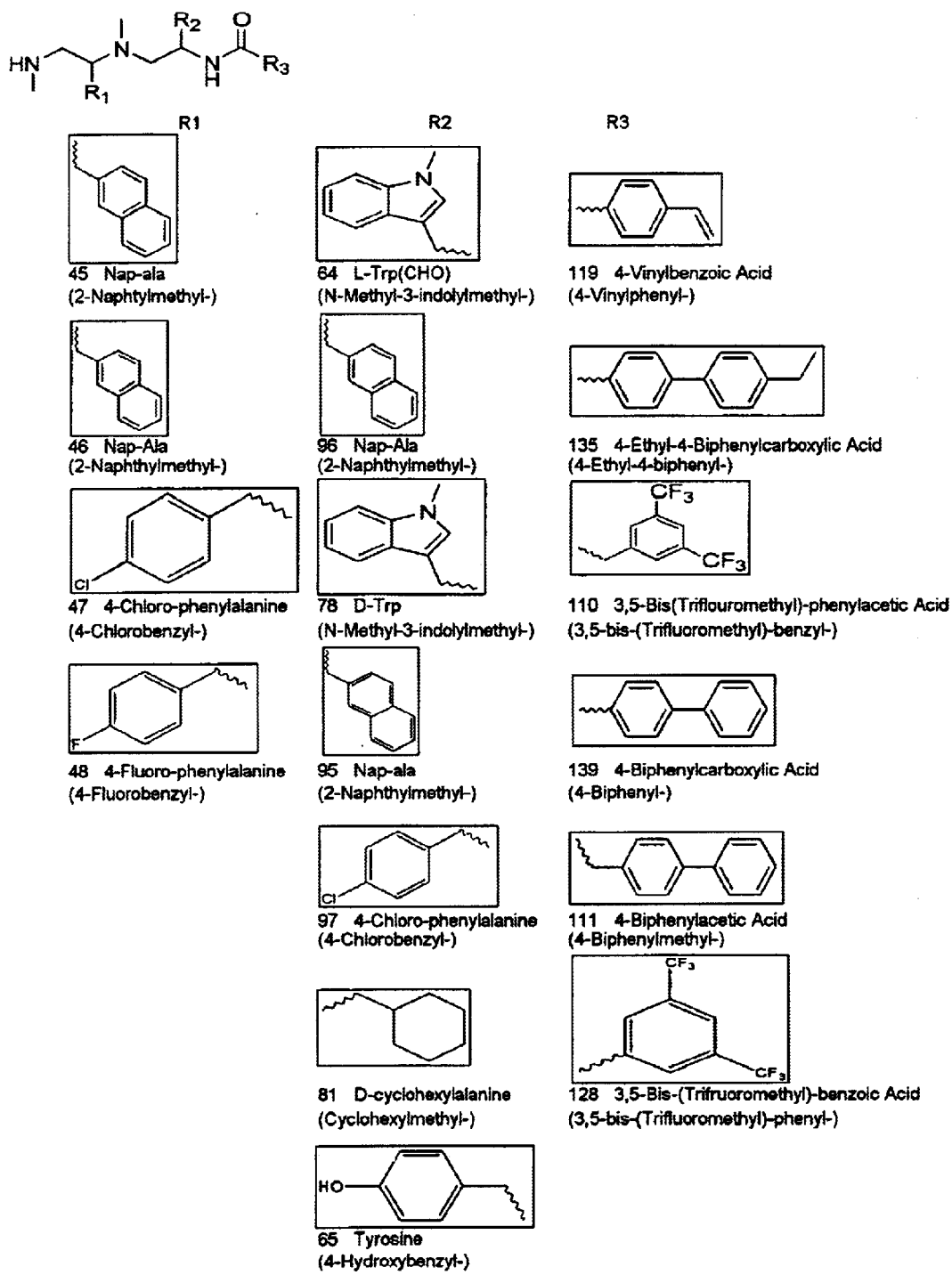
FIG. 4 shows structures of the defined functionalities in the mixtures found to be derepressors of an XIAP-inhibited caspase in the TPI914 N-acyltriamine positional scanning combinatorial library. The first chemical name listed below each box is for the reagent from which the R group was derived and the second chemical name listed below each box is the name of the functional group at the respective R position. Each functional group has the same steriochemistry as the reagent from which it was derived.
Figure 5:
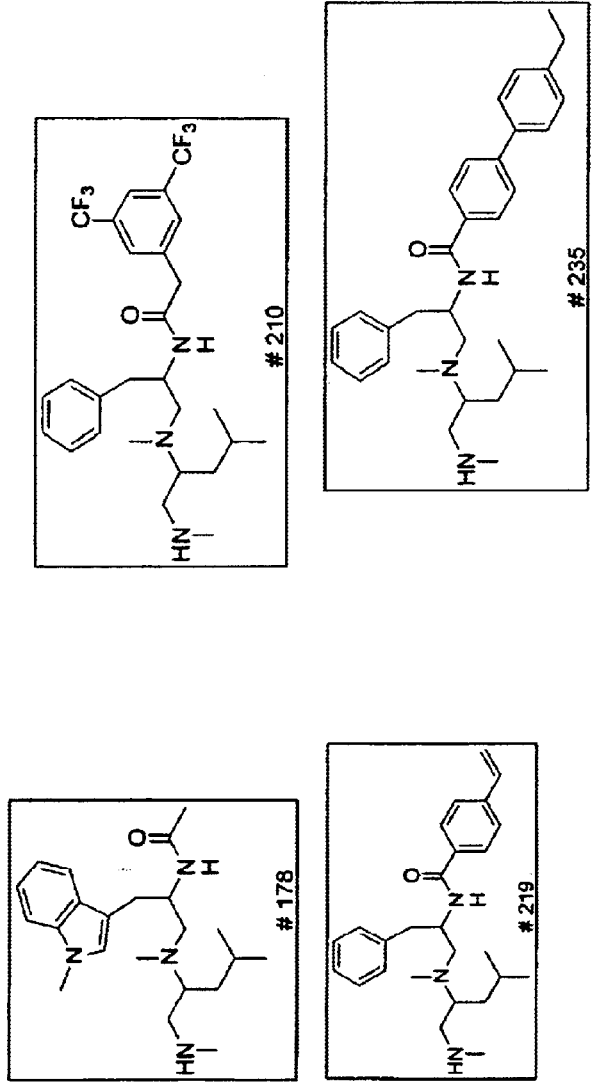
FIG. 5 shows structures for the individual compounds found to be derepressors of an XIAP-inhibited caspase in the TPI914 N-acyltriamine library. The first chemical name listed at each table entry is for the reagent from which the R group was derived and the second chemical name listed is the name of the functional group at the respective R position. Each functional group has the same steriochemistry as the reagent from which it was derived.

An agent that derepresses an IAP-inhibited caspase can have a core structure corresponding to an N-acyltriamine such as TP914 shown in FIG. 4. An agent having the TPI914 core structure can be substituted, for example, at position R1 derived from an amino acid side chain group of Nap-Ala or 4-Fluoro-phenylalanine; at position R2 derived from an amino acid side chain group of L-Trp, Nap-Ala, D-Trp, 4-chlorophenylalanine, D-cyclohexylalanine or Tyr; and at R3 with the functional group derived from 4-vinylbenzoic acid, 4-ethyl-4-biphenylcarboxylic acid, 3,5-Bis (trifluoromethyl)-phenylacetic acid, 4-biphenylcarboxylic acid, 4-biphenylacetic acid or 3,5-bis-(trifluoromethyl)-benzoic acid as shown in FIG. 4. An agent having the TPI914 core structure can be substituted at R1 with a functional group derived from an amino acid side chain group of Leu, at R2 with a functional group derived from an amino acid side chain group of D-Trp and at R3 with methyl; at R1 with a functional group derived from an amino acid side chain group of Leu, at R2 with a functional group derived from an amino acid side chain group of Phe and at R3 with the functional group derived from 3,5-Bis (trifluoromethyl)-phenylacetic acid; at R1 with a functional group derived from an amino acid side chain group of Leu, at R2 with a functional group derived from an amino acid side chain group of Phe and at R3 with the functional group derived from 4-vinylbenzoic acid; or at R1 with a functional group derived from an amino acid side chain group of Leu, at R2 with a functional group derived from an amino acid side chain group of Phe and at R3 with the functional group derived from 4-ethyl-4-biphenylcarboxylic acid each as shown in FIG. 5.

Those skilled in the art will recognize that libraries having the core structure of TPI914, TPI927, TPI759 or TPI882 can be combinatorialized at one or more position. A combinatorialized position refers to a position which is variously substituted with different moieties such that a library of molecules combinatorialized at the position is a mixture of molecules that differ in chemical structure at that position. Such libraries can be used to identify agents that derepress an IAP-inhibited caspase, for example, in a screen utilizing positional scanning as described in Example VI. Thus, any one of positions R1, R2 or R3 can be held fixed to a discrete moiety while the remaining two positions are combinatorialized, thereby generating sublibraries based on which position is fixed. Moreover, one can add additional positions to the core structure that can be combinatorialized or held constant while one or more other positions are combinatorialized. Thus, different or more diverse libraries can be created based on a particular core structure or on a species identified from the library as capable of derepressing an IAP-inhibited caspase.

Those skilled in the art will understand that an agent of the invention having a core structure corresponding to TPI914, TPI927, TPI759 or TPI882 can further include one or more attached moieties such as a peptide moiety. An agent of the invention can be multivalent, as described above, in which case the attached moiety can be one or more core structures corresponding to TPI914, TPI927, TPI759 or TPI882; a core peptide having a sequence described above; or a combination of one or more of these core structures and core peptides.

An agent that is capable of derepressing an IAP-inhibited caspase, whether based on a peptide or non-peptide core structure can include a moiety known to naturally occur in biological proteins. Such moieties when part of a protein are commonly referred to as amino acid R-groups. These R groups can be characterized by a variety of physical or chemical properties. Taking the essential amino acids as an example, the R groups found on Gly, Ala, Val, Leu, or Ile have the characteristic of being non-polar; polar R groups include the sulfhydril moiety of Cys, the thioether of Met, hydroxyl moieties of Ser and Thr, and amide moieties of Asn and Gln; Asp and Glu are characterized as polar acidic groups due to the presence of carboxylic acid moieties; polar basic R groups include Lys which has an amino moiety, Arg which has a guanidino moiety and His which has an imidazole with secondary amines; and Phe, Trp, Tyr, and His are characterized as aromatic amino acids due to the presence of phenyl or heterocyclic rings. An agent of the invention can include one or more of these moieties or characteristics, thereby rendering the agent capable of derepressing an IAP-inhibited caspase.

An agent of the invention can also be described or characterized according to other moieties or combinations of moieties that when present renders the agent capable of derepressing an IAP-inhibited caspase. Definitions for various moieties that can be present in the agents of the invention are set forth below.

As used herein, the term "alkyl," alone or in combination, refers to a saturated, straight-chain or branched-chain hydrocarbon moiety containing from 1 to 10, preferably from 1 to 6 and more preferably from 1 to 4, carbon atoms. Examples of such moieties include, but are not limited to, methyl, ethyl, n-propyl, iso-propyl, n-butyl, iso-butyl, sec-butyl, tert-butyl, pentyl, iso-amyl, hexyl, decyl and the like.

The term "alkene," alone or in combination, refers to a straight-chain or branched-chain hydrocarbon moiety having at least one carbon-carbon double bond in a total of from 2 to 10, preferably from 2 to 6 and more preferably from 2 to 4, carbon atoms. Examples of such moieties include, but are not limited to, ethenyl, E- and Z-propenyl, isopropenyl, E- and Z-butenyl, E- and Z-isobutenyl, E- and Z-pentenyl, decenyl, methylidene (=CH$_2$), ethylidene (—CH=CH—), propylidene (—CH$_2$—CH=CH—) and the like.

The term "alkyne," alone or in combination, refers to a straight-chain or branched-chain hydrocarbon moiety having at least one carbon-carbon triple bond in a total of from 2 to 10, preferably from 2 to 6 and more preferably from 2 to 4, carbon atoms. Examples of such moieties include, but are not limited to, ethynyl (acetylenyl), propynyl (propargyl), butynyl, hexynyl, decynyl and the like.

The term "cycloalkyl," alone or in combination, refers to a saturated, cyclic arrangement of carbon atoms which number from 3 to 8 and preferably from 3 to 6, carbon atoms. Examples of such cycloalkyl moieties include, but are not limited to, cyclopropyl, cyclobutyl, cyclopentyl, cyclohexyl and the like.

The term "aryl" refers to a carbocyclic (consisting entirely of carbon and hydrogen) aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl" groups, as defined in this application may independently contain one to four substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, 1,2-dioxyethylene, alkoxy, alkenoxy or alkynoxy, alkylamino, alkenylamino, alkynylamino, aliphatic or aromatic acyl, alkoxy-carbonylamino, alkylsulfonylamino, morpholinocarbonylamino, thiomorpholinocarbonylamino, N-alkyl guanidino, aralkylaminosulfonyl; aralkoxyalkyl; N-aralkoxyurea; N-hydroxylurea; N-alkenylurea; N,N-(alkyl, hydroxyl)urea; heterocyclyl; thioaryloxy-substituted aryl; N,N-(aryl, alkyl) hydrazino; Ar'-substituted sulfonylheterocyclyl; aralkyl-substituted heterocyclyl; cycloalkyl and cycloakenyl-substituted heterocyclyl; cycloalkyl-fused aryl; aryloxy-substituted alkyl; heterocyclylamino; aliphatic or aromatic acylaminocarbonyl; aliphatic or aromatic acyl-substituted alkenyl; Ar'-substituted aminocarbonyloxy; Ar', Ar'-disubstituted aryl; aliphatic or aromatic acyl-substituted acyl; cycloalkylcarbonylalkyl; cycloalkyl-substituted amino; aryloxycarbonylalkyl; phosphorodiamidyl acid or ester;

"Ar'" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy," alone or in combination, refers to an alkyl ether moiety, wherein the term "alkyl" is as defined above. Examples of suitable alkyl ether moieties include, but are not limited to, methoxy, ethoxy, n-propoxy, iso-propoxy, n-butoxy, iso-butoxy, sec-butoxy, tert-butoxy and the like.

The term "alkenoxy," alone or in combination, refers to a moiety of formula alkenyl-O—, wherein the term "alkenyl" is as defined above. Examples of suitable alkenoxy moieties include, but are not limited to, allyloxy, E- and Z-3-methyl-2-propenoxy and the like.

The term "thioalkoxy" refers to a thioether moiety of formula alkyl-S—, wherein alkyl is as defined above.

The term "alkylamino," alone or in combination, refers to a mono- or di-alkyl-substituted amino group (i.e., a group of formula alkyl-NH— or (alkyl)$_2$—N—), wherein the term "alkyl" is as defined above. Examples of suitable alkylamino moieties include, but are not limited to, methylamino, ethylamino, propylamino, isopropylamino, t-butylamino, N,N-diethylamino and the like.

The term "amide" refers to either —N(R$^1$)—C(=O)— or —C(=O)—N(R$^1$)— where (R$^1$) is defined herein to include hydrogen as well as other groups. The term "substituted amide" refers to the situation where (R$^1$) is not hydrogen, while the term "unsubstituted amide" refers to the situation where (R$^1$) is hydrogen.

The term "aryloxy," alone or in combination, refers to a moiety of formula aryl-O—, wherein aryl is as defined above. Examples of aryloxy moieties include, but are not limited to, phenoxy, naphthoxy, pyridyloxy and the like.

The term "arylamino," alone or in combination, refers to a moiety of formula aryl-NH—, wherein aryl is as defined above. Examples of arylamino moieties include, but are not limited to, phenylamino (anilido), naphthylamino, 2-, 3- and 4-pyridylamino and the like.

The term "aryl-fused cycloalkyl," alone or in combination, refers to a cycloalkyl moiety which shares two adjacent atoms with an aryl moiety, wherein the terms "cycloalkyl" and "aryl" are as defined above. An example of an aryl-fused cycloalkyl moiety is a benzofused cyclobutyl group.

The term "alkylcarbonylamino," alone or in combination, refers to a moiety of formula alkyl-CONH, wherein the term "alkyl" is as defined above.

The term "alkoxycarbonylamino," alone or in combination, refers to a moiety of formula alkyl-OCONH—, wherein the term "alkyl" is as defined above.

The term "alkylsulfonylamino," alone or in combination, refers to a moiety of formula alkyl-SO$_2$NH—, wherein the term "alkyl" is as defined above.

The term "arylsulfonylamino," alone or in combination, refers to a moiety of formula aryl-SO$_2$NH—, wherein the term "aryl" is as defined above.

The term "N-alkylurea," alone or in combination, refers to a moiety of formula alkyl-NH—CO—NH—, wherein the term "alkyl" is as defined above.

The term "N-arylurea," alone or in combination, refers to a moiety of formula aryl-NH—CO—NH—, wherein the term "aryl" is as defined above.

The term "halogen" means fluorine, chlorine, bromine and iodine.

In view of the above definitions, other chemical terms used throughout this application can be easily understood by those of skill in the art. Terms may be used alone or combined to describe a combination of moieties according to accepted chemical nomenclature.

An agent of the invention can be synthesized using reagents and conditions well known to yield products having predictable moieties or characteristics. For example, peptides can be synthesized in large numbers at relatively low cost and they can be readily modified to exhibit diverse properties (see, for example, Rees et al., *Protein Engineering: A Practical Approach* (IRL Press 1992)). A peptide derepressor of an IAP-inhibited caspase can be synthesized using a modification of the solid phase peptide synthesis method (Merrifield (*J. Am. Chem. Soc.*, 85:2149 (1964); Houghten, U.S. Pat. No. 4,631,211, issued Dec. 23, 1986) or can be synthesized using standard solution methods well known in the art (see, for example, Bodanszky, M., *Principles of Peptide Synthesis* 2nd ed. (Springer-Verlag, 1988 and 1993, suppl.)). Peptides prepared by the method of Merrifield can be synthesized using an automated peptide synthesizer such as the Applied Biosystems 431A-01 Peptide Synthesizer (Mountain View, Calif.) or using a manual peptide synthesis method (Houghten, supra, 1986).

Furthermore, combinatorial methods such as those described below can be used to make an agent that derepresses an IAP-inhibited caspase. A library can be synthesized to have candidate agents with particular moieties such as those defined above or described in the Examples set forth below. Additionally, the synthetic conditions can be selected to produce a library of candidate compounds with particular characteristics inherent in one or more of the moieties described herein such as the characteristics described above for amino acid R groups. For example, a library can be synthesized to have characteristics of SMAC a naturally occurring IAP inhibitor. The N-terminal region of SMAC has been shown to mediate binding to and inhibition of IAPs (see Srinivasula et al., *Nature* 410:112–116 (2001), Wu et al., *Nature* 408:1008–1012 (2000), Liu et al., Nature 408:1004–1008 (2000)). Accordingly, this N-terminal domain can be used to guide library synthesis such that reactants and conditions are chosen to selectively incorporate similar moieties and characteristics into the candidate agents in the library. Similar strategies can be employed using agents described herein or identified by the methods of the invention, wherein a library is made to selectively contain characteristics or moieties found in a particular agent or common to a plurality of agents. Such a design strategy increases the probability that an effective derepressor of an IAP-inhibited caspase will be identified.

An agent of the invention that is capable of derepressing an IAP-inhibited caspase can be identified in a screen or otherwise characterized according to any of a variety of functional properties described herein.

In one embodiment a derepressor of an IAP-inhibited caspase is identified or otherwise characterized based on its ability to allow caspase activity in the presence of an IAP. For example, the effectiveness of a compound of the invention can be determined according to the ratio of caspase activity for an IAP-inhibited caspase in the presence and absence of an agent of the invention.

An exemplary assay for identifying a compound that derepresses an IAP-inhibited caspase is provided in Example I and use of the assay to identify such derepressor compounds is demonstrated in Examples I through VI. As described below in the Examples, a ratio of $V_{max}$ in the presence and absence of the agent for an IAP-inhibited caspase that is at least about 1.7, depending upon assay conditions, is indicative of an effective derepressor of an IAP-inhibited caspase. Those skilled in the art will understand that a value for this ratio that is indicative of effectiveness will depend upon the concentration of the agent used and the $IC_{50}$ of the agent. Accordingly, when higher concentrations of the agent are used the threshold value for the ratio of $V_{max}$ in the presence and absence of the agent can be at least about 2 at least about 2.5, at least about 3 or at least about 4 or higher. When lower concentrations of the agent are used this ratio can be as low as at least about 1.5, at least about 1.3 at least about 1 or lower. Thus, it can be appropriate to express the ratio in combination with the relative amount of agent to IAP present in the assay including, for example, 1 molar equivalent of agent per IAP, 2 molar equivalents of agent per IAP, 5 molar equivalents of agent per IAP, 10 molar equivalents of agent per IAP or 50 molar equivalents of agent per IAP or higher.

An agent that derepresses an IAP-inhibited caspase can also be identified by its affinity for an IAP or a caspase-binding fragment thereof, for example, in a binding assay. It will be understood that a functional fragment of an IAP, caspase or both can be used in a binding assay to identify a derepressor of an IAP-inhibited caspase. Affinity of an agent for an IAP determined using a binding assay can, if desired, be quantified by an equilibrium dissociation constant ($K_d$) or equilibrium association constant ($K_a$). An agent that derepresses an IAP-inhibited caspase can be identified as an agent that has a $K_d$ that is in the micromolar range including, for example, less than about $1 \times 10^{-6}$ M, $1 \times 10^{-7}$ M, or $1 \times 10^{-8}$ M. Higher affinity agents can also be identified including an agent having nanomolar range affinity such as a $K_d$ less than about $1 \times 10^{-9}$ M, $1 \times 10^{-10}$ M or $1 \times 10^{-11}$ M. An agent of the invention can also have picomolar affinity including, for example, a $K_d$ that is less than $1 \times 10^{-12}$ M.

Alternatively, the effectiveness of an agent at derepressing an IAP-inhibited caspase can be determined based on inhibition of the association between an IAP and caspase, for example, in an inhibition binding assay. It will be understood that a functional fragment of an IAP, caspase or both can be used in an inhibition binding assay. Alternatively, a derepressor of an IAP-inhibited caspase can be identified based on its ability to inhibit binding between IAP and another inhibitor such as SMAC. An exemplary assay for determining inhibition of IAP binding to SMAC is provided in Example VII. Inhibition can be quantified, if desired, by an equilibrium inhibition constant, such as $K_i$. Values for $K_i$ can be determined by performing derepression assays, such as those described herein, with increasing concentrations of the agent and a fixed concentration of each binding partner. Binding or inhibition can be analyzed to determine the equilibrium constants described above using well known kinetic analysis such as those described in Segel, *Enzyme Kinetics* John Wiley and Sons, New York (1975). An agent that derepresses an IAP-inhibited caspase can be identified as those having $K_i$ in the micromolar, nanomolar or picomolar ranges such as those ranges and values described above for $K_d$.

Accordingly, the invention provides a complex having an IAP bound to an agent, the agent having a core peptide or core structure of the invention including, for example, those core structures described above. The complex can be isolated from at least one other cellular component normally occurring with the IAP in nature. For example, the complex can be in a purified state being substantially free of other cellular components that normally occur with the IAP in nature. The complex can also occur in a recombinant cell that does not normally express the IAP.

The invention further provides conjugates including a moiety linked to an agent that derepresses an IAP-inhibited caspase. A conjugate of the invention can include a moiety useful for targeting the agent to a particular cell or for increasing the stability or biological half life of the agent that derepresses an IAP-inhibited caspase. For example, a moiety can be a particular antibody, functional fragment thereof, or other binding polypeptide that has specificity for a particular cell in which it is desired to promote apoptosis, such as a tumor cell. Any moiety capable of targeting the agent to a cell in which an IAP-inhibited caspase is to be derepressed can be used as a conjugate.

A conjugate of an agent that derepresses an IAP-inhibited caspase can also be a moiety capable of introducing the agent to the cytosol of a cell or otherwise facilitating passage of the agent through the cell membrane. An agent can be introduced into the cell by, for example, a heterologous targeting domain or using a lipid based carrier. Thus, the invention provides cytosolic delivery of an agent that derepresses an IAP-inhibited caspase.

A moiety can also be a drug delivery vehicle such as a chambered microdevice, a cell, a liposome or a virus that provides stability or properties otherwise advantageous for administration of the agent that derepresses an IAP-inhibited caspase. Generally, such microdevices, should be nontoxic and, if desired, biodegradable. Various moieties, including microcapsules, which can contain an agent, and methods for linking a moiety, including a chambered microdevice, to a therapeutic agent are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988); see, also, Hermanson, supra, 1996).

In addition, a derepressor of an IAP-inhibited caspase formulation can be incorporated into biodegradable polymers allowing for sustained release of the compound, the polymers being implanted in the vicinity of where drug delivery is desired, for example, at the site of a tumor or implanted so that the agent is released systemically over time. Osmotic minipumps also can be used to provide controlled delivery of specific concentrations of the derepressor of an IAP-inhibited caspase species and formulations through cannulae to the site of interest, such as directly into a tumor growth or into the vascular supply of a tumor. The biodegradable polymers and their use are described, for example, in detail in Brem et al., *J. Neurosurg.* 74:441–446 (1991).

A conjugate of the invention can include a moiety that is a label. A labeled agent that binds to an IAP and/or caspase can be used to identify the subcellular localization of the IAP and/or caspase or to identify a previously unidentified IAP or caspase. A labeled agent that binds to an IAP and/or caspase can also be used to identify other molecules that interact with an IAP and/or caspase. As described in further detail below, such a binding competition assay can be used to identify an agent that derepresses an IAP-inhibited caspase. A label that can be incorporated as a mioety includes, for example, a fluorophore, chromophore, paramagnetic spin label, radionucleotide, or binding group having specificity for another molecule that can be detected.

A labeled agent of the invention can be useful for identifying cells within a tissue that are inhibited from apoptosis by an IAP-inhibited caspase. Thus, the labeled agent can be used in a diagnostic method to identify cells for which administration of a derepressor of an IAP-inhibited caspase will allow apoptosis to proceed. The method can include steps of administering a labeled agent of the invention to a tissue and identifying one or more cells that incorporate the labeled agent. The labeled agent can be administered using methods for in vivo delivery as described above. The diagnostic methods can be used at a variety of resolutions. For example, the method can be carried out to identify a tissue containing cells labeled by the agent. Alternatively, higher resolution methods can be used to identify a particular cell or cell type within a tissue that is labeled in the presence of an IAP-inhibited caspase. Because the diagnostic methods can be used to distinguish a cell for which administration of a derepressor of an IAP-inhibited caspase will allow apoptosis to proceed from non-labeled cells, the methods can be useful for guiding in the choice of targeting or delivery conjugate to use in a therapeutic method of the invention.

The diagnostic method can be performed in vitro in which case the labeled agent can be administered by injection or by soaking the tissue in a solution containing the labeled agent. Again the methods can be used at a resolution sufficient to distinguish within a tissue a cell having an IAP-inhibited caspase over those that are not inhibited from apoptosis in this way. Such resolution can be achieved for example, by use of a microscopic based technique. Further resolution can provide subcellular localization of an IAP-inhibited caspase. Subcellular localization can be used to determine an appropriate cytosolic delivery conjugate or to further identify the role of apoptosis in the particular tissue or cells under study.

The invention also provides a pharmaceutical composition containing a derepressor of an IAP-inhibited caspase and a pharmaceutical carrier. Such compositions can be used in the apoptosis promoting methods of the invention to inhibit, treat or reduce the severity of a pathological condition characterized by a pathologically reduced level of apoptosis. For example, a derepressor of an IAP-inhibited caspase can be administered as a solution or suspension together with a pharmaceutically acceptable medium.

The derepressor of an IAP-inhibited caspase formulations include those applicable for parenteral administration such as subcutaneous, intraperitoneal, intramuscular, intravenous, intradermal, intracranial, intratracheal, and epidural administration. As well as formulations applicable for oral, rectal, ophthalmic (including intravitreal or intracameral), nasal, topical (including buccal and sublingual), intrauterine, or vaginal administration. The derepressor of an IAP-inhibited caspase formulation can be presented in unit dosage form and can be prepared by pharmaceutical techniques well known to those skilled in the art. Such techniques include the step of bringing into association the active ingredient and a pharmaceutical carrier or excipient.

Formulations suitable for parenteral administration include aqueous and non-aqueous sterile injection solutions such as the pharmaceutically acceptable media described above. The solutions can additionally contain, for example, anti-oxidants, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

A pharmaceutically acceptable medium can additionally contain physiologically acceptable compounds that act, for example, to stabilize the derepressor of an IAP-inhibited caspase agent. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; lipids or liposomes; or other stabilizers or excipients. As described previously, derepressor of an IAP-inhibited caspase formulation also can be formulated with a pharmaceutically acceptable medium such as a biodegradable polymer. All of the above-described pharmaceutical carriers and media can be what is termed in the art pharmaceutical grade which means that they are of sufficient purity and quality for use in humans and are distinguishable from comparable reagents in research grade formulations.

The invention also provides a composition including a derepressor of an IAP-inhibited caspase and a molecule having therapeutic activity. A molecule included with a derepressor of the invention can be a compound having activity against a condition characterized by a pathologically reduced level of apoptosis. For example, the compound can have activity against cancer. An exemplary compound that has activity against prostate cancer and that can be used in combination with a derepressor compound of the invention is VP-16 (etoposide). As demonstrated by the results of Example X, administration of VP-16 with either TPI792-33 or TPI792-35 had a more potent effect on killing cancer cells than any of these compounds alone.

Other anti-cancer drugs can also be used in a composition with a derepressor of an IAP-inhibited caspase including, but not limited to, an alkylating agent such as mechlorethamine, chlorambucil, cyclophosphamide, melphalan, ifosfamide; an antimetabolite such as methotrexate, 6-mercaptopurine, 5-fluorouracil or cytarabine; an antibody such as Rituxan, Herceptin, or MabThera; a plant alkaloid such as vinblastine or vincristine, or etoposide; an antibiotic such as doxorubicin, daunomycin, bleomycin, or mitomycin; a nitrosurea such as carmustine or lomustine; an inorganic ion such as cisplatin; a biological response modifier such as interferon; an enzyme such as aspariginase; or a hormone such as tamoxifen or flutamide. These and other anti-cancer compounds are known in the art and formulations suitable for pharmaceutical use are known as described, for example, in *The Merck Manual* 16$^{th}$ Ed., Merck Res. Labs., Rahway N.J. (1992).

The invention further provides a kit, including at least one compound of the invention that has activity as a derepressor of an IAP-inhibited caspase and a second compound having therapeutic activity. A compound of the invention that can be included in a kit includes, for example, a compound having a core peptide selected from the group consisting of Core peptides 4 through 39 and 42 through 55, or having a core structure selected from any of the structures shown in FIGS. 5, 9A–9C, 10A–10F, 14B, and 21A–24T, wherein the compound derepresses an IAP-inhibited caspase. Such kits are useful, for example, in the treatment of a condition characterized by a pathologically reduced level of apoptosis. For example, a kit including VP-16 with either TPI792-33 or TPI792-35 can be used to treat prostate cancer.

A suitable kit includes compounds as separately packaged formulations or in a mixed formulation, so long as the compounds are provided in an amount sufficient to have a therapeutic effect following at least one administration of each compound. The formulations can be any of those described above, or otherwise known to be appropriate for the particular compound and mode of administration.

The contents of a kit of the invention are housed in packaging material or other suitable physical structure, preferably to provide a sterile, contaminant-free environment. In addition, the packaging material contains instructions indicating how the materials within the kit can be administered for treatment of a condition characterized by a pathologically reduced level of apoptosis. The instructions for use typically include a tangible expression describing the route of administration or, if required, methods for preparing the formulation for administration. The instructions can also include identification of potential effects from use of the kit's contents or a warning regarding improper use of the contents of the kit.

The invention provides a method of identifying an agent that derepresses an IAP-inhibited caspase. The method includes the steps of (a) contacting an IAP and a caspase with an agent suspected of being able to derepress an IAP-inhibited caspase, wherein the caspase is an IAP-inhibited caspase that is inhibited by the IAP, wherein the contacting occurs under conditions that allow caspase activity in the absence of the IAP; and (b) detecting derepression of the IAP-inhibited caspase.

Derepression of the IAP-inhibited caspase can be detected as an increase in an IAP-inhibited caspase activity including, for example, proteolytic activity. Proteolytic activity can be measured in an in vitro assay using a specific substrate. For example, a continuous fluorometric assay can be used to measure hydrolysis rates by following release of either 7-amino-4-trifluoromethyl-coumarin (AFC) from DEVD (SEQ ID NO:2) that is derivatized with a C-terminal aminomethylcoumarin, YVAD (SEQ ID NO:3) that is derivatized with a C-terminal aminomethylcoumarin (Tyr-Val-Ala-Asp-aminomethylcoumarin), or carbobenzoxy-Glu-Val-Asp-aminomethylcoumarin; or by following the release of p-nitroanilide (pNA) from similar peptides labeled with pNA, as described in U.S. Pat. No. 6,228,603 B1.

An immunoblot or other chromatography based assay can be used to detect proteolysis of a substrate by caspase according to altered molecular weight of the products compared to the substrate. For example, the proteolytic activity of an upstream initiator caspase, such as caspase-9, can be determined based on processing of a downstream effector pro-caspase, such as pro-caspase-3, to the mature form in an immunoblot assay as described in U.S. Pat. No. 6,228,603 B1. Comparison of the results of such an assay for an IAP-inhibited caspase in the presence and absence of an agent of the invention can be used to identify a derepressor of the IAP-inhibited caspase according to a relative increase in caspase activity in the presence of the agent.

Proteolytic activity of a caspase can also be determined by identifying morphological changes in a cell or a cell nucleus characteristic of apoptosis. Such changes that are characteristic of apoptosis include, for example, chromatin condensation, nuclear fragmentation, cell shrinkage, or cell blebbing leading to the eventual breakage into small membrane surrounded fragments termed apoptotic bodies. Thus, an agent that is a derepressor of an IAP-inhibited caspase can be identified according to the ability to cause a characteristic apoptotic change when added to a cell that is prevented from undergoing apoptosis by an IAP-inhibited caspase. A similar assay can be performed on a cell free extract derived from such a cell so long as an apoptotic change such as chromatin condensation or nuclear fragmentation can be distinguished in the presence and absence of the added agent.

Derepression of an IAP-inhibited caspase can also be detected as disassociation of an IAP-caspase species. An IAP-inhibited caspase can be identified as a caspase having an associated IAP using binding assays known in the art. Such a complex can be identified according to molecular weight or size using, for example, non-denaturing polyacrylamide gel electrophoresis, size exclusion chromatography, or analytical centrifugation. An IAP-caspase complex can also be identified using a co-precipitation technique. For example, an IAP-caspase complex can be identified due to the ability of an antibody to co-precipitate with both partners but not with one or the other partner alone. Similar, techniques can be used when either the IAP or caspase has been modified by a recombinant DNA method to incorporate an affinity tag such as glutathione-S-transferase (Amersham Pharmacia; Piscataway, N.J.), which can be precipitated with glutathione beads; polyhistidine tag (Qiagen; Chatsworth, Calif.), which can be precipitated with Nickel NTA sepharose; antibody epitopes such as the flag peptide (Sigma; St Louis, Mo.), which can be immunoprecipitated; or other known affinity tag. An agent that prevents IAP-caspase complex formation or otherwise causes dissociation of the complex can be identified in such an assay as a derepressor of an IAP-inhibited caspase.

The caspases are present in cells as precursor polypeptides referred to as procaspases. Caspase activation occurs due to proteolytic processing of the procaspase. For example, caspase-3 is a heterotetramer composed of approximately 17–20 kDa and 11 kDa polypeptides that are formed by proteolysis of a 32 kDa polypeptide precursor, pro-caspase-3. Cleavage of the pro-caspase-3 proceeds in two steps. The first cleavage results in production of a partially processed large subunit (22–24 kDa) that still contains the pro-domain, and a smaller, fully processed, subunit of about 11 kDa. In the second step, the pro-domain is cleaved from the partially processed large subunit, probably by an autocatalytic process, to produce the 17–20 kDa mature, fully processed large subunit of the caspase-3 enzyme. Removal of the pro-domain, however, is not necessary for protease activation, as the partially processed caspase also has caspase activity.

The methods of the invention for identifying an agent that derepresses an IAP-inhibited caspase can be used to identify a caspase that is prevented from being processed to a mature, fully proteolytically active form due to the presence of an IAP. For example, the methods can be used to identify an agent that prevents or suppresses an IAP from inhibiting processing of a procaspase to a caspase. Because processing of a procaspase to a caspase will coincide with an increase in caspase proteolytic activity, the methods described above for determining proteolytic activity can be used in a method for identifying an agent that prevents or suppresses an IAP from inhibiting processing of a procaspase to a caspase. Similarly, a binding assay, such as those described above, can be used to identify a procaspase-IAP complex according to the combined molecular weight of the partners. An agent that prevents complex formation or causes the complex to dissociate can be identified in such an assay as a derepressor of an IAP-inhibited caspase. A caspase that is prevented from being processed to a mature, fully proteolytically active form due to the presence of an IAP can also be identified according to differences in molecular weight or size of the mature and procaspase forms. Thus, an agent that, when contacted with a procaspase in the presence of an inhibitory IAP, causes a change in molecular weight or size indicative of the mature form can be identified as a derepressor of an IAP-inhibited caspase.

The methods of the invention can be used to identify a derepressor of an IAP-inhibited caspase that has specificity for a particular IAP or caspase or combination of a particular IAP and caspase. For example, the invention provides screening assays for identifying agents that alter the specific binding of a eukaryotic IAP such as XIAP, c-IAP-1 or c-IAP-2 and a caspase such as caspase-3, caspase-7 or caspase-9. Any IAP, including any eukaryotic IAP, can be used in a method of the invention in combination with the appropriate caspase. Other IAP proteins that are involved in regulating particular caspases can be identified using the methods disclosed herein, then the particular combination of caspase and IAP can be used in a screening assay to identify an agent that modulates the regulation of caspase activation by the IAP or that alters the specific association of the IAP and caspase.

As disclosed herein, invention core peptides were identified by screening combinatorial libraries having core tetrapeptide and hexapeptide structures. In view of the disclosed methods, the skilled artisan would recognize that combinatorial libraries of peptides having more than six amino acids or less than four amino acids also can be screened to identify other core peptides that derepress an IAP-inhibited caspase. Furthermore, while the disclosed methods can be used to initially identify core peptides that derepress an IAP-inhibited caspase, those skilled in the art would know that the methods can be used in an iterative fashion to optimize or to identify additional core peptides that derepress an IAP-inhibited caspase, as described below.

It is expected that those skilled in the art can use combinatorial synthetic methods coupled to rapid screening methods to optimize and identify additional derepressors with increased binding affinity for an IAP or increased activity in derepressing an IAP-inhibited caspase, thereby possessing enhanced therapeutic potential.

The iterative approach is well-known in the art and is set forth, in general, in Houghten et al., *Nature*, 354, 84–86 (1991); and Dooley et al., *Science*, 266, 2019–2022 (1994); both of which are incorporated herein by reference. In the iterative approach, for example, sublibraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various organic libraries and for various peptide libraries (see, for example, R. Houghten et al. PCT/US91/08694 and U.S. Pat. No. 5,556,762, both of which are incorporated herein by reference). In the positional scanning approach sublibraries are made defining only one variable with each set of sublibraries and all possible sublibraires with each single variable defined (and all other possibilities at all of the other variable positions) is made and tested. From the instant description one skilled in the art could synthesize libraries wherein 2 fixed positions are defined at a time. From the testing of each single-variable defined library, the optimum substituent at that position is determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Phage display methods provide a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

An invention derepressor of an IAP-inhibited caspase that contains peptide moieties can be synthesized using amino acids, the active groups of which are protected as required using, for example, a t-butyldicarbonate (t-BOC) group or a fluorenylmethoxy carbonyl (FMOC) group. Amino acids and amino acid analogs can be purchased commercially (Sigma Chemical Co., St. Louis Mo.; Advanced Chemtec, Louisville Ky.) or synthesized using methods known in the art. Peptides synthesized using the solid phase method can be attached to a variety of resins, including, for example, 4-methylbenzhydrylamine (MBHA), 4-(oxymethyl)-phenylacetamido methyl and 4-(hydroxymethyl) phenoxymethyl-copoly(styrene-1% divinylbenzene (Wang resin), all of which are commercially available, or to p-nitrobenzophenone oxime polymer (oxime resin), which can be synthesized as described by De Grado and Kaiser, *J. Org. Chem.* 47:3258 (1982).

The choice of amino acids or amino acid analogs incorporated into an invention peptide will depend, in part, on the specific physical, chemical or biological characteristics required of the derepressor of an IAP-inhibited caspase. Such characteristics are determined by whether, for example, the peptide is to be used in vivo or in vitro, and, when used in vivo, by the route by which the invention peptide will be administered or the location in a subject to which it will be directed. For example, the derepressor of IAP-inhibited caspase core peptides exemplified herein can be synthesized using only L-amino acids. However, the skilled artisan would know that any or all of the amino acids in a peptide of the invention can be a naturally occurring L-amino acid, a non-naturally occurring D-amino acid or an amino acid analog, provided the peptide can derepress an IAP-inhibited caspase.

The choice of including an L-amino acid or a D-amino acid in the invention peptides depends, in part, on the desired characteristics of the peptide. For example, the incorporation of one or more D-amino acids can confer increased stability on the peptide in vitro or in vivo. The incorporation of one or more D-amino acids also can increase or decrease the activity, such as IAP binding affinity, of the peptide as determined, for example, using the assay described herein in Example VII or other well known methods for determining the binding affinity of a particular peptide to a particular protein.

As set forth above, invention peptides can be either linear, cyclic or multivalent, and the like, which conformations can be achieved using methods well-known in the art. As used herein a "cyclic" peptide refers to analogs of synthetic linear peptides that can be made by chemically converting the structures to cyclic forms. Cyclization of linear peptides can modulate bioactivity by increasing or decreasing the potency of binding to the target protein (Pelton, J. T., et al., *Proc. Natl. Acad. Sci., U.S.A.*, 82:236–239). Linear peptides are very flexible and tend to adopt many different conformations in solution. Cyclization acts to constrain the number of conformations available in solution, and thus, can favor a conformation having a higher affinity for IAP or more potent activity as a derepressor of an IAP-inhibited caspase.

Cyclization of linear peptides is accomplished either by forming a peptide bond between the free N-terminal and C-terminal ends (homodetic cyclopeptides) or by forming a new covalent bond between amino acid backbone and/or side chain groups located near the N- or C-terminal ends (heterodetic cyclopeptides) (Bodanszky, N., 1984, supra). The latter cyclizations use alternate chemical strategies to form covalent bonds, e.g. disulfides, lactones, ethers, or thioethers. Linear peptides of five or more amino acid residues, as described herein, can be cyclized relatively easily. The propensity of the peptide to form a beta-turn conformation in the central four residues facilitates the formation of both homo- and heterodetic cyclopeptides. The presence of proline or glycine residues at the N- or C-terminal ends also facilitates the formation of cyclopeptides, especially from linear peptides shorter than six residues in length.

An agent of the invention can be multivalent with respect to the number of derepressor IAP-inhibited caspase sequences or moieties are present per molecule. The sequences or moieties present in a multivalent agent can be either the same or different. Exemplary multivalent peptides can be produced using the well-known multiple antigen peptide system (MAPS; see, e.g., Briand et al., 1992, *J. Immunol Meth.*, 156(2):255–265; Schott et al., 1996, *Cell Immun.*, 174(2):199–209, and the like). An agent that is multivalent with respect to the number of derepressor TAP-inhibited caspase sequences or moieties present can be useful for interacting with an IAP having more than one BIR domain. For example, a single agent can be made to contain two or more sequences or moieties that interact with separate BIR domains on the same TAP. The presence of multiple interacting partners in the multivalent agent and TAP can increase affinity or specificity of the interaction.

In some cases, it can be desirable to allow a derepressor of an IAP-inhibited caspase to remain active for only a short period of time. In those cases, the incorporation of one or more L-amino acids in the agent can allow, for example, endogenous peptidases in a subject to digest the agent in vivo, thereby limiting the subject's exposure to the derepressor. In one embodiment, the agent, whether based on a peptide backbone or other structure, can include a peptide linkage through an L-aspartate moiety or residue. Degradation of the L-aspartate containing agent by the caspases that it derepresses can provide a feedback control mechanism minimizing the extent of apoptosis allowed by the agent. The skilled artisan can determine the desirable characteristics required of an invention agent by taking into consideration, for example, the age and general health of a subject, and the like. The half life in a subject of a peptide having, for example, one or more D-amino acids substituted for a corresponding L-amino acid can be determined using methods well known to those in the field of pharmacology.

Selective modification of the reactive groups in a peptide also can impart desirable characteristics to a derepressor of an IAP-inhibited caspase. An invention peptide can be manipulated while still attached to the resin to obtain, for example, an N-terminal modified peptide such as an N-acetylated peptide. Alternatively, the peptide can be removed from the resin using hydrogen fluoride or an equivalent cleaving reagent and then modified. Agents synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus and methods for amidation of the C-terminus.

Also encompassed within the scope of invention peptides are peptide analogs. As used herein, the term "peptide analog" includes any peptide having an amino acid sequence substantially the same as a sequence specifically shown herein, such as Core peptides 1 through 55, in which one or more residues have been conservatively substituted with a functionally similar residue and which displays the ability to functionally mimic an invention lectin-binding peptide as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

As used herein the phrase "conservative substitution" also includes the use of a chemically derivatized residue in place of a non-derivatized residue, provided that such peptide displays the required IAP binding or inhibiting activity. A chemical derivative can include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides of the present invention also include any peptide having one or more additions, deletions or combination of additions and deletions of residues, relative to the sequence of a peptide whose sequence is shown herein, so long as the required IAP binding or inhibiting activity is maintained.

Those skilled in the art will recognize from the guidance provided herein that an agent of the invention can include a core peptide or core structure that is modified, derivatized, or substituted with an analogs or derivative so long as the agent is capable of derepressing an IAP-inhibited caspase. Such alterations in a core peptide or core structure can be made by well known synthetic methods such as those described herein. An agent so altered can be tested for activity using the methods described herein such as the derepression assay described in Example I or the polarization binding assay described in Example VII.

An agent identified as a derepressor of an IAP-inhibited caspase can be tested using an assay for determining caspase proteolytic activity or binding of IAP and caspase in the presence or absence of the agent including, for example, the assays described above. An agent that is identified as capable of derepressing an IAP-inhibited caspase using such assays can be further combinatorialized at one or more positions using the iteration approach described above. Alternatively, an identified derepressor or plurality of derepressors can be used as a basis for the rational design of second generation agents. For example, common structural features between a plurality of validated agents can be used to guide the synthesis of a generalized structure incorporating those shared features. Structural information regarding an agent when bound to an IAP or caspase can also be used to design a second generation agent that retains or improves upon moieties identified as providing favorable interactions while removing moieties that lead to unfavorable interactions with the caspase or IAP.

The invention provides a method of identifying an agent that derepresses an IAP-inhibited caspase. The method includes the steps of (a) detecting a labeled derepressor of an IAP-inhibited caspase bound to an IAP or caspase; (b) contacting the bound IAP or caspase with a candidate agent, the candidate agent suspected of being able to derepress an IAP-inhibited caspase; and (c) detecting dissociation of the labeled derepressor of an IAP-inhibited caspase from the IAP or caspase, whereby the candidate agent is identified as an agent that derepresses an IAP-inhibited caspase. A labeled derepressor of an IAP-inhibited caspase used in the method can have a core motif selected from a core peptide of the invention such as Core peptides 4 through 39 and 42 through 55 or a core structure selected from TPI759, TPI882, TPI914 or TPI927. The methods can be used to identify a better derepressor of an IAP-inhibited caspase in a screening format as described above and in the Examples.

A derepressor of an IAP-inhibited caspase used in a method of the invention can be labeled with any of a variety of labels including, for example, those described above. A labeled derepressor that is bound to an IAP or caspase can be detected according to a known measurable property of the label. For example, a fluorophore can be detected based on the excitation or emission wavelengths of the fluorophore, fluorescence polarization of the fluorophore, or intensity of fluorescence emitted from the fluorophore. Alternatively, detection can be based on a difference in a measurable property of the label for the bound and unbound state. For example, as demonstrated in Example VII, difference in fluorescence polarization due to the slower rotation of a substrate bound to an IAP compared to the unbound substrate can be used to detect association. Other measurable differences that can be used to determine association of a fluorophore-labeled agent with an IAP or caspase include, for example, different emission intensity due to the presence or absence of a quenching agent, difference in emission wavelength due to the presence or absence of a fluorescence resonance energy transfer (FRET) donor or acceptor, or difference in emission wavelength due to differences in fluorophore conformation or environment.

Dissociation of the labeled derepressor of an IAP-inhibited caspase from the IAP or caspase can be detected as absence or reduction in the amount of label from the IAP or caspase in the presence of a competitive binding candidate agent or as a reversal of a change that occurs upon association of the labeled agent with a caspase or IAP in the presence of a competitive binding candidate agent. Thus, dissociation can be detected in the presence of a non-labeled candidate agent as a reduction or loss of radioactivity of the IAP or caspase in the presence of a radionucloetide labeled derepressor, reduction or loss of electromagnetic absorbance at a specified wavelength for the IAP or caspase in the presence of a chromophore labeled derepressor, reduction or loss of magnetic signal at a specified field strength or radio frequency for the IAP or caspase in the presence of a paramagnetic spin labeled derepressor or reduction or loss of a secondary label associated with the IAP or caspase in the presence of a derepressor that is labeled with a binding group for the secondary label. An example of dissociation measured by the reversal of a change occurring upon association is provided in Example VII, where a difference in polarization due to the faster rotation of a dissociated substrate compared to the IAP-bound substrate is used to detect dissociation.

Other changes in a property of a label that can be detected to determine association or dissociation of an appropriately-labeled derepressor and IAP or caspase include, for example, absorption and emission of heat, absorption and emission of electromagnetic radiation, affinity for a receptor, molecular weight, density, mass, electric charge, conductivity, magnetic moment of nuclei, spin state of electrons, polarity, molecular shape, or molecular size. Properties of the surrounding environment that can change upon association or dissociation of an appropriately labeled derepressor and IAP or caspase include, for example, temperature and refractive index of surrounding solvent. Association and dissociation of a derepressor from an IAP or caspase can be measured based on any of a variety of properties of a labeled derepressor or of the complex between a derepressor and IAP or caspase using well known methods including, for example, equilibrium binding analysis, competition assays, and kinetic assays as described in Segel, *Enzyme Kinetics* John Wiley and Sons, New York (1975), and Kyte, *Mechanism in Protein Chemistry* Garland Pub. (1995).

The invention further provides a method for identifying a derepressor of an IAP-inhibited caspase in a database. A database of molecules such as peptides or small molecules can be queried with the structure of a derepressor of an IAP-inhibited caspase to identify candidate agents having a moiety identical or similar to the query structure. A candidate agent identified in a database search can be synthesized, isolated or otherwise obtained using known methods and then tested for its level of activity as a derepressor of an IAP-inhibited caspase using the assays described above and in the Examples.

For peptide based derepressors, a query can be made to a database based on amino acid sequence (primary structure) or three dimensional structure (tertiary structure) or a combination of both to identify peptides or proteins having identical or substantially similar structures. Methods for comparing primary sequence structure which can be used to determine that two sequences are substantially the same are well known in the art as are databases including, for example, SwissProt and GenPept. For example, one method for determining if two sequences are substantially the same is BLAST, Basic Local Alignment Search Tool, which can be used according to default parameters as described by Tatiana et al., *FEMS Microbial Lett.* 174:247–250 (1999) or on the National Center for Biotechnology Information web page. BLAST is a set of similarity search programs designed to examine all available sequence databases and can function to search for similarities in amino acid or nucleic acid sequences. A BLAST search provides search scores that have a well-defined statistical interpretation. Furthermore, BLAST uses a heuristic algorithm that seeks local alignments and is therefore able to detect relationships among sequences which share only isolated regions of similarity including, for example, protein domains (Altschul et al., *J. Mol. Biol.* 215:403–410 (1990)).

In addition to the originally described BLAST (Altschul et al., supra, 1990), modifications to the algorithm have been made (Altschul et al., *Nucleic Acids Res.* 25:3389–3402 (1997)). One modification is Gapped BLAST, which allows gaps, either insertions or deletions, to be introduced into alignments. Allowing gaps in alignments tends to reflect biologic relationships more closely. For example, gapped BLAST can be used to identify sequence identity within similar domains of two or more polypeptides. A second modification is PSI-BLAST, which is a sensitive way to search for sequence homologs. PSI-BLAST performs an initial Gapped BLAST search and uses information from any significant alignments to construct a position-specific score matrix, which replaces the query sequence for the next round of database searching. A PSI-BLAST search is often more sensitive to weak but biologically relevant sequence similarities.

A second resource that can be used to determine if two sequences are substantially the same is PROSITE, available on the world wide web at ExPASy. PROSITE is a method of determining the function of uncharacterized polypeptides translated from genomic or cDNA sequences (Bairoch et al., *Nucleic Acids Res.* 25:217–221 (1997)). PROSITE consists of a database of biologically significant sites and patterns that can be used to identify which known family of polypeptides, if any, the new sequence belongs. Using this or a similar algorithm, a polypeptide that is substantially the same as another polypeptide can be identified by the occurrence in its sequence of a particular cluster of amino acid residues, which can be called a pattern, motif, signature or fingerprint, that is substantially the same as a particular cluster of amino acid residues in a reference polypeptide including, for example, those found in similar domains. PROSITE uses a computer algorithm to search for motifs that identify polypeptides as family members. PROSITE also maintains a compilation of previously identified motifs, which can be used to determine if a newly identified polypeptide is a member of a known family.

Tertiary structure of a derepressor of an IAP-inhibited caspase can be determined by a theoretical method such as ab initio protein folding using algorithms known in the art or by an empirical method such as X-ray crystallographic or nuclear magnetic resonance based structure determination. A structural model of a derepressor can be used in an algorithm that compares polypeptide structure including, for example, SCOP, CATH, or FSSP which are reviewed in Hadley and Jones, *Structure* 7:1099–1112 (1999) and regions having a particular fold or conformation used as a region for sequence comparison to a second polypeptide to identify substantially similar regions.

Similar database searching methods can be used for non-peptide based derepressors or to query a database of non-peptide based candidate agents based on structure. A database can be searched, for example, by querying based on chemical property information or on structural information. In the latter approach, an algorithm based on finding a match to a template can be used as described, for example, in Martin, "Database Searching in Drug Design," *J. Med. Chem.* 35:2145–2154 (1992).

A derepressor of an IAP-inhibited caspase can also be identified in a database using the results of a positional scanning synthetic combinatorial library as a query. Such results can be represented as a motif and the motif used to search a database for a derepressor of an IAP-inhibited caspase. Motif searches are generated from screening results of positional scanning synthetic combinatorial libraries, and contained in each position are amino acids corresponding to mixtures having an activity threshold greater than a specified value. An example of an activity threshold is the ratio of $V_{max}$ for caspase activity in the presence and absence of a candidate agent as described in Example I. Motif based database searching is known in the art as described, for example, in Hemmer et al., *Nat. Med.* 5:1375–1382 (1999), Hemmer et al., *J. Exp. Med.* 185:1651–1659 (1997) and Hemmer et al., *Immunol Today* 19:163–168 (1998).

Alternatively, results from a positional scanning synthetic combinatorial library can be represented as a score matrix and the score matrix used to query for other derepressors of an IAP-inhibited caspase in a sequence database. Methods for identifying candidate peptides or proteins based on score-matrix based searches of a databases are described in Zhao et al., *J. Immunol.* 167:2130–2141 (2001). Briefly, a matrix is constructed in which columns represent positions, rows represent the 20 amino acids and each is correlated with a score. The score for a particular position and amino acid is based on assay results for the mixture of a positional scanning synthetic combinatorial library corresponding to that amino acid defined at that position. For example, each score can correspond to the ratio of $V_{max}$ for caspase activity in the presence and absence of the mixture corresponding to the amino acid defined at the particular position. The scoring matrix is then used to search for candidate derepressors of an IAP-inhibited caspase by moving the scoring matrix across database entries in 1 amino acid increments. A score is calculated for the database entries searched and each is ranked. Those having a score above a predetermined cutoff are identified as candidate derepressors of an IAP-inhibited caspase.

The invention provides a method of derepressing an IAP-inhibited caspase, by contacting an IAP-inhibited caspase with an effective amount of an agent to derepress an IAP-inhibited caspase, the agent having a core motif selected from a core peptide of the invention, such as core peptides 4 through 39 and 42 through 55, or a core structure of the invention such as TPI759, TPI882, TPI914 or TPI927.

For inhibiting a caspase inhibitory activity of an inhibitor of apoptosis protein (IAP), the IAP-inhibited caspase is contacted with an amount of derepressor effective to derepress the IAP-inhibited caspase. Thus, an effective amount of the agent is an amount that is sufficient to yield an increase in caspase proteolytic activity from the derepressed IAP-inhibited caspase compared to the caspase activity for an IAP-inhibited caspase. An increase in proteolytic activity from a derepressed IAP-inhibited caspase can be determined using any of the methods described above in reference to a method for identifying a derepressor of an IAP-inhibited caspase.

An agent of the invention can be contacted with an IAP-inhibited caspase under conditions suitable for caspase activity to occur once an IAP is inhibited from inhibiting the caspase. Such conditions include those described in Example I. The agent that is contacted with the IAP-inhibited caspase can be present in a mixture of compounds, in an isolated form or in substantially pure form. As described above, a mixture of compounds can be contacted with an IAP-inhibited caspase in a screening method employing positional scanning or iteration. Such a mixture can be identified as having the ability to derepress an IAP-inhibited caspase. The mixture can be used in the methods of the invention to derepress an IAP inhibited caspase. Alternatively, a particular species in the mixture having such activity can be further defined by isolating individual species in the mixture and repeating the derepression assay or performing a second assay for derepression of an IAP-inhibited caspase. An agent that derepresses an IAP-inhibited caspase can be contacted with the IAP-inhibited caspase in a substantially pure form, as a conjugate or in a formulation as described above.

In a further embodiment of the invention an IAP-inhibited caspase can be contacted with an agent of the invention in a cell. Accordingly, the invention provides a method of promoting apoptosis in a cell, by contacting the cell with an effective amount of an agent to derepress an IAP-inhibited caspase, the agent having a core motif selected from a core peptide of the invention, such as Core peptides 4 through 39 and 42 through 55, or a core structure of the invention such as TPI759, TPI882, TPI914 or TPI927.

Methods described herein for cytosolic delivery of an IAP-inhibited caspase, such as attachment of a moiety of conjugate, can be used in a method of promoting apoptosis in a cell. An effective amount of the agent can be identified as an amount sufficient to allow apoptosis to occur in the cell. Methods of determining morphological changes in a cell or nucleus that are characteristic of apoptosis, such as those described above in relation to identifying a derepressor of an IAP-inhibited caspase, can be used to monitor apoptosis while performing a method of promoting apoptosis in a cell.

The invention also provides a method for reducing the ability of a population of cells to survive ex vivo. The method can include the steps of contacting the cells with an agent of the invention, wherein the agent derepresses an IAP-inhibited caspase. The cells can be contacted with the agent using the methods described above for promoting apoptosis in a cell. The methods can be used to remove a particular subpopulation of cells in a sample using the targeting methods described above, such as the attachment of a targeting moiety to the agent.

The methods of the invention can be carried out in a cell from any organism in which apoptosis can occur when an IAP-inhibited caspase is derepressed including, for example, a eukaryotic cell, such as a mammalian cell, human cell, non human-primate cell, mouse cell, hamster cell, or other animal cell; an invertebrate cell such as a fly or nematode cell or a yeast cell. Various cell types can be used in the methods of the invention including, for example, a tumor cell, stem cell, neural cell, fat cell, hamatopoietic cell, liver cell or muscle cell. In particular the methods are useful for inducing apoptosis in aberrantly regulated cells including, for example, cells that exhibit uncontrolled cell proliferation as well as cells that exhibit dysfunction in specific phases of the cell cycle, leading to altered proliferative characteristics or morphological phenotypes. Specific examples of aberrantly regulated cell types include neoplastic cells such as cancer and hyperplastic cells characteristic of tissue hyperplasia. Another specific example includes immune cells that become aberrantly activated or fail to down regulate following stimulation. Autoimmune diseases are mediated by such aberrantly regulated immune cells. Aberrantly regulated cells also includes cells that are biochemically or physiologically dysfunctional. Other types of aberrant regulation of cell function or proliferation are known to those skilled in the art and are similarly target cells of the invention applicable for apoptotic destruction using the methods of the invention.

Because a number of characteristic changes associated with apoptosis of a cell are due to the proteolytic activity of caspases, the methods can be used to induce characteristic changes of apoptosis. For example, caspase induced proteolysis of lamin B, which is involved in attachment of chromatin to the nuclear envelope, can be responsible for collapse of the chromatin associated with apoptosis (Martin and Green, supra, 1995). Caspase induced proteolysis of the 45 kDa subunit of DNA fragmentation factor (DFF-45) activates a pathway leading to fragmentation of genomic DNA into nucleosomal fragments (Liu et al., *Cell* 89:175–184 (1997)). In addition, caspase induced proteolysis of PARP can prevent the ability of PARP to repair DNA damage, further contributing to the morphologic changes associated with apoptosis. Thus, the methods of the invention can be used to induce collapse of the chromatin and fragmentation of genomic DNA associated with apoptosis. Other caspase target proteins include sterol regulatory element binding proteins; retinoblastoma (RB) protein; DNA-dependent kinase; U1 70-K kinase; and the large subunit of the DNA replication complex (Wang et al., *EMBO J.* 15:1012–1020 (1996); Takahashi et al., *Proc. Natl. Acad. Sci., USA* 93:8395–8400 (1996); Casciola-Rosen et al., *J. Exp. Med.* 183:1957–1964 (1996); and Ubeda and Habener, *J. Biol. Chem.* 272:19562–19568 (1997)) each of which can be induced to be proteolyzed by the methods of the invention.

In mammalian cells, activation of caspases is achieved through at least two independent mechanisms, which are initiated by distinct caspases but result in activation of common "executioner" caspases. Apoptosis initiated by ligand binding to the Fas receptor is one well described cell death pathway. In this pathway, binding of a ligand to Fas allows the intracellular domain of Fas to bind the intracellular MORT1 (FADD) protein, which, in turn, binds to caspase-8 (MACH; FLICE; Mch5; see Boldin et al., *Cell* 85:803–815 (1996); Muzio et al., *Cell* 85:817–827 (1996)). These results define caspase-8 as an upstream caspase involved in the Fas cell death pathway. In addition, caspase-3 is activated in the Fas cell death pathway, suggesting that an upstream protease such as caspase-8 or a protease activated by caspase-8 is involved in caspase-3 activation. Accordingly, the methods of the invention can be used to directly derepress IAP inhibited-caspase-8 thereby effectively derepressing the downstream caspase-3 protease.

Caspase activation also can involve cytochrome c, which in mammalian cells is often released from mitochondria into the cytosol during apoptosis (Liu et al., *Cell* 86:147–157 (1996); Kharbanda et al., *Proc. Natl. Acad. Sci., USA* 94:6939–6942 (1997); Kluck et al., *Science* 275:1132–1136 (1997); and Yang et al., *Science* 275:1129–1132 (1997)). Upon entering the cytosol, cytochrome c induces the ATP- or dATP-dependent formation of a complex of proteins that results in proteolytic activation of pro-caspase-3 and apoptotic destruction of nuclei (Liu et al., supra, 1996). Among the members of this complex are the CED-4 homolog Apaf-1, and caspase-9 (Apaf-3; Liu et al., supra, 1996; Li et al., *Cell* 91:479–489 (1997); Zou et al., *Cell* 90:405–413 (1997)). XIAP, c-IAP-1 and c-IAP-2 suppress apoptosis induced by stimuli known to cause release of cytochrome c from mitochondria and can inhibit caspase activation induced by cytochrome c in vitro. Thus, the agents and methods of the invention can be used to allow apoptosis to occur in response to release of cytochrome c from mitochondria by suppressing inhibition of a caspase by XIAP, c-IAP-1 or c-IAP-2.

The invention further provides a method of reducing the severity of a pathologic condition in an individual, by administering to an individual having a pathologic condition characterized by a pathologically reduced level of apoptosis, an effective amount of an agent to derepress an IAP-inhibited caspase. Examples of conditions characterized by pathologically reduced levels of apoptosis that can be treated in a method of the invention include, but are not limited to, restenosis; autoimmune disease such as lupus or Rheumatoid Arthritis; allograft rejection, proliferative lesions of the skin such as Eczema; or benign prostate hypertrophy The agent can have a core motif selected from a core peptide of the invention, such as Core peptides 4 through 39 and 42 through 55, or a core structure of the invention such as TPI759, TPI882, TPI914 or TPI927.

An effective amount of an agent that derepresses an IAP-inhibited caspase when used to treat a pathological condition is an amount required to allow an increase in apoptosis when administered to an individual. The dosage of an agent of the invention required to be therapeutically effective will depend, for example, on the pathological condition to be treated, the route and form of administration, the weight and condition of the individual, and previous or concurrent therapies. The appropriate amount considered to be an effective dose for a particular application of the method can be determined by those skilled in the art, using the guidance provided herein. For example, the amount can be extrapolated from in vitro or in vivo assays as described previously. One skilled in the art will recognize that the condition of the patient can be monitored throughout the course of therapy and that the amount of the agent that is administered can be adjusted accordingly.

For treating or reducing the severity of a pathological condition, an effective amount is an efficious amount of the agent capable of increasing apoptosis that is pathologically reduced. An effective amount can be, for example, between about 10 $\mu$g/kg to 500 mg/kg body weight, for example, between about 0.1 mg/kg to 100 mg/kg, or preferably between about 1 mg/kg to 50 mg/kg, depending on the treatment regimen. For example, if an agent or formulation containing the agent is administered from one to several times a day, then a lower dose would be needed than if a formulation were administered weekly, or monthly or less frequently. Similarly, formulations that allow for timed-release of the agent, such as those described above, would provide for the continuous release of a smaller amount of derepressor of apoptosis than would be administered as a single bolus dose. For example, an agent of the invention can be administered at between about 1–5 mg/kg/week.

Formulations of a derepressor of an IAP-inhibited caspase, variants and combinations thereof can also be delivered in an alternating administrations so as to combine their apoptosis increasing effects over time. For example, an agent having a core peptide or structure of the invention can be administered in a single bolus dose followed by multiple administrations of one or more such agents species or variant alone, or in combination with a different formulation of such an agent or formulation of a different agent. Whether simultaneous or alternating delivery of the agent formulation, variant or combination thereof, the mode of administration can be any of those types of administrations described previously and will depend on the particular therapeutic need and efficacy of the derepressor of an IAP-inhibited caspase selected for the purpose. Determining which agent, formulation, species and variants to combine in a temporally administered regime, will depend on the pathological condition to be treated and the specific physical characteristics of the individual affected with the disease. Those skilled in the art will know or can determine a specific regime of administration which is effective for a particular application using the teachings and guidance provided herein together with diagnostic and clinical criteria known within the field of art of the particular pathological condition.

The methods of treating a pathological condition characterized by pathologically reduced apoptosis additionally can be practiced in conjunction with other therapies. For example, for treating cancer, the methods of the invention can be practiced prior to, during, or subsequent to conventional cancer treatments such as surgery, chemotherapy, including administration of cytokines and growth factors, radiation or other methods known in the art. As set forth above and demonstrated by the results of Example X, TPI792-33 or TPI792-35 can be administered in conjunction with VP-16 to treat cancer.

Similarly, for treating pathological conditions which include infectious disease, the methods of the invention can be practiced prior to, during, or subsequent to conventional treatments, such as antibiotic administration, against infectious agents or other methods known in the art. Treatment of pathological conditions of autoimmune disorders also can be accomplished by combining the methods of the invention for derepressing an IAP-inhibited caspase with conventional treatments for the particular autoimmune diseases. Conventional treatments include, for example, chemotherapy, steroid therapy, insulin and other growth factor and cytokine therapy, passive immunity, inhibitors of T cell receptor binding and T cell receptor vaccination. The methods of the invention can be administered in conjunction with these or other methods known in the art and at various times prior, during or subsequent to initiation of conventional treatments. For a description of treatments for pathological conditions characterized by aberrant cell growth see, for example, *The Merck Manual,* Sixteenth Ed, (Berkow, R., Editor) Rahway, N.J., 1992. Furthermore, anti-cancer drugs including, for example, any of those set forth above with regard to combination compositions, can be administered prior to, during, or subsequent to administration of a derepressor of an IAP-inhibited caspase in a method of treatment.

As described above, administration of a formulation of an agent that derepresses an IAP-inhibited caspase can be, for example, simultaneous with or delivered in alternative administrations with the conventional therapy, including multiple administrations. Simultaneous administration can be, for example, together in the same formulation or in different formulations delivered at about the same time or immediately in sequence. Alternating administrations can be, for example, delivering an agent of the invention and a conventional therapeutic treatment in temporally separate administrations. As described previously, the temporally separate administrations of an agent of the invention and conventional therapy can similarly use different modes of delivery and routes.

A condition characterized by a pathologically reduced level of apoptosis that can be treated using the agents and methods of the invention include, for example, cancer, hyperplasia, autoimmune disease and restenosis. A growing number of human diseases have been classified as autoimmune and include, for example, rheumatoid arthritis, myasthenia gravis, multiple sclerosis, psoriasis, systemic lupus erythematosus, autoimmune thyroiditis, Graves' disease, inflammatory bowel disease, autoimmune uveoretinitis, polymyositis and diabetes. Animal models for many conditions characterized by a pathologically reduced level of apoptosis have been developed and can be employed for predictive assessment of therapeutic treatments employing an agent that derepresses an IAP-inhibited caspase.

Moreover, pharmaceutical compositions of a derepressor of IAP-inhibited caspase can be reliably extrapolated for the treatment of these conditions from such animal models.

Those skilled in the art will know how to determine efficacy or amounts of an agent of the invention to administer based on the results of routine tests in a relevant animal model. The amount of an agent to be administered can be determined in a clinical setting as well based on the response in a treated individual. Modulation of efficacy, will depend on the pathological condition and the extent to which progression of apoptosis is desired for treatment or reduction in the severity of the pathological condition. Modulation can be accomplished by adjusting the particular agent used to derepress an IAP-inhibited caspase, formulation, or dosing strategy. Based on the guidance provided herein, those skilled in the art will be able to modulate efficacy in response to well known indicators of the severity of the particular condition being treated. For a description of indicators for the various pathological conditions described herein or otherwise known to be characterized by a pathologically reduced level of apoptosis see, for example, *The Merck Manual*, Sixteenth Ed, (Berkow, R., Editor) Rahway, N.J., 1992.

The following examples are intended to illustrate but not limit the present invention.

EXAMPLE I

Identification of Derepressors of an IAP-Inhibited Caspase from Hexapeptide Libraries This example demonstrates an IAP derepression assay. This Example further demonstrates a positional-scanning approach to identifying agents that are capable of derepressing an IAP-inhibited caspase.

The DCR390 library consisting of 120 mixtures of hexapeptides was synthesized using methods known in the art as described in R. Houghten et al. PCT/US91/08694 and U.S. Pat. No. 5,556,762. Each mixture was made up of a population of hexapeptides all of which had the same amino acid at a defined position and any combination of the 20 essential amino acids at the remaining 5 positions. Each mixture is identified by the position number where the defined amino acid occurs (numbered from 1 to 6 going from the amino-terminus to carboxy-terminus of the hexapeptide) and the identity of the defined amino acid. Thus, as shown in the first column of Table I, the mixture having a tryptophan at position 1 and all combinations of the 20 amino acids at positions 2 through 5 is identified as "position 1, W."

The DCR390 library was screened using the assay set forth below. Based on the mixtures identified from the DCR390 library screen as being capable of derepressing an IAP-inhibited caspase, additional defined positions were incorporated into the TPI1239 and TPI1328 sublibraries, and the sublibraries screened using the same assay.

Caspase activity was assayed by release of 7-amino-4-trifluoromethyl-coumarin (AFC) from Ac-DEVD-AFC synthetic peptides using a Molecular Devices Spectromax 340 (see Zhou et al., *J. Biol. Chem.* 272:7797–7800 (1997)). Candidate mixtures were screened for the ability to derepress an IAP-inhibited caspase by measuring AFC hydrolysis rates for mixtures containing purified recombinant caspase-3, Ac-DEVD-AFC, and GST-XIAP in the presence and absence of the candidate agent. The ratio of $V_{max}$ for hydrolysis of Ac-DEVD-AFC in the presence and absence of the candidate mixture was calculated and used to identify those that contain an agent that derepresses an IAP-inhibited caspase. The ratio=($V_{max}$ when candidate mixture, caspase 3 and XIAP are present)/($V_{max}$ when caspase 3 and XIAP are present).

Screening of each mixture from the DCR390, TPI1239 or TPI1328 library, respectively, using the above described assay was carried out as follows. Each mixture was aliquoted in a 25 microliter volume and in duplicate to a well of a 96 well microtiter plate. Into the first set of duplicate wells was added 25 microliters of caspase assay buffer (50 mM HEPES, pH 7.4, 100 mM NaCl, 10% sucrose, 10 mM DTT, 1 mM EDTA and 0.1% CHAPS) and into the second set of wells was added 25 microliters of a stock solution of 40 nM XIAP in caspase assay buffer. Each microtiter plate also had the following controls: (1) a buffer blank well to which was added 25 microliters of caspase assay buffer and 25 microliters of peptide carrier solvent, (2) an XIAP control well to which was added 25 microliters of peptide carrier solvent and 25 microliters of a stock solution of 40 nM XIAP in caspase assay buffer, and (3) a SMAC control well to which was added 25 microliters of a stock solution of 40 nM XIAP in caspase assay buffer, and 2.5 microliters of 4 mM SMAC peptide (H-Ala-Val-Pro-Ile-Ala-Gln-Lys-NH$_2$, SEQ ID NO:5) Into each of the sample and control wells was added 25 microliters of 0.64 nM caspase-3 solution followed by 25 microliters of 0.4 mM Ac-DEVD-AFC substrate. Fluorescence of liberated AFC was immediately detected from each well for 30 minutes at 30 second intervals. The Vmax for hydrolysis of AC-DEVD-AFC from each well was measured using the softmax software package.

Results of the screen for the DCR390 library are shown in Table I. Sets of mixtures having the same position fixed with different respective amino acids are arranged in 6 sections identified with the position number. Within each of the six sections are 3 columns showing (1) the identity of the fixed amino acid, (2) the apparent velocity of the reaction when candidate mixture, caspase 3 and XIAP are present, and (3) the apparent velocity of the reaction when candidate mixture, and caspase 3 are present. Also shown in each section are results for the XIAP control reaction. The mixtures in each section are arranged in descending order according to apparent velocity in the second column. Those mixtures having significantly higher apparent velocities compared to the XIAP control reaction are listed above the horizontal line and are thereby identified as containing an agent capable of derepressing an XIAP-inhibited caspase.

TABLE I

| Amino Acid | DCR 390 | |
|---|---|---|
| | XIAP + Mixtures | Mixtures |
| Position 1 | | |
| W | 43 | 63 |
| A | 35 | 67 |
| Y | 35 | 63 |
| F | 34 | 61 |
| C | 30 | 62 |
| L | 26 | 63 |
| I | 23 | 64 |
| E | 22 | 64 |
| T | 22 | 62 |
| V | 20 | 60 |
| M | 19 | 65 |
| G | 17 | 65 |
| P | 17 | 64 |
| Q | 17 | 66 |
| XIAP | 16 | 64 |
| R | 16 | 65 |

TABLE I-continued

DCR 390

| Amino Acid | XIAP + Mixtures | Mixtures |
|---|---|---|
| XIAP | 15 | 64 |
| H | 15 | 63 |
| K | 15 | 65 |
| S | 15 | 65 |
| D | 14 | 67 |
| N | 13 | 63 |
| XIAPX1.5 | 24 | |
| Position 2 | | |
| W | 57 | 58 |
| F | 44 | 58 |
| L | 38 | 61 |
| C | 36 | 64 |
| I | 32 | 61 |
| V | 30 | 59 |
| Y | 30 | 61 |
| A | 20 | 62 |
| D | 20 | 67 |
| P | 20 | 60 |
| R | 20 | 58 |
| XIAP | 19 | 63 |
| XIAP | 19 | 63 |
| G | 19 | 58 |
| H | 19 | 58 |
| M | 19 | 60 |
| E | 18 | 67 |
| N | 18 | 64 |
| T | 18 | 59 |
| Q | 17 | 59 |
| S | 17 | 59 |
| K | 16 | 61 |
| XIAPX1.5 | 29 | |
| Position 3 | | |
| F | 50 | 64 |
| I | 36 | 65 |
| W | 34 | 65 |
| L | 26 | 65 |
| C | 20 | 64 |
| V | 19 | 62 |
| A | 16 | 67 |
| H | 16 | 70 |
| K | 15 | 67 |
| Y | 14 | 63 |
| XIAP | 13 | 64 |
| XIAP | 13 | 64 |
| D | 13 | 66 |
| T | 13 | 62 |
| M | 12 | 67 |
| N | 12 | 64 |
| R | 12 | 67 |
| E | 11 | 63 |
| G | 11 | 63 |
| P | 11 | 67 |
| S | 11 | 68 |
| Q | 10 | 63 |
| XIAPX1.5 | 20 | |
| Position 4 | | |
| W | 52 | 63 |
| F | 37 | 61 |
| L | 23 | 61 |
| Y | 17 | 64 |
| C | 15 | 60 |
| I | 15 | 60 |
| V | 13 | 63 |
| XIAP | 12 | 61 |
| M | 12 | 64 |
| N | 12 | 63 |
| A | 11 | 64 |
| XIAP | 10 | 61 |
| D | 10 | 63 |
| E | 10 | 59 |
| G | 10 | 60 |
| H | 10 | 59 |
| P | 10 | 66 |
| Q | 10 | 64 |
| S | 10 | 62 |
| K | 9 | 60 |
| R | 9 | 62 |
| T | 9 | 62 |
| XIAPX1.5 | 18 | |
| Position 5 | | |
| W | 44 | 56 |
| Y | 23 | 57 |
| V | 15 | 57 |
| I | 14 | 57 |
| L | 14 | 52 |
| A | 13 | 57 |
| C | 12 | 54 |
| F | 12 | 53 |
| XIAP | 11 | 52 |
| XIAP | 11 | 52 |
| H | 11 | 57 |
| K | 11 | 55 |
| S | 11 | 57 |
| T | 11 | 56 |
| D | 10 | 54 |
| E | 10 | 53 |
| M | 10 | 49 |
| P | 10 | 54 |
| G | 9 | 57 |
| N | 9 | 52 |
| Q | 9 | 54 |
| R | 9 | 52 |
| XIAP1.5 | 17 | |
| Position 6 | | |
| W | 23 | 51 |
| R | 22 | 52 |
| A | 13 | 53 |
| C | 12 | 51 |
| G | 12 | 51 |
| K | 12 | 53 |
| Q | 11 | 50 |
| XIAP | 10 | 51 |
| XIAP | 10 | 51 |
| S | 10 | 53 |
| Y | 10 | 51 |
| D | 9 | 50 |
| E | 9 | 49 |
| L | 9 | 53 |
| M | 9 | 51 |
| N | 9 | 50 |
| T | 9 | 53 |
| V | 9 | 51 |
| F | 8 | 50 |
| H | 8 | 51 |
| I | 8 | 53 |
| P | 8 | 49 |
| XIAPX1.5 | 15 | |

Based on the results of the DCR390 screen, the TPI1239 library was synthesized and screened using the above-described caspase assay. In particular mixtures were synthesized having positions 5 and 6 defined as tryptophan, positions 3 and/or 4 defined variously, and the remaining positions randomized with the 20 essential amino acids as set forth in Table II. As shown in Table II, in the absence of XIAP the mixtures had an insignificant effect on caspase activity. Mixtures having ratios of 1.9 or higher in the presence of XIAP were identified as containing an agent capable of derepressing an IAP-inhibited caspase.

TABLE II

| | TPI 1239 | |
|---|---|---|
| Mixture | $\dfrac{V_{max}(\text{mix} + \text{casp3})}{V_{max}(\text{casp3})}$ | $\dfrac{V_{max}(\text{mix} + \text{casp3} + \text{XIAP})}{V_{max}(\text{casp3} + \text{XIAP})}$ |
| caspase 3 | 1.0 ± 0.0 | 5.1 ± 2.3 |
| Xiap + caspase3 | 0.2 ± 0.1 | 1.0 ± 0.0 |
| SMAC | 0.8 ± 0.0 | 3.8 ± 1.7 |
| XXFWWW SEQ ID NO: 11 | 0.9 ± 0.0 | 0.8 ± 0.1 |
| XXLWWW SEQ ID NO: 12 | 0.9 ± 0.0 | 0.7 ± 0.1 |
| XXWLWW SEQ ID NO: 13 | 0.9 ± 0.0 | 0.7 ± 0.1 |
| XXWWWW SEQ ID NO: 14 | 0.9 ± 0.0 | 0.8 ± 0.1 |
| XXXTWW | 0.8 ± 0.0 | 4.2 ± 1.6 |
| XXXAWW | 0.9 ± 0.0 | 3.7 ± 1.6 |
| XXXSWW | 0.8 ± 0.0 | 3.4 ± 1.1 |
| XXXQWW | 0.8 ± 0.0 | 2.4 ± 0.4 |
| XXXKWW | 0.9 ± 0.0 | 2.3 ± 1.0 |
| XXXVWW | 0.9 ± 0.0 | 2.2 ± 0.5 |
| XXXRWW | 0.9 ± 0.0 | 2.1 ± 0.2 |
| XXXHWW | 0.9 ± 0.0 | 2.1 ± 0.6 |
| XXXNWW | 0.9 ± 0.0 | 1.9 ± 0.5 |
| XXXPWW | 0.9 ± 0.0 | 1.5 ± 0.2 |
| XXXYWW | 0.9 ± 0.0 | 1.2 ± 0.3 |
| XXXDWW | 0.9 ± 0.0 | 1.1 ± 0.2 |
| XXXIWW | 0.9 ± 0.0 | 0.9 ± 0.1 |
| XXXLWW | 0.9 ± 0.0 | 0.9 ± 0.1 |
| XXXCWW | 0.9 ± 0.0 | 0.8 ± 0.2 |
| XXXEWW | 0.9 ± 0.0 | 0.8 ± 0.2 |
| XXXGWW | 0.9 ± 0.0 | 0.7 ± 0.1 |
| XXXMWW | 0.9 ± 0.0 | 0.6 ± 0.2 |
| XXXFWW | 0.9 ± 0.0 | 0.6 ± 0.1 |
| XXXWWW | 0.8 ± 0.0 | not determined |
| XXXXWW | 1.0 ± 0.0 | 2.0 ± 0.3 |

The mixtures identified from the TPI1239 library as containing an agent capable of derepressing an IAP-inhibited caspase were further analyzed for dose response. The dose response data is provided in FIGS. 11A–11C which shows that the mixtures had no effect on caspase activity. The most active mixtures were found to have alanine, lysine or threonine at position 4, tryptophan at positions 5 and 6 and mixtures at positions 1 through 3.

Based on the results of the DCR390 and TPI1239 library screens, the TPI1328 library was synthesized and screened using the above-described caspase assay. For each mixture in the TPI1328 library, 3 to 4 positions were defined and the remaining positions were combinatorialized with all 20 of the essential amino acids including Ala, Asp, Glu, Phe, Gly, His, Ile, Lys, Leu, Met, Asn, Pro, Gln, Arg, Ser, Thr, Val, Trp, Cys or Tyr. Position 4 was defined with Ala, Lys or a mixture of Ala, Lys and Thr (the mixture is referred to as "3X" or "A,K,T").

Figure 1B:
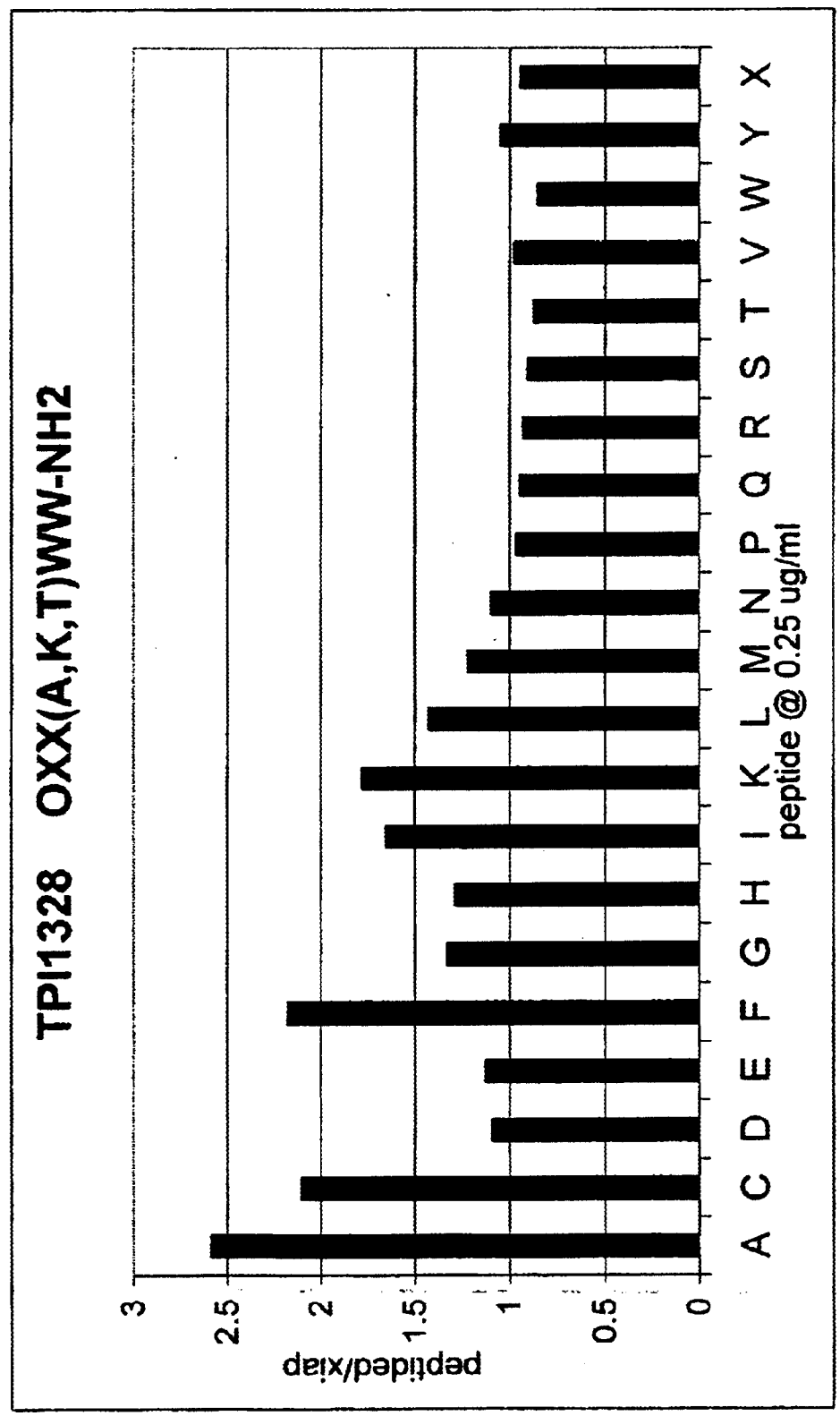
Figure 3B:
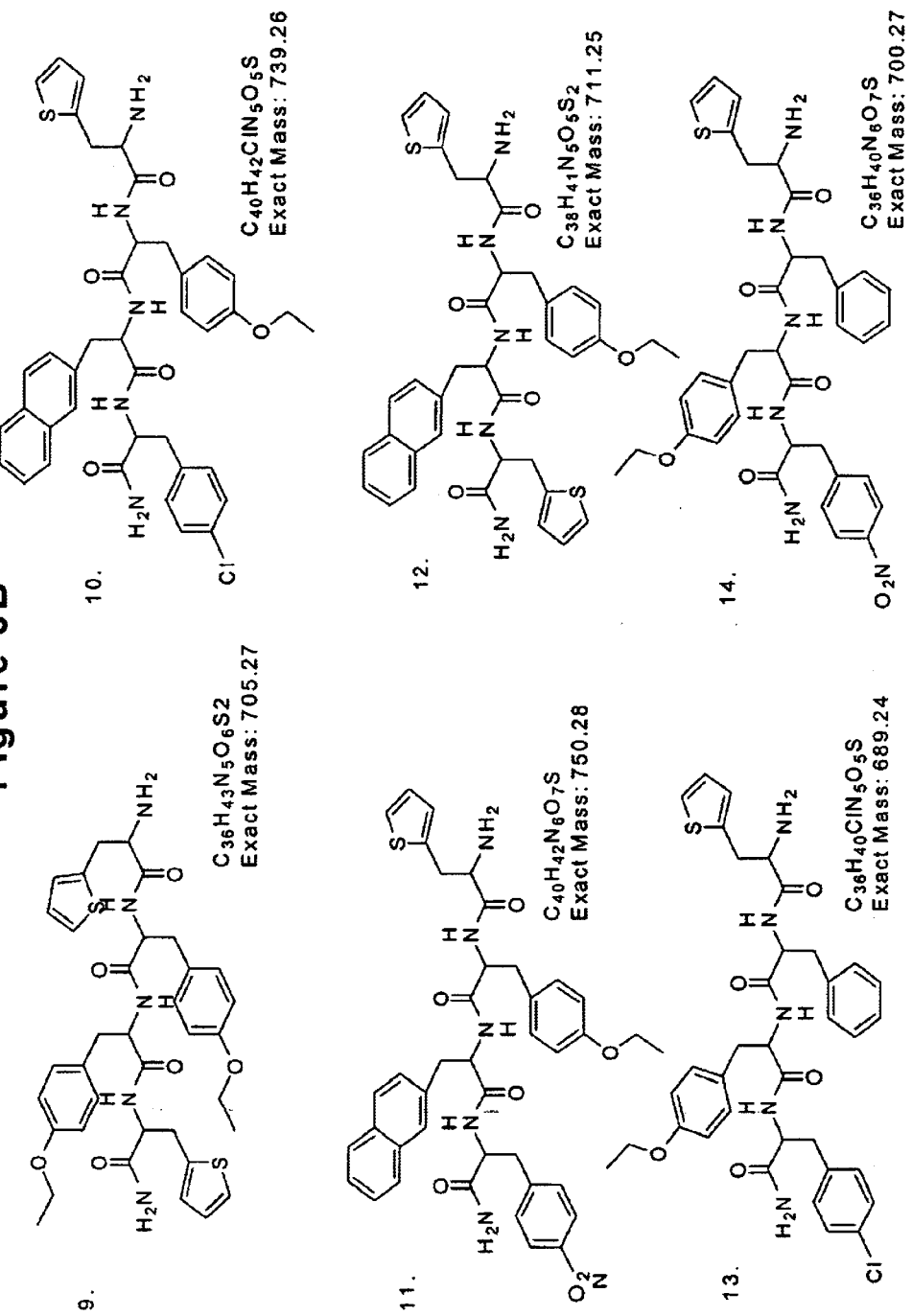
Figure 3C:
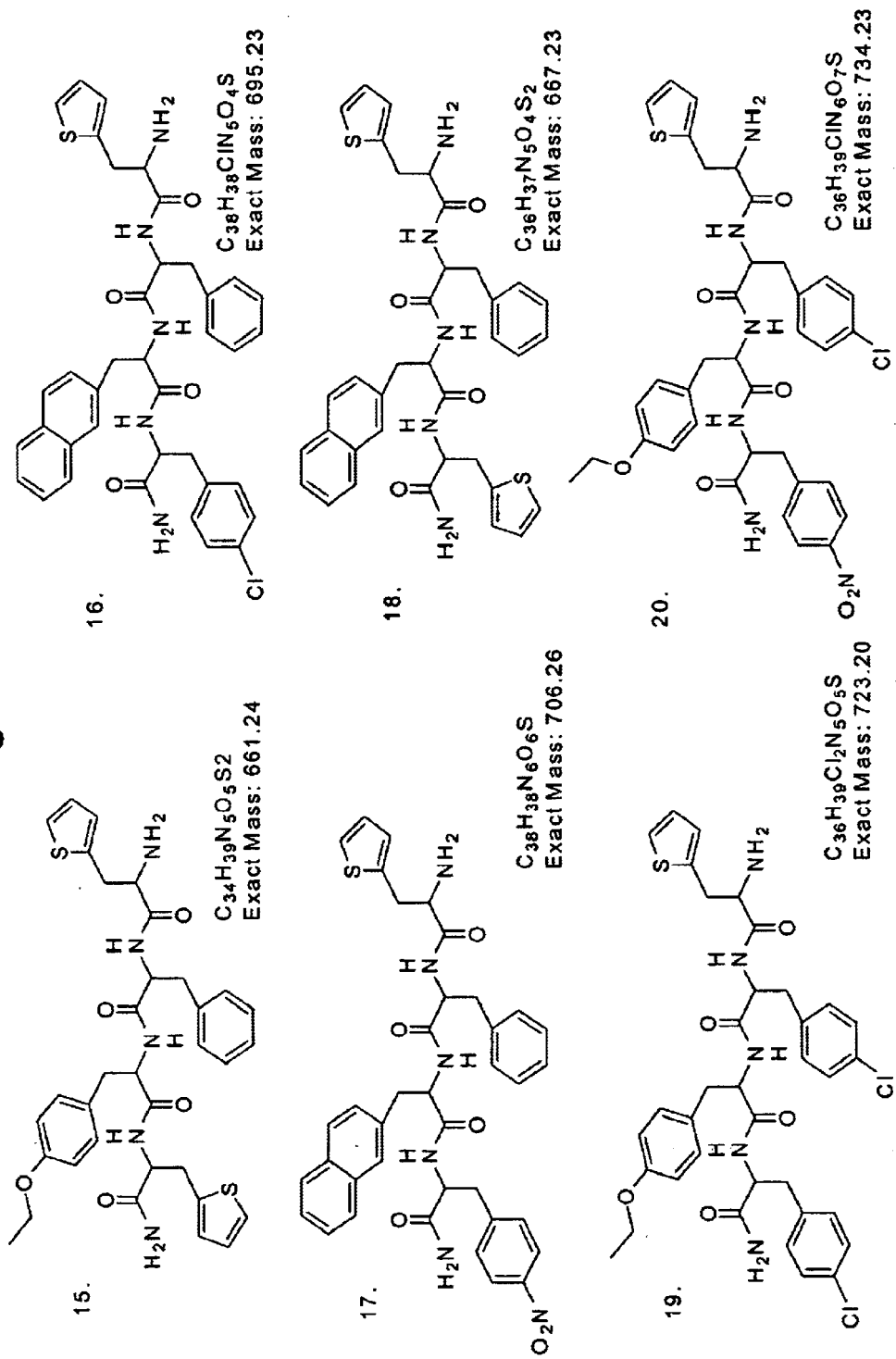
Figure 3D:
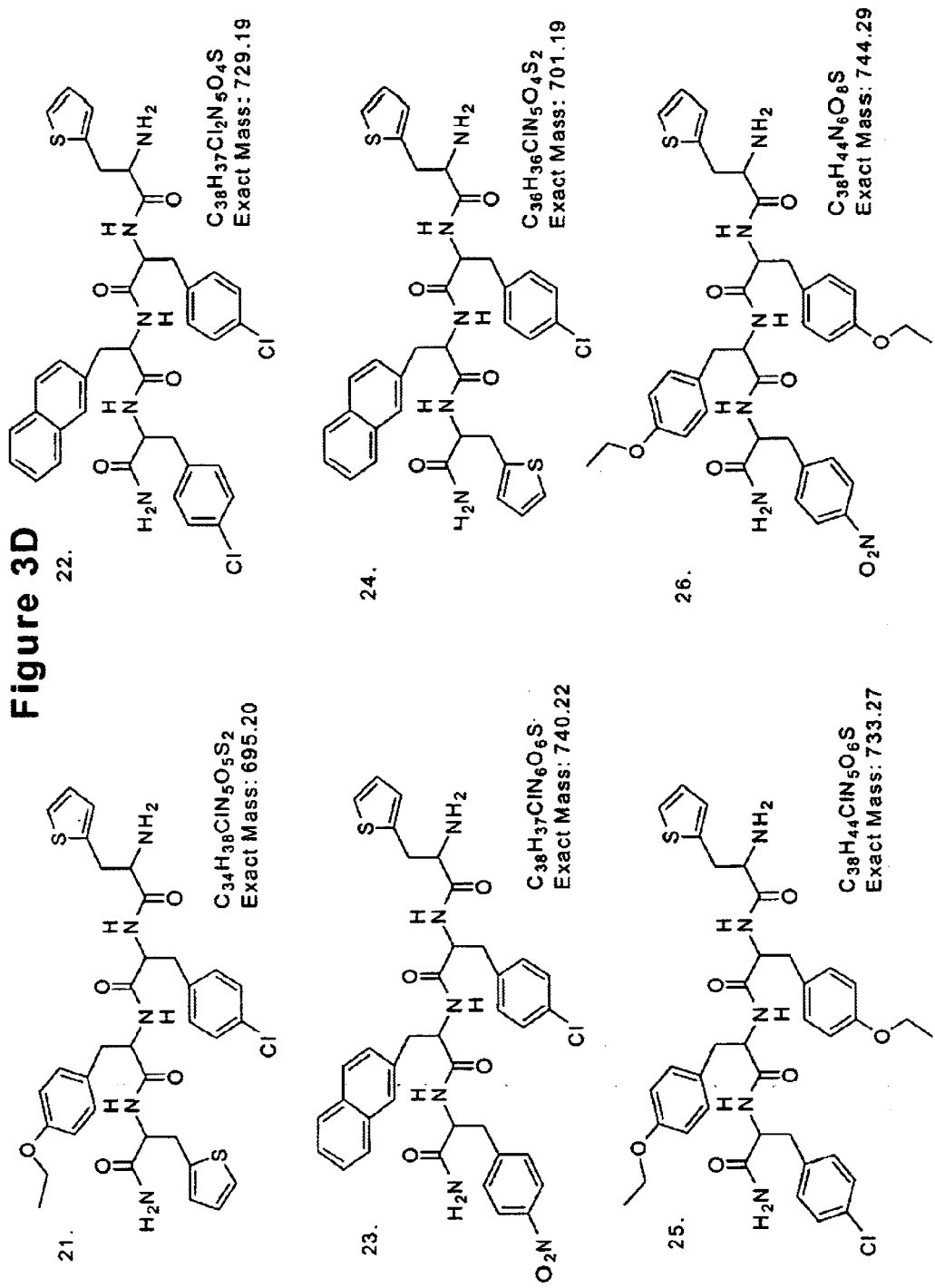
Figure 3E:
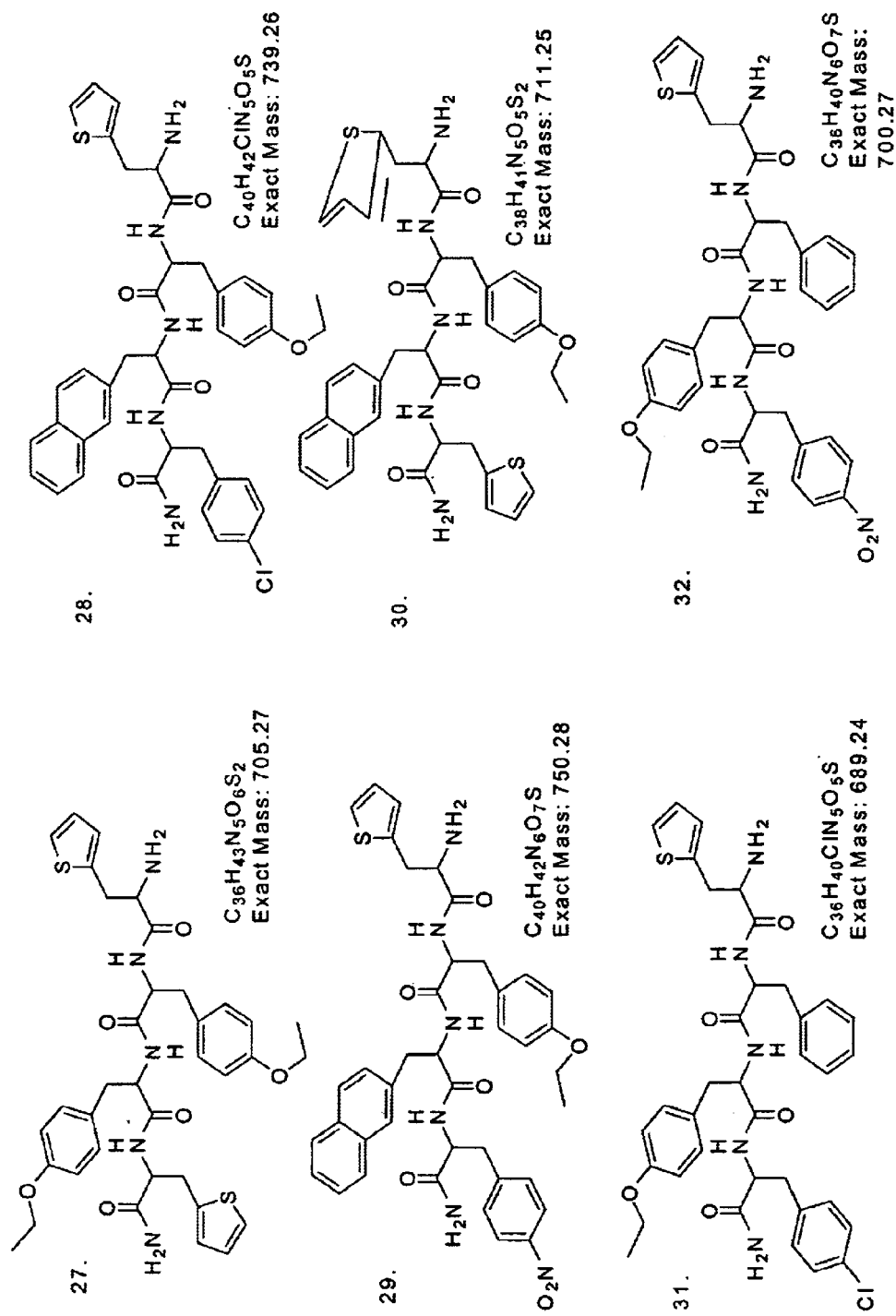
Figure 3F:
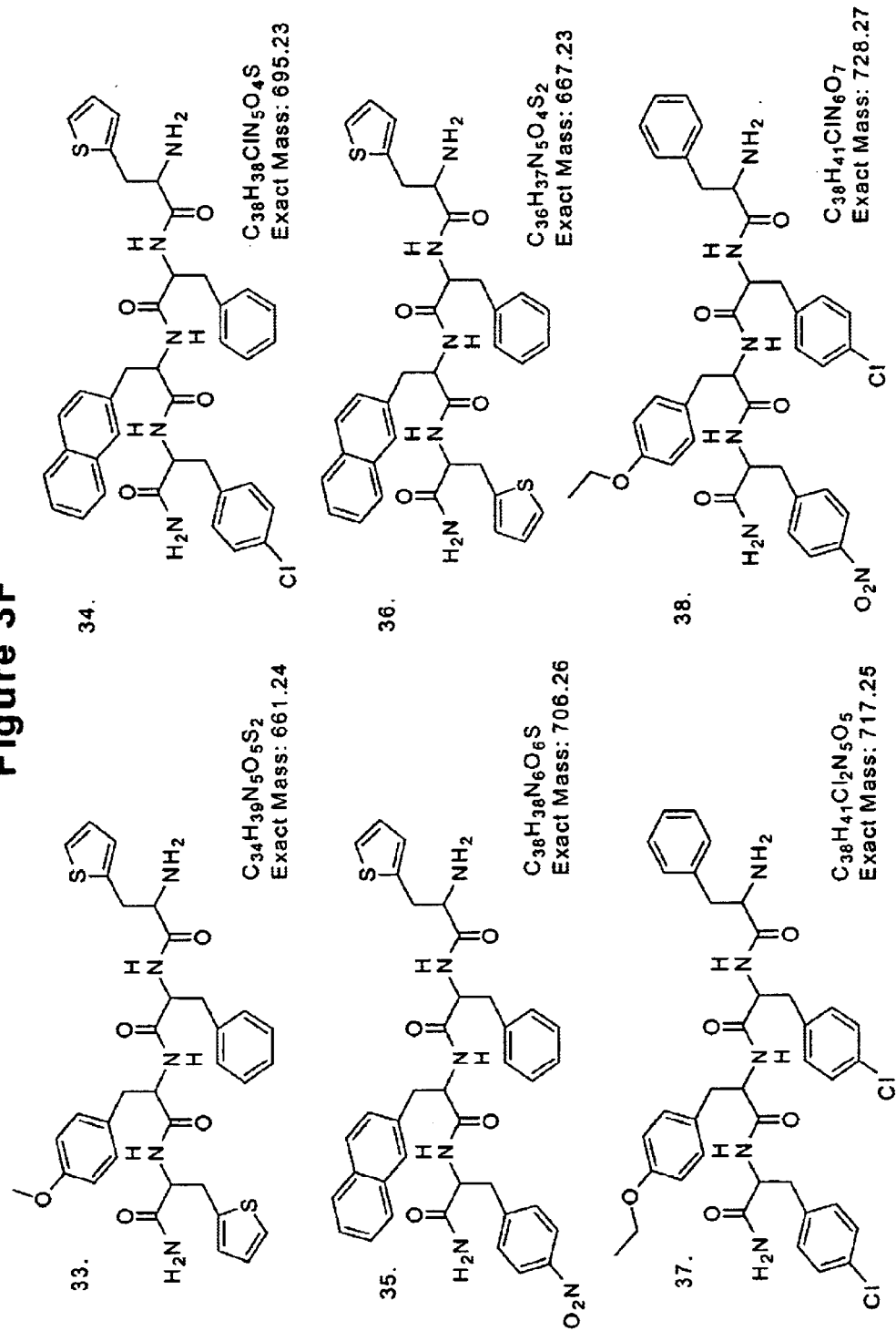
Figure 3G:
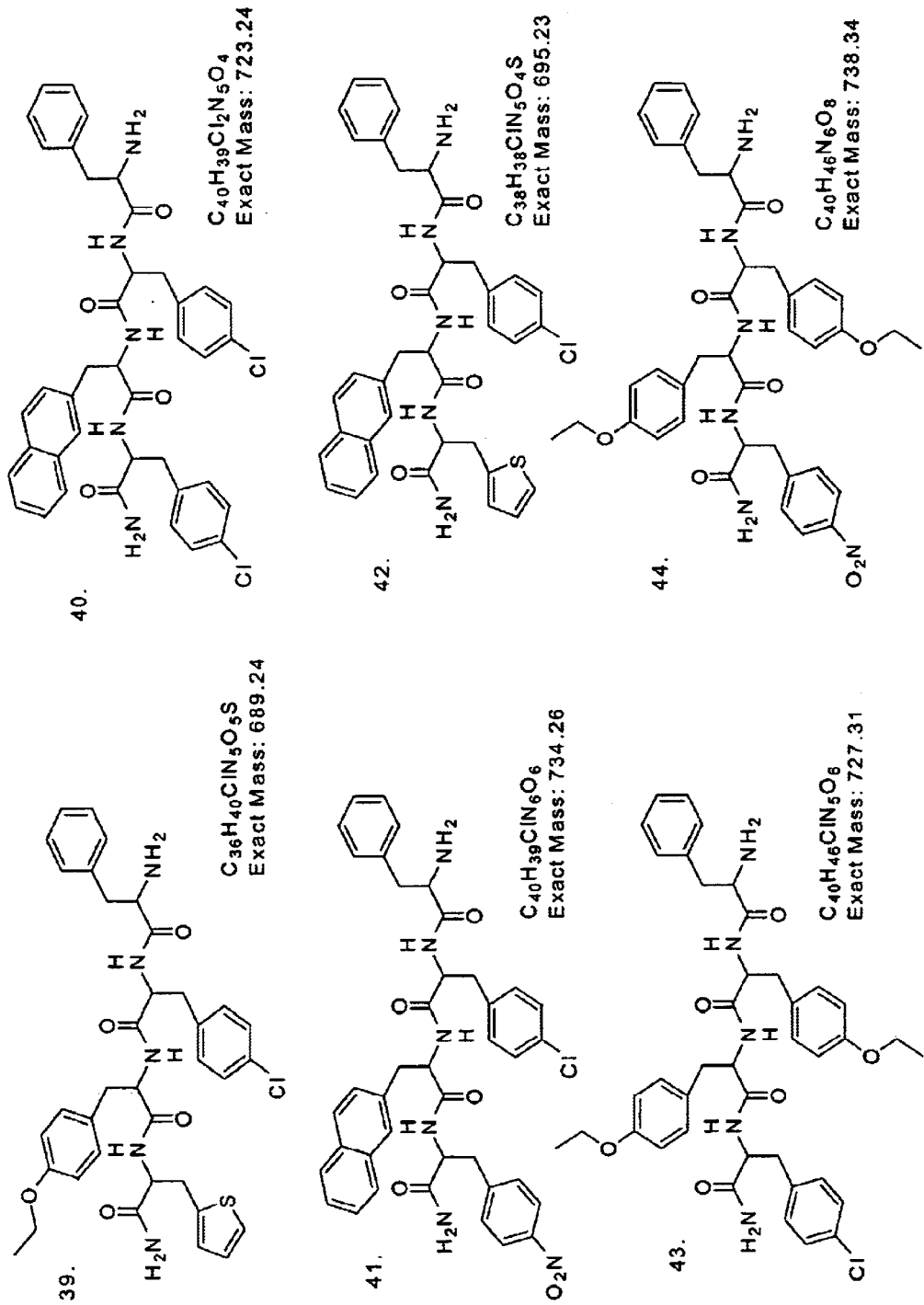
Figure 3H:
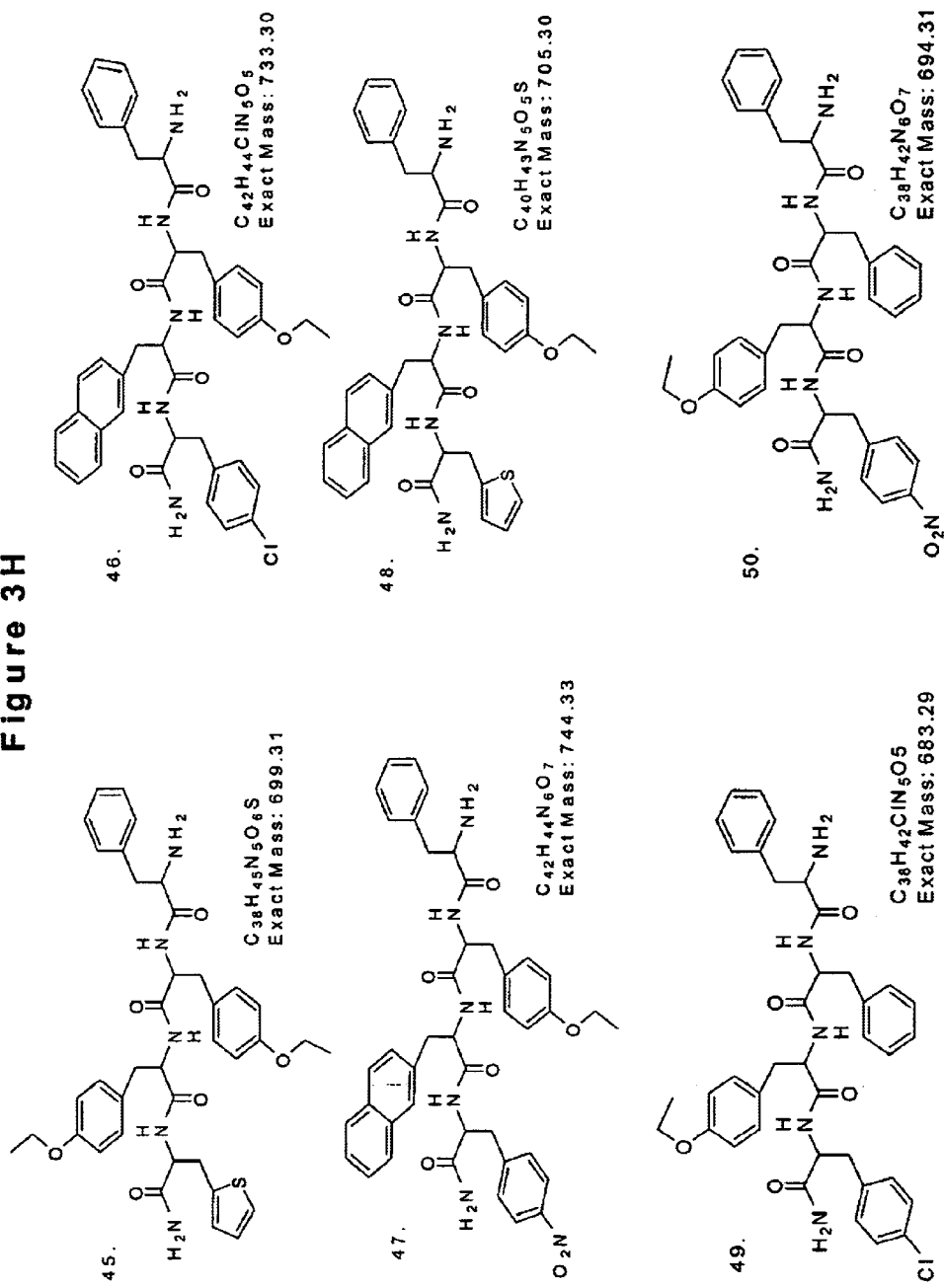
Figure 31:
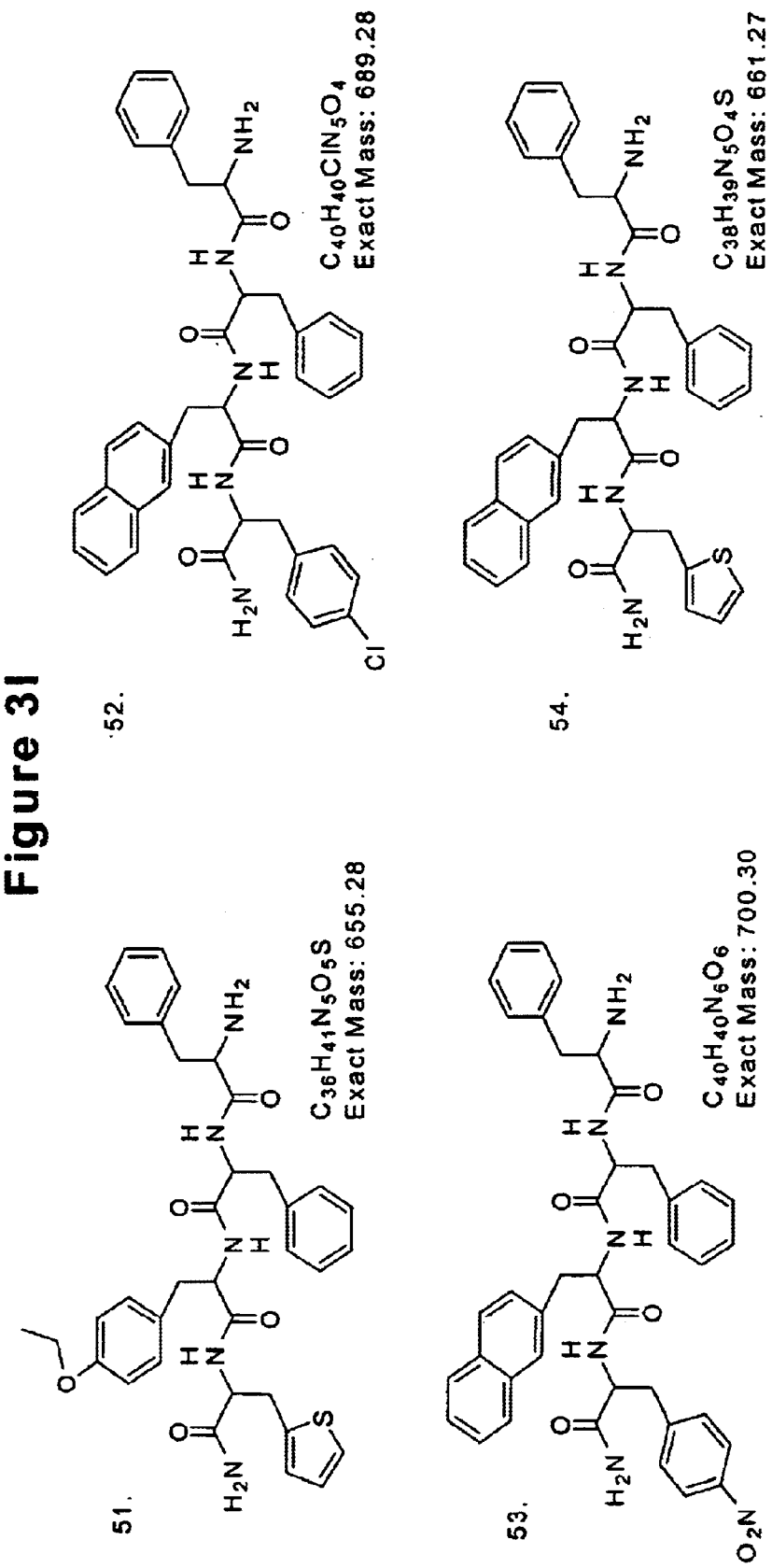

Various TPI1328 sublibraries that were screened and values obtained for the ratio of Vmax for hydrolysis of Ac-DEVD-AFC in the presence and absence of each mixture are plotted in FIGS. 1A and 1B. In FIGS. 1A and 1B and Table III, "X" represents a mixture of all 20 essential amino acids and "O" represents the location of the defined position, the identity of the amino acid at the defined position being plotted on the x axis. Candidates having a ratio over 1.7 were identified as being derepressors of XIAP-inhibited caspase-3. A list of derepressors of XIAP-inhibited caspase-3 identified from the TPI1328 library is provided in Table III.

TABLE III

| Pos 1 | Pos 2 | Pos 3 | Pos 4 | Pos 5 | Pos 6 | SEQ ID NO: |
|---|---|---|---|---|---|---|
| X | X | Ala | Ala | Trp | Trp | 7 |
| X | X | Gly | Ala | Trp | Trp | 8 |
| X | X | Arg | Ala | Trp | Trp | 9 |
| X | X | X | Ala | Trp | Trp | |
| X | X | Cys | Lys | Trp | Trp | 10 |
| X | X | Leu | Lys | Trp | Trp | 15 |
| X | X | Gly | 3X | Trp | Trp | |
| X | X | Arg | 3X | Trp | Trp | |
| X | X | Thr | 3X | Trp | Trp | |
| X | X | Val | 3X | Trp | Trp | |
| X | Thr | X | 3X | Trp | Trp | |
| X | Tyr | X | 3X | Trp | Trp | |
| Ala | X | X | 3X | Trp | Trp | |
| Cys | X | X | 3X | Trp | Trp | |
| Phe | X | X | 3X | Trp | Trp | |
| Lys | X | X | 3X | Trp | Trp | |

EXAMPLE II

Identification of Derepressors of an IAP-Inhibited Caspase from the TPI1332 and TPI1352 Individual Tetrapeptide Libraries This Example demonstrates identification of agents from the TPI1332 and TPI1352 tetrapeptide libraries that are capable of derepressing an XIAP-inhibited caspase-3.

The TPI1332 and TPI1352 tetrapeptide libraries were synthesized identically with the exception that the formyl protecting groups on tryptophan were removed by different procedures. The deprotection step used for the TPI1332 library was less complete leaving the possibility that some of the tryptophan residues present on candidate compounds used in the screen retained formyl protecting groups. The deprotecting chemistry used for the TPI1352 library was substantially complete, however resulted in the formation of polymeric structures for a subset of the species in the library.

Candidates from the TPI1332 and TPI1352 libraries were screened using the derepression assay described in Example I. The ratios of $V_{max}$ for hydrolysis of Ac-DEVD-AFC in the presence and absence of each species of the TPI1332 and TPI1352 libraries were determined and those having values greater than 2.4 were identified as derepressors of an IAP-inhibited caspase.

A list of derepressors of XIAP-inhibited caspase-3 identified from the TPI1332 and TPI1352 tetrapeptide libraries is provided in Table IV. Agents identified in both libraries are indicted as "1332/1352."

TABLE IV

| Agent | Position 1 | Position 2 | Position 3 | Position 4 |
|---|---|---|---|---|
| 1332/1352-1 | L-Ala | L-Trp | L-Trp | L-ThiAla |
| 1332/1352-2 | L-Ala | L-Trp | L-Trp | L-pClPhe |
| 1332/1352-47 | L-Ala | D-Trp | L-Trp | L-ThiAla |
| 1332-13 | L-Ala | D-Nal | L-Trp | L-Nal |
| 1332-24 | D-Trp | D-Trp | L-Trp | D-Nal |
| 1332-41 | L-Cha | D-Nal | L-Trp | L-ThiAla |
| 1352-5 | L-Ala | L-Trp | L-Trp | L-3I-Tyr |
| 1352-6 | L-Ala | D-Trp | L-Trp | L-ThiAla |
| 1352-32 | L-Cha | L-Trp | L-Trp | L-pClPhe |
| 1352-46 | L-Ala | D-Trp | L-Trp | D-Trp |
| 1352-48 | L-Ala | D-Trp | D-Phe | D-Trp |
| 1352-64 | L-Nal | D-Trp | D-Phe | D-Trp |
| 1352-66 | L-Nal | D-Cha | L-Trp | D-Trp |
| 1352-72 | L-Nal | D-ThiAla | D-Phe | D-Trp |

EXAMPLE III

Identification of Individual Peptide Derepressors of an IAP-Inhibited Caspase from the TPI792 Library This Example demonstrates identification of agents from the TPI792 library that are capable of derepressing an XIAP-inhibited caspase-3.

The TPI792 library is based on a tetrapeptide backbone. The species of the TPI792 library were screened in the derepression assay described in Example I. A list of derepressors of XIAP-inhibited caspase-3 identified from the TPI792 library is provided in Table V. Structures for the TPI792 core peptides that were tested are shown in FIGS. 20A and 20B.

TABLE V

| Agent | Pos 1 | Pos 2 | Pos 3 | Pos 4 | LC µg/ml |
|---|---|---|---|---|---|
| 792-3 | D-Nal | Lys-εFmoc | L-pClPhe | Lys-εFmoc | 2 |
| 792-9 | D-Nal | D-pClPhe | L-pClPhe | Lys-εFmoc | 10 |
| 792-15 | D-Nal | L-Nal | L-pClPhe | D-Lys-εFmoc | 2 |
| 792-17 | D-Nal | L-Nal | D-Lys(Fm) | Lys-εFmoc | 2 |
| 792-19 | L-ThiAla | Lys-εFmoc | D-Nal | Lys-εFmoc | 2 |
| 792-22 | L-ThiAla | Lys-εFmoc | L-pClPhe | D-pFPhe | 2 |
| 792-27 | L-ThiAla | D-pClPhe | L-pClPhe | Lys-εFmoc | 2 |
| 792-33 | L-ThiAla | L-Nal | L-pClPhe | Lys-εFmoc | 0.4 |
| 792-35 | L-ThiAla | L-Nal | D-Lys(Fm) | D-Lys-εFmoc | 2 |

The dose response of the agents identified from the TPI792 library were determined by repeating the derepression assay with variable concentrations of the agent. Four concentrations were chosen: 0.4, 2, 10 and 50 micrograms per milliliter. From this data the Lowest concentration with a ratio of 2 or higher in the derepression assay (LC) was determined and shown in Table V. The lowest LC value determined from the TPI792 library was 0.4 micrograms per milliliter for TP1792-33.

EXAMPLE IV

Identification of Derepressors of an IAP-Inhibited Caspase from the TPI1313 Library This Example demonstrates identification of agents from the TPI1313 library that are capable of derepressing an XIAP-inhibited caspase-3.

The TPI1313 library is based on a tetrapeptide backbone. The species of the TPI1313 library, listed in FIGS. 2A and 2C and shown in FIGS. 3A–3I, were screened in the derepression assay described in Example I. A list of derepressors of XIAP-inhibited caspase-3 identified from the TPI1313 library is provided in Table VI.

TABLE VI

| Agent | Pos 1 | Pos 2 | Pos 3 | Pos 4 |
|---|---|---|---|---|
| 1313-4 | L-ThiAla | D-pCL-Phe | D-Nal | D-pCL-Phe |
| 1313-5 | L-ThiAla | D-pCL-Phe | D-Nal | D-pNO$_2$Phe |
| 1313-7 | L-ThiAla | D-OEt-Tyr | D-OEt-Tyr | D-pCL-Phe |
| 1313-40 | Phe | D-pCL-Phe | D-Nal | D-pCL-Phe |

The dose response of the agents identified from the TPI1313 library were determined by repeating the derepression assay with variable concentrations of the agent. Four concentrations were chosen: 0.4, 2, 10 and 50 micrograms per milliliter. From this data the apparent IC$_{50}$ was determined. The lowest IC$_{50}$ value determined from the TPI1313 library range from 3.9 to 6.3 micrograms per milliliter TPI1313-7.

EXAMPLE V

Identification of Derepressors of an IAP-Inhibited Caspase from the TPI1325 Library This Example demonstrates identification of agents from the TPI1325 library that are capable of derepressing an XIAP-inhibited caspase-3.

The TPI1325 library was screened in the derepression assay described in Example I. For each species aliqouted in the assay 1 position was fixed (i.e. having a single known amino acid R group) and three positions were combinatorialized. Thus, each "mixture" identified from the TPI1325 library represents a mixture of compounds where $X_1$ and $X_2$ are selected from Ala, Asp, Glu, Phe, Gly, His, Ile, Lys, Leu, Met, Asn, Pro, Gln, Arg, Ser, Thr, Val, Trp or Tyr and $X_3$ includes any one of Ala, Lys and Thr.

A list of derepressors of XIAP-inhibited caspase-3 identified from the TPI1325 library is provided in Table VII.

TABLE VII

| Mixture | Pos 1 | Pos 2 | Pos 3 | Pos 4 |
|---|---|---|---|---|
| 1325-10 | L-Ala | L-Met | $X_1$ | $X_2$ |
| 1325-15 | L-Ala | L-Ser | $X_1$ | $X_2$ |
| 1325-16 | L-Ala | L-Thr | $X_1$ | $X_2$ |
| 1325-18 | L-Ala | L-Trp | $X_1$ | $X_2$ |
| 1325-44 | L-Ala | L-ThiAla | $X_1$ | $X_2$ |
| 1325-61 | L-Ala | $X_1$ | $X_2$ | $X_3$ |
| 1325-64 | $X_1$ | $X_2$ | L-Trp | D-Trp |

The dose response of the agents identified from the TPI1325 library were determined by repeating the derepression assay with variable concentrations of the agent. Four concentrations were chosen: 0.4, 2, 10 and 50 micrograms per milliliter. From this data the apparent IC$_{50}$ was determined. The lowest IC$_{50}$ value determined from the TPI1325 library was 12 micrograms per milliliter for TPI1325-15.

EXAMPLE VI

Identification of Derepressors of an IAP-Inhibited Caspase from the TPI914, TPI927, TPI759 and TPI882 Libraries This Example demonstrates identification of agents, from non-peptide based libraries, that are capable of derepressing an XIAP-inhibited caspase-3.

The TPI914, TPI927, TPI759 and TPI882 libraries were screened using positional scanning-(as described in U.S. Pat. No. 5,556,762) in combination with the derepression assay described in Example I.

Analysis was started with combinatorial libraries in which at least one position was defined. Hits were identified as those mixtures producing a mixture/XIAP ratio that was greater than or equal to 2. Following analysis of the first library, libraries of increasing definition were screened until a discrete library was prepared in which all positions were defined. Hits from this defined library were then checked for a dose response which yielded the IC50 values listed below.

The TPI914 N-acyltriamine library included 50 amino acid R groups at position R1, 50 amino acid R groups at position R2 and 50 acid derivatives at position R3 for a total diversity of 125,000 species. Mixtures having a defined functionality at one of the R positions and identified by positional scanning of the TPI914 library as having a peptide/XIAP ratio greater than or equal to about 1.8 when present at 25 micrograms, per milliliter in the derepression assay were identified and are shown in FIG. 4. Control agents having a peptide/XIAP ratio greater than or equal to about 1.8 when present at 6.25 micrograms per milliliter or 12.5 micrograms per milliliter in the derepression assay were identified and are shown in FIG. 5.

The TPI927 polyphenylurea library included 48 amino acid R groups at position R1, 48 amino acid R groups at position R2 and 39 acid derivatives at position R3 for a total diversity of 89,856 species. Mixtures having a defined functionality at one of the R positions and identified by positional scanning of the TPI927 library as having a peptide/XIAP ratio greater than or equal to about 1.8 when present at 4 micrograms per milliliter in the derepression assay were identified and are shown in FIGS. 6A and 6B. Control agents having a peptide/XIAP ratio greater than or equal to about 1.8 when present at 25 micrograms per milliliter in the derepression assay were identified and are shown in FIGS. 9A–9C.

The TPI759 N-benzyl-1,4,5-trisusbstituted-2,3-diketopiperazine library included 29 amino acid R groups at position R1, 27 amino acid R groups at position R2 and 40 acid derivatives at position R3 for a total diversity of 31,320 species. Mixtures having a defined functionality at one of the R positions and identified by positional scanning of the TPI759 library as having a peptide/XIAP ratio greater than or equal to about 2.0 (or in the case of the sublibrary where R3 was fixed, a ratio of 1.9 or higher) when present at 25 micrograms per milliliter in the derepression assay were identified and are shown in FIGS. 8A–8F.

The TPI882 C-6-acylamino bicyclic guanidine library included 43 amino acid R groups at position R1, 41 acid derivatives at R2 and 41 acid derivatives at R3 for a total diversity of 72,283 species. Mixtures having a defined functionality at one of the R positions and identified by positional scanning of the TPI882 library as having a peptide/XIAP ratio greater than or equal to about 1.9 when present at 5 micrograms per milliliter in the derepression assay were identified and are shown in FIGS. 7A–7F. Control agents having a peptide/XIAP ratio greater than or equal to about 2.0 when present at 8 micrograms per milliliter in the derepression assay were identified and are shown in FIGS. 10A–10F.

EXAMPLE VII

SMAC Competition Assay

This Example describes an assay useful for determining the binding affinity of a derepressor of an IAP-inhibited caspase for an IAP, or functional fragment thereof.

A polarization based binding assay was used to detect binding between rhodamine labeled SMAC (rhodamine-SMAC) and the XIAP fragments BIR2 or BIR3RING. The assay is based on the decrease in mobility that occurs for rhodamine-SMAC when associated with XIAP or functional fragments thereof which is detected as a reduction in polarization for bound rhodamine-SMAC compared to free (unbound) rhodamine-SMAC.

Binding affinity of rhodamine-SMAC for a glutathione-S-transferase-BIR2 fusion protein (GST-BIR2) or BIR3RING was determined as follows. A 1 milliliter reaction cocktail was made to include 100 mM $NaPO_4$, 0.01% bovine gamma globulin, and 20 nM rhodamine-SMAC. 0.1 ml aliquots taken from the reaction cocktail were placed into the 8 wells of a column in 96 well assay plate. Twelve such columns were set up each with a different concentration of GST-BIR2 ranging from 0 to 495 nM. Polarization of Rhodamine in each well was read in an LJL Analyst HT with excitation at 530 nm and emission at 580 nm. Data was averaged for 8 samples having the same concentration of GST-BIR2 then plotted as a function of millipolars vs. the concentration of GST-BIR2. The same procedure was followed for BIR3RING. Rhodamine-SMAC at 20 nM had a $K_d$ for GST-BIR2 of 100 nM and a $K_d$ for BIR3RING of 80 nM.

The polarization assay was used to identify agents having the ability to compete with SMAC for binding to XIAP.

Unlabelled SMAC was titrated against a solution containing 20 nM rhodamine-SMAC and 225 nM GST-BIR2. Unlabeled SMAC was titrated in the range of 0 to 20 uM in 4 uM increments. Again 8–0.1 ml samples were counted for each concentration of unlabeled SMAC allowing for the determination of a standard error. Data was plotted as a function of millipolars vs SMAC and $IC_{50}$ values determined. The $IC_{50}$ value of the SMAC titration was 12 $\mu$M. Identical procedures were followed for titration of unlabeled SMAC against a rhodamine-SMAC and BIR3RING containing solution. In this case, the $IC_{50}$ value of SMAC was 8 $\mu$M.

Candidate agents from a library are added to a solution containing 20 nM rhodamine-SMAC and 225 nM GST-Bir2. Fluorescence polarization is determined for each sample and those candidates that show a decrease in polarization compared to a control reaction containing 20 nM rhodamine-SMAC and 225 nM GST-Bir2 are identified as derepressors of an IAP-inhibited caspase. As a control, fluorescence polarization is also determined for the library sample in the absence of GST-BIR2.

An agent identified as a derepressor of an IAP-inhibited caspase is titrated against a solution of rhodamine-SMAC and GST-BIR2. Polarization is determined at each concentration of the agent as described above. Data is plotted as a function of millipolars vs. SMAC and binding constants determined also as described above.

EXAMPLE VIII

Screening of Individual Compounds from the TPI914, TPI927, TPI759 and TPI882 Libraries This example describes screening of individual agents derived from TPI914, TPI927, TPI759 and TPI882 libraries and identification of individual agents that Derepress an IAP-Inhibited Caspase.

Individual agents were synthesized based on the active agents identified in Example VI. Selected agents based on the TPI914 derepressors shown in FIG. 5 were synthesized and are identified as agents TPI1349-1 through TPI1349-34 in FIGS. 21A–21E. Selected agents based on the TPI927 derepressors shown in FIGS. 9A–9C were synthesized and are identified as agents TPI1396-1 through TPI1396-65 in FIGS. 22A–22M. Selected agents based on the TPI759 derepressors shown in FIGS. 8A–8F were synthesized and are identified as agents TPI1391-1 through TPI1391-36 in FIGS. 23A–23H. Selected agents based on the TPI882 derepressors shown in FIGS. 10A–10F were synthesized and are identified as agents TPI1400-1 through TPI1400-58 in FIGS. 24A–24L.

The SMAC competition assay was used to evaluate the agents shown in FIGS. 21A–24T. Each compound was titrated against a solution of rhodamine labeled SMAC tetrapeptide, AVPI (SEQ ID NO:4), and full length XIAP under the conditions described in Example VII. Polarization was determined at each concentration of the IAP antagonist, data was plotted as a function of millipolars vs. compound concentration. The lowest concentration of each agent having a ratio of 1.8 or higher as determined from the plots is shown in the last column of the tables shown in FIGS. 21A–24T ([lowest] ug/ml).

EXAMPLE IX

Peptidyl and Non-Peptidyl Compounds Restore Caspase Activity of IAP-Inhibited Caspase in vitro This example demonstrates an assay for determining potency of peptidyl and non-peptidyl derepressors of IAP-inhibited caspases in vitro. This example also identifies peptidyl and non-peptidyl compounds having potency at restoring caspase activity of IAP-inhibited caspase in vitro.

The SMAC competition assay was used to evaluate peptidyl IAP antagonists identified from screens of the TPI792 library and non-peptidyl IAP antagonists identified from screens of the TPI1391 and TPI1396 libraries. Each compound was titrated against a solution of rhodamine labeled SMAC tetrapeptide, AVPI (SEQ ID NO:4), and full length XIAP under the conditions described in Example VII. Polarization was determined at each concentration of the IAP antagonist, data was plotted as a function of millipolars vs. compound concentration, and the EC50 binding constants were determined from the plots. As a control unlabeled SMAC tetrapeptide, AVPI (SEQ ID NO:4) was also assayed.

Table VIII summarizes the results of the SMAC competition assay for IAP antagonists identified from the TPI792, TPI1391 and TPI1396 libraries. The EC50 was determined, by calculating the amount of compound necessary to restore Caspase-3 activity to 50% of maximum velocity (Vmax). Two of the most potent tetramer peptides were TPI792-33 and TPI792-35 which displayed enzyme derepression activities in vitro that were 5.2 to 2.5 fold better than SMAC peptide, respectively. The most potent diketopiperazine based compounds included TPI1391-21, TPI1391-28 and TPI1391-34 which exhibited potencies 3.4 to 4.8 fold more active than SMAC peptide. The most potent phenyl-urea compounds included TPI1396-22, TPI1396-34 and TPI1396-28 which exhibited potencies that were 3.8 to 5.2 fold more active than SMAC peptide.

TABLE VIII

|  | EC50 ($\mu$M) | Relative Potency |
|---|---|---|
| Natural peptides |  |  |
| SMAC AVPI tetrapeptide (SEQ ID NO:4) | 125 | 1.0 |
| Un-natural peptides |  |  |
| TPI792-33 | 24 | 5.2 |
| TPI792-35 | 51 | 2.5 |
| Diketopiperazines |  |  |
| TPI1391-21 | 37 | 3.4 |
| TPI1391-28 | 26 | 4.8 |
| TPI1391-34 | >1000 | N/A |
| Diphenyl and Triphenyl Ureas |  |  |
| TPI1396-22 | 24 | 5.2 |
| TPI1396-34 | 33 | 3.8 |
| TPI1396-28 | >1000 | N/A |

These results demonstrate that peptidyl compounds TPI792-33 and TPI792-35; diketopiperazine based compounds TPI1391-21, TPI1391-28 and TPI1391-34; and phenyl-urea compounds TPI1396-22, TPI1396-34 and TPI1396-28 derepressed XIAP inhibited caspase in vitro and did so with more potency than the SMAC AVPI tetrapeptide (SEQ ID NO:4).

EXAMPLE X

Peptidyl Compounds TPI792-33 and TPI792-35 Kill Tumor Cells

This example demonstrates an assay for determining potency of derepresors of IAP-inhibited caspases in cell cultures. This example also demonstrates that TPI792-33 and TPI792-35 reduce the viability of tumor cells in culture.

The TPI792-33 and TPI792-35 compounds were assayed to determine their effects on tumor cell viability. As shown in FIG. 12, TPI792-33 and TPI792-35 are tetrapeptides composed of unnatural amino acids that differ in their amino acid sequence at the third position. The TPI792-33 and TPI792-35 compounds both have L-3-(2-thienyl)-alanyl, L-(2-naphthyl)-alanyl, and L-($\epsilon$-fluorenylmethyloxy-carbonyl)-lysine moieties at positions 1 (N-terminus), 2 and 4, respectively, but differ at position 3 where TPI792-33 has L-p-chloro-phenylalanyl and TPI792-35 has a D-($\epsilon$-fluorenylmethyloxycarbonyl)-lysyl moiety.

Cells from the prostate cancer cell line, ALVA31 express XIAP, as well as other IAP-family proteins. The in vivo effects of TPI792-33 or TPI792-35, either individually or in combination with the cytotoxic anticancer drug VP-16 (etoposide), on derepression of XIAP-inhibited caspase and viability of ALVA31 cells was determined as follows. ALVA31 prostate cancer cells were seeded onto 96 well plates ($10^4$ cells/well) in 100 $\mu$L RPMI containing 2.5% fetal bovine serum (FBS). After 24 hours, the IAP antagonists TPI792-33, TPI792-35 or the SMAC AVPI tetrapeptide (SEQ ID NO:4) was added at a final concentration of 40 $\mu$M with or without VP-16 (100 $\mu$M final concentration). After another 24 hrs incubation, cell viability was measured by the XTT dye-reduction assay (Roche, Molecular Biochemicals; Indianapolis, Ind.) and trypan blue dye exclusion assay.

Figure 13:
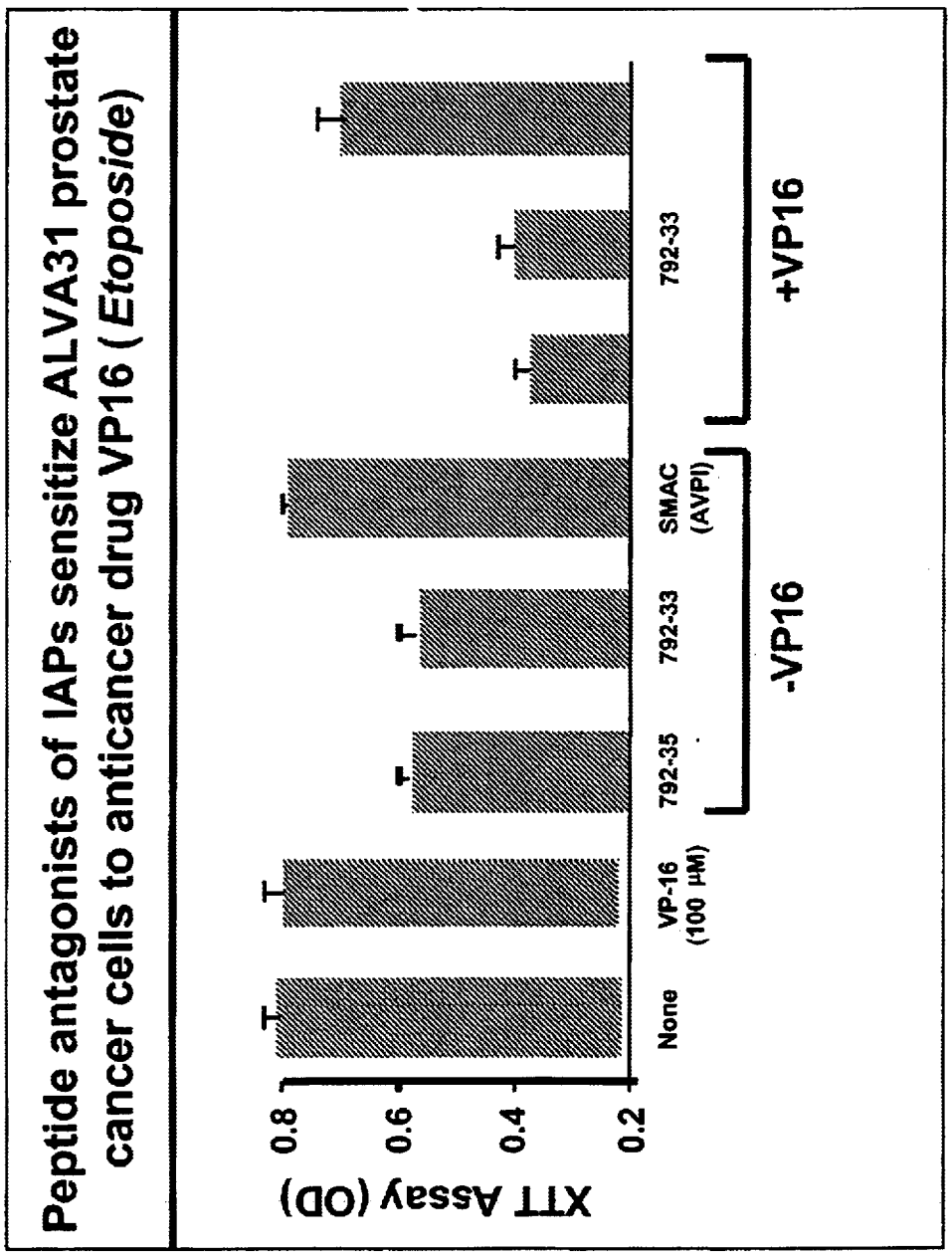
FIG. 13 shows the effects of VP-16 (etoposide), TPI792-35, TPI792-33 and the SMAC AVPI tetrapeptide (SEQ ID NO:4) on prostate cancer cell viability.

Anti-cancer drug VP-16 (etoposide), when administered alone to ALVA31 cells, had essentially no effect on the viability of the cells in the XTT dye-reduction assay (FIG. 13) and trypan blue dye exclusion assay. The SMAC AVPI tetrapeptide (SEQ ID NO:4), when administered alone to the ALVA31 cells, also had no effect on cell viability. In contrast, the TPI792-33 and TPI792-35 peptides reduced viability of these prostate cancer cells by nearly half. Moreover, the combination of VP-16 with these peptides resulted in more potent tumor cell killing compared to VP-16 alone. By comparison, the SMAC peptide was inactive, failing to significantly reduce the relative number of viable tumor cells under the same culture conditions.

These results demonstrate that TPI792-33 and TPI792-35 display markedly improved cellular activity compared to wild-type AVPI peptide from SMAC (SEQ ID NO:4). Furthermore, these results indicate that TPI792-33 and TPI792-35 have the effect of increasing apoptosis in tumor cells by derepressing IAP-inhibited caspase. These results also demonstrate that TPI792-33 and TPI792-35 sensitize prostate cancer cells to the anticancer drug VP-16.

EXAMPLE XI

Non-Peptidyl Compounds TPI1396-34 and TPI1396-28 Kill Tumor Cells

This example demonstrates that phenyl urea compounds identified from the TPI1396 library and diketopiperazine compounds identified from the TPI1391 library reduce the viability of tumor cells in culture. This example further demonstrates that cell killing activity for TPI1396-34 and TPI1391-28 is specific for tumor cells.

The following assay was used to test the ability of individual compounds from the TPI1396 and TPI1391 libraries to induce apoptosis of cultured tumor cell lines. Each of the compounds listed in Table IX was individually added to Jurkat leukemia cells ($6.25 \times 10^5$ cells/mL) in RPMI containing 2.5% FBS at various concentrations for 20 hours. After incubation, cells were washed and stained with FITC-conjugated Annexin V antibody and propidium iodide (Biovision; Mountain View, Calif.). Cells were incubated for 20 minutes at room temperature in the dark and fluorescence was measured by flow cytometry (FACScan, Immunocytometry system; Becton-Dickinson; San Jose, Calif.). Cells staining positive for Annexin V were deemed non-viable.

As shown in Table IX, these compounds were able to induce cell death in a concentration dependent manner. Although SMAC was able to reduce cell viability by about 16% when present at 50 $\mu$M, several TPI1396-34 and TPI1391-28 compounds reduce cell viability by about 85 to 94%. Thus, compounds identified from the TPI1396-34 and TPI1391-28 libraries were about 5 to 6 fold more potent than SMAC at inducing apoptosis in tumor cells.

TABLE IX

| | Concentration $\mu$M | | | | | | |
|---|---|---|---|---|---|---|---|
| | 100 | 50 | 25 | 10 | 5 | 5 | 1 |
| TPI1391 % nonviable cells | | | | | | | |
| 1391-28 | | 91 | 87 | 55 | 12 | 28 | 19 |
| 1391-21 | | 94 | 91 | 44 | 11 | 18 | 16 |
| 1391-25 | | 87 | 90 | 60 | 22 | 49 | 16 |
| 1391-17 | | 91 | 88 | 45 | N.T. | 25 | 13 |
| 1391-5 | | 88 | 88 | 36 | N.T. | | 17 |
| 1391-1 | | 91 | 69 | 20 | N.T. | | 18 |
| 1391-4 | | 86 | 90 | 48 | 12 | 18 | 20 |
| TPI1396 % nonviable cells | | | | | | | |
| 1396-34 | | 85 | 83 | 62 | 73 | 51 | 13 |
| 1396-12 | | 85 | 89 | 89 | 95 | 95 | 15 |
| 1396-11 | | 90 | 90 | 90 | 97 | 95 | 14 |
| 1396-10 | | 13 | 14 | 13 | | | 13 |
| SMAC | 15 | 16 | 16 | | 12 | | |

The TPI1396-34 and TPI1391-28 compounds were further tested as set forth below. FIG. 14 (Panel B) shows the structures for phenyl urea TPI1396-34 and diketopiperazine TPI1391-28. Both of these compounds were shown to induce apoptosis of cultured tumor cell lines in a concentration-dependent manner using the assay described above, except that compounds were added in the range of 0 to 20 $\mu$M.

Figure 15:
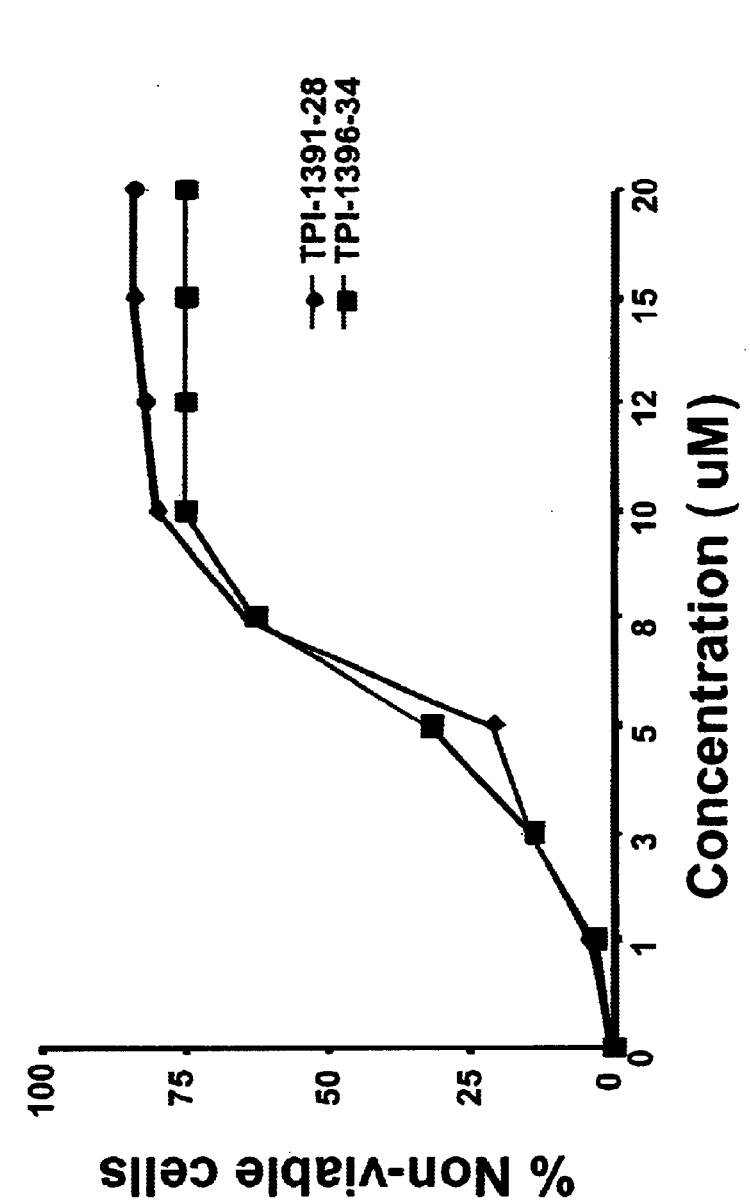
FIG. 15 shows concentration-dependent killing of Jurkat leukemia cells by TPI1391-28 and TPI1396-34.

As shown in FIG. 15, TPI1396-34 and TPI1391-28 killed Jurkat leukemia cells with $EC_{50}$ values of about 6.5 $\mu$M following a one-day exposure. Control compounds having the same core pharmacophore structure but with different substituents at the R group which prevent binding to XIAP, did not significantly reduce the viability of Jurkat leukemia cells under the assay conditions.

Comparison of cell killing by TPI1396-34 and TPI1391-28 to the respective control compounds is shown in FIG. 16. One day treatment of Jurkat leukemia cells with 5 $\mu$M or 8 $\mu$M of TPI1396-34, killed about 75% and 85% of cells, respectively. One day treatment of Jurkat leukemia cells with 5 $\mu$M or 8 $\mu$M of TPI1391-28, killed about 45% and 80% of cells, respectively. In contrast, the control compounds had no significant effect on the viability of these leukemia cells compared to untreated cells, indicating that the cytotoxic activity of these compounds is specific. Under the same assay conditions, 5 or 8 $\mu$M of the SMAC AVPI tetrapeptide (SEQ ID NO:4) had no significant effect on the viability of these leukemia cells, confirming that TPI1396-34 and TPI1391-28 had far greater potency than SMAC.

A comparison of the effects of TPI1396-34 on normal bone marrow cells versus Jurkat leukemia cells was performed as follows. TPI1396-34 (5 $\mu$M) was incubated with Jurkat cells or normal bone marrow mononuclear cells ($6.25 \times 10^5$/mL) in RPMI and 2.5% FBS for 20 hours. After incubation, cells were washed, stained with FITC-conjugated Annexin V antibody and propidium iodide, and fluorescence measured by flow cytometry as described above.

Figure 17:
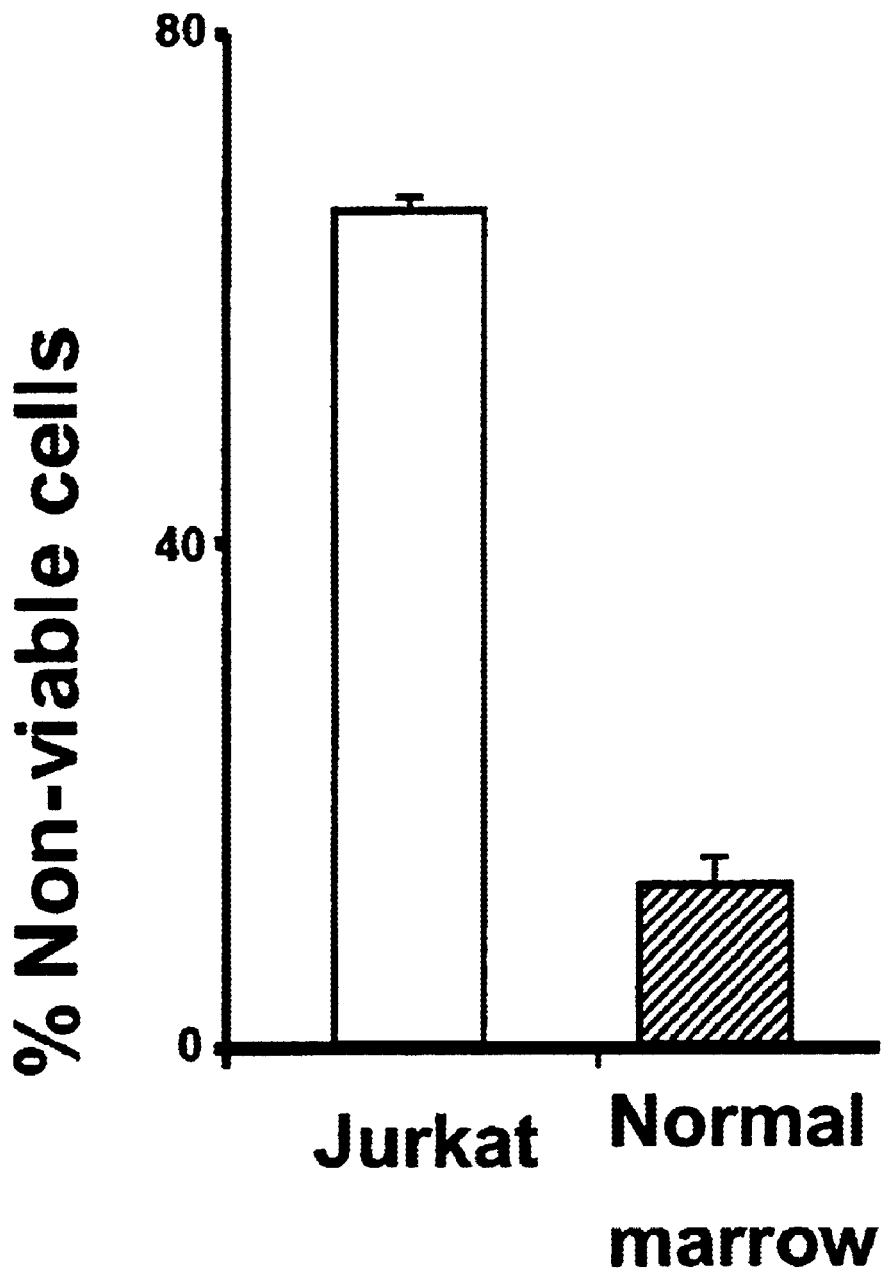
FIG. 17 shows a comparison of the effects of TPI1396-34 and TPI1391-28 on normal bone marrow cells versus Jurkat leukemia cells.

As shown in FIG. 17, TPI1396-34 and TPI1391-28 caused little toxicity to normal bone marrow cells under the same culture conditions where robust killing of the leukemia cells was observed. These results demonstrate that the TPI1396-34 and TPI1391-28 selectively kill tumor cells compared to normal cells.

EXAMPLE XII

Killing of Tumor Cells by TPI1396-34 is Mediated by XIAP

This Example describes the effects of over-expressing wild type and mutant XIAP on tumor cell killing by TPI1396-34.

U937 leukemia cells ($6.25 \times 10^5$ cells/mL) that had been stably transfected with either a Neo-control plasmid (U937-Neo cells) or a plasmid encoding XIAP (U937-XIAP cells) were treated with 5 or 8 $\mu$M of TPI1396-34 in RPMI and 2.5% FBS for 20 hours. After incubation, cells were washed, stained with FITC-conjugated Annexin V antibody and propidium iodide, and fluorescence measured by flow cytometry as described in Example X.

Figure 18:
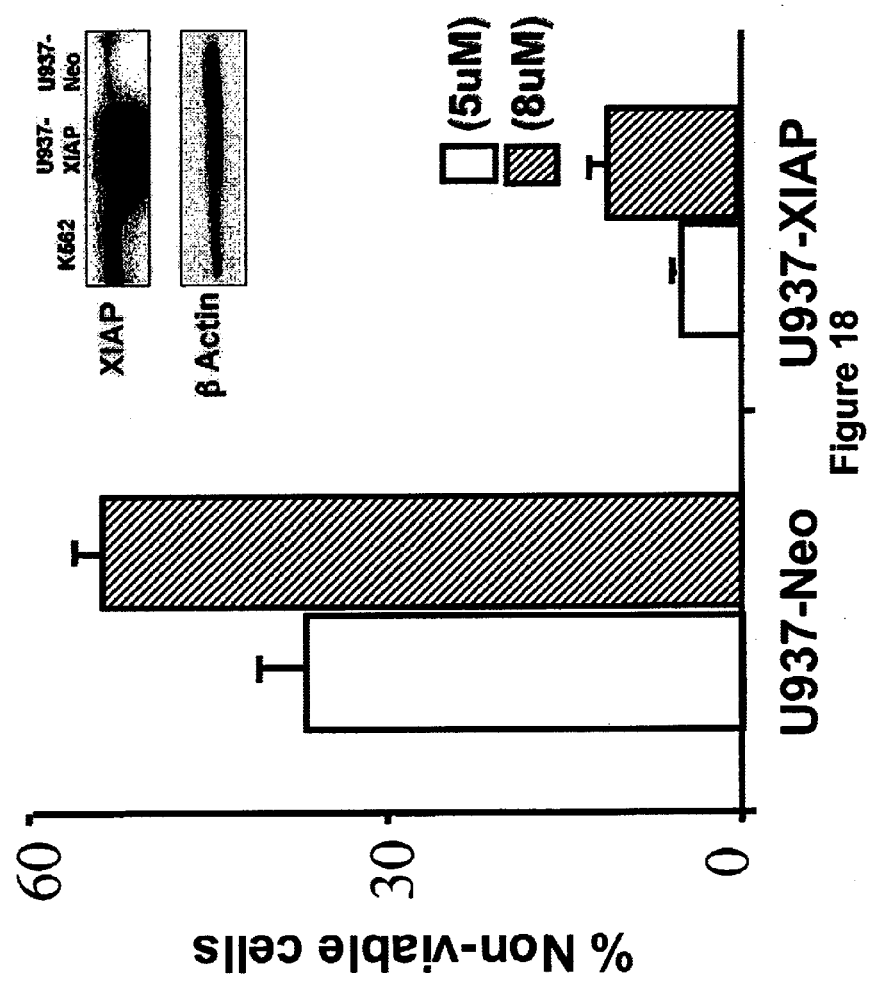
FIG. 18 shows the effects of over-expression of wild-type XIAP on the apoptogenic activity of TPI1396-34.

As shown in FIG. 18, over-expression of XIAP rendered U937 cells resistant to TPI1396-34. Comparisons of the effects of TPI1396-34 on U937—Neo and U937-XIAP cells demonstrated that over-expression of XIAP correlated with resistance to apoptosis induction by this agent. The increased resistance of tumor cells to the apoptogenic effects of TPI1396-34 when the cells over-express XIAP indicates that TPI1396-34 induces apoptosis by binding to XIAP.

Over-expression of XIAP in the U937-XIAP cells compared to vector transfected control cells was confirmed by immunoblotting (upper right panel). Expression of XIAP in K562 cells was included as a control, as these cells are known to express XIAP endogenously. Equal amounts of protein were subjected to SDS-PAGE (4–20% gradient gels from ISC BioExpress, Kaysville, Utah), followed by transfer to nitrocellulose membranes. Membranes were probed with monoclonal mouse-anti human XIAP (0.25 $\mu$g/mL) (Transduction Laboratories, Lexington, Ky.) or monoclonal mouse-anti $\beta$-actin (1:3000 v/v) (Sigma Inc, Milwaukee, Wis.). Secondary antibodies consisted of horseradish peroxidase (HRP)-conjugated goat anti-mouse IgG (Bio-Rad, Hercules, Calif.). Detection was performed by the enhanced chemiluminescence (ECL) method.

In addition to transfecting the cells with full-length XIAP, analogous assays were performed with HeLa cells transfected with plasmids over-expressing various XIAP mutants.

HeLa cells were transiently transfected with plasmids encoding full-length, wild-type XIAP versus deletion mutants having only the BIR2 (Caspase-3/7 suppressing) domain, BIR3 (Caspase-9 suppressing) domain, or a mutant in which both of the putative SMAC-binding pockets in BIR2 and BIR3 had been mutated to no longer bind Caspases. The mutant was produced by site-directed mutagenesis to modify positions 148, 219, 223, 314 and 323 to contain alanine. HeLa cells were also transiently transfected with plasmids encoding Bcl-XL, an anti-apoptotic protein that operates upstream of Caspases to suppress Cytochrome C release from mitochondria. HeLa cells (2.5× $10^5$) were seeded onto six well plates in 2 mL DMEM H21 with 5% FBS. After 24 hrs, cells were transfected (Gene Porter) with plasmids. At 48 hrs after transfection, cells were treated with 5 μM of TPI1396-34 for 20 hours. Both floating and adherent cells were then recovered from cultures, washed, and apoptosis was determined by Annexin V staining using flow cytometry.

Figure 19:
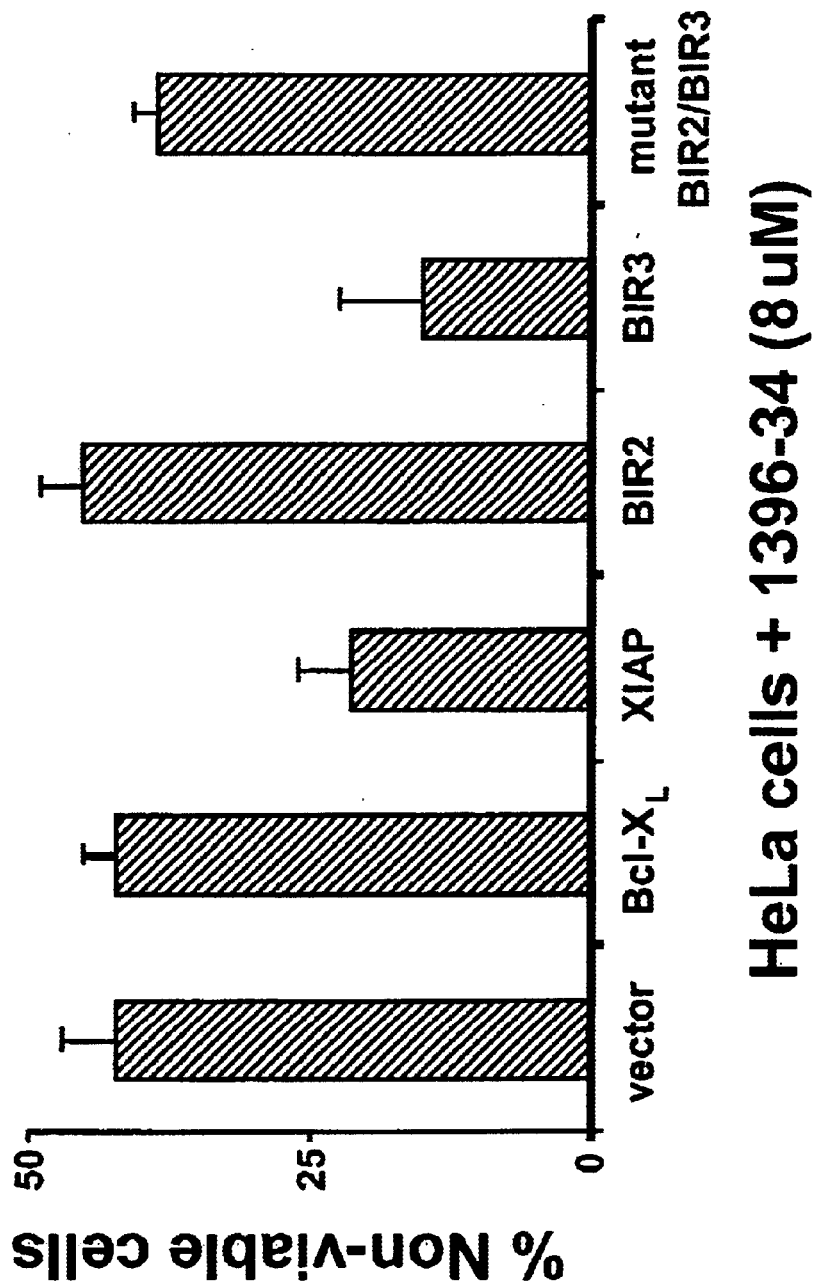
FIG. 19 shows the effects of over-expression of wild-type XIAP on the apoptogenic activity of TPI1396-34.
Figure 21L:
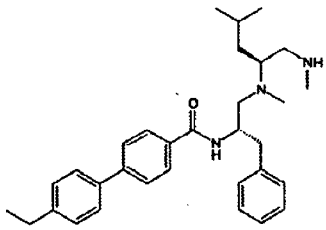
FIGS. 21A–21C show structures for agents TPI1349-1 through TPI1349-34 along with respective molecular weights, masses and lowest concentration of each agent having a ratio of 1.8 or higher in SMAC competition assays.
Figure 22W:
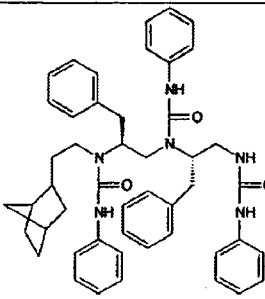
Figure 24T:
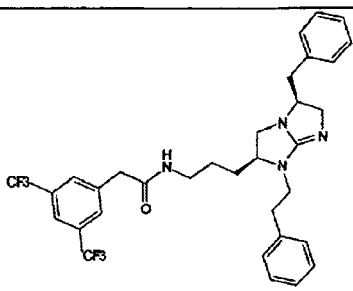

As shown in FIG. 19, TPI1396-34 induced apoptosis in HeLa cells transfected with a control vector. Apoptosis induced by TPI1396-34 was not blocked by over-expressing Bcl-XL, consistent with the fact that Bcl-XL operates upstream of XIAP. In contrast, HeLa cells over-expressing full-length XIAP were protected from TPI1396-34. In addition, cells expressing a mutant of XIAP in which the SMAC-binding pocket of XIAP was mutated were not protected from the chemical compound nor were cells expressing a mutant comprised of only the BIR2 domain. Cells expressing the BIR3 domain were protected from the apoptogenic activity of TPI-1396-34. Taken together, these results indicate that TPI1396-34 induces apoptosis of tumor cell lines in culture by targeting XIAP.

EXAMPLE XIII

Identification of Compounds that Inhibit IAPs Other than XIAP

This example describes an assay that can be used to determine the effects of derepressors of XIAP-inhibited caspases on other IAPs.

Immunohistochemical analysis of prostate cancers indicates that cIAP1 and cIAP2 are commonly over-expressed in these tumors. Both cIAP1 and cIAP2 are Caspase inhibitors (Roy, EMBO J. 16:6914–6925 (1997)) and they each bind SMAC (Du et al., Cell 102:33–42 (2000); Chai et al., Nature 406:855–862 (2000)). Moreover, molecular modeling studies indicate that some of the BIRs of cIAP1 and cIAP2 are likely to bind SMAC, having great structural similarity to XIAP. These observations indicate that derepressors of XIAP-inhibited caspases can have activity against caspases inhibited by these other IAPs.

To confirm that derepressors of XIAP-inhibited caspases have activity against caspases inhibited by these other IAPs the following assays are performed. Competition of the compounds with the SMAC peptide for binding to BIRs on XIAP is assayed. To accomplish this, the compounds are tested in SMAC competition assays in which FITC-conjugated SMAC tetrapeptide AVPI (SEQ ID NO:4) or FITC-conjugated HtrA2 tetra-peptide AVPS (SEQ ID NO:6) are bound to BIRs from XIAP. Rather than expressing full-length XIAP, fragments of XIAP containing only the BIR2 or BIR3 domains are expressed, as described in Takahashi et al., J. Biol. Chem. 273:7787–7790 (1998) and Deveraux et al., EMBO J. 17:2215–2223 (1998). These assays will determine if the compound functions as a SMAC-mimic, and also whether the compound targets BIR2 (the domain that inhibits Caspases-3 and -7), BIR3 (the domain that inhibits Caspase-9), both, or neither of these domains.

Additionally, enzyme depression assays are performed using BIR2 or BIR3 domains to pinpoint the domain in XIAP that is targeted by a compound. Recombinant purified BIR2 is mixed with Caspase-3, and BIR3 with Caspase-9, then the activity of these proteases is measured against specific fluorigenic substrate peptides (Ac-DEVD-AFC for Caspase-3 versus Ac-LEHD-AFC for Caspase-9) in the presence and absence of a compound in an effort to pinpoint whether the compound targets BIR2, BIR3, both or neither of these domains in the XIAP protein. These results can be used for structure-based optimization of compounds using molecular modeling of the published structures of XIAP, BIR2 (Sun et al., Nature 401:818–821 (1999) and Riedl et al., Cell 104:791–800 (2001)), and BIR3 (Liu et al., Nature 408:1004–1008 (2000)).

With respect to cIAP1 and cIAP2, similar enzyme derepression and SMAC competition assays are performed using full-length cIAP1 and cIAP2, as well as fragments containing individual BIR domains, thus determining whether the compounds cross-inhibit these other members of the IAP-family.

If a compound does inhibit cIAP1, cIAP2, or both of these proteins, then the potency of the compound can be improved through medicinal and combinatorial chemistry. Assays can be performed to contrast retention versus loss of cIAP1/cIAP2 activity in vitro with activity of compounds in cell-based assays. Structure activity relationship studies of this type indicate whether the optimal compound has selective specificity for XIAP versus pan-reactivity against several IAPs. The compounds with these different profiles (selective versus broad-spectrum activity) are contrasted with respect to toxicity issues, to obtain a compound with a desired balance between efficacy and safety.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. An isolated agent selected from the group consisting of TPI1396-11, TPI1396-12, TPI1396-22 or TPI1396-34, wherein said agent derepresses an IAP-inhibited caspase.

2. The agent of claim 1, wherein said agent derepresses an XIAP-inhibited caspase.

3. The agent of claim 1, wherein said agent derepresses an XIAP-inhibited caspase-3.

4. A composition comprising an isolated agent selected from the group consisting of of TPI1396-11, TPI1396-12, TPI1396-22 or TPI1396-34, and a pharmaceutically acceptable carrier.

5. The isolated agent of claim 1, which is TPI1396-11.
6. The isolated agent of claim 1, which is TPI1396-12.
7. The isolated agent of claim 1, which is TPI1396-22.
8. The isolated agent of claim 1, which is TPI1396-34.
9. The composition of claim 4, comprising TPI1396-11.
10. The composition of claim 4, comprising TPI1396-12.
11. The composition of claim 4, comprising TPI1396-22.
12. The composition of claim 4, comprising TPI1396-34.

* * * * *

SEQUENCE LISTING

<160> NUMBER OF SEQ ID NOS: 15

<210> SEQ ID NO 1
<211> LENGTH: 5
<212> TYPE: PRT
<213> ORGANISM: Artificial Sequence

```
<220> FEATURE:
<223> OTHER INFORMATION: synthetic construct
<220> FEATURE:
<221> NAME/KEY: VARIANT
<222> LOCATION: 4
<223> OTHER INFORMATION: Xaa = Any Amino Acid

<400> SEQUENCE: 1

Gln Ala Cys Xaa Gly
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic construct

<400> SEQUENCE: 2

Asp Glu Val Asp
1

<210> SEQ ID NO 3
<211> LENGTH: 4
<212> TYPE: PRT
<213> ORGANISM: Artificial Sequence
<220> FEATURE:
<223> OTHER INFORMATION: synthetic construct

<400> SEQUENCE: 3

Tyr Val Ala Asp
1

<210> SEQ ID NO 4
<211> LENGTH: 4
<212> TYPE: PRT
<213> ORGANISM: Artificial Sequence
<220> FEATURE:
<223> OTHER INFORMATION: synthetic construct

<400> SEQUENCE: 4

Ala Val Pro Ile
1

<210> SEQ ID NO 5
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 7
<223> OTHER INFORMATION: at the C-terminus
<220> FEATURE:
<221> NAME/KEY: MOD_RES
<222> LOCATION: 1
<223> OTHER INFORMATION: hydrogenated at the N-terminus

<400> SEQUENCE: 5

Ala Val Pro Ile Ala Gln Lys
1               5

<210> SEQ ID NO 6
<211> LENGTH: 4
<212> TYPE: PRT
<213> ORGANISM: Artificial Sequence
<220> FEATURE:
<223> OTHER INFORMATION: synthetic peptide
```

```
<400> SEQUENCE: 6

Ala Val Pro Ser
1

<210> SEQ ID NO 7
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 7

Xaa Xaa Ala Ala Trp Trp
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 8

Xaa Xaa Gly Ala Trp Trp
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 9

Xaa Xaa Arg Ala Trp Trp
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 10

Xaa Xaa Cys Lys Trp Trp
1               5

<210> SEQ ID NO 11
<211> LENGTH: 6
<212> TYPE: PRT
<213> ORGANISM: Artificial Sequence
```

-continued

```
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 11

Xaa Xaa Phe Trp Trp Trp
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 12

Xaa Xaa Leu Trp Trp Trp
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 13

Xaa Xaa Trp Leu Trp Trp
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 14

Xaa Xaa Trp Trp Trp Trp
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
```

```
-continued

<222> LOCATION: (1)...(2)
<223> OTHER INFORMATION: Xaa=any amino acid

<400> SEQUENCE: 15

Xaa Xaa Leu Lys Trp Trp
1               5
```